(12) United States Patent
Iwata-Reuyl et al.

(10) Patent No.: US 7,364,882 B1
(45) Date of Patent: Apr. 29, 2008

(54) ENZYMATIC REDUCTION OF A NITRILE CONTAINING COMPOUND TO THE CORRESPONDING AMINE

(75) Inventors: Dirk Iwata-Reuyl, Corbett, OR (US); Valérie de Crecy-Lagard, Gainesville, FL (US); Steven G. Van Lanen, Madison, WI (US)

(73) Assignees: State of Oregon Acting by and Through the State Board of Higher Education on Behalf of Portland State University, Portland, OR (US); Scripps Research Institute, La Jolla, CA (US)

( * ) Notice: Subject to any disclaimer, the term of this patent is extended or adjusted under 35 U.S.C. 154(b) by 0 days.

(21) Appl. No.: 11/235,933

(22) Filed: Sep. 26, 2005

Related U.S. Application Data

(60) Provisional application No. 60/612,879, filed on Sep. 24, 2004.

(51) Int. Cl.
  *C12P 13/00* (2006.01)
  *C12P 21/06* (2006.01)
  *C12N 9/00* (2006.01)
  *C12N 1/21* (2006.01)

(52) U.S. Cl. ............... 435/128; 435/69.1; 435/189; 435/471; 435/252.3

(58) Field of Classification Search ............... 435/128, 435/69.1, 471, 189
See application file for complete search history.

(56) References Cited

U.S. PATENT DOCUMENTS 6,872,555 B2   3/2005   Heyer et al.

OTHER PUBLICATIONS

Accession No. CAB13248 (Jul. 07, 2003).
Bai et al., "Hypermodification of tRNA in Thermophilic Archaea," *J. Biol. Chem.* 275:28731-28738 (2000). Note: article originally e-published on Jun. 20, 2000.
Beardall et al., "Mutagenesis of the tRNA Modifying Enzyme TGT from Archaea," *2001 Northwest Regional Meeting of the American Chemical Society*, Jun. 14-17, 2001, Hosted by Seattle University, Seattle Washington.
Reader et al., "Identification of Four Genes Necessary for Biosynthesis of the Modified Nucleoside Queuosine," *J. Biol. Chem.* 279:6280-6285 (2004).
Van Lanen et al., "From Cyclohydrolase to Oxidoreductase: Discovery of Nitrile Reductase Activity in a Common Fold," *Proc. Natl. Acad. Sci. USA* 102:4264-4269 (2005). Note: article originally e-published on Mar. 14, 2005.
Van Lanen et al., "tRNA Modification by S-Adenosylmethionine:tRNA Ribosyltransferase-Isomerase," *J. Biol. Chem.* 278:10491-10499 (2003). Note: article originally e-published on Jan. 16, 2003.

*Primary Examiner*—Rebecca E. Prouty
*Assistant Examiner*—Younus Meah
(74) *Attorney, Agent, or Firm*—Klarquist Sparkman, LLP

(57) ABSTRACT

A new class of enzymes that catalyze the conversion of a nitrile containing compound to the corresponding amine (such as a primary amine) are disclosed. Such enzymes are referred to herein as nitrile oxido-reductases. Methods of using the enzymes to reduce a nitrile to a amine, for example in vitro or in vivo, are provided. Such methods provide the first biocatalysis method for reducing nitrites to amines, and provides an alternative to currently used methods, which generally utilize harsh reaction conditions and the production of hazardous waste. While the hydrolysis of nitrites to amides and carboxylic acids via biocatalysis has found extensive use in industry, the lack of a known nitrile oxido-reductase has precluded the application of biocatalysis to nitrile reduction.

36 Claims, 22 Drawing Sheets
(15 of 22 Drawing Sheet(s) Filed in Color)

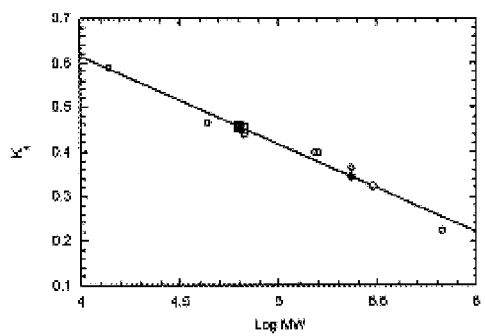
FIG. 4
FIG. 5
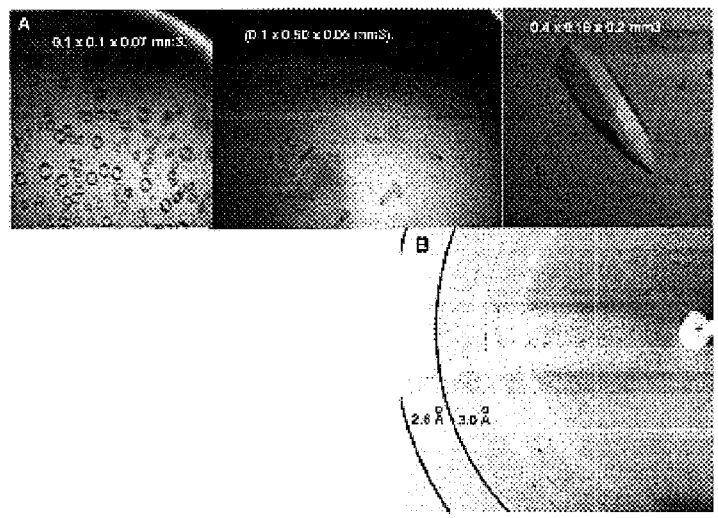
FIG. 7

*Alignment of class I (YkvM) QueF family members*

|   | 10 | 20 | 30 | 40 | Majority |
|---|---|---|---|---|---|
| 1 | | | | | A.aeo |
| 1 | | | | | A.tum |
| 1 | | | | | B.abo |
| 1 | | | | | B.aeo |
| 1 | | | | | B.ant |
| 1 | | | | | B.mel |
| 1 | | | | | B.sub |
| 1 | | | | | B.sui |
| 1 | | | | | B.the |
| 1 | | | | | C.cre |
| 1 | | | | | C.jej1 |
| 1 | | | | | C.tep |
| 1 | | | | | G.vio |
| 1 | | | | | H.pyl1 |
| 1 | | | | | H.pyl2 |
| 1 | S R L W K R L R L S | P W R T S L T R V C | I D V I L I E K L N | Y Y A L I P R V P E | J.Gle1 |
| 1 | - - M F N Q E R I S | | | | J.Gle2 |
| 1 | | | | | K.pne1 |
| 1 | | | | M | L.int1 |
| 1 | | | | | M.lot |
| 1 | | | | | M.mag |
| 1 | | | | | N.aro |
| 1 | | | | | N.eur |
| 1 | | | | | N.gon |
| 1 | | | | | N.men1 |
| 1 | | | | | N.men2 |
| 1 | | | | | N.PCC |
| 1 | | | | | N.pun |
| 1 | | | | | O.ihe |
| 1 | | | | | P.gin |
| 1 | | | | | P.mar |
| 1 | | | | | P.mar1 |
| 1 | | | | | P.mar2 |
| 1 | | | | | P.spl |
| 1 | | | | | S.mel |
| 1 | | | | | S.mut |
| 1 | | | | | S.par |
| 1 | | | | | S.PC |
| 1 | | | | | S.TM |
| 1 | | | | | S.WH |
| 1 | | | | | T.elo1 |
| 1 | | | | | T.mar |
| 1 | | | | | T.ten |
| 1 | | | | | W.suc |

```
          N Y G K P P T G - - - - - - - - - - - - - - - - - - - - - - - - - - - - - - - - -  Majority
                      210                 220                 230                 240
123   R S D E N Y G                                                                           A.aeo
149   Q T G A A P E G V W L P D Q G V A P Y R G R G                                           A.tum
133   Q T G A A P L N V W I P E Q G V A N Y R G R G                                           B.abo
136   N Y G R P G T K Y E Q M A D Y R M M N H D L Y P E T I D N R                             B.aeo
131   Q T G R V P K G L W V P E Q G V A P Y R G R G                                           B.ant
133   Q T G A A P L N V W I P E Q G V A N Y R G R G                                           B.mel
136   N Y G K P G T K Y E K M A E Y R M M N H D L Y P E T I D N R                             B.sub
133   Q T G A A P L N V W I P E Q G V A N Y R G R G                                           B.sui
131   N Y G R P G T K F E Q M A E H R L M N R E                                               B.the
129   Q T G P A P E G L W V P D Q G V A P Y R G R G                                           C.cre
120   R S D M V V P K                                                                         C.jej1
110   V S Y S K S K E                                                                         C.tep
131   R H T R P G T                                                                           G.vio
130   N Y A I K - - E Y Q D F K E K R L L N A K                                               H.pyl1
130   N Y A I K - - E Y Q D F K E K R L L D A K                                               H.pyl2
178   H S G M G K T P E K D G I S                                                             J.Gle1
140   D T E M N P K K R K R                                                                   J.Gle2
 95   T F P P P A A S P V N N K Q F H N L R A F R R A Q G C G N A V R R A I V I T G           K.pne1
130   R E V K K P                                                                             L.int1
131   Q T G A P P E G A W L P D T G V A P Y R G R G                                           M.loc
129   Q T G P S P E G L W L P D Q G V A G Y R G R G                                           M.mag
144   Q S G P P P A G L W L P D Q G V A P Y R G R G                                           N.aro
113   A E H R K K G W Q P Q P P V L L E V F E Q Q F N T H C                                   N.eur
135   N Y G K A G T E F E A L A R K R L F E H D A Q                                           N.gon
135   N Y G K A G T E F E T L A R K R L F E H D A Q                                           N.men1
135   N Y G K A G T E F E A L A R K R L F E H D A Q                                           N.men2
133   R H T K                                                                                 N.PCC
134   R H H K Y P S                                                                           N.pun
136   N Y G R P G T K F E Q M A D Q R L I Q H D M Y P E K I D N R                             O.ihe
134   N Y G K P G S R Y E L L A E K R M E T H H                                               P.gin
128   S H G S R Q P C                                                                         P.mar
130   Y S G Q K R N                                                                           P.mar1
128   S H G L K N N C                                                                         P.mar2
115   V T Y P D E A                                                                           P.sp1
132   Q T G N P P E G V W L P D Q G V E T Y R G R G                                           S.mel
133   N Y G R P N T K Y E E M A A Y R L M N H D L Y P E T I D N R                             S.mut
142   D F V P P R A G W R D S N - F F V N P - A C R I A H - - - - - V R L                     S.par
130   E Y H Q E K A S                                                                         S.PC
149   Q S G T I P E G V W I P D Q G V P P Y R G R G                                           S.TM
126   S H G T R Q P C                                                                         S.WH
123   E H H R Q T E S L C                                                                     T.elo1
126   G S L E G K K S G E V E                                                                 T.mar
127   A R Y E K E E Y                                                                         T.ten
120   D S K K N                                                                               W.suc
```

FIG. 9F

|  | Majority |
|---|---|
| 129 | A.aeo |
| 171 | A.tum |
| 155 | B.abo |
| 165 | B.aeo |
| 153 | B.ant |
| 155 | B.mel |
| 165 | B.sub |
| 155 | B.sui |
| 151 | B.the |
| 151 | C.cre |
| 127 | C.jej1 |
| 117 | C.tep |
| 137 | G.vio |
| 148 | H.pyl1 |
| 148 | H.pyl2 |
| 191 | J.Gle1 |
| 150 | J.Gle2 |
| 135 R P | K.pne1 |
| 135 | L.int1 |
| 153 | M.lot |
| 151 | M.mag |
| 166 | N.aro |
| 139 | N.eur |
| 157 | N.gon |
| 157 | N.men1 |
| 157 | N.men2 |
| 136 | N.PCC |
| 140 | N.pun |
| 165 | O.ihe |
| 154 | P.gin |
| 135 | P.mar |
| 136 | P.mar1 |
| 135 | P.mar2 |
| 121 | P.sp1 |
| 154 | S.mel |
| 162 | S.mut |
| 168 | S.par |
| 137 | S.PC |
| 171 | S.TM |
| 133 | S.WH |
| 132 | T.elo1 |
| 137 | T.mar |
| 134 | T.ten |
| 124 | W.suc |

```
              P D Y L E N A A S G - - - K V V E E T L V S H L L K S N C L I T G Q P D W G S V  Majority
                              290             300              310              320
      170  A E W L K D C T S S - - - D V V E E T L V S H  L      L I Q          G S L  A.act
      162  N E H L A S V A E G - - - E V V E E T L V S H  L      P V S          G S V  A.ple
      280  A E L L R C D P A - - - - R R V E Q V L H S H  L      P V S          G S L  A.vin
      145  P S F L M I N S E R - - - K I I K E D L Y T H  F      P V Q          A S I  B.aph
      186  P Q L L Q C A P G - - - - D E V E E T L A T R  L      P V G          A S L  B.bro
      156  P Q L L Q C A P G - - - - D E V E E T L A T R  L      P V G          A S L  B.par
      156  P Q L L Q C A P G - - - - D E V E E T L A T R  L      P V G          A S L  B.per
      162  P E I L S A D S - - - - T A I V S E T L C S N  L      L V G          G S V  C.vio
      162  P N L L S T S Q - - - - - E T V T E T L Y S H  L      P V G          G S I  C.bur
      164  T D Y L E N A T S G E - - K V V E T L V S H    L      L I H          G S I  E.col1
      164  T D Y L E N A T S G E - - K V V E E T L V S H  L      L I H          G S I  E.col2
      164  T D Y L E N A T S G E - - K V V E E T L V S H  L      L I H          G S I  E.col3
      164  T D Y L E N A T S G E - - K V V E E T L V S H  L      L I H          G S L  E.col4
      164  T D Y L E N A T C G E - - K V V E E T L V S H  L      L I H          G S L  E.col5
      162  A N N L K D C V S D - - - E I V E E K L V S H  L      L I N          G T L  H.inf
      162  A Q Y L E H S A E G - - - E E V E R T L V S H  L      L I G          G S V  H.duc
      162  P N L L E R C T N K - - - Q N V E E K L V S H  L      L I N          G T V  H.som1
      162  P N L L E R C T N K - - - Q N V E E K L V S H  L      L I N          G T V  H.som2
      162  P E I L T N C T H D - - - Q M V K E S L V S H  L      L I N          G T L  P.mul
      164  R H Y L Q N A A Q G P - - Q - V E E V L V S H  L      L I H          G S V  P.lum
      160  P E L L R C D A G - - - - R I V E E Q L Y S H  L      P V G          G T L  P.aer
      160  P E L L R C N P E - - - - R V V E E T L V S H  L      P V G          G S V  P.put
      188  P E L L C C D D S - - - - R V V A E S V H S H  L      P V S          G S V  P.syr1
      160  P E L L R C D D S - - - - Q V I E E A V H S H  L      P V S          G S V  P.syr2
      159  E T L L S A E Q E - - - E S P V E E T L V S H  L      L V G          G S V  R.met
      159  P G L L H A D Q D - - - E S P V E E V L V S H  L      L V G          G S V  R.sol
      156  N S L I E Y E D - - - - - V L V E E I N S H    L      L V G          G T I  R.con
      156  N S L I E Y E D - - - - - V L V E E I Y S N    F      L V G          G T I  R.pro
      156  N S L I E Y E D - - - - - V L V E E I N S N    L      L V G          G T I  R.sib
      164  T D Y L Q H A V S G E - - K Q V E E T L V S H  L      L I H          G S I  S.ent1
      164  T D Y L Q H A V S G E - - K Q V E E T L V S H  L      L I H          G S I  S.ent2
      164  T D Y L Q H A V S G E - - K Q V S E T L V S H  L      L I H          G S I  S.ent3
      164  T D Y L Q H A V S G E - - K Q V E E T L V S H  L      L I H          G S I  S.typ
      179  P E Y L E N S T D E K - - Q I V A E T L N S N  L      L I S          G S V  S.one
      164  T D Y L E N A T S G E - - K V V E E T L V S H  L      L I H          G S I  S.fle1
      164  T D Y L E N A T S G E - - K V V E E T L V S H  L      L I H          G S I  S.fle2
      169  D A L L Q G A A Q G - - - E E V S E V L H S H  L      L I N          G S V  V.cho
      163  A D L L A G A A G E - - - D Q V E E V L H S H  L      L I N          G S V  V.par
      163  D R L L E G A A G E - - - E N V T E T L H S H  L      L I N          G S V  V.vul1
      163  D R L L E G A A G E - - - E W V T E T L H S H  L      L I N          G S V  V.vul2
      153  A D Y L A T H A G - - - - T V V E E V L A S A  L      P V G          A S V  X.cam
      153  A A Y L C A H A Q - - - - P V V E R V L T S A  L      P V G          A S V  X.axo
      153  P D Y L S N V A Q N L I E E M V E E T L T S T  F      P V G          A S V  X.fas1
      153  P D Y L S N V A Q N L V E E M V E E T L T S T  F      P V G          A S V  X.fas2
      153  P D Y L S N V A Q N F V E E M V E E T L T S T  F      P V G          A S V  X.fas3
      153  P D Y L S N V A Q N L V E E M V E E T L T S T  F      P V G          A S V  X.fas4
      164  A D Y L Q G A A - G K - - D E V E E S L V S H  L      L I H          G S V  Y.pes1
      164  A D Y L Q G A A - G K - - D E V E E S L V S H  L      L I H          G S V  Y.pes2
```

FIG. 10H

```
              Q I R Y R G R K I D R E K L L R Y L V S F R H H N E F H E Q C V E R I P N D L L  Majority
                            330             340              350             360
207  Q I H    V    K Q I N R E Q L    R    I I S F    Q H N E    H    Q    V    I F C    L M  A.act
199  Q I H    V    K K L N R E K L    R    L V S F    E H N E    H    Q    V    I F I    L I  A.ple
316  V V D    H    P A L D P A S L    A    V V S F    Q H A D    H    Q    V    I F L    L L  A.vin
182  Y I A    T    L S I N H A S L    R    L I S F    S H N E    H    E    I    I P N    I N  B.aph
222  Q V R    R    R P I D R A A L    K    V V S F    Q H A E    H    H    V    I F G    I M  B.bro
192  Q V R    R    R P I D R A A L    K    V V S F    Q H A E    H    H    V    I F G    I M  B.par
192  Q V R    R    R P I D R A A L    K    V V S F    Q H A E    H    H    V    I F G    I M  B.per
196  S I R    T    P K I D R E A L    R    L I G F    R H N E    H    Q    V    I F V    V L  C.vio
197  E I H    T    P K I D H V Q L    K    I I S Y    N H E H    H    A    V    F F M    I L  C.bur
202  Q I Q    R    R Q I D R E K L    R    L V S F    H H N E    H    Q    V    I F N    L L  E.col1
202  Q I Q    R    R Q I D R E K L    R    L V S F    H H N E    H    Q    V    I P N    L L  E.col2
202  Q I Q    R    R Q I D R E K L    R    L V S F    H H N E    H    Q    V    I F N    L L  E.col3
202  Q I Q    R    R Q I D R E K L    R    L V S F    H H N E    H    Q    V    I F N    L L  E.col4
202  Q I Q    R    R Q I D R E K L    R    L V S F    H H N E    H    Q    V    I F N    L L  E.col5
199  H I H    V    K K I N Q E K L    R    V V S F    Q H M E    H    Q    V    I F C    L M  H.inf
199  Q I H    V    K K I N R E K L    R    L V S F    R H N E    H    Q    V    I F I    L M  H.duc
199  Q I H    I    N Q I N R E K L    R    L I S F    Q H N E    H    Q    V    I F C    L M  H.som1
199  Q I H    I    N Q I N R E K L    R    L I S F    Q H N E    H    Q    V    I F C    L M  H.som2
199  Q I R    E    K Q I D R E K L    R    I I S F    Q H N E    H    Q    V    I F C    L M  P.mul
201  Q I H    K    S K I N R E A L    R    L I S F    H H N E    H    Q    V    I F S    L Q  P.lum
196  V V D    R    P A L D P A S L    A    L V S F    Q H Q D    H    Q    V    I F L    L Q  P.aer
196  V V Q    K    R A L D H A S L    T    L I S F    Q H A D    H    Q    V    I Y L    L K  P.put
224  V V E    R    A A L D H A S L    A    I V S F    Q R S D    H    Q    V    I F L    L Q  P.syr1
196  V V E    R    A A L D H A S L    A    I V S F    Q H S D    H    Q    V    I F L    L Q  P.syr2
196  Q I R    V    A P I D Q E G L    K    L I S F    N H N E    H    Q    V    I F P    V M  R.met
196  Q I R    V    A P I N Q E G L    K    L I S F    E H N E    H    Q    V    I P M    I Q  R.sol
191  V I K    K    K K L K Y D S F    R    L I S F    N C N E    A    Q    A    I F T    I K  R.con
191  V I K    K    K K L K Y D S F    R    L I S F    N F N E    A    Q    A    I F I    I K  R.pro
191  V I K    K    K K L K Y D S F    K    L I S F    N C N E    A    Q    A    I F T    I K  R.sib
202  Q I Q    R    R K I D R E K L    R    L V S F    H H N E    H    Q    V    I F N    I L  S.ent1
202  Q I Q    R    R K I D R E K L    R    L V S F    H H N E    H    Q    V    I F N    I L  S.ent2
202  Q I Q    R    R K I D R E K L    R    L V S F    H H N E    H    Q    V    I F N    L L  S.ent3
202  Q I Q    R    R K I D R E K L    R    L V S F    H H N E    H    Q    V    I P N    I L  S.typ
217  M I R    Q    P K I D R E K L    R    L I S F    Q H M E    H    Q    V    I F V    L K  S.one
202  Q I Q    R    R Q I D R E K L    R    L V S F    H H N E    H    Q    V    I F N    L L  S.fle1
202  Q I Q    R    R Q I D R E K L    R    L V S F    H H N E    H    Q    V    I F N    L L  S.fle2
206  E I A    H    A K M N R E A L    R    L V S F    E H M E    H    Q    V    I F T    I M  V.cho
200  E I R    Q    A K I D R E K L    R    L V S F    E H N E    H    Q    V    I F T    L M  V.par
200  E I R    Q    H K I D R E K L    R    L V S F    E H N E    H    Q    V    I F T    L M  V.vul1
200  E I R    Q    H K I D R E K L    R    L V S F    E H N E    H    Q    V    I F T    L M  V.vul2
189  T L R    R    A P I D R E G L    R    L V S F    D H A D    H    Q    V    I F Q    L L  X.cam
189  T L R    R    A P I D R E G L    R    L V S F    D H A D    H    Q    V    I F N    V L  X.axo
193  T V R    F    V P I D H E G L    R    F I S F    H H A E    H    Q    V    I F Q    V L  X.fas1
193  T V R    F    M P I D H E G L    R    F I S F    H H A E    H    Q    V    I F Q    V L  X.fas2
193  T V R    F    V P I D H E G L    R    F I S F    H H A E    H    Q    V    I F Q    V L  X.fas3
193  T V R    F    M P I D H E G L    R    F I S F    H H A E    H    Q    V    I F Q    V L  X.fas4
201  Q I H    R    P Q I D H E A L    R    L V S F    H H N E    H    Q    V    I F N    I M  Y.pes1
201  Q I H    R    P Q I D H E A L    R    L V S F    H H N E    H    Q    V    I F N    I M  Y.pes2
```

|     | A R Q |        | Majority |
|-----|-------|--------|----------|
| 285 | A     |        | A.act    |
| 277 | A     |        | A.ple    |
| 394 | A     |        | A.vin    |
| 260 | A     |        | B.aph    |
| 301 | A     |        | B.bro    |
| 271 | A     |        | B.par    |
| 271 | A     |        | B.per    |
| 277 | A     |        | C.vio    |
| 276 | F     |        | C.bur    |
| 280 | V     |        | E.col1   |
| 280 | V     |        | E.col2   |
| 280 | V     |        | E.col3   |
| 280 | V     |        | E.col4   |
| 280 | V     |        | E.col5   |
| 277 | A     |        | H.inf    |
| 277 | A     |        | H.duc    |
| 277 | A     |        | H.som1   |
| 277 | A     |        | H.som2   |
| 277 | A     |        | P.mul    |
| 280 | A     |        | P.lum    |
| 274 | V     |        | P.aer    |
| 274 | V     |        | P.put    |
| 302 | A     |        | P.syr1   |
| 274 | A     |        | P.syr2   |
| 275 | A     |        | R.met    |
| 275 | A     |        | R.sol    |
| 271 | I     |        | R.con    |
| 271 | I     |        | R.pro    |
| 271 | I     |        | R.sib    |
| 280 | A     |        | S.ent1   |
| 280 | A     |        | S.ent2   |
| 280 | A     |        | S.ent3   |
| 280 | A     |        | S.typ    |
| 293 | A     |        | S.one    |
| 280 | V     |        | S.fle1   |
| 280 | V     |        | S.fle2   |
| 285 | A     |        | V.cho    |
| 279 | A     |        | V.par    |
| 279 | A     |        | V.vul1   |
| 279 | A     |        | V.vul2   |
| 269 | L     |        | X.cam    |
| 269 | L     |        | X.axo    |
| 273 | P     |        | X.fas1   |
| 273 | P     |        | X.fas2   |
| 273 | P     |        | X.fas3   |
| 273 | P     |        | X.fas4   |
| 279 | A     |        | Y.pes1   |
| 279 | A     |        | Y.pes2   |

FIG. 10K

SEQUENCE LISTING

```
<160> NUMBER OF SEQ ID NOS: 95

<210> SEQ ID NO 1
<211> LENGTH: 498
<212> TYPE: DNA
<213> ORGANISM: Bacillus subtilis
<220> FEATURE:
<221> NAME/KEY: CDS
<222> LOCATION: (1)..(498)

<400> SEQUENCE: 1 atg acg aca aga aaa gaa tca gaa tta gaa ggt gta aca ttg cta ggc        48
Met Thr Thr Arg Lys Glu Ser Glu Leu Glu Gly Val Thr Leu Leu Gly
1               5                   10                  15 aat caa ggt aca aat tat ttg ttc gaa tat gca ccg gac gtg ctg gaa        96
Asn Gln Gly Thr Asn Tyr Leu Phe Glu Tyr Ala Pro Asp Val Leu Glu
            20                  25                  30 tcc ttc cct aat aaa cat gta aac cgt gat tac ttt gta aaa ttc aat       144
Ser Phe Pro Asn Lys His Val Asn Arg Asp Tyr Phe Val Lys Phe Asn
        35                  40                  45 tgc ccg gaa ttc aca tct tta tgt cct aaa aca ggc cag cct gac ttt       192
Cys Pro Glu Phe Thr Ser Leu Cys Pro Lys Thr Gly Gln Pro Asp Phe
    50                  55                  60 gcg aca atc tac atc agc tac att cct gat gaa aaa atg gtt gaa agc       240
Ala Thr Ile Tyr Ile Ser Tyr Ile Pro Asp Glu Lys Met Val Glu Ser
65                  70                  75                  80 aaa tca tta aag ctg tat cta ttc agc ttc aga aac cat ggt gac ttc       288
Lys Ser Leu Lys Leu Tyr Leu Phe Ser Phe Arg Asn His Gly Asp Phe
```

-continued

```
                    85                  90                  95
cac gag gac tgc atg aat atc atc atg aac gac ttg att gaa tta atg    336
His Glu Asp Cys Met Asn Ile Ile Met Asn Asp Leu Ile Glu Leu Met
                100                 105                 110 gac ccg cgc tac att gaa gta tgg ggc aaa ttc acg cca aga ggc gga    384
Asp Pro Arg Tyr Ile Glu Val Trp Gly Lys Phe Thr Pro Arg Gly Gly
            115                 120                 125 att tcc att gat ccg tac aca aac tac gga aag cct ggc acg aag tat    432
Ile Ser Ile Asp Pro Tyr Thr Asn Tyr Gly Lys Pro Gly Thr Lys Tyr
        130                 135                 140 gag aaa atg gcc gaa tac cgt atg atg aac cat gat ttg tat ccg gag    480
Glu Lys Met Ala Glu Tyr Arg Met Met Asn His Asp Leu Tyr Pro Glu
145                 150                 155                 160 aca att gat aat cgt taa                                            498
Thr Ile Asp Asn Arg
                165

<210> SEQ ID NO 2
<211> LENGTH: 165
<212> TYPE: PRT
<213> ORGANISM: Bacillus subtilis

<400> SEQUENCE: 2

Met Thr Thr Arg Lys Glu Ser Glu Leu Glu Gly Val Thr Leu Leu Gly
1               5                   10                  15

Asn Gln Gly Thr Asn Tyr Leu Phe Glu Tyr Ala Pro Asp Val Leu Glu
            20                  25                  30

Ser Phe Pro Asn Lys His Val Asn Arg Asp Tyr Phe Val Lys Phe Asn
        35                  40                  45

Cys Pro Glu Phe Thr Ser Leu Cys Pro Lys Thr Gly Gln Pro Asp Phe
    50                  55                  60

Ala Thr Ile Tyr Ile Ser Tyr Ile Pro Asp Glu Lys Met Val Glu Ser
65                  70                  75                  80

Lys Ser Leu Lys Leu Tyr Leu Phe Ser Phe Arg Asn His Gly Asp Phe
                85                  90                  95

His Glu Asp Cys Met Asn Ile Ile Met Asn Asp Leu Ile Glu Leu Met
                100                 105                 110

Asp Pro Arg Tyr Ile Glu Val Trp Gly Lys Phe Thr Pro Arg Gly Gly
            115                 120                 125

Ile Ser Ile Asp Pro Tyr Thr Asn Tyr Gly Lys Pro Gly Thr Lys Tyr
        130                 135                 140

Glu Lys Met Ala Glu Tyr Arg Met Met Asn His Asp Leu Tyr Pro Glu
145                 150                 155                 160

Thr Ile Asp Asn Arg
                165

<210> SEQ ID NO 3
<211> LENGTH: 849
<212> TYPE: DNA
<213> ORGANISM: Escherichia coli
<220> FEATURE:
<221> NAME/KEY: CDS
<222> LOCATION: (1)..(849)

<400> SEQUENCE: 3 atg tct tct tat gca aac cat cag gca ctt gcg ggc ctg act ctt gga    48
Met Ser Ser Tyr Ala Asn His Gln Ala Leu Ala Gly Leu Thr Leu Gly
1               5                   10                  15 aaa tca acc gat tac cgg gat acc tat gac gcc agc cta ctg caa ggc    96
```

```
                                                                        -continued Lys Ser Thr Asp Tyr Arg Asp Thr Tyr Asp Ala Ser Leu Leu Gln Gly
             20                  25                  30 gtt cca cgc agc ctg aat cgc gac ccg ctg ggt ctg aaa gcg gat aac      144
Val Pro Arg Ser Leu Asn Arg Asp Pro Leu Gly Leu Lys Ala Asp Asn
             35                  40                  45 ctg cct ttt cac ggt acg gat atc tgg acg ctg tat gaa ctt tcc tgg      192
Leu Pro Phe His Gly Thr Asp Ile Trp Thr Leu Tyr Glu Leu Ser Trp
 50                  55                  60 ctg aat gcg aaa ggt ttg ccg cag gtc gct gtc ggt cat gtt gaa ctt      240
Leu Asn Ala Lys Gly Leu Pro Gln Val Ala Val Gly His Val Glu Leu
 65                  70                  75                  80 gat tac acc agc gta aat ctg att gag tcg aag agt ttt aag ctc tat      288
Asp Tyr Thr Ser Val Asn Leu Ile Glu Ser Lys Ser Phe Lys Leu Tyr
                 85                  90                  95 ctc aac agt ttt aac cag acg cgt ttt aat aac tgg gat gag gtg cgc      336
Leu Asn Ser Phe Asn Gln Thr Arg Phe Asn Asn Trp Asp Glu Val Arg
            100                 105                 110 cag acg ctg gag cgc gac tta agc act tgc gct cag ggt aag att agc      384
Gln Thr Leu Glu Arg Asp Leu Ser Thr Cys Ala Gln Gly Lys Ile Ser
            115                 120                 125 gtg gcg tta tat cgt ctt gat gaa ctg gaa ggc cag ccg ata ggt cat      432
Val Ala Leu Tyr Arg Leu Asp Glu Leu Glu Gly Gln Pro Ile Gly His
        130                 135                 140 ttt aat ggc act tgc att gat gac cag gat atc act atc gat aac tat      480
Phe Asn Gly Thr Cys Ile Asp Asp Gln Asp Ile Thr Ile Asp Asn Tyr
145                 150                 155                 160 gaa ttc act act gac tat ctg gag aat gcc acc tgt ggt gaa aaa gta      528
Glu Phe Thr Thr Asp Tyr Leu Glu Asn Ala Thr Cys Gly Glu Lys Val
                165                 170                 175 gtg gaa gag acg ctt gtc agc cac ctg ctg aaa tca aac tgc ctg atc      576
Val Glu Glu Thr Leu Val Ser His Leu Leu Lys Ser Asn Cys Leu Ile
            180                 185                 190 acc cat caa cca gat tgg ggt tcg ctc caa att cag tat cgt gga cgc      624
Thr His Gln Pro Asp Trp Gly Ser Leu Gln Ile Gln Tyr Arg Gly Arg
            195                 200                 205 caa att gac aga gaa aaa ctg ctg cgt tac ctg gtc tca ttc cgt cat      672
Gln Ile Asp Arg Glu Lys Leu Leu Arg Tyr Leu Val Ser Phe Arg His
        210                 215                 220 cac aac gag ttc cac gaa cag tgc gtg gaa cgc atc ttt aat gac ctg      720
His Asn Glu Phe His Glu Gln Cys Val Glu Arg Ile Phe Asn Asp Leu
225                 230                 235                 240 tta cgc ttc tgc cag cca gaa aaa ttg agc gtt tac gca cgt tat acc      768
Leu Arg Phe Cys Gln Pro Glu Lys Leu Ser Val Tyr Ala Arg Tyr Thr
                245                 250                 255 cgt cgt ggc ggt ctg gac att aac ccg tgg cgc agt aat agc gat ttt      816
Arg Arg Gly Gly Leu Asp Ile Asn Pro Trp Arg Ser Asn Ser Asp Phe
            260                 265                 270 gtc cca tcg acc aca aga ctg gtt cgg caa taa                          849
Val Pro Ser Thr Thr Arg Leu Val Arg Gln
            275                 280

<210> SEQ ID NO 4
<211> LENGTH: 282
<212> TYPE: PRT
<213> ORGANISM: Escherichia coli

<400> SEQUENCE: 4

Met Ser Ser Tyr Ala Asn His Gln Ala Leu Ala Gly Leu Thr Leu Gly
1               5                   10                  15

Lys Ser Thr Asp Tyr Arg Asp Thr Tyr Asp Ala Ser Leu Leu Gln Gly
```

-continued

```
                      20                  25                  30
Val Pro Arg Ser Leu Asn Arg Asp Pro Leu Gly Leu Lys Ala Asp Asn
         35                  40                  45

Leu Pro Phe His Gly Thr Asp Ile Trp Thr Leu Tyr Glu Leu Ser Trp
 50                  55                  60

Leu Asn Ala Lys Gly Leu Pro Gln Val Ala Val Gly His Val Glu Leu
 65                  70                  75                  80

Asp Tyr Thr Ser Val Asn Leu Ile Glu Ser Lys Ser Phe Lys Leu Tyr
                 85                  90                  95

Leu Asn Ser Phe Asn Gln Thr Arg Phe Asn Asn Trp Asp Glu Val Arg
             100                 105                 110

Gln Thr Leu Glu Arg Asp Leu Ser Thr Cys Ala Gln Gly Lys Ile Ser
         115                 120                 125

Val Ala Leu Tyr Arg Leu Asp Glu Leu Glu Gly Gln Pro Ile Gly His
 130                 135                 140

Phe Asn Gly Thr Cys Ile Asp Asp Gln Asp Ile Thr Ile Asp Asn Tyr
145                 150                 155                 160

Glu Phe Thr Thr Asp Tyr Leu Glu Asn Ala Thr Cys Gly Glu Lys Val
                165                 170                 175

Val Glu Glu Thr Leu Val Ser His Leu Leu Lys Ser Asn Cys Leu Ile
             180                 185                 190

Thr His Gln Pro Asp Trp Gly Ser Leu Gln Ile Gln Tyr Arg Gly Arg
         195                 200                 205

Gln Ile Asp Arg Glu Lys Leu Leu Arg Tyr Leu Val Ser Phe Arg His
 210                 215                 220

His Asn Glu Phe His Glu Gln Cys Val Glu Arg Ile Phe Asn Asp Leu
225                 230                 235                 240

Leu Arg Phe Cys Gln Pro Glu Lys Leu Ser Val Tyr Ala Arg Tyr Thr
                245                 250                 255

Arg Arg Gly Gly Leu Asp Ile Asn Pro Trp Arg Ser Asn Ser Asp Phe
             260                 265                 270

Val Pro Ser Thr Thr Arg Leu Val Arg Gln
         275                 280
```

```
<210> SEQ ID NO 5
<211> LENGTH: 8
<212> TYPE: PRT
<213> ORGANISM: Artificial
<220> FEATURE:
<223> OTHER INFORMATION: QueF motif
<220> FEATURE:
<221> NAME/KEY: MISC_FEATURE
<222> LOCATION: (2)..(2)
<223> OTHER INFORMATION: X at position 2 is S or L
<220> FEATURE:
<221> NAME/KEY: MISC_FEATURE
<222> LOCATION: (4)..(4)
<223> OTHER INFORMATION: X at position 4 is S or A
<220> FEATURE:
<221> NAME/KEY: MISC_FEATURE
<222> LOCATION: (5)..(5)
<223> OTHER INFORMATION: X at position 5 is a hydrophobic amino acid
<220> FEATURE:
<221> NAME/KEY: MISC_FEATURE
<222> LOCATION: (7)..(7)
<223> OTHER INFORMATION: X at position 7 is  L or Y
<220> FEATURE:
<221> NAME/KEY: MISC_FEATURE
<222> LOCATION: (8)..(8)
<223> OTHER INFORMATION: X at position 8 is F, Y or W.

<400> SEQUENCE: 5
```

```
Glu Xaa Lys Xaa Xaa Lys Xaa Xaa
1               5
```

<210> SEQ ID NO 6
<211> LENGTH: 129
<212> TYPE: PRT
<213> ORGANISM: Aquifex aeolicus VF5

<400> SEQUENCE: 6

```
Met Glu Ala Lys Glu Lys Tyr Gly Glu Ile Glu Ile Glu Lys Ala
1               5                   10                  15

Gln Leu Glu Ala Trp Pro Asn Pro Asn Pro Glu Arg Asp Tyr Met Ile
                20                  25                  30

Glu Ile Thr Phe Pro Glu Phe Thr Cys Leu Cys Pro Arg Ser Gly Tyr
            35                  40                  45

Pro Asp Phe Ala Thr Ile Lys Ile Arg Tyr Ile Pro Asp Lys Tyr Ile
        50                  55                  60

Val Glu Leu Lys Ser Leu Lys Leu Trp Leu Asn Lys Phe Arg Asn Arg
65                  70                  75                  80

Tyr Ile Ser His Glu Ala Ala Thr Asn Glu Ile Tyr Gln Ala Leu Tyr
                85                  90                  95

Asp Leu Leu Lys Pro Arg Phe Leu Glu Val Val Gly Asp Phe His Pro
            100                 105                 110

Arg Gly Asn Val His Thr Val Val Arg Val Arg Ser Asp Glu Asn Tyr
        115                 120                 125

Gly
```

<210> SEQ ID NO 7
<211> LENGTH: 171
<212> TYPE: PRT
<213> ORGANISM: Agrobacterium tumefaciens

<400> SEQUENCE: 7

```
Met Asn Ser Pro Gly Arg Asn Asp Pro Val Leu Asn Asn Gln Glu Phe
1               5                   10                  15

Cys Met Ser Val Thr Asp Val Ser Gly Leu Ser Gln Leu Gly Thr Lys
                20                  25                  30

Val Asp Thr Pro Glu Ser Pro Glu Lys Ala Val Leu Glu Lys Val Pro
            35                  40                  45

Asn Gly Asn Ala Gly Thr Asp Tyr Val Val Arg Phe Thr Ala Pro Glu
        50                  55                  60

Phe Thr Ser Leu Cys Pro Met Thr Gly Gln Pro Asp Phe Ala His Ile
65                  70                  75                  80

Val Ile Asp Tyr Ile Pro Gly Asp Phe Leu Val Glu Ser Lys Ser Leu
                85                  90                  95

Lys Leu Phe Leu Gln Ser Phe Arg Asn His Gly Ala Phe His Glu Asp
            100                 105                 110

Cys Ser Val Tyr Ile Ala Lys Arg Leu Val Glu Leu Gln Pro Lys
        115                 120                 125

Trp Leu Arg Ile Gly Ala Tyr Trp Pro Arg Gly Ile Pro Ile
130                 135                 140

Asp Val Phe Trp Gln Thr Gly Ala Ala Pro Glu Gly Val Trp Leu Pro
145                 150                 155                 160

Asp Gln Gly Val Ala Pro Tyr Arg Gly Arg Gly
                165                 170
```

```
<210> SEQ ID NO 8
<211> LENGTH: 155
<212> TYPE: PRT
<213> ORGANISM: Brucella abortus

<400> SEQUENCE: 8

Met Ser Glu As

```
                165

<210> SEQ ID NO 10
<211> LENGTH: 153
<212> TYPE: PRT
<213> ORGANISM: Unknown
<220> FEATURE:
<223> OTHER INFORMATION: exemplary nitrile oxidoreductase

<400> SEQUENCE: 10

Met Thr Thr Met Ala Lys Lys Ser Leu Gln Leu Gly Arg Ala Val Glu
1               5                   10                  15

Trp Pro His Thr Pro Glu Glu Ala Gln Leu Asp Arg Val Pro Asn Pro
            20                  25                  30

Gln Lys Gly Thr Asp Tyr Leu Val Arg Phe Thr Val Pro Glu Phe Thr
        35                  40                  45

Ser Leu Cys Pro Val Thr Gly Gln Pro Asp Phe Ala His Leu Met Ile
    50                  55                  60

Asp Tyr Ala Pro Gly Pro Trp Leu Leu Glu Ser Lys Ser Leu Lys Leu
65                  70                  75                  80

Tyr Ile Ala Ser Phe Arg Asn His Gly Ala Phe His Glu Asp Cys Thr
                85                  90                  95

Val Met Ile Gly Lys Arg Ile Ala Ser Glu Ile Lys Pro Lys Trp Leu
            100                 105                 110

Arg Ile Gly Gly Tyr Trp Tyr Pro Arg Gly Gly Ile Pro Ile Asp Val
        115                 120                 125

Phe Trp Gln Thr Gly Arg Val Pro Lys Gly Leu Trp Val Pro Glu Gln
    130                 135                 140

Gly Val Ala Pro Tyr Arg Gly Arg Gly
145                 150

<210> SEQ ID NO 11
<211> LENGTH: 155
<212> TYPE: PRT
<213> ORGANISM: Brucella melitensis

<400> SEQUENCE: 11

Met Ser Glu Asn Thr Ile Tyr Ser Gly Leu Lys Gln Leu Gly Ser His
1               5                   10                  15

Thr Asp Ile Pro Leu Thr Pro Glu Glu Ala Val Leu Glu Arg Val Ala
            20                  25                  30

Asn Pro Gln Glu Gly Thr Pro Tyr Cys Val Arg Phe Thr Ala Pro Glu
        35                  40                  45

Phe Ser Ser Leu Cys Pro Met Thr Gly Gln Pro Asp Phe Ala His Leu
    50                  55                  60

Val Ile Asp Tyr Val Pro Gly Lys Trp Leu Val Glu Ser Lys Ser Leu
65                  70                  75                  80

Lys Leu Phe Leu Phe Ser Phe Arg Asn His Gly Ala Phe His Glu Asp
                85                  90                  95

Cys Thr Val Thr Ile Gly Lys Arg Leu Val Asp Leu Leu Glu Pro Glu
            100                 105                 110

Trp Leu Arg Ile Gly Gly Tyr Trp Tyr Pro Arg Gly Gly Ile Pro Ile
        115                 120                 125

Asp Val Phe Tyr Gln Thr Gly Ala Ala Pro Leu Asn Val Trp Ile Pro
    130                 135                 140

Glu Gln Gly Val Ala Asn Tyr Arg Gly Arg Gly
145                 150                 155
```

<210> SEQ ID NO 12
<211> LENGTH: 155
<212> TYPE: PRT
<213> ORGANISM: Brucella suis

<400> SEQUENCE: 12

Met Ser

```
<211> LENGTH: 151
<212> TYPE: PRT
<213> ORGANISM: Caulobacter crescentus

<400> SEQUENCE: 14

Met Thr Asp Leu Asn Val Thr Gln Leu Gly Arg Val Val Asp Ala Pro
1               5                   10                  15

Glu Ser Pro Glu Ala Ala Val Leu Glu Arg Val Pro Asn Pro Gln Ser
            20                  25                  30

Asp Val Leu Tyr Leu Ala Arg Phe Val Ala Pro Glu Phe Thr Ser Leu
        35                  40                  45

Cys Pro Val Thr Gly Gln Pro Asp Phe Ala His Leu Val Ile Asp Tyr
50                  55                  60

Ala Pro Gly Asp Trp Leu Ile Glu Ser Lys Ser Leu Lys Leu Tyr Leu
65                  70                  75                  80

Thr Ser Phe Arg Asn His Gly Ser Phe His Glu Asp Cys Thr Val Lys
                85                  90                  95

Val Ala Arg Lys Ile Val Glu Ile Ala Gln Pro Arg Trp Leu Arg Ile
            100                 105                 110

Gly Gly Tyr Trp Tyr Pro Arg Gly Gly Ile Pro Ile Asp Val Phe Trp
        115                 120                 125

Gln Thr Gly Pro Ala Pro Glu Gly Leu Trp Val Pro Asp Gln Gly Val
130                 135                 140

Ala Pro Tyr Arg Gly Arg Gly
145                 150

<210> SEQ ID NO 15
<211> LENGTH: 127
<212> TYPE: PRT
<213> ORGANISM: Campylobacter jejuni

<400> SEQUENCE: 15

Met Arg Tyr Gly Glu Lys Glu Ile Lys Glu Phe Asp Val Glu Asn Met
1               5                   10                  15

Glu Ile Trp Pro Asn Asp Ala Lys Asn Asp Tyr Ile Ile Lys Ile Thr
            20                  25                  30

Leu Pro Glu Phe Met Cys Cys Cys Pro Arg Ser Gly Tyr Pro Asp Phe
        35                  40                  45

Ala Thr Ile Tyr Leu Glu Tyr Met Pro Asp Lys Phe Val Val Glu Leu
50                  55                  60

Lys Ala Ile Lys Leu Tyr Ile Asn Thr Phe Met Tyr Arg Asn Val Ser
65                  70                  75                  80

His Glu Ala Ser Ile Asn Glu Ile Tyr Asn Thr Leu Lys Asp Lys Leu
                85                  90                  95

Lys Pro Lys Trp Ile Lys Val Val Gly Asp Phe Asn Pro Arg Gly Asn
            100                 105                 110

Val His Thr Val Ile Glu Cys Arg Ser Asp Met Val Val Pro Lys
        115                 120                 125

<210> SEQ ID NO 16
<211> LENGTH: 117
<212> TYPE: PRT
<213> ORGANISM: Chlorobium tepidum

<400> SEQUENCE: 16

Met Asn Lys Glu Ile Ile Glu Val Phe Asp Asn Thr Tyr Pro Asp Arg
1               5                   10                  15
```

-continued

```
Asp Tyr Thr Ile Glu Ile Ile Asn Pro Glu Phe Thr Ser Val Cys Pro
                20                  25                  30

Lys Thr Gly Leu Pro Asp Phe Gly Thr Ile Thr Val Asn Tyr Val Pro
         35                  40                  45

Asp Lys Ser Cys Ile Glu Leu Lys Ser Leu Lys Tyr Tyr Phe Leu Glu
 50                  55                  60

Phe Arg Asn Ala Gly Ile Phe Tyr Glu Asn Ile Thr Asn Arg Ile Leu
 65                  70                  75                  80

Asp Asp Leu Val Glu Ala Cys Gln Pro Arg Arg Met Thr Val Lys Thr
                 85                  90                  95

Glu Trp Asn Ala Arg Gly Gly Ile Thr Glu Thr Val Thr Val Ser Tyr
            100                 105                 110

Ser Lys Ser Lys Glu
        115
```

<210> SEQ ID NO 17
<211> LENGTH: 137
<212> TYPE: PRT
<213> ORGANISM: Gloeobacter violaceus

<400> SEQUENCE: 17

```
Met Ser Asp Leu Pro Val Ala Pro Thr Pro Ala Glu Pro Val Lys Tyr
 1               5                  10                  15

Gly Glu Arg Ala Ile Glu Ala Gly Gln Leu Ile Thr Phe Pro Asn Pro
                20                  25                  30

Arg Pro Gly Arg Asp Tyr Asp Ile His Ile Thr Leu Pro Glu Phe Thr
         35                  40                  45

Cys Lys Cys Pro Phe Ser Gly Tyr Pro Asp Phe Ala Thr Ile Tyr Leu
 50                  55                  60

Thr Tyr Val Pro His Glu Lys Val Val Glu Leu Lys Ala Leu Lys Leu
 65                  70                  75                  80

Tyr Val Asn Ser Phe Arg Asp Arg Tyr Ile Ser His Glu Glu Val Val
                 85                  90                  95

His Val Val Leu Asp Asp Phe Val Ala Ala Asp Pro Leu Arg Val
            100                 105                 110

Gln Ile Lys Gly Asp Phe Asn Pro Arg Gly Asn Val His Met Val Val
        115                 120                 125

Glu Ala Arg His Thr Arg Pro Gly Thr
        130                 135
```

<210> SEQ ID NO 18
<211> LENGTH: 148
<212> TYPE: PRT
<213> ORGANISM: Helicobacter pylori

<400> SEQUENCE: 18

```
Met Thr Pro Glu Leu Asn Leu Lys Ser Leu Gly Ala Lys Thr Pro Tyr
 1               5                  10                  15

Ile Phe Glu Tyr Asn Ser Gln Leu Leu Glu Ala Phe Pro Asn Pro Asn
                20                  25                  30

Pro Asn Leu Asp Pro Leu Ile Thr Leu Glu Cys Lys Glu Phe Thr Ser
         35                  40                  45

Leu Cys Pro Ile Thr Ser Gln Pro Asp Phe Gly Val Ile Phe Ile Arg
 50                  55                  60

Tyr Ile Pro Lys Asp Lys Met Val Glu Ser Lys Ser Leu Lys Leu Tyr
 65                  70                  75                  80
```

```
Leu Phe Ser Tyr Arg Asn His Gly Ser Phe His Glu Ser Cys Ile Asn
            85                  90                  95

Thr Ile Leu Leu Asp Leu Val Arg Leu Leu Glu Pro Lys Tyr Leu Glu
            100                 105                 110

Val Tyr Gly Asp Phe Ala Ser Arg Gly Gly Ile Ala Ile Lys Pro Phe
            115                 120                 125

Val Asn Tyr Ala Ile Lys Glu Tyr Gln Asp Phe Lys Glu Lys Arg Leu
            130                 135                 140

Leu Asn Ala Lys
145

<210> SEQ ID NO 19
<211> LENGTH: 148
<212> TYPE: PRT
<213> ORGANISM: Helicobacter pylori

<400> SEQUENCE: 19

Met Thr Pro Glu Ser Asn Leu Lys Ser Leu Gly Ala Lys Thr Pro Tyr
1               5                   10                  15

Ile Phe Glu Tyr Asn Ser Asp Leu Leu Glu Ala Phe Pro Asn Pro Asn
            20                  25                  30

Pro Asn Leu Asp Pro Leu Ile Thr Leu Glu Cys Lys Glu Phe Thr Ser
            35                  40                  45

Leu Cys Pro Ile Thr Ser Gln Pro Asp Phe Gly Val Ile Phe Ile Arg
        50                  55                  60

Tyr Ile Pro Lys Asp Lys Met Val Glu Ser Lys Ser Leu Lys Leu Tyr
65                  70                  75                  80

Leu Phe Ser Tyr Arg Asn His Gly Ser Phe His Glu Ser Cys Ile Asn
            85                  90                  95

Thr Ile Leu Leu Asp Leu Val Gln Leu Leu Glu Pro Lys Tyr Leu Glu
            100                 105                 110

Val Tyr Gly Asp Phe Val Ser Arg Gly Gly Ile Ala Ile Lys Pro Phe
            115                 120                 125

Val Asn Tyr Ala Ile Lys Glu Tyr Gln Asp Phe Lys Glu Lys Arg Leu
            130                 135                 140

Leu Asp Ala Lys
145

<210> SEQ ID NO 20
<211> LENGTH: 191
<212> TYPE: PRT
<213> ORGANISM: Unknown
<220> FEATURE:
<223> OTHER INFORMATION: exemplary nitrile oxidoreductase

<400> SEQUENCE: 20

Ser Arg Leu Trp Lys Arg Leu Arg Leu Ser Pro Trp Arg Thr Ser Leu
1               5                   10                  15

Thr Arg Val Cys Ile Asp Val Ile Leu Ile Glu Lys Leu Asn Tyr Tyr
            20                  25                  30

Ala Leu Ile Pro Arg Val Pro Glu Thr Thr Met Pro Ser Ser Lys Lys
            35                  40                  45

Glu Lys Lys Ser Ser Thr Gln Ser Thr Leu Lys Lys Thr Ala Tyr Gly
        50                  55                  60

Glu Thr Ala Ile Gln Gln Asn Gln Leu Glu Lys Trp Pro Ala Pro Glu
65                  70                  75                  80

Ser Thr Ala Pro Leu Glu Ile Arg Ile Ser Tyr Pro Glu Phe Thr Cys
```

```
                    85                  90                  95
Leu Cys Pro Arg Ser Gly Tyr Pro Asp Phe Ala Thr Ile His Leu Arg
            100                 105                 110

Tyr Arg Pro Ser Gly Phe Ile Val Glu Leu Lys Ser Leu Lys Leu Tyr
        115                 120                 125

Leu Asn Ser Phe Arg Asn Arg Ala Ile Ser His Glu Glu Thr Ala Ala
    130                 135                 140

Thr Leu Phe Arg Asp Leu Glu Asn Leu Leu Arg Pro Asp Phe Leu Glu
145                 150                 155                 160

Ile Val Ala Asp Phe Asn Val Arg Gly Asn Val Lys Thr Val Ile Thr
                165                 170                 175

Leu His Ser Gly Met Gly Lys Thr Pro Glu Lys Asp Gly Ile Ser
            180                 185                 190

<210> SEQ ID NO 21
<211> LENGTH: 150
<212> TYPE: PRT
<213> ORGANISM: Unknown
<220> FEATURE:
<223> OTHER INFORMATION: exemplary nitrile oxidoreductase

<400> SEQUENCE: 21

Met Phe Asn Gln Glu Arg Ile Ser Asp Val Ala Pro Pro Lys Lys Thr
1               5                   10                  15

Lys Thr Thr Glu Ala Ser Thr Ser Tyr Gly Glu Gln Ala Ile Glu Thr
            20                  25                  30

Asn Arg Leu Glu Gly Trp Pro Asn Pro Glu Lys Glu Gln Ser Tyr Arg
        35                  40                  45

Ile His Leu Ser Tyr Pro Glu Phe Thr Cys Leu Cys Pro Arg Ser Gly
    50                  55                  60

Tyr Pro Asp Phe Ala Thr Ile Glu Ile Asn Tyr Val Pro Asp Arg Thr
65                  70                  75                  80

Ile Val Glu Leu Arg Ser Leu Lys Leu Tyr Leu Asn Gly Phe Arg Asn
                85                  90                  95

Arg Arg Ile Ser His Glu Ala Ala Ile Asn Thr Ile Phe Arg Asp Leu
            100                 105                 110

His Glu Leu Leu Ser Pro Arg Glu Met Asp Val Thr Gly Asp Phe Asn
        115                 120                 125

Val Arg Gly Asn Leu Lys Thr Val Ile Arg Val Asp Thr Glu Met Asn
    130                 135                 140

Pro Lys Lys Arg Lys Arg
145                 150

<210> SEQ ID NO 22
<211> LENGTH: 134
<212> TYPE: PRT
<213> ORGANISM: Klebsiella pneumoniae

<400> SEQUENCE: 22

Met Glu Glu Thr Leu Val Ser His Leu Leu Lys Ser Asn Cys Leu Ile
1               5                   10                  15

Thr His Gln Pro Asp Trp Gly Ser Val Gln Ile Gln Tyr Arg Gly Ala
            20                  25                  30

Lys Ile Asp Arg Glu Gln Leu Leu Arg Tyr Leu Val Ser Phe Arg His
        35                  40                  45

His Asn Glu Phe His Glu Gln Cys Val Glu Arg Ile Phe Asn Asp Ile
    50                  55                  60
```

```
Leu Arg Phe Cys Gln Pro Glu Ser Leu Ser Val Tyr Ala Arg Tyr Thr
 65                  70                  75                  80

Arg Ala Ala Val Trp Ile Ser Thr Pro Gly Ala Ala Met Ala Thr Phe
                 85                  90                  95

Pro Pro Pro Pro Ala Ala Ser Pro Val Asn Asn Lys Gln Phe His Asn
            100                 105                 110

Leu Arg Ala Phe Arg Arg Ala Gln Gly Cys Gly Asn Ala Val Arg Arg
            115                 120                 125

Ala Ile Val Ile Thr Gly
            130

<210> SEQ ID NO 23
<211> LENGTH: 135
<212> TYPE: PRT
<213> ORGANISM: Leptospira interrogans

<400> SEQUENCE: 23

Met Ser Met Lys Thr Asn His Pro Glu Thr Tyr Asp Gly Arg Gln Asp
 1               5                  10                  15

His Ile Pro Ser Leu Gln Thr Pro Glu Ile Glu Ser Phe Thr Asn Val
             20                  25                  30

Tyr Glu Gly Lys Asp Tyr Thr Ile Asp Phe Thr Val Pro Glu Phe Thr
         35                  40                  45

Ala Val Cys Pro Lys Thr Gly Leu Pro Asp Phe Gly Val Ile Leu Val
     50                  55                  60

Ser Tyr Ile Pro Asn Lys Arg Cys Ile Glu Leu Lys Ser Phe Lys Glu
 65                  70                  75                  80

Tyr Ile Leu Ser Tyr Arg Asn Val Gly Ile Phe His Glu Phe Leu Val
                 85                  90                  95

Asn Lys Ile Leu Glu Asp Val Ile Lys Ser Ile Asp Pro Lys Tyr Leu
            100                 105                 110

Lys Val Ile Gly Asp Tyr Asn Ala Arg Gly Gly Ile Lys Thr Ile Val
            115                 120                 125

Thr Arg Glu Tyr Lys Lys Pro
            130                 135

<210> SEQ ID NO 24
<211> LENGTH: 153
<212> TYPE: PRT
<213> ORGANISM: Mesorhizobium loti

<400> SEQUENCE: 24

Met Ile Asp Thr Lys Thr Leu Thr Gln Leu Gly Ala His Val Glu Thr
 1               5                  10                  15

Pro Gln Ser Pro Glu Ala Ala Val Leu Glu Thr Val Pro Phe Ser Arg
             20                  25                  30

Gly Asp Gly Pro Pro Ala Ile Val Arg Phe Thr Cys Pro Glu Phe Thr
         35                  40                  45

Ser Leu Cys Pro Val Thr Gly Gln Pro Asp Phe Ala His Ile Val Ile
     50                  55                  60

Asp Tyr Ala Pro Asp Ala Ala Leu Val Glu Ser Lys Ser Leu Lys Leu
 65                  70                  75                  80

Phe Met Thr Ser Phe Arg Asn His Gly Ala Phe His Glu Asp Cys Thr
                 85                  90                  95

Val Met Ile Gly Arg Arg Ile Val Ala Ala Thr Lys Pro Leu Trp Leu
            100                 105                 110
```

```
Arg Ile Gly Gly Tyr Trp Tyr Pro Arg Gly Gly Ile Pro Ile Asp Val
            115                 120                 125

Phe Trp Gln Thr Gly Ala Pro Pro Glu Gly Ala Trp Leu Pro Asp Thr
130                 135                 140

Gly Val Ala Pro Tyr Arg Gly Arg Gly
145                 150

<210> SEQ ID NO 25
<211> LENGTH: 151
<212> TYPE: PRT
<213> ORGANISM: Magnetospirillum magnetotacticum

<400> SEQUENCE: 25

Met Ala Asp Leu Ser Leu Thr Gln Leu Gly Gln Ser Thr Ala Leu Pro
1               5                   10                  15

Asp Asn Pro Asp Lys Ala Val Leu Glu Thr Val Pro Asn Pro His Pro
            20                  25                  30

Gly Thr Leu Tyr Leu Val Arg Phe Thr Ala Pro Glu Phe Thr Ser Leu
        35                  40                  45

Cys Pro Ile Thr Gly Gln Pro Asp Phe Ala Gln Leu Val Ile Asp Tyr
50                  55                  60

Ala Pro Glu Gly Ala Leu Val Glu Ser Lys Ser Leu Lys Leu Phe Leu
65                  70                  75                  80

Gly Ser Phe Arg Asn His Gly Ala Phe His Glu Asp Cys Thr Ile Ala
                85                  90                  95

Ile Ala Lys Arg Leu Val Ala Ala Cys Ala Pro Lys Trp Leu Arg Ile
            100                 105                 110

Gly Gly Tyr Trp Tyr Pro Arg Gly Gly Ile Pro Ile Asp Val Phe Trp
        115                 120                 125

Gln Thr Gly Pro Ser Pro Glu Gly Leu Trp Leu Pro Asp Gln Gly Val
130                 135                 140

Ala Gly Tyr Arg Gly Arg Gly
145                 150

<210> SEQ ID NO 26
<211> LENGTH: 129
<212> TYPE: PRT
<213> ORGANISM: Novosphingobium aromaticivorans DSM 12444

<400> SEQUENCE: 26

Met Leu Asp Tyr Val Ala Asn Pro Arg Pro Gly Ala Leu Tyr Met Ile
1               5                   10                  15

Arg Phe Ala Ala Pro Glu Phe Thr Ser Leu Cys Pro Val Thr Gly Gln
            20                  25                  30

Pro Asp Phe Ala His Leu Val Ile Asp Tyr Ala Pro Gly Glu Cys Ile
        35                  40                  45

Val Glu Ser Lys Ala Leu Lys Leu Phe Leu Gly Ser Phe Arg Asn His
50                  55                  60

Ala Gly Phe His Glu Asp Val Thr Val Gly Ile Gly Gln Arg Leu Phe
65                  70                  75                  80

Asp Glu Met Lys Pro Gln Trp Leu Arg Ile Gly Gly Tyr Trp Tyr Pro
                85                  90                  95

Arg Gly Gly Ile Pro Ile Asp Val Phe Trp Gln Ser Gly Pro Pro Pro
            100                 105                 110

Ala Gly Leu Trp Leu Pro Asp Gln Gly Val Ala Pro Tyr Arg Gly Arg
        115                 120                 125
```

```
<210> SEQ ID NO 27
<211> LENGTH: 139
<212> TYPE: PRT
<213> ORGANISM: Nitrosomonas europaea

<400> SEQUENCE: 27

Met Thr Thr Gln Pro Ser Lys Gln Leu Glu Thr Phe Glu Asn Pro Val
1               5                   10                  15

Gln Thr Arg Asp Tyr Arg Ile His Met Glu Ile Pro Glu Phe Thr Cys
            20                  25                  30

Leu Cys Pro Lys Thr Gly Gln Pro Asp Phe Ala Arg Leu Thr Leu Asp
        35                  40                  45

Tyr Ile Pro Asp Lys Lys Cys Ile Glu Leu Lys Ser Leu Lys Leu Tyr
    50                  55                  60

Ile Trp Ser Tyr Arg Asp Glu Gly Ala Phe His Glu Ala Val Thr Asn
65                  70                  75                  80

Arg Ile Leu Asp Asp Leu Val Ala Ala Met Lys Pro Arg Phe Ile Arg
                85                  90                  95

Leu Thr Ser Lys Phe Tyr Val Arg Gly Gly Ile Phe Thr Asn Val Val
            100                 105                 110

Ala Glu His Arg Lys Lys Gly Trp Gln Pro Gln Pro Val Leu Leu
        115                 120                 125

Glu Val Phe Glu Gln Gln Phe Asn Thr His Gly
    130                 135

<210> SEQ ID NO 28
<211> LENGTH: 157
<212> TYPE: PRT
<213> ORGANISM: Neisseria gonorrhoeae

<400> SEQUENCE: 28

Met Ser Arg Asn Asn Glu Glu Leu Gln Gly Ile Ser Leu Leu Gly Asn
1               5                   10                  15

Gln Lys Thr Gln Tyr Pro Thr Gly Tyr Ala Pro Glu Ile Leu Glu Ala
            20                  25                  30

Phe Asp Asn Lys His Pro Asp Asn Asp Tyr Val Lys Phe Val Cys
        35                  40                  45

Pro Glu Phe Thr Ser Leu Cys Pro Met Thr Gly Gln Pro Asp Phe Ala
    50                  55                  60

Thr Ile Val Ile Arg Tyr Ile Pro His Ile Lys Met Val Glu Ser Lys
65                  70                  75                  80

Ser Leu Lys Leu Tyr Leu Phe Ser Phe Arg Asn His Gly Asp Phe His
                85                  90                  95

Glu Asp Cys Val Asn Ile Ile Met Lys Asp Leu Ile Ala Leu Met Asp
            100                 105                 110

Pro Lys Tyr Ile Glu Val Phe Gly Glu Phe Thr Pro Arg Gly Gly Ile
        115                 120                 125

Ala Val His Pro Phe Ala Asn Tyr Gly Lys Ala Gly Thr Glu Phe Glu
    130                 135                 140

Ala Leu Ala Arg Lys Arg Leu Phe Glu His Asp Ala Gln
145                 150                 155

<210> SEQ ID NO 29
<211> LENGTH: 157
```

```
<212> TYPE: PRT
<213> ORGANISM: Neisseria meningitidis

<400> SEQUENCE: 29

Met Ser Arg Asn Asn Glu Glu Leu Gln Gly Ile Ser Leu Leu Gly Asn
1               5                   10                  15

Gln Lys Thr Gln Tyr Pro Thr Gly Tyr Ala Pro Glu Ile Leu Glu Ala
            20                  25                  30

Phe Asp Asn Lys His Pro Asp Asn Asp Tyr Phe Val Lys Phe Val Cys
        35                  40                  45

Pro Glu Phe Thr Ser Leu Cys Pro Met Thr Gly Gln Pro Asp Phe Ala
    50                  55                  60

Thr Ile Tyr Ile Arg Tyr Ile Pro His Ile Lys Met Val Glu Ser Lys
65                  70                  75                  80

Ser Leu Lys Leu Tyr Leu Phe Ser Phe Arg Asn His Gly Asp Phe His
                85                  90                  95

Glu Asp Cys Val Asn Ile Ile Met Lys Asp Leu Ile Ala Leu Met Asp
            100                 105                 110

Pro Lys Tyr Ile Glu Val Phe Gly Glu Phe Thr Pro Arg Gly Gly Ile
        115                 120                 125

Ala Ile His Pro Phe Ala Asn Tyr Gly Lys Ala Gly Thr Glu Phe Glu
    130                 135                 140

Thr Leu Ala Arg Lys Arg Leu Phe Glu His Asp Ala Gln
145                 150                 155

<210> SEQ ID NO 30
<211> LENGTH: 157
<212> TYPE: PRT
<213> ORGANISM: Neisseria meningitidis

<400> SEQUENCE: 30

Met Ser Arg Asn Thr Glu Glu Leu Gln Gly Ile Ser Leu Leu Gly Asn
1               5                   10                  15

Gln Lys Thr Arg Tyr Pro Thr Gly Tyr Ala Pro Glu Ile Leu Glu Ala
            20                  25                  30

Phe Asp Asn Lys His Pro Asp Asn Asp Tyr Phe Val Lys Phe Val Cys
        35                  40                  45

Pro Glu Phe Thr Ser Leu Cys Pro Met Thr Gly Gln Pro Asp Phe Ala
    50                  55                  60

Thr Ile Tyr Ile Arg Tyr Ile Pro His Ile Lys Met Val Glu Ser Lys
65                  70                  75                  80

Ser Leu Lys Leu Tyr Leu Phe Ser Phe Arg Asn His Gly Asp Phe His
                85                  90                  95

Glu Asp Cys Val Asn Ile Ile Met Lys Asp Leu Ile Ala Leu Met Asp
            100                 105                 110

Pro Lys Tyr Ile Glu Val Phe Gly Glu Phe Thr Pro Arg Gly Gly Ile
        115                 120                 125

Ala Ile His Pro Phe Ala Asn Tyr Gly Lys Ala Gly Thr Glu Phe Glu
    130                 135                 140

Ala Leu Ala Arg Lys Arg Leu Phe Glu His Asp Ala Gln
145                 150                 155

<210> SEQ ID NO 31
<211> LENGTH: 136
<212> TYPE: PRT
<213> ORGANISM: Nostoc sp.
```

-continued

```
<400> SEQUENCE: 31

Met Ser Asn Ser Ser Pro Glu Thr Val Ser Gln Pro Ser Gln Glu Val
1               5                   10                  15

Lys Tyr Gly Glu Arg Glu Ile Ala Glu Gly Gln Leu Ile Thr Phe Pro
            20                  25                  30

Asn Pro Arg Val Gly Arg Arg Tyr Asp Ile Asn Ile Thr Leu Pro Glu
        35                  40                  45

Phe Thr Cys Lys Cys Pro Phe Ser Gly Tyr Pro Asp Phe Ala Thr Ile
    50                  55                  60

Tyr Ile Thr Tyr Val Pro Asp Glu Arg Val Val Glu Leu Lys Ala Leu
65                  70                  75                  80

Lys Leu Tyr Ile Asn Ser Tyr Arg Asp Arg Tyr Ile Ser His Glu Glu
                85                  90                  95

Ser Ala Asn Gln Ile Leu Asp Asp Phe Val Ala Ala Cys Asp Pro Leu
            100                 105                 110

Glu Ala Asn Val Lys Ala Asp Phe Thr Pro Arg Gly Asn Val His Thr
        115                 120                 125

Val Val Glu Val Arg His Thr Lys
    130                 135

<210> SEQ ID NO 32
<211> LENGTH: 140
<212> TYPE: PRT
<213> ORGANISM: Nostoc sp. PCC73102

<400> SEQUENCE: 32

Met Thr Thr Asp Lys Leu Pro Glu Ser Val Ser Gln Thr Thr Gln Glu
1               5                   10                  15

Met Lys Tyr Gly Glu Arg Asp Ile Ala Glu Gly Lys Leu Ile Thr Phe
            20                  25                  30

Pro Asn Pro Arg Val Gly Arg Arg Tyr Asp Ile Asn Ile Thr Leu Pro
        35                  40                  45

Glu Phe Thr Cys Lys Cys Pro Phe Ser Gly Tyr Pro Asp Phe Ala Thr
    50                  55                  60

Ile Tyr Val Thr Tyr Ile Pro Asp Glu Arg Val Val Glu Leu Lys Ala
65                  70                  75                  80

Leu Lys Leu Tyr Ile Asn Ser Tyr Arg Asp Arg Tyr Ile Ser His Glu
                85                  90                  95

Glu Ser Ala Asn Gln Ile Leu Asp Asp Phe Val Ala Ala Cys Asp Pro
            100                 105                 110

Leu Glu Ala Thr Val Lys Ala Asp Phe Thr Pro Arg Gly Asn Val His
        115                 120                 125

Thr Val Val Glu Val Arg His His Lys Tyr Pro Ser
    130                 135                 140

<210> SEQ ID NO 33
<211> LENGTH: 165
<212> TYPE: PRT
<213> ORGANISM: Oceanobacillus iheyensis HTE831

<400> SEQUENCE: 33

Met Val Gly Arg Asp Glu Asn Glu Leu Gln Asp Val Gln Leu Leu Gly
1               5                   10                  15

Ser Gln Gly Thr Thr Tyr Asp Phe Asn Tyr Thr Pro Glu Val Leu Glu
            20                  25                  30

Val Phe Asp Asn Lys His Val Ser Arg Asp Tyr Phe Val Lys Phe Asn
```

```
                35                  40                  45
Cys Pro Glu Phe Thr Thr Leu Cys Pro Lys Thr Asn Gln Pro Asp Phe
             50                  55                  60

Gly Thr Ile Tyr Ile Ser Tyr Ile Pro Asp Ile Lys Met Val Glu Ser
 65                  70                  75                  80

Lys Ser Leu Lys Leu Tyr Leu Phe Ser Phe Arg Asn His Gly Asp Phe
                 85                  90                  95

His Glu Asp Cys Ile Asn Ile Ile Met Asn Asp Leu Ile Asp Leu Met
            100                 105                 110

Asn Pro Arg Tyr Ile Glu Val Arg Gly Lys Phe Thr Pro Arg Gly Gly
        115                 120                 125

Ile Ser Ile Asp Pro Tyr Cys Asn Tyr Gly Arg Pro Gly Thr Lys Phe
    130                 135                 140

Glu Gln Met Ala Asp Gln Arg Leu Ile Gln His Asp Met Tyr Pro Glu
145                 150                 155                 160

Lys Ile Asp Asn Arg
                165

<210> SEQ ID NO 34
<211> LENGTH: 154
<212> TYPE: PRT
<213> ORGANISM: Porphyromonas gingivalis

<400> SEQUENCE: 34

Met Thr Gly Ile Arg Glu Gly Glu Lys Glu Leu Ser Leu Leu Gly Ser
1               5                  10                  15

Lys Thr Glu Tyr Arg Asn Asp Tyr Ala Pro Glu Val Leu Glu Ala Phe
             20                  25                  30

Thr Asn Lys His Gln Glu Asn Asp Tyr Trp Val Arg Phe Asn Cys Pro
         35                  40                  45

Glu Phe Thr Ser Leu Cys Pro Ile Thr Gly Gln Pro Asp Phe Ala Thr
     50                  55                  60

Ile Tyr Ile Asn Tyr Ile Pro Asp Val Lys Met Val Glu Ser Lys Ser
 65                  70                  75                  80

Leu Lys Leu Tyr Leu Phe Ser Phe Arg Asn His Gly Ala Phe His Glu
                 85                  90                  95

Asp Cys Val Asn Ile Ile Met Lys Asp Leu Ile Ala Leu Met Gln Pro
            100                 105                 110

Arg Tyr Ile Glu Val Trp Gly Asp Phe Thr Pro Arg Gly Gly Ile Ser
        115                 120                 125

Ile Val Pro Phe Cys Asn Tyr Gly Lys Pro Gly Ser Arg Tyr Glu Leu
    130                 135                 140

Leu Ala Glu Lys Arg Met Glu Thr His His
145                 150

<210> SEQ ID NO 35
<211> LENGTH: 135
<212> TYPE: PRT
<213> ORGANISM: Prochlorococcus marinus str. MIT 9313

<400> SEQUENCE: 35

Met Ser Ser Thr Gln Ala Gln Ala Ser Lys Thr Leu Tyr Gly Glu Arg
1               5                  10                  15

Val Ile Ala Glu Gly Glu Leu Ile Cys Phe Asp Asn Pro Arg Pro Glu
             20                  25                  30

Arg Pro Tyr Glu Ile Ser Ile Glu Leu Pro Glu Phe Thr Cys Gln Cys
```

```
                35                  40                  45
Pro Phe Ser Gly Tyr Pro Asp Phe Ala Val Leu Arg Leu Leu Tyr Gln
    50                  55                  60

Pro Gly Ser Arg Val Ile Glu Leu Lys Ala Ile Lys Leu Tyr Val Asn
65                  70                  75                  80

Ser Tyr Arg Asn Cys Thr Ile Ser His Glu Ala Ala Asn Lys Ile
                85                  90                  95

Leu Asp Asp Leu Val Val Ala Cys Asn Pro Val Trp Met Gln Leu Glu
                100                 105                 110

Ala Asp Phe Asn Pro Arg Gly Asn Val His Thr Val Arg Val Ser
                115                 120                 125

His Gly Ser Arg Gln Pro Cys
    130                 135

<210> SEQ ID NO 36
<211> LENGTH: 136
<212> TYPE: PRT
<213> ORGANISM: Prochlorococcus marinus subsp. pastoris str. CCMP1986

<400> SEQUENCE: 36

Met Gly Thr Ala Asn Leu His Asp Ser Thr Asn Lys Pro Leu Tyr Gly
1               5                   10                  15

Glu Arg Ile Ile Glu Glu Ser Asn Ile Ile Cys Phe Glu Asn Pro Asn
                20                  25                  30

Lys Lys Arg Ile Tyr Glu Ile Ser Ile Glu Leu Pro Glu Phe Thr Cys
                35                  40                  45

Lys Cys Pro Phe Ser Gly Tyr Pro Asp Phe Ala Lys Leu Asn Ile Tyr
    50                  55                  60

Tyr Gln Pro Asn Met Lys Val Tyr Glu Leu Lys Ser Leu Lys Leu Tyr
65                  70                  75                  80

Ile Asn Lys Phe Arg Asp Leu Lys Ile Ser His Glu Glu Val Val Asn
                85                  90                  95

Arg Ile Met Asp Asp Leu Leu Lys Ala Ala Val Pro His Trp Ile His
                100                 105                 110

Leu Asn Ala Asp Phe Asn Pro Arg Gly Asn Val Ser Met Lys Leu Asp
                115                 120                 125

Ile Tyr Ser Gly Gln Lys Arg Asn
    130                 135

<210> SEQ ID NO 37
<211> LENGTH: 135
<212> TYPE: PRT
<213> ORGANISM: Prochlorococcus marinus subsp. marinus str. CCMP1375

<400> SEQUENCE: 37

Met Thr Ile Ser Glu Lys Ser Asn Glu Ser Glu Leu Tyr Gly Glu Arg
1               5                   10                  15

Phe Ile Ser Asp Ala Glu Ile Val Cys Phe Pro Asn Pro Ser Pro Asn
                20                  25                  30

Arg Thr Tyr Glu Ile Ser Ile Glu Leu Pro Glu Phe Thr Cys Gln Cys
                35                  40                  45

Pro Phe Ser Gly Tyr Pro Asp Phe Ala Ile Ile Arg Leu Leu Tyr Gln
    50                  55                  60

Pro Gly Glu Lys Val Leu Glu Leu Lys Ser Met Lys Leu Tyr Val Asn
65                  70                  75                  80

Ser Phe Arg Asn Arg Lys Ile Ser His Glu Glu Val Ala Asn Lys Met
```

```
                    85                  90                  95
Leu Asp Asp Phe Val Ala Ala Asn Pro Ser Trp Met Gln Leu Glu
            100                 105                 110
Ala Asp Phe Asn Pro Arg Gly Asn Val His Thr Val Arg Val Ser
            115                 120                 125
His Gly Leu Lys Asn Asn Cys
            130                 135

<210> SEQ ID NO 38
<211> LENGTH: 121
<212> TYPE: PRT
<213> ORGANISM: Rhodopirellula baltica SH 1

<400> SEQUENCE: 38

Met Ser Asp Thr Ala Ser Phe Arg Asp Thr Leu Glu Val Phe Glu Asn
1               5                   10                  15

Pro Ala Pro Thr Arg Asn Phe Thr Ile Glu His His Cys Pro Glu Phe
            20                  25                  30

Thr Ser Val Cys Pro Lys Thr Gly Gln Pro Asp Tyr Gly Thr Ile Val
        35                  40                  45

Phe Thr Tyr Val Pro Asp Arg Val Cys Val Glu Leu Lys Ser Leu Lys
    50                  55                  60

Met Tyr Leu Gln Lys Phe Arg Asn Glu Gly Ile Phe Tyr Glu Gln Val
65                  70                  75                  80

Thr Asn Arg Ile Leu Asp Asp Phe Val Ala Val Val Gln Pro Arg Lys
                85                  90                  95

Val Thr Val Glu Ser Lys Trp Thr Pro Arg Gly Gly Leu Asn Ser Asn
            100                 105                 110

Ile Ile Val Thr Tyr Pro Asp Glu Ala
            115                 120

<210> SEQ ID NO 39
<211> LENGTH: 154
<212> TYPE: PRT
<213> ORGANISM: Sinorhizobium meliloti

<400> SEQUENCE: 39

Met Thr Lys Thr Asp Val Ser Gly Leu Ser Gln Leu Gly Ala Lys Val
1               5                   10                  15

Asp Leu Pro Gln Ser Pro Glu Glu Ala Val Leu Glu Arg Val Pro Ser
            20                  25                  30

Gly His Gly Gly Thr Asp Phe Val Arg Phe Thr Ala Pro Glu Phe
        35                  40                  45

Thr Ser Leu Cys Pro Met Thr Gly Gln Pro Asp Phe Ala His Ile Val
    50                  55                  60

Ile Asp Tyr Val Pro Asp Gly Trp Leu Val Glu Ser Lys Ser Leu Lys
65                  70                  75                  80

Leu Phe Leu His Ser Phe Arg Asn His Gly Ala Phe His Glu Asp Cys
                85                  90                  95

Thr Ile Glu Ile Ala Lys Arg Leu Val Ser Leu Ser Pro Lys Trp
            100                 105                 110

Leu Arg Ile Gly Ala Tyr Trp Tyr Pro Arg Gly Gly Ile Pro Ile Asp
            115                 120                 125

Val Phe Trp Gln Thr Gly Asn Pro Pro Glu Gly Val Trp Leu Pro Asp
            130                 135                 140

Gln Gly Val Pro Thr Tyr Arg Gly Arg Gly
```

```
145                 150

<210> SEQ ID NO 40
<211> LENGTH: 162
<212> TYPE: PRT
<213> ORGANISM: Streptococcus mutans

<400> SEQUENCE: 40

Met Ser Gln Glu Glu Ile Lys Asp Leu Thr Leu Leu Gly Asn Gln Lys
1               5                   10                  15

Thr Asn Tyr Asn Phe Asp Tyr Asp Leu Asn Ile Leu Glu Ala Phe Asp
            20                  25                  30

Asn Arg His Gln Asp Asn Asp Tyr Phe Ile Lys Phe Asn Cys Pro Glu
        35                  40                  45

Phe Thr Ser Leu Cys Pro Ile Thr Gly Gln Pro Asp Phe Ala Thr Ile
    50                  55                  60

Tyr Leu Ser Tyr Ile Pro Asp Lys Lys Cys Val Glu Ser Lys Ser Leu
65                  70                  75                  80

Lys Leu Tyr Leu Phe Ser Tyr Arg Asn His Gly Asp Phe His Glu Asn
                85                  90                  95

Cys Ile Asn Thr Ile Gly Lys Asp Leu Val Asp Leu Leu Gln Pro Arg
            100                 105                 110

Tyr Leu Glu Val Trp Gly Lys Phe Thr Pro Arg Gly Gly Ile Ser Ile
        115                 120                 125

Asp Pro Tyr Tyr Asn Tyr Gly Arg Pro Asn Thr Lys Tyr Glu Glu Met
    130                 135                 140

Ala Ala Tyr Arg Leu Met Asn His Asp Leu Tyr Pro Glu Thr Ile Asp
145                 150                 155                 160

Asn Arg

<210> SEQ ID NO 41
<211> LENGTH: 168
<212> TYPE: PRT
<213> ORGANISM: Unknown
<220> FEATURE:
<223> OTHER INFORMATION: exemplary nitrile oxidoreductase

<400> SEQUENCE: 41

Met Arg Leu His Arg Leu Asp Glu Leu Glu Gly Gln Pro Val Ala His
1               5                   10                  15

Phe His Gly Ala Cys Ile Asp Asp Gln Asp Ile Ser Ile Asp Asn Tyr
            20                  25                  30

Gln Phe Thr Thr Asp Tyr Leu Gln His Ala Val Ser Gly Glu Lys Gln
        35                  40                  45

Val Glu Glu Thr Leu Val Ser His Leu Leu Lys Ser Asn Cys Leu Ile
    50                  55                  60

Thr His Gln Pro Asp Trp Gly Ala Ile Gln Ile Gln Ile Arg Gly Arg
65                  70                  75                  80

Lys Ile Asp Arg Glu Lys Leu Leu Arg Tyr Leu Val Ser Phe Arg His
                85                  90                  95

His Asn Glu Phe His Glu Gln Cys Val Glu Arg Ile Phe Asn Asp Ile
            100                 105                 110

Leu Arg Phe Cys Gln Pro Glu Thr Leu Ser Ile Tyr Ala Arg Tyr Thr
        115                 120                 125

Arg Gly Gly Leu Asp Ile Asn Pro Trp Arg Ser Asn Thr Asp Phe Val
    130                 135                 140
```

```
Pro Pro Arg Ala Gly Trp Arg Asp Ser Asn Phe Phe Val Asn Phe Ala
145                 150                 155                 160

Cys Arg Ile Ala His Val Arg Leu
                165
```

<210> SEQ ID NO 42
<211> LENGTH: 137
<212> TYPE: PRT
<213> ORGANISM: Synechocystis sp.

<400> SEQUENCE: 42

```
Met Thr Glu Thr Thr Ile Thr Thr Ser Asp Asn Val Glu Lys Tyr Gly
1               5                   10                  15

Glu Arg Glu Ile Arg Asp Ala Gln Leu Ile Thr Phe Pro Asn Pro Arg
            20                  25                  30

Pro Gly Arg Arg Tyr Asp Val His Ile Thr Leu Pro Glu Phe Thr Cys
        35                  40                  45

Lys Cys Pro Phe Ser Gly Tyr Pro Asp Phe Ala Thr Leu Tyr Leu Thr
50                  55                  60

Tyr Cys Pro Asp Gln Lys Val Val Glu Leu Lys Ser Ile Lys Leu Tyr
65                  70                  75                  80

Ile Asn Ser Tyr Arg Asp Arg His Ile Pro His Glu Glu Val Thr Asn
                85                  90                  95

Gln Ile Leu Asp Asp Phe Val Ala Val Ala Asn Pro Leu Tyr Ala Arg
            100                 105                 110

Leu Lys Ala Asp Phe Asn Pro Arg Gly Asn Val His Thr Val Ile Glu
        115                 120                 125

Val Glu Tyr His Gln Glu Lys Ala Ser
    130                 135
```

<210> SEQ ID NO 43
<211> LENGTH: 171
<212> TYPE: PRT
<213> ORGANISM: Silicibacter sp. TM1040

<400> SEQUENCE: 43

```
Met Ser Ser Ser Gly Ala Thr Asn Val Ala Ser Asp Val Met Glu Ser
1               5                   10                  15

Ser Met Ser Glu Asp Ile Tyr Gln Asn Leu Lys Gln Leu Gly Gly Glu
            20                  25                  30

Thr Arg Ile Pro Ala Ser Pro Glu Glu Ala Glu Leu Glu Arg Val Ala
        35                  40                  45

Asn Pro Gln Ala Asp Val Ala Tyr Asn Val Arg Phe Thr Ala Pro Glu
50                  55                  60

Phe Thr Ser Leu Cys Pro Met Thr Gly Gln Pro Asp Phe Ala His Leu
65                  70                  75                  80

Val Ile Asp Tyr Val Pro Gly Pro Trp Leu Val Glu Ser Lys Ser Leu
                85                  90                  95

Lys Leu Phe Leu Thr Ser Phe Arg Asn His Gly Ala Phe His Glu Asp
            100                 105                 110

Cys Thr Ile Ser Ile Ala Arg Arg Leu Val Asp Phe Leu Asp Pro Gln
        115                 120                 125

Trp Leu Arg Ile Gly Gly Tyr Trp Tyr Pro Arg Gly Gly Ile Pro Ile
        130                 135                 140

Asp Val Phe Trp Gln Ser Gly Thr Ile Pro Glu Gly Val Trp Ile Pro
145                 150                 155                 160
```

-continued

Asp Gln Gly Val Pro Pro Tyr Arg Gly Arg Gly
                165                 170

<210> SEQ ID NO 44
<211> LENGTH: 133
<212> TYPE: PRT
<213> ORGANISM: Synechococcus WH8102

<400> SEQUENCE: 44

Met Thr Asp Gln Leu Thr Gln Thr Pro Leu Tyr Gly Glu Arg Ala Ile
1               5                   10                  15

Ala Glu Ala Glu Leu Ile Cys Phe Asp Asn Pro Arg Pro Gly Arg Pro
            20                  25                  30

Tyr Glu Val Ser Ile Glu Leu Pro Glu Phe Thr Cys Lys Cys Pro Phe
        35                  40                  45

Ser Ser Tyr Pro Asp Phe Ala Val Leu Arg Leu Ile Tyr Gln Pro Gly
    50                  55                  60

Pro Arg Val Val Glu Leu Lys Ala Ile Lys Leu Tyr Val Asn Ser Tyr
65                  70                  75                  80

Arg Asp Gln Ser Ile Ser His Glu Glu Val Thr Asn Arg Ile Leu Asp
                85                  90                  95

Asp Leu Val Ala Ala Thr Asp Pro Val Trp Met Gln Leu Glu Ala Asp
            100                 105                 110

Phe Asn Pro Arg Gly Asn Val His Thr Val Arg Val Ser His Gly
        115                 120                 125

Thr Arg Gln Pro Cys
    130

<210> SEQ ID NO 45
<211> LENGTH: 132
<212> TYPE: PRT
<213> ORGANISM: Thermosynechococcus elongatus BP-1

<400> SEQUENCE: 45

Met Gln Val Ser Glu Met Lys Tyr Gly Glu Arg Ala Ile Gln Glu Gly
1               5                   10                  15

Gln Leu Ile Thr Phe Pro Asn Pro Arg Pro Gly Arg Gln Tyr Thr Ile
            20                  25                  30

Glu Ile Thr Leu Pro Glu Phe Thr Cys Lys Cys Pro Phe Ser Gly Tyr
        35                  40                  45

Pro Asp Phe Ala Thr Leu Tyr Val Ser Tyr Ile Pro His Glu Lys Val
    50                  55                  60

Val Glu Leu Lys Ala Ile Lys Leu Tyr Ile Asn Ser Tyr Arg Asp Arg
65                  70                  75                  80

Tyr Ile Ser His Glu Glu Ala Val Asn Gln Val Leu Asp Asp Leu Val
                85                  90                  95

Ala Ala Cys Asp Pro Leu Tyr Met Lys Ile Lys Gly Asp Phe Ala Pro
            100                 105                 110

Arg Gly Asn Val His Thr Val Ile Thr Val Glu His His Arg Gln Thr
        115                 120                 125

Glu Ser Leu Cys
    130

<210> SEQ ID NO 46
<211> LENGTH: 137
<212> TYPE: PRT
<213> ORGANISM: Thermotoga maritima

<400> SEQUENCE: 46

Met Pro Lys Ala Glu Gly Arg Ile Phe Asp Phe Lys Gly His Asp Ala
1               5                   10                  15

Ile Arg Thr Asp Phe Leu Glu Ala Ile Asp Phe Asp Gly Lys Asp Glu
            20                  25                  30

Tyr Ile Lys Ile Glu Thr Asp Glu Phe Ser Ala Val Cys Pro Phe Ser
        35                  40                  45

Gly Leu Pro Asp Ile Gly Arg Val Ile Ile Glu Tyr Tyr Pro Asp Gly
    50                  55                  60

Gly Lys Ile Val Glu Leu Lys Ser Leu Lys Tyr Tyr Phe Val Ser Phe
65                  70                  75                  80

Arg Asn Val Gly Ile Tyr Gln Glu Ala Thr Lys Arg Ile Tyr Glu
                85                  90                  95

Asp Leu Lys Asn Leu Leu Lys Thr Asp Arg Ile Arg Val Thr Val Ile
                100                 105                 110

Tyr Asn Ile Arg Gly Gly Ile Lys Thr Thr Thr Gln Met Gly Ser Leu
            115                 120                 125

Glu Gly Lys Lys Ser Gly Glu Val Glu
        130                 135

<210> SEQ ID NO 47
<211> LENGTH: 134
<212> TYPE: PRT
<213> ORGANISM: Thermoanaerobacter tengcongensis MB4

<400> SEQUENCE: 47

Met Thr Asp Lys Tyr Lys Glu Arg Arg Phe Asp Ile Tyr Gly Tyr Glu
1               5                   10                  15

Lys Ile Asp Lys Glu Val Leu Glu Ser Ile Glu Tyr Glu Tyr Pro Glu
            20                  25                  30

Lys Asn Thr Ile Val Glu Tyr Ile Thr Asp Glu Phe Ser Ser Val Cys
        35                  40                  45

Pro Trp Thr Gly Leu Pro Asp Asn Ala Lys Leu Thr Ile Arg Tyr Ile
    50                  55                  60

Pro His Lys Lys Leu Val Glu Leu Lys Ser Leu Lys Tyr Tyr Leu Thr
65                  70                  75                  80

Ser Tyr Arg Asn Val Gly Ile Leu Gln Glu His Ala Ile Asn Arg Ile
                85                  90                  95

Leu Asp Asp Leu Val Glu Phe Leu Gln Pro Lys Phe Met Glu Ile Ile
                100                 105                 110

Gly Glu Phe Gln Glu Arg Gly Gly Ile Ala Thr Arg Ile Ile Ala Arg
            115                 120                 125

Tyr Glu Lys Glu Glu Tyr
        130

<210> SEQ ID NO 48
<211> LENGTH: 124
<212> TYPE: PRT
<213> ORGANISM: Wolinella succinogenes

<400> SEQUENCE: 48

Met Arg Tyr Gly Glu Met Glu Val Lys Asn Phe Asn Pro Glu Glu Ile
1               5                   10                  15

Glu Val Trp Pro Asn Arg Asn Asp Arg His Tyr Thr Ile Lys Ile Thr
            20                  25                  30

Leu Pro Glu Phe Ser Cys Leu Cys Pro Arg Ser Gly Tyr Pro Asp Tyr

```
                35                  40                  45
Ala Thr Val Tyr Ile Glu Tyr Val Pro Ser Ser Leu Val Glu Leu
        50                  55                  60

Lys Ala Ile Lys Leu Tyr Ile Asn Ser Phe Arg Asp Arg His Val Ser
65                  70                  75                  80

His Glu Asp Ser Ala Asn Glu Ile Tyr Asp Leu Leu Tyr Lys Lys Leu
                85                  90                  95

Ser Pro Lys Glu Leu Tyr Leu Lys Met Asp Phe Asn Pro Arg Gly Asn
            100                 105                 110

Val His Thr Ile Ile Glu Ile Asp Ser Lys Lys Asn
            115                 120

<210> SEQ ID NO 49
<211> LENGTH: 287
<212> TYPE: PRT
<213> ORGANISM: Actinobacillus actinomycetemcomitans

<400> SEQUENCE: 49

Met Ala Leu Ala Ile Arg Lys Ile Met Asn Tyr Gln Asp Pro Ser Leu
1               5                   10                  15

Asn Ala Leu Lys Leu Gly Gln Gln Thr Lys Tyr Ala Glu Lys Tyr Asp
            20                  25                  30

Arg Thr Leu Leu Gln Pro Val Pro Arg His Leu Asn Arg Asp Ser Leu
        35                  40                  45

Gly Ile Thr Gln Ile Gln Pro Phe Ser Thr Gly Ala Asp Ile Trp Thr
    50                  55                  60

Ala Tyr Glu Ile Ser Trp Leu Asn Pro Lys Gly Val Pro Gln Val Ala
65                  70                  75                  80

Ile Ala Asp Val Gln Ile Asp Phe Arg Ser Glu Asn Leu Ile Glu Ser
                85                  90                  95

Lys Ser Phe Lys Leu Tyr Leu Asn Ser Phe Asn Gln Thr Lys Phe Ala
            100                 105                 110

Asp Leu Val Asp Val Gln His Ile Leu Gln Gln Asp Leu Gln Asp Cys
        115                 120                 125

Ala Lys Gly Glu Val Lys Val Arg Leu Asn Ser Leu Ala Asn Tyr Thr
    130                 135                 140

Asp Gln Pro Ile Ala Met Leu His Gly Asp Cys Ile Asp Gly Leu Asp
145                 150                 155                 160

Ile Asp Ile Glu Asp Tyr Ala Phe Asn Ala Glu Trp Leu Lys Asp Cys
                165                 170                 175

Thr Ser Ser Asp Val Val Glu Glu Thr Leu Val Ser His Leu Leu Lys
            180                 185                 190

Ser Asn Cys Leu Ile Thr Ser Gln Pro Asp Trp Gly Ser Val Gln Ile
        195                 200                 205

His Tyr Val Gly Lys Gln Ile Asn Arg Glu Gln Leu Leu Arg Tyr Ile
    210                 215                 220

Ile Ser Phe Arg Gln His Asn Glu Phe His Glu Gln Cys Val Glu Arg
225                 230                 235                 240

Ile Phe Cys Asp Leu Met His Tyr Ala Lys Pro Glu Lys Leu Thr Val
                245                 250                 255

Tyr Ala Arg Tyr Thr Arg Arg Gly Gly Leu Asp Ile Asn Pro Tyr Arg
            260                 265                 270

Ser Asn Phe Glu Pro Leu Pro Pro Asn Leu Arg Leu Ala Arg Gln
        275                 280                 285
```

<210> SEQ ID NO 50
<211> LENGTH: 279
<212> TYPE: PRT
<213> ORGANISM: Actinobacillus pleuropneumoniae

<400> SEQUENCE: 50

```
Met Asn Tyr Asn Asp Lys Ser Leu Ser Ala Leu Lys Leu Gly Gln Lys
1               5                   10                  15

Thr Glu Tyr Lys Ser Glu Tyr Asp Pro Thr Leu Leu Gln Pro Val Pro
            20                  25                  30

Arg Lys Leu Asn Arg Asp Gly Leu Gly Ile Thr Glu Gln Gln Pro Phe
        35                  40                  45

Asp Arg Gly Ala Asp Val Trp Thr Cys Tyr Glu Leu Ser Trp Leu Asn
    50                  55                  60

Glu Asn Gly Leu Pro Gln Val Ala Ile Ala Asp Val Ala Ile Asp Phe
65                  70                  75                  80

Arg Ser Glu Asn Leu Ile Glu Ser Lys Ser Phe Lys Leu Tyr Leu Asn
                85                  90                  95

Ser Phe Asn Gln Thr Lys Phe Ala Ser Leu Glu Gln Val Glu Gln Thr
            100                 105                 110

Leu Ala Lys Asp Leu Ser Gln Cys Ala Ser Gly Gln Val Ser Val Lys
        115                 120                 125

Val Tyr Lys Leu Ser Ala Tyr Thr Gln Gln Pro Ile Val Asp Phe Ala
    130                 135                 140

Gly Glu Cys Ile Asp Glu Gln Asp Ile Gln Ile Asp Ser Tyr Glu Phe
145                 150                 155                 160

Ser Asn Glu His Leu Ala Ser Val Ala Glu Gly Glu Val Val Glu Glu
                165                 170                 175

Thr Leu Val Ser His Leu Leu Lys Ser Asn Cys Leu Ile Thr Ser Gln
            180                 185                 190

Pro Asp Trp Gly Ser Val Gln Ile His Tyr Val Gly Lys Lys Leu Asn
        195                 200                 205

Arg Glu Lys Leu Leu Arg Tyr Leu Val Ser Phe Arg Glu His Asn Glu
    210                 215                 220

Phe His Glu Gln Cys Val Glu Arg Ile Phe Ile Asp Leu Ile Gln Phe
225                 230                 235                 240

Thr Gln Pro Glu Lys Leu Thr Val Tyr Ala Arg Tyr Thr Arg Arg Gly
                245                 250                 255

Gly Leu Asp Ile Asn Pro Phe Arg Ser Asn Phe Glu Ser Val Pro Gln
            260                 265                 270

Asn Leu Arg Met Ala Arg Gln
        275
```

<210> SEQ ID NO 51
<211> LENGTH: 276
<212> TYPE: PRT
<213> ORGANISM: Azotobacter vinelandii

<400> SEQUENCE: 51

```
Met His Pro Ala Ala Glu Asp Ser Pro Leu Gly Lys Ser Ser Glu Tyr
1               5                   10                  15

Leu Asp Thr Tyr Thr Pro Ser Leu Leu Phe Pro Ile Pro Arg Ala Pro
            20                  25                  30

Lys Trp Ala Glu Leu Gly Leu Ala Ala Glu Asn Leu Pro Tyr Arg Gly
        35                  40                  45
```

Val Asp Val Trp Asn Cys Tyr Glu Leu Ser Trp Leu Leu Pro Ser Gly
 50                  55                  60

Lys Pro Val Val Ala Val Gly Glu Phe Val Ile Pro Ala Asp Ser Pro
 65                  70                  75                  80

Asn Ile Val Glu Ser Lys Ser Phe Lys Leu Tyr Leu Asn Ser Leu Asn
                 85                  90                  95

Gln Thr Val Phe Ala Asp Arg Glu Ala Leu Arg Gln Thr Leu Ala Arg
            100                 105                 110

Asp Leu Ser Ala Ala Thr Gly Ala Pro Val Ala Val Arg Leu Arg Ser
        115                 120                 125

Leu Gly Glu Val Gln Glu Gln Gly Val Ala Ala Leu Pro Gly Gln Cys
    130                 135                 140

Ile Asp Glu Leu Asp Val Thr Ile Gly Arg Tyr Gly Gln Pro Ser Ala
145                 150                 155                 160

Glu Leu Leu Arg Cys Asp Pro Ala Arg Arg Val Glu Gln Val Leu His
                165                 170                 175

Ser His Leu Leu Lys Ser Asn Cys Pro Val Thr Gly Gln Pro Asp Trp
            180                 185                 190

Gly Ser Leu Val Val Asp Tyr His Gly Pro Ala Leu Asp Pro Ala Ser
        195                 200                 205

Leu Leu Ala Tyr Val Val Ser Phe Arg Gln His Ala Asp Phe His Glu
    210                 215                 220

Gln Cys Val Glu Arg Ile Phe Leu Asp Leu Leu Arg Leu Leu Glu Pro
225                 230                 235                 240

Gly Arg Leu Thr Val Tyr Ala Arg Tyr Val Arg Arg Gly Gly Leu Asp
                245                 250                 255

Ile Asn Pro Trp Arg Ser Thr Gly Ala Val Val Ala Asp Asn Arg Arg
            260                 265                 270

Leu Ala Arg Gln
        275

<210> SEQ ID NO 52
<211> LENGTH: 262
<212> TYPE: PRT
<213> ORGANISM: Buchnera aphidicola

<400> SEQUENCE: 52

Met Ser Leu Lys Ile Asn Asn Phe Asn Phe Leu Arg Pro Ile Ser Arg
1               5                   10                  15

Lys Lys His Arg Lys Lys Ile Lys Leu Asn Cys Leu Asn Leu Pro Phe
            20                  25                  30

Lys Gly Lys Asp Ile Trp Thr Leu Tyr Glu Leu Ser Trp Leu Asn Lys
        35                  40                  45

Asn Gly Leu Pro Gln Ile Ala Ile Ala Lys Ile Glu Ile Asp Val Asn
 50                  55                  60

Ser Ala Asn Ile Ile Glu Ser Lys Ser Phe Lys Ile Tyr Ile Asn Ser
 65                  70                  75                  80

Phe Asn Gln Met Lys Phe Asn Asn Ile Asp Phe Ile Asn Ile Leu
                85                  90                  95

Thr Asn Asp Leu Thr Lys Cys Ile Cys Gly Gln Ile Ser Ile Lys Leu
            100                 105                 110

Phe Ser Leu Asp Ala Ile Lys Asn Glu Thr Ile Thr Asp Phe His Gly
        115                 120                 125

Ile Cys Ile Asp Asn Gln Asn Ile Lys Ile Glu Ser Tyr Lys Tyr Thr
    130                 135                 140

-continued

```
Pro Ser Phe Leu Met Ile Asn Ser Glu Arg Lys Ile Ile Lys Glu Asp
145                 150                 155                 160

Leu Tyr Thr His Leu Phe Lys Ser Asn Cys Pro Val Thr Gln Gln Pro
                165                 170                 175

Asp Trp Ala Ser Ile Tyr Ile Ala Tyr Thr Gly Leu Ser Ile Asn His
            180                 185                 190

Ala Ser Leu Leu Arg Tyr Leu Ile Ser Phe Arg Ser His Asn Glu Phe
        195                 200                 205

His Glu Glu Cys Ile Glu Arg Ile Phe Asn Asp Ile Asn Asn Ile Cys
    210                 215                 220

Lys Pro Glu Glu Leu Ser Val Tyr Ala Arg Tyr Thr Arg Arg Gly Gly
225                 230                 235                 240

Ile Asp Ile Asn Pro Trp Arg Ser Asn Thr Asn Phe Ser Pro Phe Leu
                245                 250                 255

Thr Arg Leu Ala Arg Gln
            260

<210> SEQ ID NO 53
<211> LENGTH: 303
<212> TYPE: PRT
<213> ORGANISM: Bordetella bronchiseptica

<400> SEQUENCE: 53

Met Thr Glu Ser Ala Phe His Ile Ala Lys Lys Ala Gly Arg Gly Ser
1               5                   10                  15

Ala Tyr Asn Ala Gly Ile Ile Ala Tyr Ala Asp Pro Val Ser Met Ser
            20                  25                  30

Leu Ser Asn Ala Pro Leu Gly Gln His Val Ala Tyr Pro Ser Gln Tyr
        35                  40                  45

Asp Pro Gly Leu Leu Phe Pro Ile Pro Arg Ala Thr Asn Arg Ala Ser
    50                  55                  60

Leu Gln Leu Gly Ala Thr Leu Pro Phe Thr Gly Val Asp Leu Trp Asn
65                  70                  75                  80

Ala Tyr Glu Leu Ser Trp Leu Asp Ala Arg Gly Lys Pro Arg Val Ala
                85                  90                  95

Met Ala Thr Phe Ser Phe Pro Ala Asp Ser Pro Asn Ile Val Glu Ser
            100                 105                 110

Lys Ser Phe Lys Leu Tyr Leu Asn Ser Phe Asn Gln Thr Arg Leu Pro
        115                 120                 125

Asn Ala Gln Ala Leu Arg Asp Arg Leu Glu Arg Asp Leu Ala Ala Ala
    130                 135                 140

Ala Gly Ala Pro Val Gly Leu Glu Phe Ile Ser Pro Gln Arg Phe Gly
145                 150                 155                 160

Glu Leu Asn Met Ala Glu Leu Asp Gly Ile Tyr Ile Asp Lys Leu Asp
                165                 170                 175

Ile Glu Ile Asp Thr Tyr Glu Pro Ala Pro Gln Leu Leu Gln Cys Ala
            180                 185                 190

Pro Gly Asp Glu Val Glu Glu Thr Leu Ala Thr Arg Leu Leu Lys Ser
        195                 200                 205

Asn Cys Pro Val Thr Gly Gln Pro Asp Trp Ala Ser Leu Gln Val Arg
    210                 215                 220

Tyr Arg Gly Arg Pro Ile Asp Arg Ala Ala Leu Leu Lys Tyr Val Val
225                 230                 235                 240

Ser Phe Arg Gln His Ala Glu Phe His Glu His Cys Val Glu Arg Ile

```
                       245                 250                 255
Phe Gly Asp Ile Met Arg Ala Cys Gln Pro Arg Gln Leu Thr Val Tyr
                260                 265                 270

Ala Arg Tyr Thr Arg Arg Gly Gly Leu Asp Ile Asn Pro Trp Arg Ser
            275                 280                 285

Asn Phe Glu Ser Ala Pro Pro Ala Asp Val Arg Thr Ala Arg Gln
        290                 295                 300

<210> SEQ ID NO 54
<211> LENGTH: 273
<212> TYPE: PRT
<213> ORGANISM: Bordetella parapertussis

<400> SEQUENCE: 54

Met Ser Leu Ser Asn Ala Pro Leu Gly Gln His Val Ala Tyr Pro Ser
1               5                   10                  15

Gln Tyr Asp Pro Gly Leu Leu Phe Pro Ile Pro Arg Ala Thr Asn Arg
            20                  25                  30

Ala Ser Leu Gln Leu Gly Ala Thr Leu Pro Phe Thr Gly Val Asp Leu
        35                  40                  45

Trp Asn Ala Tyr Glu Leu Ser Trp Leu Asp Ala Arg Gly Lys Pro Arg
    50                  55                  60

Val Ala Met Ala Thr Phe Ser Phe Pro Ala Asp Ser Pro Asn Ile Val
65                  70                  75                  80

Glu Ser Lys Ser Phe Lys Leu Tyr Leu Asn Ser Phe Asn Gln Thr Arg
                85                  90                  95

Leu Pro Asn Ala Gln Ala Leu Arg Asp Arg Leu Glu Arg Asp Leu Ala
            100                 105                 110

Ala Ala Ala Gly Ala Pro Val Gly Leu Lys Phe Ile Ser Pro Gln Arg
        115                 120                 125

Phe Gly Glu Leu Asn Met Ala Glu Leu Asp Gly Ile Tyr Ile Asp Lys
    130                 135                 140

Leu Asp Ile Glu Ile Asp Thr Tyr Glu Pro Ala Pro Gln Leu Leu Gln
145                 150                 155                 160

Cys Ala Pro Gly Asp Glu Val Glu Glu Thr Leu Ala Thr Arg Leu Leu
                165                 170                 175

Lys Ser Asn Cys Pro Val Thr Gly Gln Pro Asp Trp Ala Ser Leu Gln
            180                 185                 190

Val Arg Tyr Arg Gly Arg Pro Ile Asp Arg Ala Ala Leu Leu Lys Tyr
        195                 200                 205

Val Val Ser Phe Arg Gln His Ala Glu Phe His Glu His Cys Val Glu
    210                 215                 220

Arg Ile Phe Gly Asp Ile Met Arg Ala Cys Gln Pro Arg Gln Leu Thr
225                 230                 235                 240

Val Tyr Ala Arg Tyr Thr Arg Arg Gly Gly Leu Asp Ile Asn Pro Trp
                245                 250                 255

Arg Ser Asn Phe Glu Ser Ala Pro Pro Ala Asp Val Arg Thr Ala Arg
            260                 265                 270

Gln

<210> SEQ ID NO 55
<211> LENGTH: 273
<212> TYPE: PRT
<213> ORGANISM: Bordetella pertussis

<400> SEQUENCE: 55
```

```
Met Ser Leu Ser Asn Ala Pro Leu Gly Gln His Val Ala Tyr Pro Ser
1               5                   10                  15

Gln Tyr Asp Pro Gly Leu Leu Phe Pro Ile Pro Arg Ala Thr Asn Arg
            20                  25                  30

Ala Ser Leu Gln Leu Gly Ala Ala Leu Pro Phe Thr Gly Val Asp Leu
        35                  40                  45

Trp Asn Ala Tyr Glu Leu Ser Trp Leu Asp Ala Arg Gly Lys Pro Arg
50                  55                  60

Val Ala Met Ala Thr Phe Ser Phe Pro Ala Asp Ser Pro Asn Ile Val
65                  70                  75                  80

Glu Ser Lys Ser Phe Lys Leu Tyr Leu Asn Ser Phe Asn Gln Thr Arg
                85                  90                  95

Leu Pro Asn Ala Gln Ala Leu Arg Asp Arg Leu Glu Arg Asp Leu Ala
            100                 105                 110

Ala Ala Ala Gly Ala Pro Val Gly Leu Glu Phe Ile Ser Pro Gln Arg
        115                 120                 125

Phe Gly Glu Leu Asn Met Ala Glu Leu Asp Gly Ile Tyr Ile Asp Lys
    130                 135                 140

Leu Asp Ile Glu Ile Asp Thr Tyr Glu Pro Ala Pro Gln Leu Leu Gln
145                 150                 155                 160

Cys Ala Pro Gly Asp Glu Val Glu Glu Thr Leu Ala Thr Arg Leu Leu
                165                 170                 175

Lys Ser Asn Cys Pro Val Thr Gly Gln Pro Asp Trp Ala Ser Leu Gln
            180                 185                 190

Val Arg Tyr Arg Gly Arg Pro Ile Asp Arg Ala Ala Leu Leu Lys Tyr
        195                 200                 205

Val Val Ser Phe Arg Gln His Ala Glu Phe His Glu His Cys Val Glu
    210                 215                 220

Arg Ile Phe Gly Asp Ile Met Arg Ala Cys Gln Pro Arg Gln Leu Thr
225                 230                 235                 240

Val Tyr Ala Arg Tyr Thr Arg Arg Gly Gly Leu Asp Ile Asn Pro Trp
                245                 250                 255

Arg Ser Asn Phe Glu Ser Ala Pro Pro Ala Asp Val Arg Thr Ala Arg
            260                 265                 270

Gln
```

<210> SEQ ID NO 56
<211> LENGTH: 279
<212> TYPE: PRT
<213> ORGANISM: Chromobacterium violaceum

<400> SEQUENCE: 56

```
Met Asn Ile His Ala Ala Thr Pro Glu His Ser Pro Leu Gly Lys Thr
1               5                   10                  15

Val Ser Tyr Gln Asp Gln Tyr Asp Pro Ser Leu Leu Phe Pro Ile Ala
            20                  25                  30

Arg Gln Thr Lys Arg Asp Glu Ile Gly Val Asp Glu Ala Ala Leu Pro
        35                  40                  45

Phe Ala Gly Val Asp Ile Trp Thr Gly Phe Glu Leu Ser Trp Leu Asn
    50                  55                  60

Ala Arg Gly Lys Pro Gln Ile Gly Ile Ala Thr Phe Arg Ile Pro Ala
65                  70                  75                  80

Gly Ser Pro Arg Leu Ile Glu Ser Lys Ser Phe Lys Leu Tyr Leu Asn
                85                  90                  95
```

-continued

```
Ser Tyr Asn Gln Thr Arg Met Asp Gly Ile Asp Ala Leu Ala Ala Gln
             100                 105                 110

Leu Ala Arg Asp Leu Ser Ala Ala Gly Ala Glu Val Ala Val Ser
         115                 120                 125

Ile Ala Leu Pro Gln Ala Phe Ala Ala Glu Arg Ile Ala Glu Leu Ala
    130                 135                 140

Gly Glu Cys Ile Asp Glu Leu Asp Ile Ala Val Asp Asn Tyr Ala Pro
145                 150                 155                 160

Cys Pro Glu Ile Leu Ser Ala Asp Ser Thr Ala Ile Val Ser Glu Thr
                165                 170                 175

Leu Cys Ser Asn Leu Leu Lys Ser Asn Cys Leu Val Thr Gly Gln Pro
            180                 185                 190

Asp Trp Gly Ser Val Ser Ile Arg Tyr Thr Gly Pro Lys Ile Asp Arg
        195                 200                 205

Glu Ala Leu Leu Arg Tyr Leu Ile Gly Phe Arg His Asn Glu Phe
    210                 215                 220

His Glu Gln Cys Val Glu Arg Ile Phe Val Asp Val Leu Arg Ala Cys
225                 230                 235                 240

Ala Pro Thr Lys Leu Thr Val Tyr Ala Arg Tyr Thr Arg Arg Gly Gly
                245                 250                 255

Leu Asp Ile Asn Pro Trp Arg Ser Asn Cys Asp Ala Ala Pro Thr Asp
            260                 265                 270

Asn Val Arg Thr Ala Arg Gln
        275

<210> SEQ ID NO 57
<211> LENGTH: 278
<212> TYPE: PRT
<213> ORGANISM: Coxiella burnetii

<400> SEQUENCE: 57

Met Ser Thr Leu Arg Val Leu His Glu Lys Ser Glu Leu Gly Lys Thr
1               5                   10                  15

Thr Val Tyr Pro Lys Glu Tyr Ala Pro His Leu Leu Leu Pro Ile Pro
            20                  25                  30

Arg Asp Leu Asn Arg Lys Thr Leu Asn Val Asn Val Ser Glu Pro Pro
        35                  40                  45

Pro Phe Tyr Gly Tyr Asp Leu Trp Asn Ala Tyr Glu Leu Ser Trp Leu
    50                  55                  60

Asn Glu Lys Gly Lys Pro Phe Ala Ala Arg Gly Glu Phe Ile Ile Pro
65                  70                  75                  80

Ala Thr Ser Ser His Leu Ile Glu Ser Lys Ser Phe Lys Leu Tyr Leu
                85                  90                  95

Asn Ser Phe Asn Asn Glu Arg Phe Ala Asp Ala Ala Val Ser Gln
            100                 105                 110

Thr Met Lys Arg Asp Leu Ser Lys Arg Val Asn Glu Ser Val Thr Val
        115                 120                 125

Asn Phe Ile Leu His Glu Thr Glu Ile Pro Val Ala Tyr Ser Pro Lys
    130                 135                 140

Gly Ser Leu Leu Asp Val Leu Asp Ile Ala Ile Asp Thr Tyr Ser Pro
145                 150                 155                 160

Asp Pro Asn Leu Leu Ser Thr Ser Gln Glu Thr Val Thr Glu Thr Leu
                165                 170                 175

Tyr Ser His Leu Leu Lys Ser Asn Cys Pro Val Thr Gly Gln Pro Asp
```

```
                180                 185                 190
Trp Gly Ser Ile Glu Ile His Tyr Thr Gly Pro Lys Ile Asp His Val
        195                 200                 205
Gln Leu Leu Lys Tyr Ile Ile Ser Tyr Arg Asn His Glu Glu Phe His
        210                 215                 220
Glu Ala Cys Val Glu Arg Phe Phe Met Asp Ile Leu Arg His Cys Arg
225                 230                 235                 240
Pro Gln Glu Leu Thr Val Gln Ala Arg Tyr Thr Arg Arg Gly Gly Leu
                245                 250                 255
Asp Ile Asn Pro Tyr Arg Ser Thr Asn Pro Thr Phe Ser Val Gln Asn
            260                 265                 270
His Arg Ser Phe Arg Gln
            275

<210> SEQ ID NO 58
<211> LENGTH: 282
<212> TYPE: PRT
<213> ORGANISM: Escherichia coli
<220> FEATURE:
<221> NAME/KEY: misc_feature
<222> LOCATION: (179)..(179)
<223> OTHER INFORMATION: Xaa can be any naturally occurring amino acid

<400> SEQUENCE: 58

Met Ser Ser Tyr Ala Asn His Gln Ala Leu Ala Gly Leu Thr Leu Gly
1               5                   10                  15
Lys Ser Thr Asp Tyr Arg Asp Thr Tyr Asp Ala Ser Leu Leu Gln Gly
            20                  25                  30
Val Pro Arg Ser Leu Asn Arg Asp Pro Leu Gly Leu Lys Ala Asp Asn
        35                  40                  45
Leu Pro Phe Gln Gly Thr Asp Ile Trp Thr Leu Tyr Glu Leu Ser Trp
    50                  55                  60
Leu Asn Ala Lys Gly Leu Pro Gln Val Ala Gly His Val Glu Leu
65                  70                  75                  80
Asp Tyr Thr Ser Val Asn Leu Ile Glu Ser Lys Ser Phe Lys Leu Tyr
                85                  90                  95
Leu Asn Ser Phe Asn Gln Thr Arg Phe Asn Asn Trp Asp Glu Val Arg
            100                 105                 110
Gln Thr Leu Glu Arg Asp Leu Ser Thr Cys Ala Gln Gly Glu Val Ser
        115                 120                 125
Val Ala Leu Tyr Arg Leu Asp Glu Leu Glu Gly Gln Pro Ile Gly His
    130                 135                 140
Phe Asn Gly Thr Cys Ile Asp Asp Gln Asp Ile Thr Ile Asp Asn Tyr
145                 150                 155                 160
Glu Phe Thr Thr Asp Tyr Leu Glu Asn Ala Thr Ser Gly Glu Lys Val
                165                 170                 175
Val Glu Xaa Thr Leu Val Ser His Leu Leu Lys Ser Asn Cys Leu Ile
            180                 185                 190
Thr His Gln Pro Asp Trp Gly Ser Ile Gln Ile Gln Tyr Arg Gly Arg
        195                 200                 205
Gln Ile Asp Arg Glu Lys Leu Leu Arg Tyr Leu Val Ser Phe Arg His
        210                 215                 220
His Asn Glu Phe His Glu Gln Cys Val Glu Arg Ile Phe Asn Asp Leu
225                 230                 235                 240
Leu Arg Phe Cys Gln Pro Glu Lys Leu Ser Val Tyr Ala Arg Tyr Thr
                245                 250                 255
```

Arg Arg Gly Gly Leu Asp Ile Asn Pro Trp Arg Ser Asn Ser Asp Phe
            260                 265                 270

Val Pro Ser Thr Thr Arg Leu Val Arg Gln
            275                 280

<210> SEQ ID NO 59
<211> LENGTH: 282
<212> TYPE: PRT
<213> ORGANISM: Escherichia coli

<400> SEQUENCE: 59

Met Ser Ser Tyr Ala Asn His Gln Ala Leu Ala Gly Leu Thr Leu Gly
1               5                   10                  15

Lys Ser Thr Asp Tyr Arg Asp Thr Tyr Asp Ala Ser Leu Leu Gln Gly
            20                  25                  30

Val Pro Arg Ser Leu Asn Arg Asp Pro Leu Gly Leu Lys Ala Asp Asn
            35                  40                  45

Leu Pro Phe Gln Gly Thr Asp Ile Trp Thr Leu Tyr Glu Leu Ser Trp
        50                  55                  60

Leu Asn Ala Lys Gly Leu Pro Gln Val Ala Val Gly His Val Glu Leu
65                  70                  75                  80

Asp Tyr Thr Ser Val Asn Leu Ile Glu Ser Lys Ser Phe Lys Leu Tyr
                85                  90                  95

Leu Asn Ser Phe Asn Gln Thr Arg Phe Asn Asn Trp Asp Glu Val Arg
            100                 105                 110

Gln Thr Leu Glu Arg Asp Leu Ser Thr Cys Ala Gln Gly Glu Val Ser
            115                 120                 125

Val Ala Leu Tyr Arg Leu Asp Glu Leu Glu Gly Gln Pro Ile Gly His
        130                 135                 140

Phe Asn Gly Thr Cys Ile Asp Asp Gln Asp Ile Thr Ile Asp Asn Tyr
145                 150                 155                 160

Glu Phe Thr Thr Asp Tyr Leu Glu Asn Ala Thr Ser Gly Glu Lys Val
                165                 170                 175

Val Glu Glu Thr Leu Val Ser His Leu Leu Lys Ser Asn Cys Leu Ile
            180                 185                 190

Thr His Gln Pro Asp Trp Gly Ser Ile Gln Ile Gln Tyr Arg Gly Arg
            195                 200                 205

Gln Ile Asp Arg Glu Lys Leu Leu Arg Tyr Leu Val Ser Phe Arg His
        210                 215                 220

His Asn Glu Phe His Glu Gln Cys Val Glu Arg Ile Phe Asn Asp Leu
225                 230                 235                 240

Leu Arg Phe Cys Gln Pro Glu Lys Leu Ser Val Tyr Ala Arg Tyr Thr
                245                 250                 255

Arg Arg Gly Gly Leu Asp Ile Asn Pro Trp Arg Ser Asn Ser Asp Phe
            260                 265                 270

Val Pro Ser Thr Thr Arg Leu Val Arg Gln
            275                 280

<210> SEQ ID NO 60
<211> LENGTH: 282
<212> TYPE: PRT
<213> ORGANISM: Escherichia coli

<400> SEQUENCE: 60

Met Ser Ser Tyr Ala Asn His Gln Ala Leu Ala Gly Leu Thr Leu Gly
1               5                   10                  15

```
Lys Ser Thr Asp Tyr Arg Asp Thr Tyr Asp Ala Ser Leu Leu Gln Gly
            20                  25                  30

Val Pro Arg Ser Leu Asn Arg Asp Pro Leu Gly Leu Lys Ala Asp Asn
            35                  40                  45

Leu Pro Phe His Gly Thr Asp Ile Trp Thr Leu Tyr Glu Leu Ser Trp
 50                  55                  60

Leu Asn Ala Lys Gly Leu Pro Gln Val Ala Val Gly His Val Glu Leu
 65                  70                  75                  80

Asp Tyr Thr Ser Val Asn Leu Ile Glu Ser Lys Ser Phe Lys Leu Tyr
                85                  90                  95

Leu Asn Ser Phe Asn Gln Thr Arg Phe Asn Asn Trp Asp Glu Val Arg
               100                 105                 110

Gln Thr Leu Glu Arg Asp Leu Ser Thr Cys Ala Gln Gly Lys Val Ser
           115                 120                 125

Val Ala Leu Tyr Arg Leu Asp Glu Leu Glu Gly Gln Pro Ile Gly His
           130                 135                 140

Phe Asn Gly Thr Cys Ile Asp Asp Gln Asp Ile Thr Ile Asp Asn Tyr
145                 150                 155                 160

Glu Phe Thr Thr Asp Tyr Leu Glu Asn Ala Thr Ser Gly Glu Lys Val
                165                 170                 175

Val Glu Glu Thr Leu Val Ser His Leu Leu Lys Ser Asn Cys Leu Ile
           180                 185                 190

Thr His Gln Pro Asp Trp Gly Ser Ile Gln Ile Gln Tyr Arg Gly Arg
           195                 200                 205

Gln Ile Asp Arg Glu Lys Leu Leu Arg Tyr Leu Val Ser Phe Arg His
       210                 215                 220

His Asn Glu Phe His Glu Gln Cys Val Glu Arg Ile Phe Asn Asp Leu
225                 230                 235                 240

Leu Arg Phe Cys Gln Pro Glu Lys Leu Ser Val Tyr Ala Arg Tyr Thr
               245                 250                 255

Arg Arg Gly Gly Leu Asp Ile Asn Pro Trp Arg Ser Asn Asn Asp Phe
           260                 265                 270

Val Pro Ser Thr Thr Arg Leu Val Arg Gln
           275                 280

<210> SEQ ID NO 61
<211> LENGTH: 282
<212> TYPE: PRT
<213> ORGANISM: Escherichia coli
<220> FEATURE:
<221> NAME/KEY: misc_feature
<222> LOCATION: (179)..(179)
<223> OTHER INFORMATION: Xaa can be any naturally occurring amino acid

<400> SEQUENCE: 61

Met Ser Ser Tyr Ala Asn His Gln Ala Leu Ala Gly Leu Thr Leu Gly
 1               5                  10                  15

Lys Ser Thr Asp Tyr Arg Asp Thr Tyr Asp Ala Ser Leu Leu Gln Gly
            20                  25                  30

Val Pro Arg Ser Leu Asn Arg Asp Pro Leu Gly Leu Lys Ala Asp Asn
            35                  40                  45

Leu Pro Phe His Gly Thr Asp Ile Trp Thr Leu Tyr Glu Leu Ser Trp
 50                  55                  60

Leu Asn Ala Lys Gly Leu Pro Gln Val Ala Val Gly His Val Glu Leu
 65                  70                  75                  80
```

Asp Tyr Thr Ser Val Asn Leu Ile Glu Ser Lys Ser Phe Lys Leu Tyr
                85                  90                  95

Leu Asn Ser Phe Asn Gln Thr Arg Phe Asn Asn Trp Asp Glu Val Arg
            100                 105                 110

Gln Thr Leu Glu Arg Asp Leu Ser Thr Cys Ala Gln Gly Lys Val Ser
        115                 120                 125

Val Ala Leu Tyr Arg Leu Asp Glu Leu Glu Gly Gln Pro Ile Gly His
    130                 135                 140

Phe Asn Gly Thr Cys Ile Asp Asp Gln Asp Ile Thr Ile Asp Asn Tyr
145                 150                 155                 160

Glu Phe Thr Thr Asp Tyr Leu Glu Asn Ala Thr Ser Gly Glu Lys Val
                165                 170                 175

Val Glu Xaa Thr Leu Val Ser His Leu Leu Lys Ser Asn Cys Leu Ile
            180                 185                 190

Thr His Gln Pro Asp Trp Gly Ser Leu Gln Ile Gln Tyr Arg Gly Arg
        195                 200                 205

Gln Ile Asp Arg Glu Lys Leu Leu Arg Tyr Leu Val Ser Phe Arg His
    210                 215                 220

His Asn Glu Phe His Glu Gln Cys Val Glu Arg Ile Phe Asn Asp Leu
225                 230                 235                 240

Leu Arg Phe Cys Gln Pro Glu Lys Leu Ser Val Tyr Ala Arg Tyr Thr
                245                 250                 255

Arg Arg Gly Gly Leu Asp Ile Asn Pro Trp Arg Ser Asn Ser Asp Phe
            260                 265                 270

Val Pro Ser Thr Thr Arg Leu Val Arg Gln
        275                 280

<210> SEQ ID NO 62
<211> LENGTH: 279
<212> TYPE: PRT
<213> ORGANISM: Haemophilus influenzae

<400> SEQUENCE: 62

Met Asn Tyr Gln Asp Asn Ser Leu Lys Ser Leu Lys Leu Gly Gln Lys
1               5                   10                  15

Thr Glu Tyr Ala Ser Gln Tyr Asp Arg Thr Leu Leu Gln Pro Val Pro
            20                  25                  30

Arg Ala Leu Asn Arg Asp Gly Leu Gly Ile Thr Gln Asn Gln Pro Phe
        35                  40                  45

Thr Ile Gly Ala Asp Ile Trp Thr Ala Tyr Glu Ile Ser Trp Leu Asn
    50                  55                  60

Glu Lys Gly Leu Pro Gln Val Ala Ile Ala Asp Ile Tyr Leu Asp Tyr
65                  70                  75                  80

Gln Ser Gln Asn Leu Ile Glu Ser Lys Ser Phe Lys Leu Tyr Leu Asn
                85                  90                  95

Ser Phe Asn Gln Ser Lys Phe Ala Asp Phe Asn Ala Val Gln Gln Thr
            100                 105                 110

Met Gln Arg Asp Leu Ser Glu Cys Ala Gln Gly Asp Val Lys Val Arg
        115                 120                 125

Leu Asn Pro Met Ala Val Tyr Asp Ser Gln Lys Ile Asp His Leu Gln
    130                 135                 140

Gly Asp Cys Ile Asp Glu Gln Asp Ile Glu Ile Thr Ser Tyr Glu Phe
145                 150                 155                 160

Asn Ala Asn Trp Leu Lys Asp Cys Val Ser Asp Glu Ile Val Glu Glu
                165                 170                 175

```
Lys Leu Val Ser His Leu Leu Lys Ser Asn Cys Leu Ile Thr Asn Gln
            180                 185                 190

Pro Asp Trp Gly Thr Leu His Ile His Tyr Val Gly Lys Lys Ile Asn
        195                 200                 205

Gln Glu Lys Leu Leu Arg Tyr Val Val Ser Phe Arg Gln His Asn Glu
    210                 215                 220

Phe His Glu Gln Cys Val Glu Arg Ile Phe Cys Asp Leu Met His Tyr
225                 230                 235                 240

Ala Lys Pro Glu Lys Leu Thr Val Tyr Ala Arg Tyr Thr Arg Arg Gly
                245                 250                 255

Gly Leu Asp Ile Asn Pro Phe Arg Ser Asn Phe Glu Asn Leu Pro Glu
            260                 265                 270

Asn Leu Arg Leu Ala Arg Gln
            275

<210> SEQ ID NO 63
<211> LENGTH: 279
<212> TYPE: PRT
<213> ORGANISM: Haemophilus ducreyi

<400> SEQUENCE: 63

Met Ser Tyr Thr Asp Thr Val Leu Ser Ser Leu Lys Leu Gly Gln Lys
1               5                   10                  15

Thr Glu Tyr Thr Gly Glu Tyr Asp Pro Thr Leu Leu Gln Ala Val Pro
            20                  25                  30

Arg Lys Leu Asn Arg Asp His Leu Gly Ile Thr Glu Gln Gln Pro Phe
        35                  40                  45

Asn Gln Gly Ala Asp Val Trp Thr Cys Tyr Glu Val Ser Trp Leu Asn
    50                  55                  60

Leu Asn Gly Leu Pro Gln Val Ala Ile Ala Glu Val Val Ile Asp Ala
65                  70                  75                  80

Asn Ser Glu Asn Leu Ile Glu Ser Lys Ser Phe Lys Leu Tyr Leu Asn
            85                  90                  95

Ser Val Asn Gln Thr Thr Phe Glu Ser Leu Glu Gln Val Glu Tyr Ile
            100                 105                 110

Ile Glu Ser Asp Leu Ser Arg Cys Ala Cys Gly Leu Val Trp Val Lys
        115                 120                 125

Ile His Lys Leu Ser Glu Tyr Lys Asn Glu Ile Ile Ala Asp Phe Ser
    130                 135                 140

Gly Glu Cys Ile Asp Glu Gln Asp Ile Glu Ile Asp Asn Tyr Gln Tyr
145                 150                 155                 160

Ser Ala Gln Tyr Leu Glu His Ser Ala Glu Gly Glu Glu Val Glu Glu
                165                 170                 175

Thr Leu Val Ser His Leu Leu Lys Ser Asn Cys Leu Ile Thr Ser Gln
            180                 185                 190

Pro Asp Trp Gly Ser Val Gln Ile His Tyr Val Gly Lys Lys Ile Asn
        195                 200                 205

Arg Glu Lys Leu Leu Arg Tyr Leu Val Ser Phe Arg Glu His Asn Glu
    210                 215                 220

Phe His Glu Gln Cys Val Glu Arg Ile Phe Thr Asp Leu Met Thr Phe
225                 230                 235                 240

Ala Lys Pro Glu Lys Leu Met Val Tyr Ala Arg Tyr Thr Arg Arg Gly
                245                 250                 255

Gly Leu Glu Ile Asn Pro Phe Arg Ala Asn Phe Asp Ala Met Pro Gln
```

His Ile Arg Met Ala Arg Gln
                275

<210> SEQ ID NO 64
<211> LENGTH: 279
<212> TYPE: PRT
<213> ORGANISM: Haemophilus somnus

<400> SEQUENCE: 64

Met Gln Tyr His Asp Gln Ser Leu Gln Thr Leu Lys Leu Gly Lys Lys
1               5                   10                  15

Thr Glu Tyr Ile Ser Thr Tyr Asp Arg Thr Leu Leu Gln Ala Val Pro
            20                  25                  30

Arg Lys Leu Asn Arg Asp Asp Leu Gly Ile Ser Thr Lys Gln Pro Phe
        35                  40                  45

Ser Phe Gly Ala Asp Ile Trp Thr Ala Tyr Glu Ile Ser Trp Leu Asn
    50                  55                  60

Leu Lys Gly Val Pro Gln Val Ala Ile Ala Asp Val Glu Ile Asp Tyr
65                  70                  75                  80

Gln Ser Glu Asn Leu Ile Glu Ser Lys Ser Phe Lys Leu Tyr Leu Asn
                85                  90                  95

Ser Phe Asn Gln Ser Gln Phe Glu Asn Leu Gln Val Glu Gln Ile
            100                 105                 110

Leu Gln Gln Asp Leu Ile Lys Cys Ala Lys Gly Gln Val Lys Val Arg
        115                 120                 125

Leu Asn Ser Leu Gln Asn Tyr Ala Gln Gln Pro Ile Ala Thr Leu Gln
    130                 135                 140

Gly Glu Cys Ile Asp Glu Gln Asp Ile Glu Ile Arg Cys Tyr Glu Phe
145                 150                 155                 160

Asp Pro Asn Leu Leu Glu Asn Cys Thr Asn Lys Gln Trp Val Glu Glu
                165                 170                 175

Lys Leu Val Ser His Leu Leu Lys Ser Asn Cys Leu Ile Thr Asn Gln
            180                 185                 190

Pro Asp Trp Gly Thr Val Gln Ile His Tyr Ile Gly Asn Gln Ile Asn
        195                 200                 205

Arg Glu Lys Leu Leu Arg Tyr Leu Ile Ser Phe Arg Gln His Asn Glu
    210                 215                 220

Phe His Glu Gln Cys Val Glu Arg Ile Phe Cys Asp Leu Met Lys Phe
225                 230                 235                 240

Ala Gln Pro Glu Lys Leu Ser Val Tyr Ala Arg Tyr Thr Arg Arg Gly
                245                 250                 255

Gly Leu Asp Ile Asn Pro Phe Arg Ser Asn Phe Glu Pro Ile Pro Leu
            260                 265                 270

Asn Gln Arg Leu Ala Arg Gln
        275

<210> SEQ ID NO 65
<211> LENGTH: 279
<212> TYPE: PRT
<213> ORGANISM: Haemophilus somnus

<400> SEQUENCE: 65

Met Gln Tyr His Asp Gln Ser Leu Gln Thr Leu Lys Leu Gly Lys Lys
1               5                   10                  15

Thr Glu Tyr Ile Ser Thr Tyr Asp Arg Thr Leu Leu Gln Ala Val Pro

-continued

```
                    20                  25                  30
Arg Lys Leu Asn Arg Asp Asp Leu Gly Ile Ser Thr Lys Gln Pro Phe
            35                  40                  45
Ser Phe Gly Ala Asp Ile Trp Thr Ala Tyr Glu Ile Ser Trp Leu Asn
        50                  55                  60
Leu Lys Gly Val Pro Gln Val Ala Ile Ala Asp Val Glu Ile Asp Tyr
65                  70                  75                  80
Gln Ser Glu Asn Leu Ile Glu Ser Lys Ser Phe Lys Leu Tyr Leu Asn
                85                  90                  95
Ser Phe Asn Gln Ser Gln Phe Glu Asn Leu Gln Val Glu Gln Ile
            100                 105                 110
Leu Gln Gln Asp Leu Ile Lys Cys Ala Lys Gly Gln Val Lys Val Arg
        115                 120                 125
Leu Asn Ser Leu Gln Asn Tyr Ala Gln Gln Pro Ile Ala Thr Leu Gln
130                 135                 140
Gly Glu Cys Ile Asp Glu Gln Asp Ile Glu Ile Leu Cys Tyr Glu Phe
145                 150                 155                 160
Asp Pro Asn Leu Leu Glu Asn Cys Thr Asn Lys Gln Trp Val Glu Glu
                165                 170                 175
Lys Leu Val Ser His Leu Leu Lys Ser Asn Cys Leu Ile Thr Asn Gln
            180                 185                 190
Pro Asp Trp Gly Thr Val Gln Ile His Tyr Ile Gly Asn Gln Ile Asn
        195                 200                 205
Arg Glu Lys Leu Leu Arg Tyr Leu Ile Ser Phe Arg Gln His Asn Glu
210                 215                 220
Phe His Glu Gln Cys Val Glu Arg Ile Phe Cys Asp Leu Met Lys Phe
225                 230                 235                 240
Ala Gln Pro Glu Lys Leu Ser Val Tyr Ala Arg Tyr Thr Arg Arg Gly
                245                 250                 255
Gly Leu Asp Ile Asn Pro Phe Arg Ser Asn Phe Glu Pro Ile Pro Leu
            260                 265                 270
Asn Gln Arg Leu Ala Arg Gln
        275

<210> SEQ ID NO 66
<211> LENGTH: 279
<212> TYPE: PRT
<213> ORGANISM: Pasteurella multocida

<400> SEQUENCE: 66

Met Gln Tyr Gln His Asp Ser Leu Asp Lys Leu Lys Leu Gly Gln Gln
1               5                   10                  15
Thr Gln Tyr Ala Ser Asn Tyr Asp His Thr Leu Leu Gln Pro Val Pro
                20                  25                  30
Arg His Leu Asn Arg Asp Thr Leu Gly Ile Thr His Thr Gln Pro Phe
            35                  40                  45
His Phe Gly Ala Asp Ile Trp Thr Ala Tyr Glu Ile Ser Trp Leu Asn
        50                  55                  60
Leu Asn Gly Leu Pro Gln Val Ala Ile Ala Asp Val Ala Ile Asp Phe
65                  70                  75                  80
Gln Ser Glu Asn Leu Ile Glu Ser Lys Ser Phe Lys Leu Tyr Leu Asn
                85                  90                  95
Ser Phe Asn Gln Ser Lys Phe Ala Thr Phe Glu Glu Val Gln Gln His
            100                 105                 110
```

-continued

Leu Thr Gln Asp Leu Ser Asn Cys Ala Lys Gly Lys Val Ser Val Lys
        115                 120                 125

Leu His Pro Leu Ser Lys Tyr Cys His Glu Pro Ile Val Glu Leu Ala
    130                 135                 140

Gly Glu Cys Ile Asp Gln Gln Asp Ile Glu Ile Asn Asp Tyr Gln Phe
145                 150                 155                 160

Asn Pro Glu Ile Leu Thr Asn Cys Thr His Asp Gln Met Val Lys Glu
                165                 170                 175

Ser Leu Val Ser His Leu Leu Lys Ser Asn Cys Leu Ile Thr Asn Gln
            180                 185                 190

Pro Asp Trp Gly Thr Leu Gln Ile Arg Tyr Glu Gly Lys Gln Ile Asp
        195                 200                 205

Arg Glu Lys Leu Leu Arg Tyr Ile Ile Ser Phe Arg Gln His Asn Glu
    210                 215                 220

Phe His Glu Gln Cys Val Glu Arg Ile Phe Cys Asp Leu Met Gln Phe
225                 230                 235                 240

Ala Lys Pro Asp Lys Leu Thr Val Tyr Ala Arg Tyr Thr Arg Arg Gly
                245                 250                 255

Gly Leu Asp Ile Asn Pro Phe Arg Ser Asn Phe Glu Ala Val Pro Asp
            260                 265                 270

Asn Gln Arg Leu Ala Arg Gln
        275

<210> SEQ ID NO 67
<211> LENGTH: 148
<212> TYPE: PRT
<213> ORGANISM: Photorhabdus luminescens

<400> SEQUENCE: 67

Asp His Phe Asn Asn Gln Pro Ile Ser Thr Phe Thr Gly Glu Cys Ile
1               5                   10                  15

Asp Asp Gln Asp Ile Glu Val Thr Glu Tyr Asp Phe Asn Arg His Tyr
            20                  25                  30

Leu Gln Asp Ala Ala Gln Gly Pro Leu Val Glu Val Leu Val Ser
        35                  40                  45

His Leu Leu Lys Ser Asn Cys Leu Ile Thr His Gln Pro Asp Trp Gly
    50                  55                  60

Ser Val Gln Ile His Tyr Lys Gly Ala Lys Ile Asn Arg Glu Ala Leu
65                  70                  75                  80

Leu Arg Tyr Leu Ile Ser Phe Arg His His Asn Glu Phe His Glu Gln
                85                  90                  95

Cys Val Glu Arg Ile Phe Asn Asp Leu Gln Gln Leu Cys Ala Pro Glu
            100                 105                 110

Lys Leu Ser Val Tyr Ala Arg Tyr Thr Arg Arg Gly Gly Leu Asp Ile
        115                 120                 125

Asn Pro Trp Arg Thr Asn Ser Ala Ser Phe Ile Pro Ala Ile Gly Arg
    130                 135                 140

Leu Ala Arg Gln
145

<210> SEQ ID NO 68
<211> LENGTH: 276
<212> TYPE: PRT
<213> ORGANISM: Pseudomonas aeruginosa

<400> SEQUENCE: 68

-continued

```
Met Gln His Pro Ala Glu His Ser Pro Leu Gly Lys Thr Ser Glu Tyr
1               5                   10                  15

Val Ser Ser Tyr Thr Pro Ser Leu Leu Phe Pro Ile Ser Arg Thr Ala
            20                  25                  30

Lys Trp Ala Glu Leu Gly Leu Ser Ala Glu Thr Leu Pro Tyr Arg Gly
        35                  40                  45

Val Asp Ile Trp Asn Cys Tyr Glu Leu Ser Trp Leu Thr Pro Ala Gly
    50                  55                  60

Lys Pro Val Val Ala Ile Gly Glu Phe Ser Ile Pro Ala Asp Ser Pro
65                  70                  75                  80

Asn Ile Ile Glu Ser Lys Ser Phe Lys Leu Tyr Leu Asn Ser Leu Asn
                85                  90                  95

Gln Ser Ala Phe Asp Ser Arg Glu Ala Leu Arg Ala Val Leu Gln Lys
            100                 105                 110

Asp Leu Ser Ala Ala Val Gly Ala Pro Val Gly Val Arg Leu Arg Ser
        115                 120                 125

Leu Asp Glu Val Ala Glu Gly Ile Gly Arg Leu Pro Gly Arg Cys
    130                 135                 140

Ile Asp Glu Leu Asp Ile Ala Val Asp Gly Tyr Glu Gln Pro Arg Pro
145                 150                 155                 160

Glu Leu Leu Arg Cys Asp Ala Gly Arg Ile Val Glu Glu Gln Leu Tyr
                165                 170                 175

Ser His Leu Leu Lys Ser Asn Cys Pro Val Thr Gly Gln Pro Asp Trp
            180                 185                 190

Gly Thr Leu Val Val Asp Tyr Arg Gly Pro Ala Leu Asp Pro Ala Ser
        195                 200                 205

Leu Leu Ala Tyr Leu Val Ser Phe Arg Gln His Gln Asp Phe His Glu
    210                 215                 220

Gln Cys Val Glu Arg Ile Phe Leu Asp Leu Gln Arg Leu Leu Gln Pro
225                 230                 235                 240

Gln Ala Leu Ser Val Tyr Ala Arg Tyr Val Arg Arg Gly Gly Leu Asp
                245                 250                 255

Ile Asn Pro Tyr Arg Ser Leu Ala Glu Val Ala Pro Asp Asn Arg Arg
            260                 265                 270

Leu Val Arg Gln
        275

<210> SEQ ID NO 69
<211> LENGTH: 276
<212> TYPE: PRT
<213> ORGANISM: Pseudomonas putida

<400> SEQUENCE: 69

Met His Pro Ala Ala Glu His Ser Pro Leu Gly Lys Ser Ser Glu Tyr
1               5                   10                  15

Ile Ala Thr Tyr Ser Pro Glu Gln Leu Phe Pro Ile Pro Arg Thr Ala
            20                  25                  30

Lys Trp Ala Glu Leu Gly Val Thr Ala Gln Thr Leu Pro Trp Gln Gly
        35                  40                  45

Val Asp Tyr Trp Asn Cys Phe Glu Leu Ser Trp Leu Leu Pro Ser Gly
    50                  55                  60

Lys Pro Val Val Ala Ile Gly Glu Phe Ala Ile Pro Ala Asp Ser Pro
65                  70                  75                  80

Asn Ile Ile Glu Ser Lys Ser Phe Lys Leu Tyr Leu Asn Ser Leu Asn
                85                  90                  95
```

```
Gln Thr Val Phe Thr Ser Leu Gly Ala Leu Gln Val Cys Leu Glu Lys
                100                 105                 110

Asp Leu Ser Ala Ala Ala Gly Lys Pro Val Gly Val Lys Val Arg Thr
            115                 120                 125

Leu Ala Glu Val Glu Ala Gln Gly Val Val Ala Leu Pro Gly Gln Cys
        130                 135                 140

Ile Asp Ala Leu Asp Val Ala Ile Ser Asn Tyr Glu Gln Pro Gln Pro
145                 150                 155                 160

Glu Leu Leu Arg Cys Asn Pro Glu Arg Val Val Glu Thr Leu His
                165                 170                 175

Ser His Leu Leu Lys Ser Asn Cys Pro Val Thr Gly Gln Pro Asp Trp
                180                 185                 190

Gly Ser Val Val Gln Tyr Lys Gly Arg Ala Leu Asp His Ala Ser
                195                 200                 205

Leu Leu Thr Tyr Leu Ile Ser Phe Arg Gln His Ala Asp Phe His Glu
        210                 215                 220

Gln Cys Val Glu Arg Ile Tyr Leu Asp Leu Lys Asn Leu Leu Gln Pro
225                 230                 235                 240

Glu His Leu Thr Val Tyr Ala Arg Tyr Val Arg Gly Gly Leu Asp
                245                 250                 255

Ile Asn Pro Tyr Arg Ser Thr Gly Pro Ile Ser Pro Asp Asn Lys Arg
                260                 265                 270

Leu Val Arg Gln
        275

<210> SEQ ID NO 70
<211> LENGTH: 304
<212> TYPE: PRT
<213> ORGANISM: Pseudomonas syringae pv. tomato str. DC3000

<400> SEQUENCE: 70

Met Ala Gly Gln Ser Gly Phe Ser Leu Lys Ala Pro Gly Lys Arg Tyr
1               5                   10                  15

Lys Leu Ala Ala Phe Ile His Asp Pro Gly Ile Ala Met His Pro Ala
            20                  25                  30

Ala Glu His Ser Pro Leu Gly Lys Ser Ser Glu Tyr Ile Ala Thr Tyr
        35                  40                  45

Thr Pro Ser Leu Leu Phe Pro Ile Pro Arg Ala Ala Lys Trp Ala Glu
    50                  55                  60

Leu Gly Leu Thr Ala Gln Thr Leu Pro Tyr Gln Gly Val Asp Phe Trp
65                  70                  75                  80

Asn Cys Tyr Glu Leu Ser Trp Leu Leu Pro Ser Gly Lys Pro Val Val
                85                  90                  95

Ala Ile Gly Glu Phe Ser Ile Pro Ala Glu Ser Pro Asn Ile Ile Glu
            100                 105                 110

Ser Lys Ser Phe Lys Leu Tyr Leu Asn Ser Leu Asn Gln Thr Ala Phe
        115                 120                 125

Ala Thr Val Glu Gln Leu Thr Ala Thr Leu Glu Gln Asp Leu Ser Ala
    130                 135                 140

Ala Ala Gly Lys Pro Val Gly Val Arg Ile Arg Ser Leu Ala Glu Ile
145                 150                 155                 160

Glu Glu Glu Gly Val Ala Ala Leu Pro Gly Val Cys Ile Asp Asp Leu
                165                 170                 175

Asp Ile Ser Val Ser Ser Tyr Asp Arg Pro Gln Pro Glu Leu Leu Cys
```

```
                    180                 185                 190
Cys Asp Asp Ser Arg Val Val Ala Glu Ser Val His Ser His Leu Leu
            195                 200                 205
Lys Ser Asn Cys Pro Val Thr Ser Gln Pro Asp Trp Gly Ser Val Val
        210                 215                 220
Val Glu Tyr Arg Gly Ala Ala Leu Asp His Ala Ser Leu Leu Ala Tyr
225                 230                 235                 240
Ile Val Ser Phe Arg Gln His Ser Asp Phe His Glu Gln Cys Val Glu
                245                 250                 255
Arg Ile Phe Leu Asp Leu Gln Arg Leu Leu Lys Pro Glu Lys Leu Thr
            260                 265                 270
Val Tyr Ala Arg Tyr Val Arg Arg Gly Leu Asp Ile Asn Pro Tyr
        275                 280                 285
Arg Ser Thr Glu Thr Leu Asp Val Asp Asn Arg Arg Leu Ala Arg Gln
        290                 295                 300
```

<210> SEQ ID NO 71
<211> LENGTH: 304
<212> TYPE: PRT
<213> ORGANISM: Pseudomonas syringae

<400> SEQUENCE: 71

```
Met Ala Gly Gln Ser Gly Phe Ser Leu Lys Ala Pro Gly Lys Arg Tyr
1               5                   10                  15
Lys Leu Ala Ala Phe Ile His Asp Pro Gly Ile Ala Met His Pro Ala
            20                  25                  30
Ala Glu His Ser Pro Leu Gly Lys Ser Ser Glu Tyr Ile Ala Thr Tyr
        35                  40                  45
Thr Pro Ser Leu Leu Phe Pro Ile Pro Arg Ala Ala Lys Trp Ala Glu
    50                  55                  60
Leu Gly Leu Thr Ala Gln Thr Leu Pro Tyr Gln Gly Val Asp Phe Trp
65                  70                  75                  80
Asn Cys Tyr Glu Leu Ser Trp Leu Leu Pro Ser Gly Lys Pro Val Val
                85                  90                  95
Ala Ile Gly Glu Phe Ser Ile Pro Ala Glu Ser Pro Asn Ile Ile Glu
            100                 105                 110
Ser Lys Ser Phe Lys Leu Tyr Leu Asn Ser Leu Asn Gln Thr Ala Phe
        115                 120                 125
Ala Thr Val Glu Gln Leu Gln Thr Thr Leu Glu Gln Asp Leu Ser Ala
    130                 135                 140
Ala Ala Gly Lys Pro Val Gly Val Arg Ile Arg Ser Leu Ala Glu Ile
145                 150                 155                 160
Glu Glu Glu Gly Val Ala Ala Leu Pro Gly Val Cys Ile Asp Asp Leu
                165                 170                 175
Asp Ile Ser Val Ser Ser Tyr Asp Arg Pro Gln Pro Glu Leu Leu Cys
            180                 185                 190
Cys Asp Asp Ser Arg Val Val Ala Glu Ser Val His Ser His Leu Leu
        195                 200                 205
Lys Ser Asn Cys Pro Val Thr Ser Gln Pro Asp Trp Gly Ser Val Val
    210                 215                 220
Val Glu Tyr Arg Gly Ala Ala Leu Asp His Ala Ser Leu Leu Ala Tyr
225                 230                 235                 240
Ile Val Ser Phe Arg Gln His Ser Asp Phe His Glu Gln Cys Val Glu
                245                 250                 255
```

```
Arg Ile Phe Leu Asp Leu Gln Arg Leu Leu Lys Pro Glu Lys Leu Thr
            260                 265                 270

Val Tyr Ala Arg Tyr Val Arg Arg Gly Gly Leu Asp Ile Asn Pro Tyr
            275                 280                 285

Arg Ser Thr Glu Thr Leu Asp Val Asp Asn Arg Arg Leu Ala Arg Gln
            290                 295                 300

<210> SEQ ID NO 72
<211> LENGTH: 277
<212> TYPE: PRT
<213> ORGANISM: Ralstonia metallidurans CH34

<400> SEQUENCE: 72

Met Thr Leu Pro Glu His Ser Pro Leu Gly Lys Pro Ser Ala Tyr Lys
1               5                   10                  15

Thr Glu Tyr Asp Ala Ser Leu Leu Phe Pro Ile Pro Arg Gln Pro Lys
            20                  25                  30

Arg Ala Glu Ile Gly Leu Pro Glu Gly Arg Ala Leu Pro Phe Phe Gly
            35                  40                  45

Val Asp Ile Trp Asn Ala Tyr Glu Val Ser Trp Leu Asn Leu Lys Gly
    50                  55                  60

Lys Pro Gln Val Ala Leu Ala Thr Phe Ile Ile Pro Ala Asp Thr Pro
65                  70                  75                  80

Asn Ile Val Glu Ser Lys Ser Phe Lys Leu Tyr Leu Asn Ser Phe Asn
                85                  90                  95

Gln Thr Lys Ile Ala Ser Pro Glu Ala Leu Gln Gln Leu Leu His His
            100                 105                 110

Asp Leu Ser Glu Ala Thr Gly Gly Thr Val Gln Val Arg Leu Val Thr
            115                 120                 125

Glu Ala Asp Leu Gly Thr Gln Lys Met Gly Glu Leu Asp Gly Leu Leu
    130                 135                 140

Leu Asp Arg Leu Asp Ile Glu Thr Asp Ile Tyr Glu Pro Asp Pro Thr
145                 150                 155                 160

Leu Leu Ser Ala Glu Gln Glu Glu Ser Pro Val Glu Glu Thr Leu Val
                165                 170                 175

Ser His Leu Leu Lys Ser Asn Cys Leu Val Thr Gly Gln Pro Asp Trp
            180                 185                 190

Gly Ser Val Gln Ile Arg Tyr Val Gly Ala Pro Ile Asp Gln Glu Gly
    195                 200                 205

Leu Leu Lys Tyr Leu Ile Ser Phe Arg Asn His Asn Glu Phe His Glu
210                 215                 220

Gln Cys Val Glu Arg Ile Phe Thr Asp Val Met Arg Met Cys Lys Pro
225                 230                 235                 240

Val Lys Leu Ala Val Tyr Ala Arg Tyr Thr Arg Arg Gly Gly Leu Asp
                245                 250                 255

Ile Asn Pro Phe Arg Thr Asn Tyr Asn Thr Pro Trp Pro Asp Asn Arg
            260                 265                 270

Arg Asn Ala Arg Gln
        275

<210> SEQ ID NO 73
<211> LENGTH: 277
<212> TYPE: PRT
<213> ORGANISM: Ralstonia solanacearum

<400> SEQUENCE: 73
```

```
Met Ser His Pro Glu His Ser Pro Leu Gly Lys Ala Ser Ala Tyr Lys
1               5                   10                  15

Thr Gln Tyr Asp Pro Ser Leu Leu Phe Pro Ile Pro Arg Gln Ala Lys
                20                  25                  30

Arg Asp Glu Ile Gly Leu Ala Ala Gly Ser Ala Leu Pro Phe Phe Gly
            35                  40                  45

Ile Asp Leu Trp Asn Leu Tyr Glu Leu Ser Trp Leu Asn Leu Lys Gly
    50                  55                  60

Lys Pro Gln Val Ala Ile Gly Thr Val Ile Val Pro Ala Asp Ser Pro
65                  70                  75                  80

Asn Ile Val Glu Ser Lys Ser Phe Lys Leu Tyr Leu Asn Thr Phe Asn
                85                  90                  95

Gln Thr Lys Val Ala Ser Ser Glu Ala Leu Gln Gln Leu Ile His His
            100                 105                 110

Asp Leu Ser Glu Ala Cys Gly Ala Pro Val Gln Val Arg Ile Val Pro
            115                 120                 125

Gln Glu Glu Phe Ala Arg Gln Lys Met Gly Glu Leu Ala Gly Leu Ser
        130                 135                 140

Leu Asp Arg Leu Asp Val Glu Thr Asp Val Tyr Gln Pro Thr Pro Gly
145                 150                 155                 160

Leu Leu His Ala Asp Gln Asp Glu Ser Pro Val Glu Val Leu Val
                165                 170                 175

Ser His Leu Leu Lys Ser Asn Cys Leu Val Thr Gly Gln Pro Asp Trp
                180                 185                 190

Gly Ser Val Gln Ile Arg Tyr Val Gly Ala Pro Ile Asn Gln Glu Gly
            195                 200                 205

Leu Leu Lys Tyr Leu Ile Ser Phe Arg Glu His Asn Glu Phe His Glu
210                 215                 220

Gln Cys Val Glu Arg Ile Phe Met Asp Ile Gln Arg Gln Cys Arg Pro
225                 230                 235                 240

Val Lys Leu Ala Val Tyr Ala Arg Tyr Thr Arg Arg Gly Gly Leu Asp
                245                 250                 255

Ile Asn Pro Phe Arg Thr Asn Phe Asn Thr Pro Trp Pro Asp Asn Leu
                260                 265                 270

Arg Asn Ala Arg Gln
            275

<210> SEQ ID NO 74
<211> LENGTH: 273
<212> TYPE: PRT
<213> ORGANISM: Rickettsia conorii

<400> SEQUENCE: 74

Met Pro Leu Ser Thr Ser Leu Leu Gly Lys Lys Ser Thr Tyr Lys Asp
1               5                   10                  15

Ser Tyr Asp Val Thr Leu Leu Phe Lys Ile Pro Arg Ile Asn Asn Arg
                20                  25                  30

Asn Glu Leu Gly Ile Asn Ser Asn Leu Pro Phe Tyr Gly Val Asp
            35                  40                  45

Val Trp Asn Thr Tyr Glu Leu Ser Cys Leu Asn Lys Asn Gly Lys Pro
    50                  55                  60

Trp Val Gly Val Gly Thr Phe Tyr Ile Pro Thr Asp Ser Glu Asn Ile
65                  70                  75                  80

Val Glu Ser Lys Ser Phe Lys Leu Tyr Leu Asn Ser Phe Asn Asn Phe
                85                  90                  95
```

```
Val Val Glu Ser Val Lys Glu Leu Glu Arg Ile Ile Leu Gln Asp Leu
            100                 105                 110

Ser Asn Val Thr His Ala Lys Val Thr Gly Arg Ile Phe Pro Ile Asn
        115                 120                 125

Thr Lys Val Glu Phe Gly Val Pro Ser Gly Lys Asn Ile Asp Asp Leu
    130                 135                 140

Asp Ile Val Cys Asn Asn Tyr Gly Ala Pro Asp Asn Ser Leu Ile Glu
145                 150                 155                 160

Tyr Glu Asp Val Leu Val Glu Glu Ile Asn Ser His Leu Leu Lys
                165                 170                 175

Ser Asn Cys Leu Val Thr Gly Gln Pro Asp Trp Gly Thr Ile Val Ile
        180                 185                 190

Lys Tyr Lys Gly Lys Lys Leu Lys Tyr Asp Ser Phe Leu Lys Tyr Leu
        195                 200                 205

Ile Ser Phe Arg Asn Cys Asn Glu Phe Ala Glu Gln Cys Ala Glu Arg
        210                 215                 220

Ile Phe Thr Asp Ile Lys Asn Ala Ile Ser Pro Asp Phe Leu Ser Ile
225                 230                 235                 240

Tyr Ile Val Tyr Ala Arg Arg Gly Gly Ile Asp Ile Cys Pro Tyr Arg
                245                 250                 255

Ser Thr Asp Lys Ser Tyr Thr Leu Pro Ser Asp Lys Arg Phe Ile Arg
        260                 265                 270

Gln

<210> SEQ ID NO 75
<211> LENGTH: 273
<212> TYPE: PRT
<213> ORGANISM: Rickettsia prowazekii

<400> SEQUENCE: 75

Met Pro Leu Ser Thr Ser Leu Leu Gly Lys Lys Asn Thr Tyr Lys Asp
1               5                   10                  15

Ser Tyr Asp Ala Thr Leu Leu Phe Lys Ile Pro Arg Ile Asn Asn Ar

-continued

```
Lys Tyr Lys Gly Lys Lys Leu Lys Tyr Asp Ser Phe Leu Arg Tyr Leu
            195                 200                 205

Ile Ser Phe Arg Asn Phe Asn Glu Phe Ala Glu Gln Cys Ala Glu Arg
210                 215                 220

Ile Phe Ile Asp Ile Lys Asn Ser Ile Asn Leu Asp Phe Leu Ser Ile
225                 230                 235                 240

Tyr Ile Val Tyr Thr Arg Arg Gly Gly Ile Asp Ile Cys Pro Tyr Arg
            245                 250                 255

Ser Thr Asp Lys Ser Tyr Thr Leu Pro Asn Asp Lys Arg Leu Ile Arg
            260                 265                 270

Gln

<210> SEQ ID NO 76
<211> LENGTH: 273
<212> TYPE: PRT
<213> ORGANISM: Rickettsia sibirica

<400> SEQUENCE: 76

Met Pro Leu Ser Thr Ser Leu Leu Gly Lys Lys Ser Thr Tyr Lys Asp
1               5                   10                  15

Ser Tyr Asp Val Thr Leu Leu Phe Lys Ile Pro Arg Ile Asn Asn Arg
            20                  25                  30

Asn Glu Leu Gly Ile Asn Ser Asn Asn Leu Pro Phe Tyr Gly Val Asp
        35                  40                  45

Val Trp Asn Thr Tyr Glu Leu Ser Cys Leu Asn Lys Asn Gly Lys Pro
50                  55                  60

Trp Val Gly Val Gly Thr Phe Tyr Ile Pro Thr Asp Ser Glu Asn Ile
65                  70                  75                  80

Val Glu Ser Lys Ser Phe Lys Leu Tyr Leu Asn Ser Phe Asn Asn Phe
                85                  90                  95

Val Val Glu Ser Val Lys Glu Leu Glu Arg Ile Ile Leu Gln Asp Leu
            100                 105                 110

Ser Asn Val Thr His Ala Lys Val Thr Gly Arg Ile Phe Pro Ile Asn
            115                 120                 125

Thr Lys Val Glu Phe Gly Val Pro Ser Gly Lys Asn Ile Asp Asp Leu
        130                 135                 140

Asp Ile Val Cys Asn Asn Tyr Gly Ala Pro Asp Asn Ser Leu Ile Glu
145                 150                 155                 160

Tyr Glu Asp Val Leu Val Glu Glu Ile Asn Ser Asn Leu Leu Lys
            165                 170                 175

Ser Asn Cys Leu Val Thr Gly Gln Pro Asp Trp Gly Thr Ile Val Ile
            180                 185                 190

Lys Tyr Lys Gly Lys Lys Leu Lys Tyr Asp Ser Phe Leu Lys Tyr Leu
            195                 200                 205

Ile Ser Phe Arg Asn Cys Asn Glu Phe Ala Glu Gln Cys Ala Glu Arg
            210                 215                 220

Ile Phe Thr Asp Ile Lys Asn Ala Ile Ser Pro Asp Phe Leu Ser Ile
225                 230                 235                 240

Tyr Ile Val Tyr Ala Arg Arg Gly Gly Ile Asp Ile Cys Pro Tyr Arg
            245                 250                 255

Ser Thr Asp Lys Ser Tyr Thr Leu Pro Ser Asp Lys Arg Phe Ile Arg
            260                 265                 270

Gln
```

<210> SEQ ID NO 77
<211> LENGTH: 282
<212> TYPE: PRT
<213> ORGANISM: Salmonella enterica

<400> SEQUENCE: 77

Met Ser Ser Tyr Glu Asn His Gln Ala Leu Asp Gly Leu Thr Leu Gly
1               5                   10                  15

Lys Ser Thr Asp Tyr Arg Asp Asn Tyr Asp Ala Ser Leu Leu Gln Gly
            20                  25                  30

Val Pro Arg Ser Leu Asn Arg Asp Pro Leu Gly Leu Thr Ala Asp Asn
        35                  40                  45

Leu Pro Phe His Gly Ala Asp Ile Trp Thr Leu Tyr Glu Leu Ser Trp
    50                  55                  60

Leu Asn Ser Gln Gly Leu Pro Gln Val Ala Val Gly His Val Glu Leu
65                  70                  75                  80

Asp Tyr Thr Ser Val Asn Leu Ile Glu Ser Lys Ser Phe Lys Leu Tyr
                85                  90                  95

Leu Asn Ser Phe Asn Gln Thr Arg Phe Asp Thr Trp Glu Thr Val Arg
            100                 105                 110

Gln Thr Leu Glu Arg Asp Leu Arg Ala Cys Ala Gln Gly Asn Val Ser
        115                 120                 125

Val Arg Leu His Arg Leu Asp Glu Leu Glu Gly Gln Pro Val Ala His
    130                 135                 140

Phe His Gly Thr Cys Ile Asp Asp Gln Asp Ile Ser Ile Asp Asn Tyr
145                 150                 155                 160

Gln Phe Thr Thr Asp Tyr Leu Gln His Ala Val Ser Gly Glu Lys Gln
                165                 170                 175

Val Glu Glu Thr Leu Val Ser His Leu Leu Lys Ser Asn Cys Leu Ile
            180                 185                 190

Thr His Gln Pro Asp Trp Gly Ser Ile Gln Ile Gln Tyr Arg Gly Arg
        195                 200                 205

Lys Ile Asp Arg Glu Lys Leu Leu Arg Tyr Leu Val Ser Phe Arg His
    210                 215                 220

His Asn Glu Phe His Glu Gln Cys Val Glu Arg Ile Phe Asn Asp Ile
225                 230                 235                 240

Leu Arg Phe Cys Gln Pro Glu Thr Leu Ser Val Tyr Ala Arg Tyr Thr
                245                 250                 255

Arg Arg Gly Gly Leu Asp Ile Asn Pro Trp Arg Ser Thr Asp Phe
            260                 265                 270

Val Pro Ala Thr Gly Arg Leu Ala Arg Gln
        275                 280

<210> SEQ ID NO 78
<211> LENGTH: 282
<212> TYPE: PRT
<213> ORGANISM: Salmonella enterica

<400> SEQUENCE: 78

Met Ser Ser Tyr Glu Asn His Gln Ala Leu Asp Gly Leu Thr Leu Gly
1               5                   10                  15

Lys Ser Thr Asp Tyr Arg Asp Asn Tyr Asp Ala Ser Leu Leu Gln Gly
            20                  25                  30

Val Pro Arg Ser Leu Asn Arg Asp Pro Leu Gly Leu Thr Ala Asp Asn
        35                  40                  45

```
Leu Pro Phe His Gly Ala Asp Ile Trp Thr Leu Tyr Glu Leu Ser Trp
 50                  55                  60

Leu Asn Ser Gln Gly Leu Pro Gln Val Ala Val Gly His Val Glu Leu
 65                  70                  75                  80

Asp Tyr Thr Ser Val Asn Leu Ile Glu Ser Lys Ser Phe Lys Leu Tyr
                 85                  90                  95

Leu Asn Ser Phe Asn Gln Thr Arg Phe Asp Thr Trp Glu Thr Val Arg
                100                 105                 110

Gln Thr Leu Glu Arg Asp Leu Arg Ala Cys Ala Gln Gly Asn Val Ser
            115                 120                 125

Val Arg Leu His Arg Leu Asp Glu Leu Glu Gly Gln Pro Val Ala His
        130                 135                 140

Phe His Gly Thr Cys Ile Asp Asp Gln Asp Ile Ser Ile Asp Asn Tyr
145                 150                 155                 160

Gln Phe Thr Thr Asp Tyr Leu Gln His Ala Val Ser Gly Glu Lys Gln
                165                 170                 175

Val Glu Glu Thr Leu Val Ser His Leu Leu Lys Ser Asn Cys Leu Ile
            180                 185                 190

Thr His Gln Pro Asp Trp Gly Ser Ile Gln Ile Gln Tyr Arg Gly Arg
        195                 200                 205

Lys Ile Asp Arg Glu Lys Leu Leu Arg Tyr Leu Val Ser Phe Arg His
    210                 215                 220

His Asn Glu Phe His Glu Gln Cys Val Glu Arg Ile Phe Asn Asp Ile
225                 230                 235                 240

Leu Arg Phe Cys Gln Pro Glu Thr Leu Ser Val Tyr Ala Arg Tyr Thr
                245                 250                 255

Arg Arg Gly Gly Leu Asp Ile Asn Pro Trp Arg Ser Asn Thr Asp Phe
            260                 265                 270

Val Pro Ala Thr Gly Arg Leu Ala Arg Gln
        275                 280

<210> SEQ ID NO 79
<211> LENGTH: 282
<212> TYPE: PRT
<213> ORGANISM: Salmonella enterica subsp. enterica serovar Choleraesuis
      str.

<400> SEQUENCE: 79

Met Ser Ser Tyr Glu Asn His Gln Ala Leu Asp Gly Leu Thr Leu Gly
 1               5                  10                  15

Lys Ser Thr Asp Tyr Arg Asp Asn Tyr Asp Ala Ser Leu Leu Gln Gly
                 20                  25                  30

Val Pro Arg Ser Leu Asn Arg Asp Pro Leu Gly Leu Thr Ala Asp Asn
            35                  40                  45

Leu Pro Phe His Gly Ala Asp Ile Trp Thr Leu Tyr Glu Leu Ser Trp
 50                  55                  60

Leu Asn Ser Gln Gly Leu Pro Gln Val Ala Val Gly His Val Glu Leu
 65                  70                  75                  80

Asp Tyr Thr Ser Val Asn Leu Ile Glu Ser Lys Ser Phe Lys Leu Tyr
                 85                  90                  95

Leu Asn Ser Phe Asn Gln Thr Arg Phe Asp Thr Trp Glu Thr Val Arg
                100                 105                 110

Gln Thr Leu Glu Arg Asp Leu Arg Ala Cys Ala Gln Gly Asn Val Ser
            115                 120                 125

Val Arg Leu His Arg Leu Asp Glu Leu Glu Gly Gln Pro Val Ala His
```

```
                130                 135                 140
Phe His Gly Thr Cys Ile Asp Asp Gln Asp Ile Ser Ile Asp Asn Tyr
145                 150                 155                 160

Gln Phe Thr Thr Asp Tyr Leu Gln His Ala Val Ser Gly Glu Lys Gln
                165                 170                 175

Val Glu Glu Thr Leu Val Ser His Leu Leu Lys Ser Asn Cys Leu Ile
                180                 185                 190

Thr His Gln Pro Asp Trp Gly Ser Ile Gln Ile Gln Tyr Arg Gly Arg
                195                 200                 205

Lys Ile Asp Arg Glu Lys Leu Leu Arg Tyr Leu Val Ser Phe Arg His
210                 215                 220

His Asn Glu Phe His Glu Gln Cys Val Glu Arg Ile Phe Asn Asp Ile
225                 230                 235                 240

Leu Arg Phe Cys Gln Pro Glu Thr Leu Ser Val Tyr Ala Arg Tyr Thr
                245                 250                 255

Arg Arg Gly Gly Leu Asp Ile Asn Pro Trp Arg Ser Asn Thr Asp Phe
                260                 265                 270

Val Pro Ala Thr Gly Arg Leu Ala Arg Gln
                275                 280

<210> SEQ ID NO 80
<211> LENGTH: 282
<212> TYPE: PRT
<213> ORGANISM: Salmonella typhimurium

<400> SEQUENCE: 80

Met Ser Ser Tyr Glu Asn His Gln Ala Leu Asp Gly Leu Thr Leu Gly
1               5                   10                  15

Lys Ser Thr Asp Tyr Arg Asp Asn Tyr Asp Val Ser Leu Leu Gln Gly
                20                  25                  30

Val Pro Arg Ser Leu Asn Arg Asp Pro Leu Gly Leu Thr Ala Asp Asn
                35                  40                  45

Leu Pro Phe His Gly Ala Asp Ile Trp Thr Leu Tyr Glu Leu Ser Trp
                50                  55                  60

Leu Asn Ser Gln Gly Leu Pro Gln Val Ala Val Gly His Val Glu Leu
65                  70                  75                  80

Asp Tyr Thr Ser Val Asn Leu Ile Glu Ser Lys Ser Phe Lys Leu Tyr
                85                  90                  95

Leu Asn Ser Phe Asn Gln Thr Arg Phe Asp Thr Trp Glu Thr Val Arg
                100                 105                 110

Gln Thr Leu Glu Arg Asp Leu Arg Ala Cys Ala Gln Gly Asn Val Ser
                115                 120                 125

Val Arg Leu His Arg Leu Asp Glu Leu Glu Gly Gln Pro Val Ala His
                130                 135                 140

Phe His Gly Thr Cys Ile Asp Asp Gln Asp Ile Ser Ile Asp Asn Tyr
145                 150                 155                 160

Gln Phe Thr Thr Asp Tyr Leu Gln His Ala Val Ser Gly Glu Lys Gln
                165                 170                 175

Val Glu Glu Thr Leu Val Ser His Leu Leu Lys Ser Asn Cys Leu Ile
                180                 185                 190

Thr His Gln Pro Asp Trp Gly Ser Ile Gln Ile Gln Tyr Arg Gly Arg
                195                 200                 205

Lys Ile Asp Arg Glu Lys Leu Leu Arg Tyr Leu Val Ser Phe Arg His
210                 215                 220
```

His Asn Glu Phe His Glu Gln Cys Val Glu Arg Ile Phe Asn Asp Ile
225                 230                 235                 240

Leu Arg Phe Cys Gln Pro Glu Thr Leu Ser Val Tyr Ala Arg Tyr Thr
            245                 250                 255

Arg Arg Gly Gly Leu Asp Ile Asn Pro Trp Arg Ser Asn Thr Asp Phe
            260                 265                 270

Val Pro Ala Thr Gly Arg Leu Ala Arg Gln
        275                 280

<210> SEQ ID NO 81
<211> LENGTH: 297
<212> TYPE: PRT
<213> ORGANISM: Shewanella oneidensis MR-1

<400> SEQUENCE: 81

Met Cys Ala Tyr Phe Asp Met Glu Thr Val Leu Met Thr Gln Asn His
1               5                   10                  15

Asp Pro Tyr Ser Asp Ala Lys Glu Leu Ala Gly Leu Thr Leu Gly Lys
            20                  25                  30

Ala Thr Asp Tyr Gln Ala Glu Tyr Asp Ala Ser Leu Leu Gln Gly Val
        35                  40                  45

Pro Arg Ser Leu Asn Arg Asn Ala Ile Asn Leu Thr Ala Glu Ser Leu
50                  55                  60

Pro Phe His Gly Ala Asp Ile Trp Thr Ala Tyr Glu Leu Ser Trp Leu
65                  70                  75                  80

Asn Ala Lys Gly Lys Pro Met Val Ala Ile Ala Asp Ile Gln Leu Ser
                85                  90                  95

His Ala Ser Gln Asn Leu Ile Glu Ser Lys Ser Phe Lys Leu Tyr Leu
            100                 105                 110

Asn Ser Phe Asn Gln Thr Lys Phe Asp Asn Leu Asp Ala Val Gln Lys
        115                 120                 125

Thr Leu Val Lys Asp Leu Ser Glu Cys Ala Gln Gly Asp Val Thr Val
130                 135                 140

Lys Ile Ile Glu Pro Lys Ser Phe Gly Ile Gln Arg Val Val Glu Leu
145                 150                 155                 160

Pro Gly Thr Cys Ile Asp Asp Leu Asp Ile Glu Val Ser Asp Tyr Asp
                165                 170                 175

Phe Asn Pro Glu Tyr Leu Glu Asn Ser Thr Asp Glu Lys Gln Ile Val
            180                 185                 190

Ala Glu Thr Leu Asn Ser Asn Leu Leu Lys Ser Asn Cys Leu Ile Thr
        195                 200                 205

Ser Gln Pro Asp Trp Gly Ser Val Met Ile Arg Tyr Gln Gly Pro Lys
210                 215                 220

Ile Asp Arg Glu Lys Leu Leu Arg Tyr Leu Ile Ser Phe Arg Gln His
225                 230                 235                 240

Asn Glu Phe His Glu Gln Cys Val Glu Arg Ile Phe Val Asp Leu Lys
                245                 250                 255

His Tyr Cys His Cys Ala Lys Leu Thr Val Tyr Ala Arg Tyr Thr Arg
            260                 265                 270

Arg Gly Gly Leu Asp Ile Asn Pro Tyr Arg Ser Asp Phe Glu His Pro
        275                 280                 285

Gly Glu Ser His Arg Leu Ala Arg Gln
        290                 295

<210> SEQ ID NO 82

```
<211> LENGTH: 282
<212> TYPE: PRT
<213> ORGANISM: Shigella flexneri

<400> SEQUENCE: 82

Met Ser Ser Tyr Ala Asn His Gln Ala Leu Ala Gly Leu Thr Leu Gly
1               5                   10                  15

Lys Ser Thr Asp Tyr Arg Asp Thr Tyr Asp Ala Ser Leu Leu Gln Gly
            20                  25                  30

Val Pro Arg Ser Leu Asn Arg Asp Pro Leu Gly Leu Lys Ala Asp Asn
        35                  40                  45

Leu Pro Phe His Gly Thr Asp Ile Trp Thr Leu Tyr Glu Leu Ser Trp
    50                  55                  60

Leu Asn Ala Lys Gly Leu Pro Gln Val Ala Val Gly His Val Glu Leu
65                  70                  75                  80

Asp Tyr Thr Ser Val Asn Leu Ile Glu Ser Lys Ser Phe Lys Leu Tyr
                85                  90                  95

Leu Asn Ser Phe Asn Gln Thr Arg Phe Asn Asn Trp Asp Glu Val Arg
            100                 105                 110

Gln Thr Leu Glu Arg Asp Leu Ser Thr Cys Ala Gln Gly Lys Ile Ser
        115                 120                 125

Val Ala Leu Tyr Arg Leu Asp Glu Leu Glu Gly Gln Pro Ile Gly His
    130                 135                 140

Phe Asn Gly Thr Cys Ile Asp Asp Gln Asp Ile Thr Ile Asp Asn Tyr
145                 150                 155                 160

Glu Phe Thr Thr Asp Tyr Leu Glu Asn Ala Thr Ser Gly Glu Lys Val
                165                 170                 175

Val Glu Glu Thr Leu Val Ser His Leu Leu Lys Ser Asn Cys Leu Ile
            180                 185                 190

Thr His Gln Pro Asp Trp Gly Ser Ile Gln Ile Gln Tyr Arg Gly Arg
        195                 200                 205

Gln Ile Asp Arg Glu Lys Leu Leu Arg Tyr Leu Val Ser Phe Arg His
    210                 215                 220

His Asn Glu Phe His Glu Gln Cys Val Glu Arg Ile Phe Asn Asp Leu
225                 230                 235                 240

Leu Arg Phe Cys Gln Pro Glu Lys Leu Ser Val Tyr Ala Arg Tyr Thr
                245                 250                 255

Arg Arg Gly Gly Leu Asp Ile Asn Pro Trp Arg Ser Asn Ser Asp Phe
            260                 265                 270

Val Pro Ser Thr Thr Arg Leu Val Arg Gln
        275                 280

<210> SEQ ID NO 83
<211> LENGTH: 282
<212> TYPE: PRT
<213> ORGANISM: Shigella flexneri

<400> SEQUENCE: 83

Met Ser Ser Tyr Ala Asn His Gln Ala Leu Ala Gly Leu Thr Leu Gly
1               5                   10                  15

Lys Ser Thr Asp Tyr Arg Asp Thr Tyr Asp Ala Ser Leu Leu Gln Gly
            20                  25                  30

Val Pro Arg Ser Leu Asn Arg Asp Pro Leu Gly Leu Lys Ala Asp Asn
        35                  40                  45

Leu Pro Phe His Gly Thr Asp Ile Trp Thr Leu Tyr Glu Leu Ser Trp
    50                  55                  60
```

```
Leu Asn Ala Lys Gly Leu Pro Gln Val Ala Val Gly His Val Glu Leu
 65                  70                  75                  80

Asp Tyr Thr Ser Val Asn Leu Ile Glu Ser Lys Ser Phe Lys Leu Tyr
                 85                  90                  95

Leu Asn Ser Phe Asn Gln Thr Arg Phe Asn Asn Trp Asp Glu Val Arg
            100                 105                 110

Gln Thr Leu Glu Arg Asp Leu Ser Thr Cys Ala Gln Gly Lys Ile Ser
        115                 120                 125

Val Ala Leu Tyr Arg Leu Asp Glu Leu Glu Gly Gln Pro Ile Gly His
130                 135                 140

Phe Asn Gly Thr Cys Ile Asp Asp Gln Asp Ile Thr Ile Asp Asn Tyr
145                 150                 155                 160

Glu Phe Thr Thr Asp Tyr Leu Glu Asn Ala Thr Ser Gly Glu Lys Val
                165                 170                 175

Val Glu Glu Thr Leu Val Ser His Leu Leu Lys Ser Asn Cys Leu Ile
            180                 185                 190

Thr His Gln Pro Asp Trp Gly Ser Ile Gln Ile Gln Tyr Arg Gly Arg
        195                 200                 205

Gln Ile Asp Arg Glu Lys Leu Leu Arg Tyr Leu Val Ser Phe Arg His
210                 215                 220

His Asn Glu Phe His Glu Gln Cys Val Glu Arg Ile Phe Asn Asp Leu
225                 230                 235                 240

Leu Arg Phe Cys Gln Pro Glu Lys Leu Ser Val Tyr Ala Arg Tyr Thr
                245                 250                 255

Arg Arg Gly Gly Leu Asp Ile Asn Pro Trp Arg Ser Asn Ser Asp Phe
            260                 265                 270

Val Pro Ser Thr Thr Arg Leu Val Arg Gln
        275                 280

<210> SEQ ID NO 84
<211> LENGTH: 287
<212> TYPE: PRT
<213> ORGANISM: Vibrio cholerae

<400> SEQUENCE: 84

Met Asn Arg Leu Lys Asn Met Ser Lys Tyr Ser Asp Ala Lys Glu Leu
  1               5                  10                  15

Ala Ser Leu Thr Leu Gly Lys Lys Thr Glu Tyr Ala Asn Gln Tyr Asp
             20                  25                  30

Pro Ser Leu Leu Gln Pro Val Pro Arg Ser Leu Asn Arg Asn Asp Leu
         35                  40                  45

His Leu Ser Ala Thr Leu Pro Phe Gln Gly Cys Asp Ile Trp Thr Leu
     50                  55                  60

Tyr Glu Leu Ser Trp Leu Asn Gln Lys Gly Leu Pro Gln Val Ala Ile
 65                  70                  75                  80

Gly Glu Val Ser Ile Pro Ala Thr Ser Ala Asn Leu Ile Glu Ser Lys
                 85                  90                  95

Ser Phe Lys Leu Tyr Leu Asn Ser Tyr Asn Gln Thr Arg Phe Ala Ser
            100                 105                 110

Trp Asp Glu Val Gln Thr Arg Leu Val His Asp Leu Ser Ala Cys Ala
        115                 120                 125

Gly Glu Thr Val Thr Val Asn Val Lys Ser Leu Asn Glu Tyr Thr Ala
130                 135                 140

Glu Pro Ile Val Thr Met Gln Gly Glu Cys Ile Asp Asp Gln Asp Ile
```

```
                145                 150                 155                 160
Glu Ile Asn Tyr Glu Phe Asp Asp Ala Leu Leu Gln Gly Ala Ala
                    165                 170                 175
Gln Gly Glu Glu Val Ser Glu Val Leu His Ser His Leu Leu Lys Ser
                180                 185                 190
Asn Cys Leu Ile Thr Asn Gln Pro Asp Trp Gly Ser Val Glu Ile Ala
                195                 200                 205
Tyr His Gly Ala Lys Met Asn Arg Glu Ala Leu Leu Arg Tyr Leu Val
        210                 215                 220
Ser Phe Arg Glu His Asn Glu Phe His Glu Gln Cys Val Glu Arg Ile
225                 230                 235                 240
Phe Thr Asp Ile Met Arg Tyr Cys Gln Pro Gln Ser Leu Thr Val Tyr
                    245                 250                 255
Ala Arg Tyr Thr Arg Arg Gly Gly Leu Asp Ile Asn Pro Phe Arg Ser
                260                 265                 270
Ser His Gln Ser Ala Pro Asn His Asn Gln Arg Met Ala Arg Gln
            275                 280                 285

<210> SEQ ID NO 85
<211> LENGTH: 281
<212> TYPE: PRT
<213> ORGANISM: Vibrio parahaemolyticus

<400> SEQUENCE: 85

Met Ser Lys Tyr Ser Asp Ala Lys Glu Leu Ala Gly Leu Thr Leu Gly
1               5                   10                  15
Lys Lys Thr Glu Tyr Ala Asn Gln Tyr Asp Ala Ser Leu Leu Gln Pro
                20                  25                  30
Val Pro Arg Ser Leu Asn Arg Asp Asp Leu Glu Leu Gly Asp Thr Leu
            35                  40                  45
Pro Phe Leu Gly His Asp Ile Trp Thr Leu Tyr Glu Leu Ser Trp Leu
        50                  55                  60
Asn Ser Lys Gly Leu Pro Gln Val Ala Val Gly Glu Val Tyr Ile Pro
65                  70                  75                  80
Ala Thr Ser Ala Asn Leu Ile Glu Ser Lys Ser Phe Lys Leu Tyr Leu
                85                  90                  95
Asn Ser Tyr Asn Gln Thr Arg Phe Ala Ser Trp Glu Glu Val Ala Glu
                100                 105                 110
Arg Leu Thr Gln Asp Leu Ser Ala Cys Ala Gly Glu Lys Val Leu Val
            115                 120                 125
Glu Val Asn Pro Val Gly His Tyr Thr Asn Gln Pro Ile Val Thr Met
        130                 135                 140
Glu Gly Glu Cys Ile Asp Asp Gln Asp Ile Glu Ile Asn Ser Tyr Asp
145                 150                 155                 160
Phe Asp Ala Asp Leu Leu Ala Gly Ala Ala Gly Glu Asp Gln Val Glu
                    165                 170                 175
Glu Val Leu His Ser His Leu Leu Lys Ser Asn Cys Leu Ile Thr Asn
                180                 185                 190
Gln Pro Asp Trp Gly Ser Val Glu Ile Arg Tyr Gln Gly Ala Lys Ile
            195                 200                 205
Asp Arg Glu Lys Leu Leu Arg Tyr Leu Val Ser Phe Arg Glu His Asn
        210                 215                 220
Glu Phe His Glu Gln Cys Val Glu Arg Ile Phe Thr Asp Leu Met Lys
225                 230                 235                 240
```

Tyr Cys Gln Pro Asn Lys Leu Thr Val Phe Ala Arg Tyr Thr Arg Arg
            245                 250                 255

Gly Gly Leu Asp Ile Asn Pro Tyr Arg Ser Thr Glu Gln Asp Lys Pro
            260                 265                 270

Ala His Asn His Arg Met Ala Arg Gln
            275                 280

<210> SEQ ID NO 86
<211> LENGTH: 281
<212> TYPE: PRT
<213> ORGANISM: Vibrio vulnificus

<400> SEQUENCE: 86

Met Ser Lys Tyr Ser Asp Ala Lys Glu Leu Ala Gly Leu Thr Leu Gly
1               5                   10                  15

Lys Lys Thr Asp Tyr Ala Asn Gln Tyr Asp Pro Ser Leu Leu Gln Pro
            20                  25                  30

Val Pro Arg Ser Leu Asn Arg Asp Leu Gln Leu Gly Asp Glu Leu
        35                  40                  45

Pro Phe Met Gly His Asp Ile Trp Thr Leu Tyr Glu Leu Ser Trp Leu
    50                  55                  60

Asn Ser Lys Gly Leu Pro Gln Val Ala Val Gly Glu Val Tyr Ile Pro
65                  70                  75                  80

Ala Thr Ser Ala Asn Leu Ile Glu Ser Lys Ser Phe Lys Leu Tyr Leu
                85                  90                  95

Asn Ser Tyr Asn Gln Thr Arg Phe Asp Ser Trp Glu Glu Val Arg Gln
            100                 105                 110

Arg Leu Ile Thr Asp Leu Ser His Cys Ala Gly Glu Ala Val Glu Val
            115                 120                 125

Ala Val Asn Ser Val Thr His Tyr Thr Gln Gln Pro Ile Val Thr Met
        130                 135                 140

Glu Gly Glu Cys Ile Asp Glu Gln Asp Ile Asp Ile Ser Ser Tyr Asp
145                 150                 155                 160

Phe Asp Asp Arg Leu Leu Glu Gly Ala Ala Gly Glu Glu Trp Val Thr
                165                 170                 175

Glu Thr Leu His Ser His Leu Leu Lys Ser Asn Cys Leu Ile Thr Asn
            180                 185                 190

Gln Pro Asp Trp Gly Ser Val Glu Ile Arg Tyr Gln Gly His Lys Ile
        195                 200                 205

Asp Arg Glu Lys Leu Leu Arg Tyr Leu Val Ser Phe Arg Glu His Asn
    210                 215                 220

Glu Phe His Glu Gln Cys Val Glu Arg Ile Phe Thr Asp Leu Met Lys
225                 230                 235                 240

Tyr Cys Gln Pro Glu Ser Leu Thr Val Phe Ala Arg Tyr Thr Arg Arg
                245                 250                 255

Gly Gly Leu Asp Ile Asn Pro Tyr Arg Ser Thr Glu Gln Ala Lys Pro
            260                 265                 270

Asp His Asn His Arg Met Ala Arg Gln
        275                 280

<210> SEQ ID NO 87
<211> LENGTH: 281
<212> TYPE: PRT
<213> ORGANISM: Vibrio vulnificus

<400> SEQUENCE: 87

```
Met Ser Lys Tyr Ser Asp Ala Lys Glu Leu Ala Gly Leu Thr Leu Gly
1               5                  10                  15

Lys Lys Thr Asp Tyr Ala Asn Gln Tyr Asp Pro Ser Leu Leu Gln Pro
            20                  25                  30

Val Pro Arg Ser Leu Asn Arg Asp Asp Leu Gln Leu Gly Asp Glu Leu
        35                  40                  45

Pro Phe Met Gly His Asp Ile Trp Thr Leu Tyr Glu Leu Ser Trp Leu
    50                  55                  60

Asn Lys Gly Leu Pro Gln Val Ala Val Gly Glu Val Tyr Ile Pro
65                  70                  75                  80

Ala Thr Ser Ala Asn Leu Ile Glu Ser Lys Ser Phe Lys Leu Tyr Leu
                85                  90                  95

Asn Ser Tyr Asn Gln Thr Arg Phe Asp Ser Trp Glu Glu Val Arg Gln
            100                 105                 110

Arg Leu Ile Thr Asp Leu Ser His Cys Ala Gly Glu Ala Val Glu Val
        115                 120                 125

Ala Val Asn Ser Val Thr His Tyr Thr Gln Gln Pro Ile Val Thr Met
    130                 135                 140

Glu Gly Glu Cys Ile Asp Glu Gln Asp Ile Asp Ile Ser Ser Tyr Asp
145                 150                 155                 160

Phe Asp Asp Arg Leu Leu Glu Gly Ala Ala Gly Glu Glu Trp Val Thr
            165                 170                 175

Glu Thr Leu His Ser His Leu Leu Lys Ser Asn Cys Leu Ile Thr Asn
        180                 185                 190

Gln Pro Asp Trp Gly Ser Val Glu Ile Arg Tyr Gln Gly His Lys Ile
    195                 200                 205

Asp Arg Glu Lys Leu Leu Arg Tyr Leu Val Ser Phe Arg Glu His Asn
210                 215                 220

Glu Phe His Glu Gln Cys Val Glu Arg Ile Phe Thr Asp Leu Met Lys
225                 230                 235                 240

Tyr Cys Gln Pro Glu Ser Leu Thr Val Phe Ala Arg Tyr Thr Arg Arg
            245                 250                 255

Gly Gly Leu Asp Ile Asn Pro Tyr Arg Ser Thr Glu Gln Ala Lys Pro
        260                 265                 270

Asp His Asn His Arg Met Ala Arg Gln
    275                 280
```

<210> SEQ ID NO 88
<211> LENGTH: 271
<212> TYPE: PRT
<213> ORGANISM: Xanthomonas campestris

<400> SEQUENCE: 88

```
Met Asn Thr Pro Glu Asp Ser Ser Leu Gly Arg Glu Val Ala Tyr Pro
1               5                  10                  15

Ser Gly Tyr Asp Pro Ser Leu Leu Phe Pro Ile Pro Arg Ala Ala Gly
            20                  25                  30

Arg Ala Ala Ile Gly Leu Arg G

Arg Phe Asn Ser Ala Glu Ala Val Arg Ala Arg Ile Ala Thr Asp Leu
            100                 105                 110

Ser Thr Arg Ala Gly Ala Asp Val Ser Val Glu Phe Gly Leu Pro Pro
            115                 120                 125

Ile Asp Ala Val Gly Glu Gly Glu Ser Ile Asp Ala Leu Asp Ile Ala
        130                 135                 140

Ile Asp Asp Tyr Gly Pro Pro Lys Ala Asp Tyr Leu Ala Thr His Ala
145                 150                 155                 160

Gly Thr Val Val Glu Glu Val Leu Ala Ser Ala Leu Leu Lys Ser Asn
                165                 170                 175

Cys Pro Val Thr Gly Gln Pro Asp Trp Ala Ser Val Thr Leu Arg Tyr
            180                 185                 190

Arg Gly Ala Pro Ile Asp Arg Glu Gly Leu Leu Arg Tyr Leu Val Ser
        195                 200                 205

Phe Arg Asp His Ala Asp Phe His Glu Gln Cys Val Glu Arg Ile Phe
    210                 215                 220

Gln Asp Leu Leu Val Arg Cys Ala Pro Gln Trp Leu Val Glu Ala
225                 230                 235                 240

Arg Tyr Thr Arg Arg Gly Gly Leu Asp Ile Asn Pro Val Arg Thr Ser
                245                 250                 255

Pro Gln Met Pro Thr Pro Leu Ser Ile Phe Arg Asp Leu Arg Gln
            260                 265                 270

<210> SEQ ID NO 89
<211> LENGTH: 271
<212> TYPE: PRT
<213> ORGANISM: Xanthomonas axonopodis

<400> SEQUENCE: 89

Met Asn Thr Pro Glu Asp Ser Thr Leu Gly Arg Glu Val Ala Tyr Pro
1               5                   10                  15

Ser Gly Tyr Asp Pro Ser Leu Leu Phe Pro Ile Pro Arg Ala Ala Gly
            20                  25                  30

Arg Gln Ala Ile Gly Leu Thr Gly Asp Leu Pro Phe Ile Gly Arg Asp
        35                  40                  45

Arg Trp His Ala Tyr Glu Leu Ser Trp Leu Asp Ala Gln Gly Lys Pro
    50                  55                  60

Cys Val Ala Thr Ala Thr Leu His Val Pro Cys Asp Ser Pro Ser Leu
65                  70                  75                  80

Ile Glu Ser Lys Ser Leu Lys Leu Tyr Leu Asn Ser Leu Asn Ala Thr
                85                  90                  95

Arg Phe Asn Ser Ala Glu Ala Val Arg Thr Arg Ile Ala Thr Asp Leu
            100                 105                 110

Ser Thr Arg Ala Gly Ala Asp Val Ala Val Glu Phe Gly Leu Pro Pro
            115                 120                 125

Ile Asp Ala Val Gly Glu Gly Glu Ser Ile Asp Ala Leu Asp Leu Ser
        130                 135                 140

Ile Asp Asp Tyr Gly Pro Pro Asn Ala Ala Tyr Leu Cys Ala His Ala
145                 150                 155                 160

Gln Pro Val Val Glu Glu Val Leu Thr Ser Ala Leu Leu Lys Ser Asn
                165                 170                 175

Cys Pro Val Thr Gly Gln Pro Asp Trp Ala Ser Val Thr Leu Arg Tyr
            180                 185                 190

Arg Gly Ala Pro Ile Asp Arg Glu Gly Leu Leu Arg Tyr Leu Val Ser

```
                195                 200                 205
Phe Arg Asp His Ala Glu Phe His Glu Gln Cys Val Glu Arg Ile Phe
    210                 215                 220
Asn Asp Val Leu Thr Gln Cys Ala Pro Gln Trp Leu Val Val Glu Ala
225                 230                 235                 240
Arg Tyr Thr Arg Arg Gly Gly Leu Asp Ile Asn Pro Leu Arg Ser Ser
                245                 250                 255
Ala Ser Val Pro Thr Pro Leu Ser Ile Phe Arg Asp Leu Arg Gln
                260                 265                 270

<210> SEQ ID NO 90
<211> LENGTH: 275
<212> TYPE: PRT
<213> ORGANISM: Xylella fastidiosa

<400> SEQUENCE: 90

Met Asn Thr Ser His Tyr Ser Val Leu Gly His Ala Val Pro Tyr Pro
1               5                   10                  15
Lys Ala Tyr Asp Pro Ser Leu Leu Phe Pro Ile Ser Arg Ala Val Gly
                20                  25                  30
Arg Ala Gln Ile Gly Ile Gly Val Val Leu Pro Phe Val Gly Glu Asp
            35                  40                  45
Arg Trp His Ala Tyr Glu Leu Ser Trp Leu Asp Ala Arg Gly Lys Pro
    50                  55                  60
Cys Val Ala Thr Ala Thr Phe His Val Pro Cys Asp Ser Pro Tyr Leu
65                  70                  75                  80
Ile Glu Ser Lys Ser Leu Lys Leu Tyr Leu Asn Ser Phe Ser Ala Glu
                85                  90                  95
Val Phe Asn Arg Ala Glu Ala Leu Arg Leu Arg Ile Ala Ala Asp Leu
            100                 105                 110
Ser Ala Cys Ala Gly Ala Ala Val Ala Val Glu Phe Gly Leu Pro Pro
        115                 120                 125
Val Gly Gly Gly Asp Lys Glu Ile Ser Leu Asp Arg Leu Asn Val Asp
    130                 135                 140
Ile Glu Asp Tyr Gly Pro Pro Asn Pro Asp Tyr Leu Ser Asn Val Ala
145                 150                 155                 160
Gln Asn Leu Ile Glu Glu Met Val Glu Glu Thr Leu Thr Ser Thr Leu
                165                 170                 175
Phe Lys Ser Asn Cys Pro Val Thr Gly Gln Pro Asp Trp Ala Ser Val
            180                 185                 190
Thr Val Arg Tyr Phe Gly Val Pro Ile Asp His Glu Gly Leu Leu Arg
        195                 200                 205
Tyr Phe Ile Ser Phe Arg His His Ala Glu Phe His Glu Gln Cys Val
    210                 215                 220
Glu Arg Ile Phe Gln Asp Val Leu Gln Arg Cys Ser Pro Gln Cys Leu
225                 230                 235                 240
Ala Val Glu Ala Arg Tyr Thr Arg Arg Gly Gly Leu Asp Ile Asn Pro
                245                 250                 255
Leu Arg Thr Thr Ser Glu Met Ala Trp Pro Ile Ser Val Phe Arg Asp
            260                 265                 270
Pro Arg Gln
        275

<210> SEQ ID NO 91
<211> LENGTH: 275
```

```
<212> TYPE: PRT
<213> ORGANISM: Xylella fastidiosa

<400> SEQUENCE: 91

Met Asn Thr Ser His Tyr Ser Val Leu Gly His Thr Val Pro Tyr Pro
1               5                   10                  15

Lys Val Tyr Asp Pro Ser Leu Leu Phe Pro Ile Ser Arg Ala Val Gly
                20                  25                  30

Arg Thr Gln Ile Gly Ile Gly Val Val Leu Pro Phe Val Gly Glu Asp
            35                  40                  45

Arg Trp His Ala Tyr Glu Leu Ser Trp Leu Asp Ala Arg Gly Lys Pro
        50                  55                  60

Cys Val Ala Thr Ala Thr Phe His Val Pro Cys Asp Ser Pro Tyr Leu
65                  70                  75                  80

Ile Glu Ser Lys Ser Leu Lys Leu Tyr Leu Asn Ser Phe Ser Ala Glu
                85                  90                  95

Val Phe Asn Arg Ala Glu Ala Leu Arg Leu Arg Ile Ala Ala Asp Leu
                100                 105                 110

Ser Ala Cys Ala Gly Ala Ala Val Ala Val Glu Phe Gly Leu Pro Pro
            115                 120                 125

Val Gly Gly Gly Asp Lys Glu Ile Ser Leu Asp Arg Leu Asn Val Asp
        130                 135                 140

Ile Glu Asp Tyr Gly Pro Pro Asn Pro Asp Tyr Leu Ser Asn Val Ala
145                 150                 155                 160

Gln Asn Leu Val Glu Glu Met Val Glu Thr Leu Thr Ser Thr Leu
                165                 170                 175

Phe Lys Ser Asn Cys Pro Val Thr Gly Gln Pro Asp Trp Ala Ser Val
                180                 185                 190

Thr Val Arg Tyr Phe Gly Met Pro Ile Asp His Glu Gly Leu Leu Arg
            195                 200                 205

Tyr Phe Ile Ser Phe Arg His His Ala Glu Phe His Glu Gln Cys Val
        210                 215                 220

Glu Arg Ile Phe Gln Asp Val Leu Gln Arg Cys Ala Pro Gln Cys Leu
225                 230                 235                 240

Ala Val Glu Ala Arg Tyr Thr Arg Arg Gly Gly Leu Asp Ile Asn Pro
                245                 250                 255

Leu Arg Thr Thr Ser Glu Met Ala Trp Pro Leu Ser Val Phe Arg Asp
                260                 265                 270

Pro Arg Gln
        275

<210> SEQ ID NO 92
<211> LENGTH: 275
<212> TYPE: PRT
<213> ORGANISM: Xylella fastidiosa

<400> SEQUENCE: 92

Met Asn Thr Ser His Tyr Ser Val Leu Gly His Thr Val Pro Tyr Pro
1               5                   10                  15

Lys Val Tyr Asp Pro Ser Leu Leu Phe Pro Ile Ser Arg Ala Val Gly
                20                  25                  30

Arg Thr Gln Ile Gly Ile Gly Val Val Leu Pro Phe Val Gly Glu Asp
            35                  40                  45

Arg Trp His Ala Tyr Glu Leu Ser Trp Leu Asp Ala Arg Gly Lys Pro
        50                  55                  60
```

Cys Val Ala Thr Ala Thr Phe His Val Pro Cys Asp Ser Pro Tyr Leu
65                  70                  75                  80

Ile Glu Ser Lys Ser Leu Lys Leu Tyr Leu Asn Ser Phe Ser Ala Glu
                85                  90                  95

Val Phe Asn Arg Ala Glu Ala Leu Arg Leu Arg Ile Ala Ala Asp Leu
            100                 105                 110

Ser Ala Cys Ala Gly Ala Ala Val Ala Val Glu Phe Gly Leu Pro Pro
        115                 120                 125

Val Gly Gly Gly Asp Lys Glu Ile Ser Leu Asp Arg Leu Asn Val Asp
    130                 135                 140

Ile Glu Asp Tyr Gly Pro Pro Asn Pro Asp Tyr Leu Ser Asn Val Ala
145                 150                 155                 160

Gln Asn Phe Val Glu Glu Met Val Glu Thr Leu Thr Ser Thr Leu
                165                 170                 175

Phe Lys Ser Asn Cys Pro Val Thr Gly Gln Pro Asp Trp Ala Ser Val
            180                 185                 190

Thr Val Arg Tyr Phe Gly Val Pro Ile Asp His Glu Gly Leu Leu Arg
        195                 200                 205

Tyr Phe Ile Ser Phe Arg His His Ala Glu Phe His Glu Gln Cys Val
    210                 215                 220

Glu Arg Ile Phe Gln Asp Val Leu Gln Arg Cys Ala Pro Gln Cys Leu
225                 230                 235                 240

Ala Val Glu Ala Arg Tyr Thr Arg Arg Gly Gly Leu Asp Ile Asn Pro
                245                 250                 255

Leu Arg Ala Thr Ser Glu Met Ala Trp Pro Leu Ser Val Phe Arg Asp
            260                 265                 270

Pro Arg Gln
        275

<210> SEQ ID NO 93
<211> LENGTH: 275
<212> TYPE: PRT
<213> ORGANISM: Xylella fastidiosa

<400> SEQUENCE: 93

Met Asn Thr Ser His Tyr Ser Val Leu Gly His Thr Val Pro Tyr Pro
1               5                   10                  15

Lys Val Tyr Asp Pro Ser Leu Leu Phe Pro Ile Ser Arg Ala Val Gly
                20                  25                  30

Arg Thr Gln Ile Gly Ile Gly Val Val Leu Pro Phe Val Gly Glu Asp
            35                  40                  45

Arg Trp His Ala Tyr Glu Leu Ser Trp Leu Asp Ala Arg Gly Lys Pro
        50                  55                  60

Cys Val Ala Thr Ala Thr Phe His Val Pro Cys Asp Ser Pro Tyr Leu
65                  70                  75                  80

Ile Glu Ser Lys Ser Leu Lys Leu Tyr Leu Asn Ser Phe Ser Ala Glu
                85                  90                  95

Val Phe Asn Arg Ala Glu Ala Leu Arg Leu Arg Ile Ala Ala Asp Leu
            100                 105                 110

Ser Ala Cys Ala Gly Ala Ala Val Ala Val Glu Phe Gly Leu Pro Pro
        115                 120                 125

Val Gly Ser Gly Asp Lys Glu Ile Ser Leu Asp Arg Leu Asn Val Asp
    130                 135                 140

Ile Glu Asp Tyr Gly Pro Pro Asn Pro Asp Tyr Leu Ser Asn Val Ala
145                 150                 155                 160

-continued

```
Gln Asn Leu Val Glu Glu Met Val Glu Thr Leu Thr Ser Thr Leu
                165                 170                 175

Phe Lys Ser Asn Cys Pro Val Thr Gly Gln Pro Asp Trp Ala Ser Val
            180                 185                 190

Thr Val Arg Tyr Phe Gly Met Pro Ile Asp His Glu Gly Leu Leu Arg
        195                 200                 205

Tyr Phe Ile Ser Phe Arg His His Ala Glu Phe His Glu Gln Cys Val
    210                 215                 220

Glu Arg Ile Phe Gln Asp Val Leu Gln Arg Cys Ala Pro Gln Cys Leu
225                 230                 235                 240

Ala Val Glu Ala Arg Tyr Thr Arg Arg Gly Gly Leu Asp Ile Asn Pro
                245                 250                 255

Leu Arg Thr Thr Ser Glu Met Ala Trp Pro Leu Ser Val Phe Arg Asp
            260                 265                 270

Pro Arg Gln
        275

<210> SEQ ID NO 94
<211> LENGTH: 281
<212> TYPE: PRT
<213> ORGANISM: Yersinia pestis

<400> SEQUENCE: 94

Met Ser Ser Tyr Gln Asn His Lys Ala Leu Ala Glu Leu Thr Leu Gly
1               5                   10                  15

Lys Pro Thr Ala Tyr Cys Asp Tyr Tyr Asp Ala Thr Leu Leu Gln Ala
                20                  25                  30

Val Pro Arg Ser Met Asn Arg Glu Pro Leu Gly Leu Tyr Pro Asp Asn
            35                  40                  45

Leu Pro Phe His Gly Ala Asp Ile Trp Thr Leu Tyr Glu Leu Ser Trp
        50                  55                  60

Leu Asn Ser Asn Gly Leu Pro Gln Val Ala Val Gly Glu Ile Ser Leu
65                  70                  75                  80

Asn Ala Asp Ser Ile Asn Leu Ile Glu Ser Lys Ser Phe Lys Leu Tyr
                85                  90                  95

Leu Asn Ser Phe Asn Gln Thr Ile Phe Ala Asp Lys Glu Ser Val Arg
            100                 105                 110

Met Thr Leu Gln Arg Asp Leu Ala Ala Cys Ala Gln Gly Asn Val Ser
        115                 120                 125

Val Ala Leu Tyr Asp Leu Asp Glu Ile Thr Gly Gln Pro Ile Ser Asn
    130                 135                 140

Phe Asn Gly Glu Cys Leu Asp Lys Gln Asp Ile Arg Ile Asp Ser Tyr
145                 150                 155                 160

Glu Phe Asn Ala Asp Tyr Leu Gln Gly Ala Ala Gly Lys Asp His Val
                165                 170                 175

Glu Glu Ser Leu Val Ser His Leu Leu Lys Ser Asn Cys Leu Ile Thr
            180                 185                 190

His Gln Pro Asp Trp Gly Ser Val Gln Ile His Tyr Arg Gly Pro Gln
        195                 200                 205

Ile Asp His Glu Ala Leu Leu Arg Tyr Leu Val Ser Phe Arg His His
    210                 215                 220

Asn Glu Phe His Glu Gln Cys Val Glu Arg Ile Phe Asn Asp Ile Met
225                 230                 235                 240

Arg Phe Cys Gln Pro Glu Thr Leu Thr Val Tyr Ala Arg Tyr Thr Arg
```

-continued

```
                245                 250                 255
Arg Gly Gly Leu Asp Ile Asn Pro Trp Arg Ser Asn Thr Asp Phe Val
                260                 265                 270

Pro Leu Thr Gly Arg Leu Ala Arg Gln
                275                 280

<210> SEQ ID NO 95
<211> LENGTH: 281
<212> TYPE: PRT
<213> ORGANISM: Yersinia pestis

<400> SEQUENCE: 95

Met Ser Ser Tyr Gln Asn His Lys Ala Leu Ala Glu Leu Thr Leu Gly
1               5                   10                  15

Lys Pro Thr Ala Tyr Cys Asp Tyr Tyr Asp Ala Thr Leu Leu Gln Ala
                20                  25                  30

Val Pro Arg Ser Met Asn Arg Glu Pro Leu Gly Leu Tyr Pro Asp Asn
                35                  40                  45

Leu Pro Phe His Gly Ala Asp Ile Trp Thr Leu Tyr Glu Leu Ser Trp
    50                  55                  60

Leu Asn Ser Asn Gly Leu Pro Gln Val Ala Val Gly Glu Ile Ser Leu
65                  70                  75                  80

Asn Ala Asp Ser Ile Asn Leu Ile Glu Ser Lys Ser Phe Lys Leu Tyr
                85                  90                  95

Leu Asn Ser Phe Asn Gln Thr Ile Phe Ala Asp Lys Glu Ser Val Arg
                100                 105                 110

Met Thr Leu Gln Arg Asp Leu Ala Ala Cys Ala Gln Gly Asn Val Ser
                115                 120                 125

Val Ala Leu Tyr Asp Leu Asp Glu Ile Thr Gly Gln Pro Ile Ser Asn
                130                 135                 140

Phe Asn Gly Glu Cys Leu Asp Lys Gln Asp Ile Arg Ile Asp Ser Tyr
145                 150                 155                 160

Glu Phe Asn Ala Asp Tyr Leu Gln Gly Ala Ala Gly Lys Asp His Val
                165                 170                 175

Glu Glu Ser Leu Val Ser His Leu Leu Lys Ser Asn Cys Leu Ile Thr
                180                 185                 190

His Gln Pro Asp Trp Gly Ser Val Gln Ile His Tyr Arg Gly Pro Gln
                195                 200                 205

Ile Asp His Glu Ala Leu Leu Arg Tyr Leu Val Ser Phe Arg His His
                210                 215                 220

Asn Glu Phe His Glu Gln Cys Val Glu Arg Ile Phe Asn Asp Ile Met
225                 230                 235                 240

Arg Phe Cys Gln Pro Glu Thr Leu Thr Val Tyr Ala Arg Tyr Thr Arg
                245                 250                 255

Arg Gly Gly Leu Asp Ile Asn Pro Trp Arg Ser Asn Thr Asp Phe Val
                260                 265                 270

Pro Leu Thr Gly Arg Leu Ala Arg Gln
                275                 280
```

ENZYMATIC REDUCTION OF A NITRILE CONTAINING COMPOUND TO THE CORRESPONDING AMINE

CROSS REFERENCE TO RELATED APPLICATION

This application claims priority to U.S. Provisional Application No. 60/612,879 filed Sep. 24, 2004, herein incorporated by reference.

STATEMENT OF GOVERNMENT SUPPORT

This invention was made with U.S. Government support under the National Institutes of Health Grant No. GM23561 and National Science Foundation Grant Nos. MCB-9733746 and MCB-0128901. The U.S. Government has certain rights in the invention.

FIELD

This disclosure relates to methods of reducing nitriles to amines, and amines produced by the method.

BACKGROUND

The demands of an increasingly environmentally conscientious society and industries need to maximize its bottom line have driven a rapid increase in the use of enzymes and microorganisms for mediating industrially important chemical transformations (Schmid et al., *Nature* 409: 258-68, 2001; Ritter, *Chem. Engin. News.* 82:25-30, 2004). Generally, enzymes possess exceptional catalytic efficiencies, operate under very mild conditions (room temperature, neutral pH, ambient pressure), exhibit high selectivity and specificity, and generate minimal waste (Wong and Whitesides (1994). *Enzymes in Synthetic Organic Chemistry*. Oxford, Pergamon). As such, enzymes have the potential to favorably impact industrial chemical processes and provide an attractive alternative to traditional chemical synthesis.

Several nitrile metabolizing enzymes have been identified and used in biocatalysis (FIG. 1). For example, the use of nitrile hydratase (NHase), which converts nitriles to amides, in the industrial synthesis of acrylamide represented the first application of biocatalysis to commodity chemical synthesis (Kobayashi et al., *Trends Biotech.* 10:402-8, 1992), and the first use of biocatalysis in the petroleum industry. Other commercial applications of NHase include the production of nicotinamide from 3-cyanopyridine (Mathew et al., *Appl. Environ. Microbiol.* 54:1030-2, 1988), the production of benzamide and thiophenamide from the corresponding nitriles, and the conversion of the nitrile groups in acrylic fibers to the corresponding amides (Tauber et al., *Appl. Environ. Microbiol.* 66:1634-8, 2000).

The enzyme nitrilase, which hydrolyzes nitriles to carboxylic acids, has also been incorporated into many commercial processes. For example, the vitamins nicotinic acid and p-aminobenzoic acid have been prepared from the nitrilase-catalyzed hydrolysis of 3-cyanopyridine and p-aminobenzonitrile, respectively. Nitrilase and NHase are also used as agents in the bioremediation of nitrile containing waste streams and in herbicide degradation (Banerjee et al., *Appl. Environ. Micro.* 60:33-44, 2002).

One area where biocatalysis has yet to impact the commercial reactions of nitriles is in their reduction to primary amines. This is due to the lack of any known enzyme capable of carrying out the reduction of nitriles to amines (FIG. 1). The reduction of nitriles to amines has traditionally been carried out by hydrogenation over various transition metal catalysts or by metal hydride reductions (March, J. (1992). *Advanced Organic Chemistry: Reactions, Mechanisms, and Structure*. New York, John Wiley & Sons). These reactions are typically non-selective, requiring the use of protecting groups when other reducible functional groups are present, and can result in the formation of unwanted byproducts.

Thus, identification of an enzyme that is capable of reducing nitriles to amines would permit biocatalysis of this reaction, and provide an alternative to the synthetic conversion of nitriles to amines.

SUMMARY

The inventors have identified a new class of enzymes capable of reducing nitriles to primary amines, referred to herein as nitrile oxido-reductases. Using a comparative genomics approach, combined with in vivo and in vitro functional data, enzymes, herein referred to as QueF, were identified that are involved in the biosynthesis of 7-cyano-7-deazaguanine (preQ$_0$), the last common intermediate in the biosynthesis of queuosine. Orthologs of QueF were found in bacteria (such as *Escherichia coli* QueF and *Bacillus subtilis* QueF), and encode a family of unique NADPH-dependent nitrile oxido-reductases that convert preQ$_0$ to 7-aminomethyl-7-deazaguanine (preQ$_1$), the subsequent step in queuosine biosynthesis. The discovery of biological nitrile reduction can be used to biocatalytically reduce nitrile-containing compounds to the corresponding primary amines. Based on the discovery that QueF is a nitrile oxido-reductase, native QueF enzymes can be mutated to engineer other nitrile oxido-reductases having specificity for other nitriles.

Methods of reducing a nitrile containing compound to an amine are provided. For example, the methods can be used to reduce a nitrile to its corresponding primary amine. The disclosed methods can be performed in vitro or in vivo. In some examples, the method includes providing a nitrile oxido-reductase (such as a recombinant nitrile oxido-reductase) and contacting the nitrile containing compound with the nitrile oxido-reductase under conditions sufficient for substantially reducing the nitrile containing compound to the corresponding amine.

Complete reduction of the nitrile containing compound is not required. For example, if the compound includes a single nitrile group, substantial reduction can include reducing at least 70% of the nitrile containing compounds in the reaction, such as at least 80%, at least 90%, at least 95%, or at least 99% of the nitrile containing compounds in the reaction. In another example, if the compound includes a more than one nitrile group, such as a di- or tri-nitrile containing-compound, substantial reduction can include reducing at least one or at least two of the two or three nitriles on the compound, and can also include reducing all of the nitriles on at least 70% of the nitrile containing compounds in the reaction, such as at least 80%, at least 90%, at least 95% or at least 99% of the nitrile containing compounds in the reaction.

Although the specification provides specific examples of combinations of nitrile containing compounds and nitrile oxido-reductases that can be used, one skilled in the art will recognize that other nitrile containing compounds and nitrile oxido-reductases that can be used, depending on the target amine. One skilled in the art will also recognize that more than one nitrile containing compound and more than one nitrile oxido-reductase can be included in a single reaction, for example to produce multiple amines.

The present disclosure also provides methods for producing an amine, such as a primary amine. In particular examples, the method includes providing a nitrile that when reduced produces the target amine, providing a nitrile oxido-reductase, and contacting the nitrile with the nitrile oxido-reductase under conditions sufficient for substantially reducing the nitrile to the amine.

Also disclosed herein are isolated proteins having nitrile oxido-reductase activity, as well as nucleic acids encoding such proteins. Such proteins and nucleic acid molecules can be used in the methods disclosed herein. The disclosed nucleic acid molecules can be part of a vector, such as a plasmid or viral vector. Also provided herein are transformed cells that include a recombinant nitrile oxido-reductase encoding nucleic acid molecule (such as a cDNA or gene sequence), for example operably linked to a promoter, thereby allowing the cells to express the corresponding recombinant nitrile oxido-reductase protein. Such cells can be used in the methods disclosed herein.

The foregoing and other features and advantages will become more apparent from the following detailed description of several embodiments, which proceeds with reference to the accompanying figures.

BRIEF DESCRIPTION OF THE FIGURES

This patent or application filed contains at least one drawing executed in color. Copies of this patent or patent application publication with color drawings will be provided by the Office upon request and payment of the necessary fee.

FIG. 4 is a schematic drawing showing the primary structure organization of the QueF class I (YkvM) and class II (YqcD) subfamilies.

FIG. 5 is a graph showing a gel filtration standard curve. Native molecular-weight determinations were done for the following: wild-type *E. coli* QueF (■), His$_6$-*E. coli* QueF (□), wild-type *B. subtilis* QueF (♦), and His$_6$-*B. subtilis* QueF (◇). The standard curve (o) was prepared using RNase (14 kDa), ovalbumin (43 kDa), bovine serum albumin (66 kDa), alcohol dehydrogenase (150 kDa), aldolase (158 kDa), catalase (232 kDa) and thyroglobulin (669 kDa). The outer and total volumes of the column were determined with blue-dextran and DNP-aspartate, respectively.

FIGS. 7A-B are digital images showing crystallization of *B. subtilis* QueF. (A): Left, manually-grown hexagonal crystals of apo *B. subtilis* QueF, Middle, trigonal crystals grown the presence of preQo, β-NADP and CaCl$_2$. Right, larger trigonal crystals. (B) 3.0-Å X-ray diffraction of trigonal QueF.

Figure 9B:
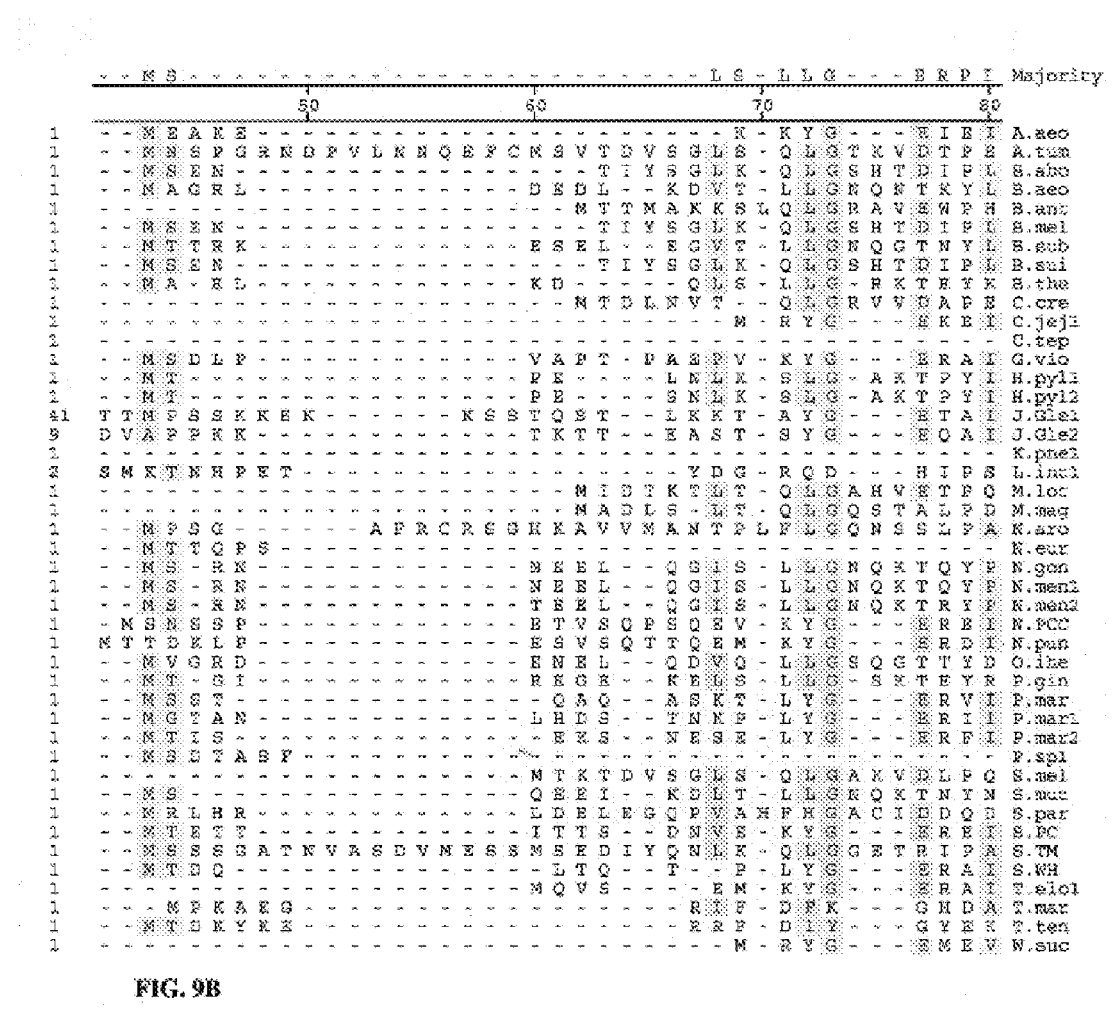
Figure 9C:
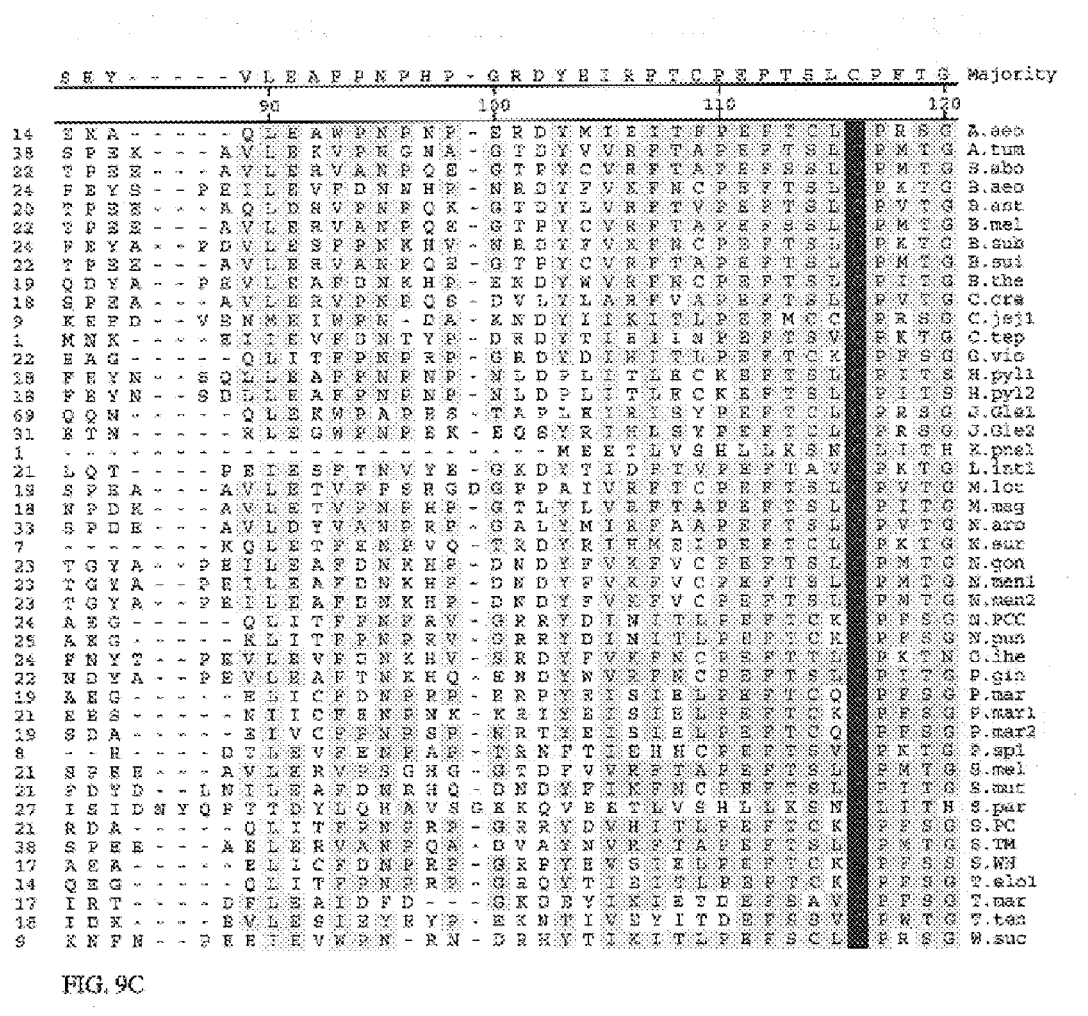
Figure 9D:
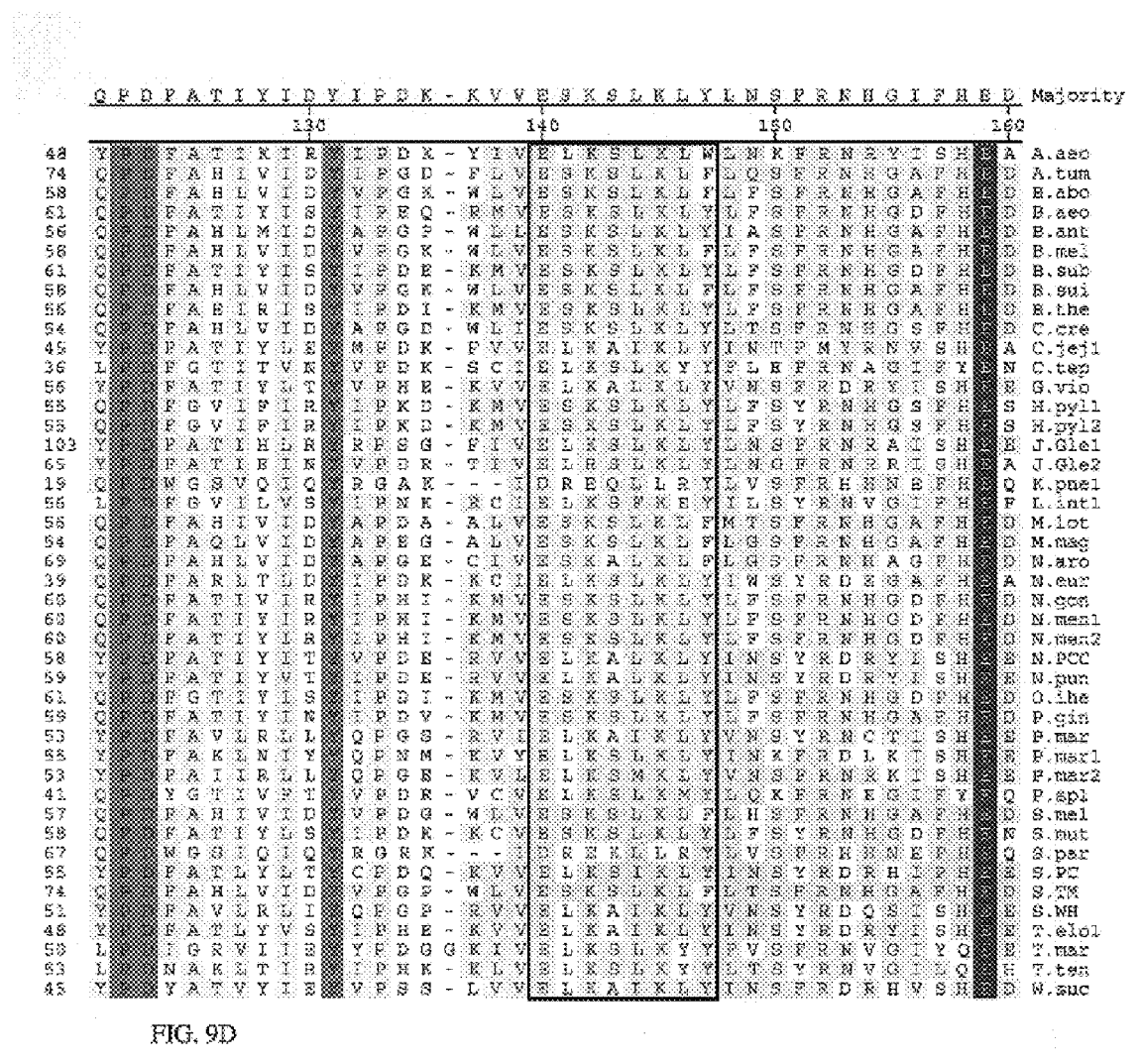
Figure 9E:
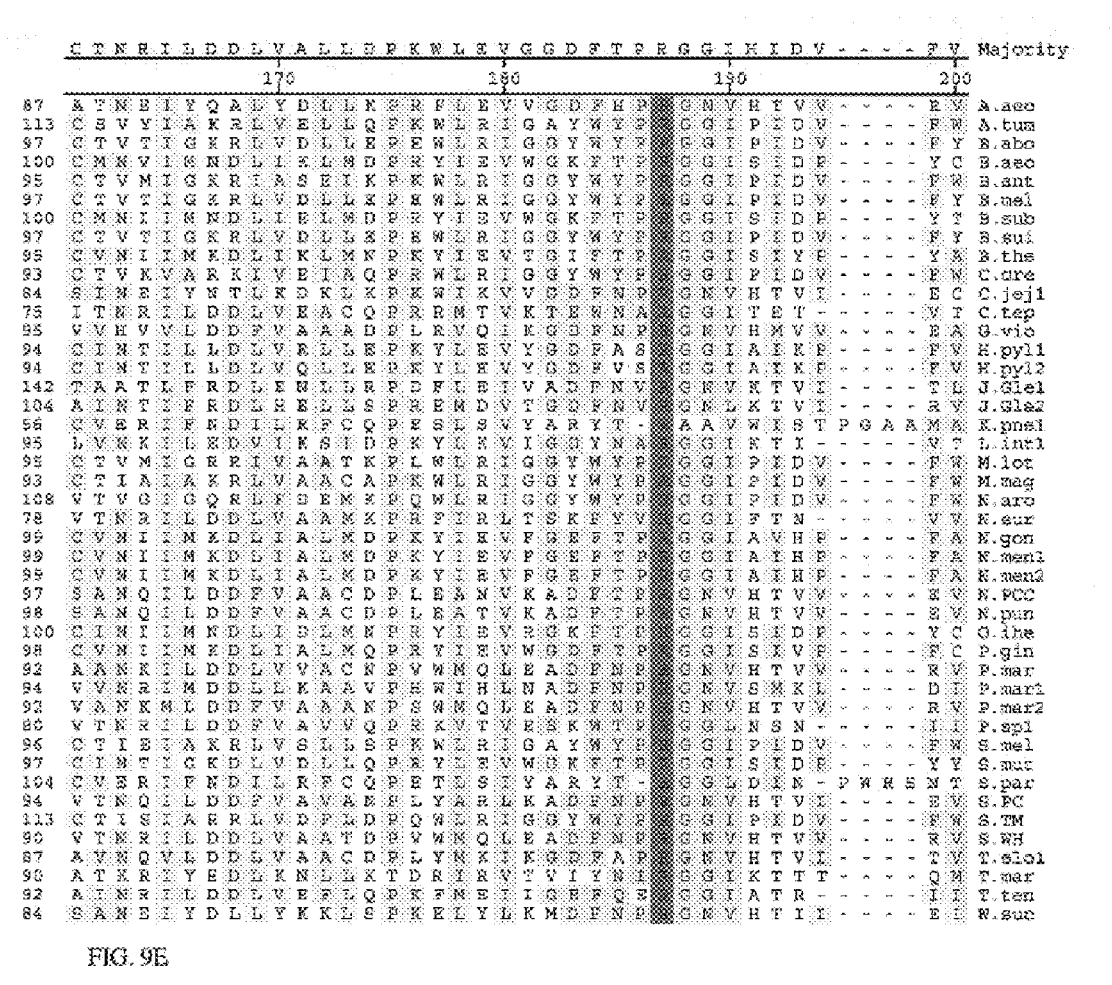

FIGS. 9A-G show the alignment of several QueF class I enzymes (SEQ ID NOS: 2 and 6-48).

Figure 10C:
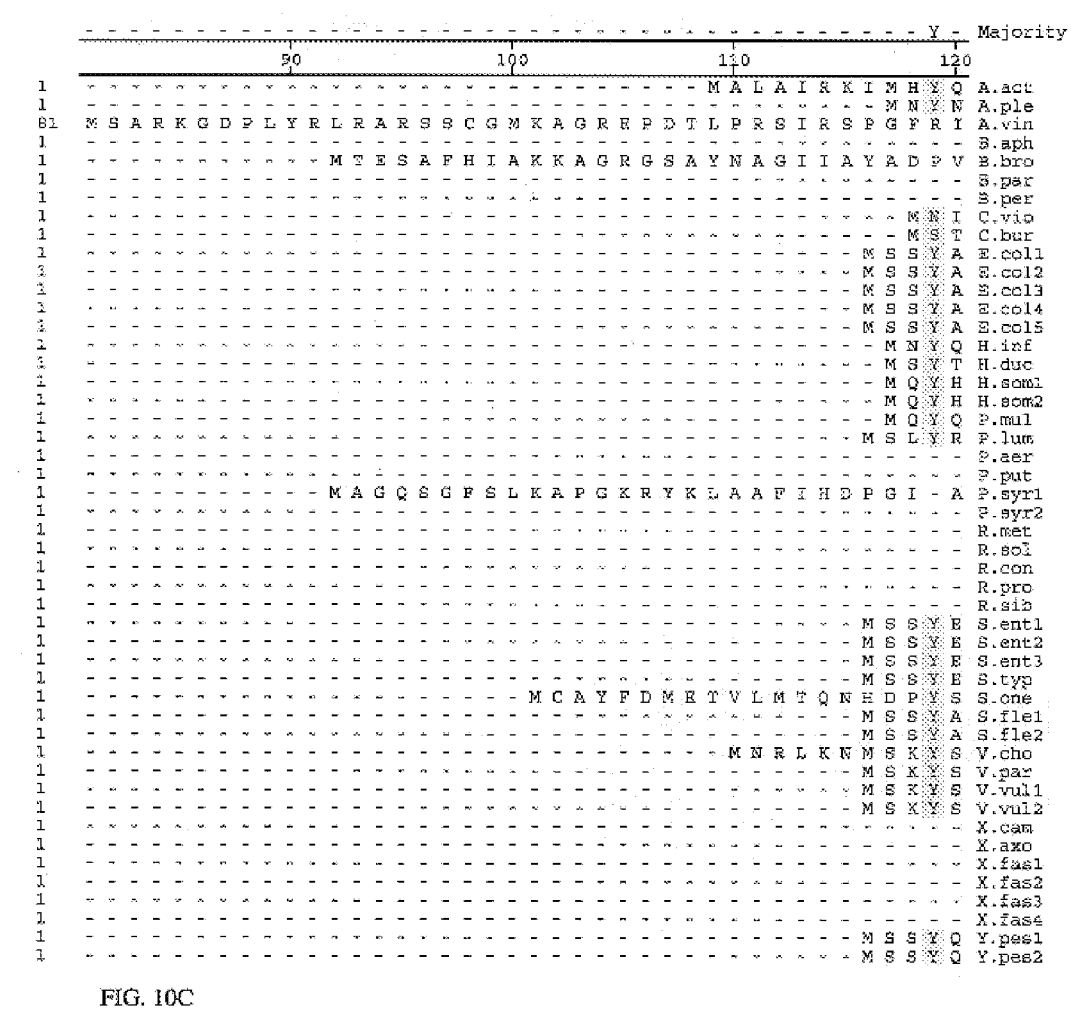
Figure 10D:
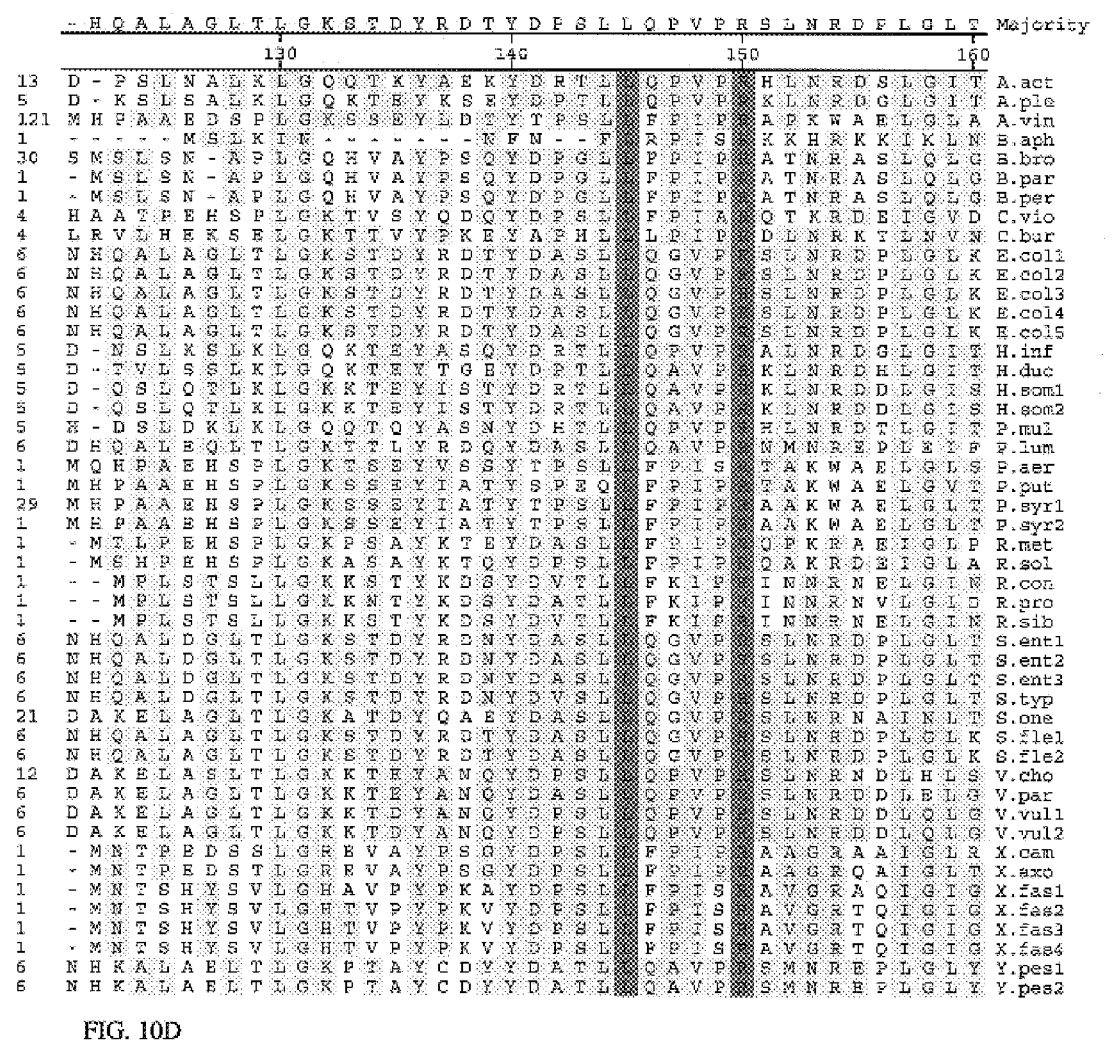
Figure 10E:
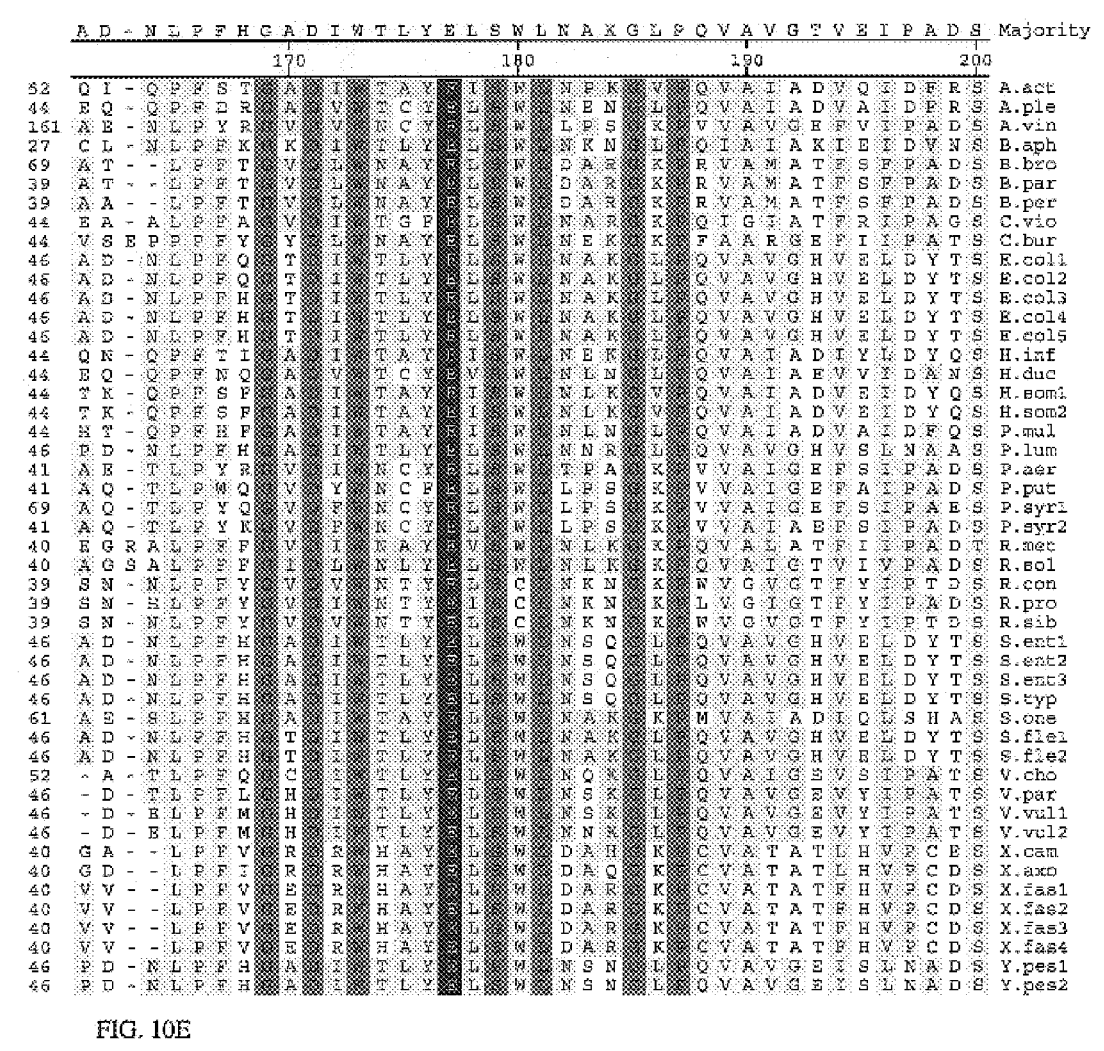
Figure 10F:
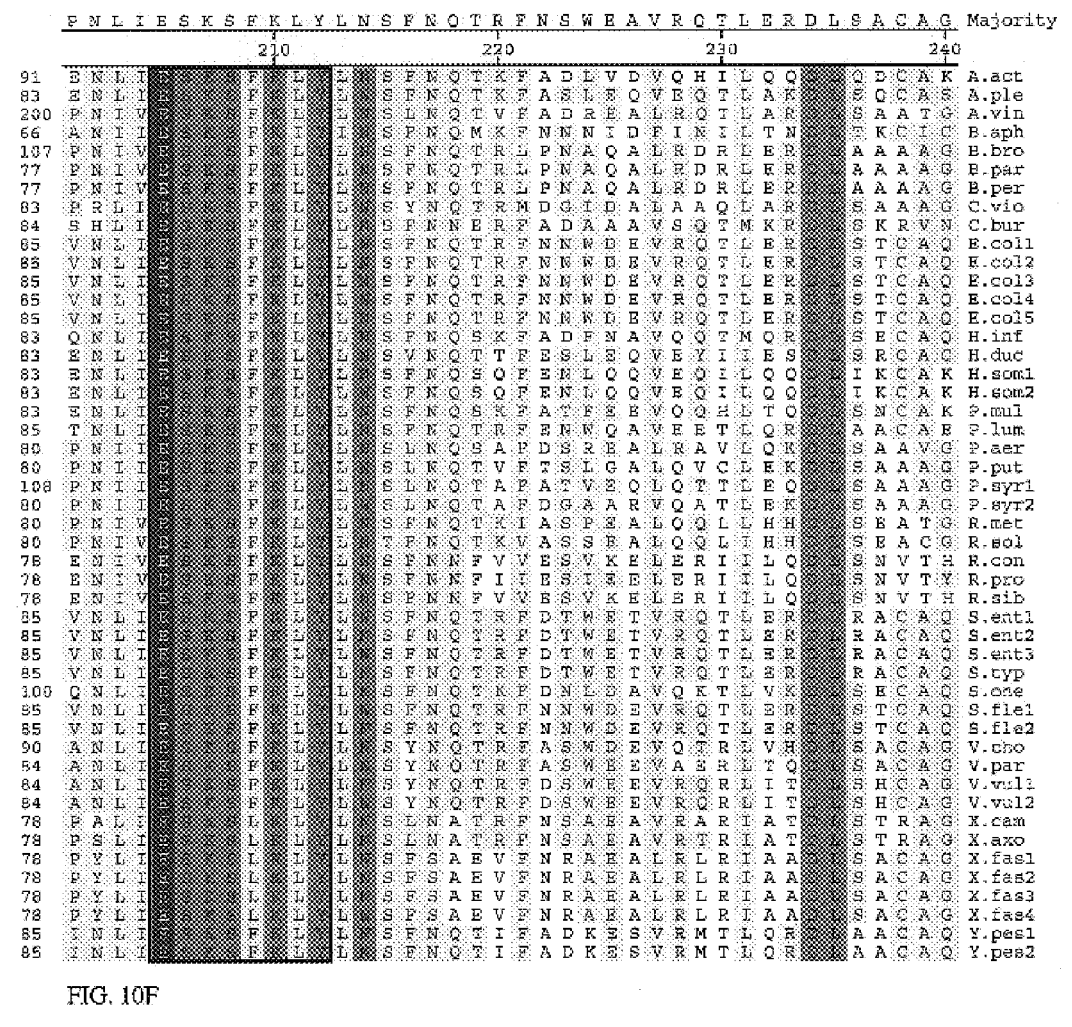
Figure 10G:
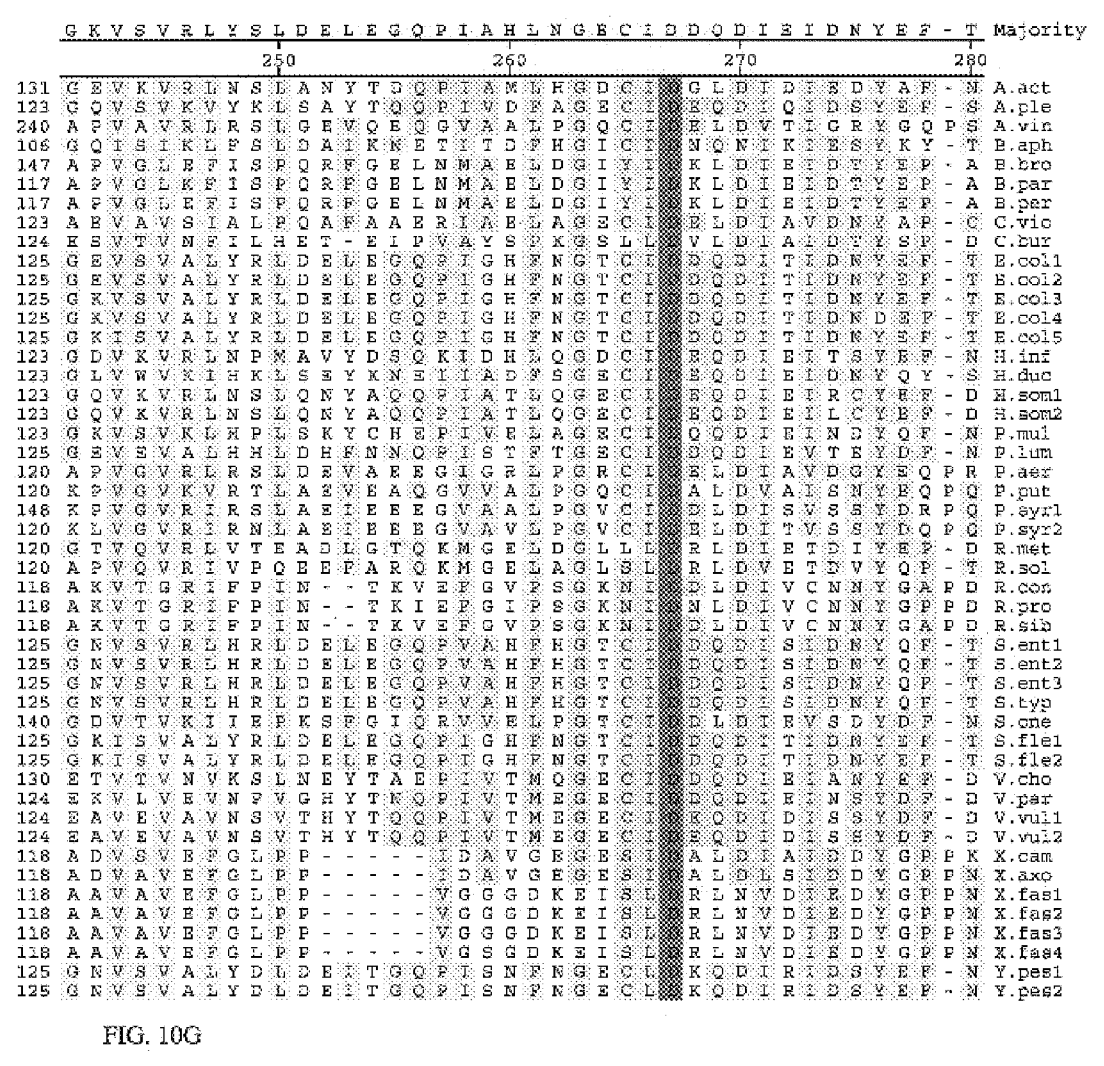

FIGS. 10A-K show the alignment of several QueF class II enzymes (SEQ ID NOS: 4 and 49-95).

SEQUENCE LISTING

Figure 1:
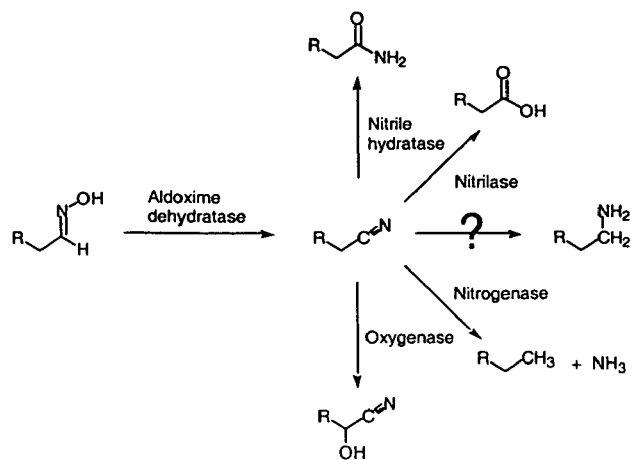
FIG. 1 is a schematic drawing illustrating known enzymes involved in the metabolism of organic nitriles.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand. In the accompanying sequence listing:

SEQ ID NO: 1 is a nucleic acid sequence of a *B. subtilis* QueF (GeneID No. 939296).

SEQ ID NO: 2 is the corresponding amino acid sequence of SEQ ID NO: 1 (GenBank Accession No. NP_389258).

SEQ ID NO: 3 is a nucleic acid sequence of a *E. coli* QueF (GeneID No: 947270; GenBank Accession No. U00096 region: 2923370 . . . 2924218).

SEQ ID NO: 4 is the corresponding amino acid sequence of SEQ ID NO: 3 (GenBank Accession No. NP_417274).

SEQ ID NO: 5 is a QueF motif amino acid sequence.

SEQ ID NO: 6 is an exemplary nitrile oxido-reductase amino acid sequence (GenBank Accession no. NP_213635).

SEQ ID NO: 7 is an exemplary nitrile oxido-reductase amino acid sequence (GenBank Accession no. NP_355229).

SEQ ID NO: 8 is an exemplary nitrile oxido-reductase amino acid sequence (GenBank Accession no. YP_221888).

SEQ ID NO: 9 is an exemplary nitrile oxido-reductase amino acid sequence.

SEQ ID NO: 10 is an exemplary nitrile oxido-reductase amino acid sequence.

SEQ ID NO: 11 is an exemplary nitrile oxido-reductase amino acid sequence (GenBank Accession no. NP_539721).

SEQ ID NO: 12 is an exemplary nitrile oxido-reductase amino acid sequence (GenBank Accession no. NP_698188).

SEQ ID NO: 13 is an exemplary nitrile oxido-reductase amino acid sequence (GenBank Accession no. AAO76671).

SEQ ID NO: 14 is an exemplary nitrile oxido-reductase amino acid sequence (GenBank Accession no. NP_421453).

SEQ ID NO: 15 is an exemplary nitrile oxido-reductase amino acid sequence (GenBank Accession no. CAB73710).

SEQ ID NO: 16 is an exemplary nitrile oxido-reductase amino acid sequence (GenBank Accession no. NP_662521).

SEQ ID NO: 17 is an exemplary nitrile oxido-reductase amino acid sequence (GenBank Accession no. BAC91534).

SEQ ID NO: 18 is an exemplary nitrile oxido-reductase amino acid sequence (GenBank Accession no. AAD08456).

SEQ ID NO: 19 is an exemplary nitrile oxido-reductase amino acid sequence (GenBank Accession no. NP_224026).

SEQ ID NO: 20 is an exemplary nitrile oxido-reductase amino acid sequence.

SEQ ID NO: 21 is an exemplary nitrile oxido-reductase amino acid sequence.

SEQ ID NO: 22 is an exemplary nitrile oxido-reductase amino acid sequence from *K. pneumoniae*.

SEQ ID NO: 23 is an exemplary nitrile oxido-reductase amino acid sequence (GenBank Accession no. NP_712266).

SEQ ID NO: 24 is an exemplary nitrile oxido-reductase amino acid sequence (GenBank Accession no. NP_10841).

SEQ ID NO: 25 is an exemplary nitrile oxido-reductase amino acid sequence (GenBank Accession no. ZP_00054688).

SEQ ID NO: 26 is an exemplary nitrile oxido-reductase amino acid sequence (GenBank Accession no. ZP_00301998).

SEQ ID NO: 27 is an exemplary nitrile oxido-reductase amino acid sequence (GenBank Accession no. NP_842285).

SEQ ID NO: 28 is an exemplary nitrile oxido-reductase amino acid sequence (GenBank Accession no. YP_208721).

SEQ ID NO: 29 is an exemplary nitrile oxido-reductase amino acid sequence (GenBank Accession no. AAF40762).

SEQ ID NO: 30 is an exemplary nitrile oxido-reductase amino acid sequence (GenBank Accession no. CAB85382).

SEQ ID NO: 31 is an exemplary nitrile oxido-reductase amino acid sequence (GenBank Accession no. BAB73119).

SEQ ID NO: 32 is an exemplary nitrile oxido-reductase amino acid sequence (GenBank Accession no. ZP_00111265).

SEQ ID NO: 33 is an exemplary nitrile oxido-reductase amino acid sequence (GenBank Accession no. BAC14166).

SEQ ID NO: 34 is an exemplary nitrile oxido-reductase amino acid sequence (GenBank Accession no. AAQ66412).

SEQ ID NO: 35 is an exemplary nitrile oxido-reductase amino acid sequence (GenBank Accession no. CAE21653).

SEQ ID NO: 36 is an exemplary nitrile oxido-reductase amino acid sequence (GenBank Accession no. NP_893578).

SEQ ID NO: 37 is an exemplary nitrile oxido-reductase amino acid sequence (GenBank Accession no. NP_876005).

SEQ ID NO: 38 is an exemplary nitrile oxido-reductase amino acid sequence (GenBank Accession no. CAD72755).

SEQ ID NO: 39 is an exemplary nitrile oxido-reductase amino acid sequence (GenBank Accession no. CAC46964).

SEQ ID NO: 40 is an exemplary nitrile oxido-reductase amino acid sequence (GenBank Accession no. AAN58623).

SEQ ID NO: 41 is an exemplary nitrile oxido-reductase amino acid sequence.

SEQ ID NO: 42 is an exemplary nitrile oxido-reductase amino acid sequence (GenBank Accession no. S77065).

SEQ ID NO: 43 is an exemplary nitrile oxido-reductase amino acid sequence (GenBank Accession no. ZP_00622845).

SEQ ID NO: 44 is an exemplary nitrile oxido-reductase amino acid sequence (GenBank Accession no. CAE06978).

SEQ ID NO: 45 is an exemplary nitrile oxido-reductase amino acid sequence (GenBank Accession no. NP_681009).

SEQ ID NO: 46 is an exemplary nitrile oxido-reductase amino acid sequence (GenBank Accession no. NP_228600).

SEQ ID NO: 47 is an exemplary nitrile oxido-reductase amino acid sequence (GenBank Accession no. NP_623163).

SEQ ID NO: 48 is an exemplary nitrile oxido-reductase amino acid sequence GenBank Accession no. NP_906277).

SEQ ID NO: 49 is an exemplary nitrile oxido-reductase amino acid sequence from *Actinobacillus actinomycetemcomitans*).

SEQ ID NO: 50 is an exemplary nitrile oxido-reductase amino acid sequence GenBank Accession no. ZP_00135322).

SEQ ID NO: 51 is an exemplary nitrile oxido-reductase amino acid sequence GenBank Accession no. ZP_00342251).

SEQ ID NO: 52 is an exemplary nitrile oxido-reductase amino acid sequence GenBank Accession no. NP_660633).

SEQ ID NO: 53 is an exemplary nitrile oxido-reductase amino acid sequence GenBank Accession no. NP_889875).

SEQ ID NO: 54 is an exemplary nitrile oxido-reductase amino acid sequence GenBank Accession no. NP_884039).

SEQ ID NO: 55 is an exemplary nitrile oxido-reductase amino acid sequence GenBank Accession no. NP_880745).

SEQ ID NO: 56 is an exemplary nitrile oxido-reductase amino acid sequence GenBank Accession no. AAQ61412).

SEQ ID NO: 57 is an exemplary nitrile oxido-reductase amino acid sequence GenBank Accession no. NP_819201).

SEQ ID NO: 58 is an exemplary nitrile oxido-reductase amino acid sequence GenBank Accession no. AAG57908).

SEQ ID NO: 59 is an exemplary nitrile oxido-reductase amino acid sequence GenBank Accession no. BAB37077).

SEQ ID NO: 60 is an exemplary nitrile oxido-reductase amino acid sequence GenBank Accession no. NP_755237).

SEQ ID NO: 61 is an exemplary *E. coli* nitrile oxido-reductase amino acid sequence.

SEQ ID NO: 62 is an exemplary nitrile oxido-reductase amino acid sequence GenBank Accession no. NP_439443).

SEQ ID NO: 63 is an exemplary nitrile oxido-reductase amino acid sequence GenBank Accession no. AAP96437).

SEQ ID NO: 64 is an exemplary nitrile oxido-reductase amino acid sequence GenBank Accession no. ZP_00122278).

SEQ ID NO: 65 is an exemplary nitrile oxido-reductase amino acid sequence GenBank Accession no. ZP_00133538).

SEQ ID NO: 66 is an exemplary nitrile oxido-reductase amino acid sequence GenBank Accession no. NP_245413).

SEQ ID NO: 67 is an exemplary nitrile oxido-reductase amino acid sequence GenBank Accession no. AAO39145).

SEQ ID NO: 68 is an exemplary nitrile oxido-reductase amino acid sequence GenBank Accession no. NP_251496).

SEQ ID NO: 69 is an exemplary nitrile oxido-reductase amino acid sequence GenBank Accession no. AAN67773).

SEQ ID NO: 70 is an exemplary nitrile oxido-reductase amino acid sequence from *Pseudomonas syringae*.

SEQ ID NO: 71 is an exemplary nitrile oxido-reductase amino acid sequence GenBank Accession no. ZP_00124356).

SEQ ID NO: 72 is an exemplary nitrile oxido-reductase amino acid sequence GenBank Accession no. ZP_00272373).

SEQ ID NO: 73 is an exemplary nitrile oxido-reductase amino acid sequence GenBank Accession no. NP_518569).

SEQ ID NO: 74 is an exemplary nitrile oxido-reductase amino acid sequence GenBank Accession no. NP_359739).

SEQ ID NO: 75 is an exemplary nitrile oxido-reductase amino acid sequence GenBank Accession no. H71715).

SEQ ID NO: 76 is an exemplary nitrile oxido-reductase amino acid sequence GenBank Accession no. EAA25828).

SEQ ID NO: 77 is an exemplary nitrile oxido-reductase amino acid sequence GenBank Accession no. NP_806572).

SEQ ID NO: 78 is an exemplary nitrile oxido-reductase amino acid sequence GenBank Accession no. NP_457363).

SEQ ID NO: 79 is an exemplary nitrile oxido-reductase amino acid sequence GenBank Accession no. YP_217894).

SEQ ID NO: 80 is an exemplary nitrile oxido-reductase amino acid sequence GenBank Accession no. AAL21847).

SEQ ID NO: 81 is an exemplary nitrile oxido-reductase amino acid sequence GenBank Accession no. NP_717220).

SEQ ID NO: 82 is an exemplary nitrile oxido-reductase amino acid sequence GenBank Accession no. AAN44295).

SEQ ID NO: 83 is an exemplary nitrile oxido-reductase amino acid sequence GenBank Accession no. AAP18120).

SEQ ID NO: 84 is an exemplary nitrile oxido-reductase amino acid sequence GenBank Accession no. AAF94064).

SEQ ID NO: 85 is an exemplary nitrile oxido-reductase amino acid sequence GenBank Accession no. NP_797080).

SEQ ID NO: 86 is an exemplary nitrile oxido-reductase amino acid sequence GenBank Accession no. AAO08830).

SEQ ID NO: 87 is an exemplary nitrile oxido-reductase amino acid sequence GenBank Accession no. NP_933680).

SEQ ID NO: 88 is an exemplary nitrile oxido-reductase amino acid sequence GenBank Accession no. NP_639130).

SEQ ID NO: 89 is an exemplary nitrile oxido-reductase amino acid sequence GenBank Accession no. AAM38688).

SEQ ID NO: 90 is an exemplary nitrile oxido-reductase amino acid sequence GenBank Accession no. NP_299662).

SEQ ID NO: 91 is an exemplary nitrile oxido-reductase amino acid sequence GenBank Accession no. ZP_00041649).

SEQ ID NO: 92 is an exemplary nitrile oxido-reductase amino acid sequence GenBank Accession no. ZP_00039169).

SEQ ID NO: 93 is an exemplary nitrile oxido-reductase amino acid sequence GenBank Accession no. NP_779599).

SEQ ID NO: 94 is an exemplary nitrile oxido-reductase amino acid sequence GenBank Accession no. CAC89876).

SEQ ID NO: 95 is an exemplary nitrile oxido-reductase amino acid sequence GenBank Accession no. NP_670446).

DETAILED DESCRIPTION

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nitrile oxido-reductase" includes single or plural nitrile oxido-reductase molecules and is considered equivalent to the phrase "comprising at least one nitrile oxido-reductase." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

NADPH reduced form of nicotinamide adenine dinucleotide phosphate preQ$_0$ 7-cyano-7-deazaguanine preQ$_1$ 7-aminomethyl-7-deazaguanine QueF An exemplary group of nitrile oxido-reductases Amine: Organic compounds containing nitrogen as the key atom in the amine functional group. Amines have structures resembling ammonia where the nitrogen is bonded to a carbon atom, and where one or more hydrogen atoms are replaced by organic groups, such as: aliphatic or substituted aliphatic groups, including alkyl, alkenyl, or alkynyl groups (or combinations thereof); substituted aliphatic groups, including without limitation, aliphatic groups substituted with halogen, oxygen, sulfur, nitrogen, combinations of such elements and a functional or groups defined by such elements; aromatic groups; substituted aromatic groups; heterocycles; or other groups, and all possible combinations of such groups. The substitution of one hydrogen atom constitutes a primary amine (such as $NH_2CH_3$); that of two atoms, a secondary amine (such as $NH(CH3)_2$); that of three atoms, a tertiary amine (such as $N(CH_3)_3$); and that of four atoms, a quaternary ammonium ion (such as $+N(CH_3)_4$), a positively charged ion isolated only in association with a negative ion.

cDNA (complementary DNA): A piece of DNA lacking internal, non-coding segments (introns) and regulatory sequences which determine transcription. cDNA can be synthesized by reverse transcription from messenger RNA extracted from cells.

Conservative substitution: One or more amino acid substitutions (for example 1, 2, 5 or 10 amino acid residues) for amino acid residues having similar biochemical properties. Typically, conservative substitutions have little to no impact on the activity of a resulting peptide. For example, a conservative substitution is an amino acid substitution in a nitrile oxido-reductase peptide (such as a QueF peptide) that does not substantially affect the ability of the peptide to reduce nitrites to amines. In a particular example, a conservative substitution is an amino acid substitution in a nitrile oxido-reductase peptide, such as a conservative substitution in any of SEQ ID NOS: 2, 4, or 6-95 that does not significantly alter the ability of the protein to reduce nitrites to amines.

An alanine scan can be used to identify amino acid residues in a peptide that can tolerate substitution. In one example, nitrile oxido-reductase activity is not altered by more than 25%, for example not more than 20%, for example not more than 10%, when an alanine, or other conservative amino acid (such as those listed below), is substituted for one or more native amino acids.

In a particular example, nitrile oxido-reductase activity is not substantially altered if the amount of reduction of a nitrile to an amine produced is not decreased by more than about 25%, such as not more than about 10%, than an amount of reduction in the presence of a nitrile oxido-reductase containing one or more conservative amino acid substitutions, as compared to an amount of reduction in the presence of a native nitrile oxido-reductase.

A peptide can be produced to contain one or more conservative substitutions by manipulating the nucleotide sequence that encodes that peptide using, for example, standard procedures such as site-directed mutagenesis or PCR. Alternatively, a peptide can be produced to contain one or more conservative substitutions by using standard peptide synthesis methods.

Substitutional variants are those in which at least one residue in the amino acid sequence has been removed and a different residue inserted in its place. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Further information about conservative substitutions can be found in, among other locations in, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988), WO 00/67796 (Curd et al.) and in standard textbooks of genetics and molecular biology.

Deletion: The removal of a sequence of a nucleic acid molecule or a protein, the regions on either side being joined together.

Detectable: Capable of having an existence or presence ascertained. For example, production of an amine from a nitrile is detectable if the signal generated from the reduction reaction (such as the oxidation of NADPH or the presence of an amine) is strong enough to be measured.

DNA: Deoxyribonucleic acid. DNA is a long chain polymer which includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a peptide. The term codon is also used for the corresponding (and complementary) sequences of three nucleotides in the mRNA into which the DNA sequence is transcribed.

Exogenous: The term "exogenous" as used herein with reference to a nucleic acid molecule (such as nucleic acid molecule that encodes a nitrile oxido-reductase) and a particular cell refers to any nucleic acid molecule that does not originate from that particular cell as found in nature. Thus, a non-naturally-occurring nucleic acid molecule is considered to be exogenous to a cell once introduced into the cell. A nucleic acid molecule that is naturally-occurring also can be exogenous to a particular cell. For example, an entire coding sequence isolated from cell X is an exogenous nucleic acid with respect to cell Y once that coding sequence is introduced into cell Y, even if X and Y are the same cell type.

Expression: The process by which a gene's coded information is converted into the structures and functions of a cell, such as a protein, transfer RNA, or ribosomal RNA. Expressed genes (or other nucleic acid sequences) include those that are transcribed into mRNA and then translated into protein and those that are transcribed into RNA but not translated into protein (for example, transfer and ribosomal RNAs).

Functionally Equivalent: Having a similar function, such as the ability of a sequence variant, fragment or fusion to have a similar function as the native sequence. For example, functionally equivalent molecules of a nitrile oxido-reductase include those molecules that retain the function of nitrile oxido-reductase, that is, the ability to reduce a nitrile to the corresponding amine. For example, functional equivalents can be provided by sequence alterations in a nitrile oxido-reductase wherein the peptide with one or more sequence alterations retains a function of the unaltered peptide, such that it retains its ability to reduce a nitrile to an amine.

Examples of sequence alterations include, but are not limited to, conservative substitutions, deletions, mutations, frameshifts, and insertions. In one example, a given peptide binds an antibody, and a functional equivalent is a peptide that binds the same antibody. Thus a functional equivalent includes peptides that have the same binding specificity as a peptide, and that can be used as a reagent in place of the peptide (such as in the production of a primary amine). In one example a functional equivalent includes a peptide wherein the binding sequence is discontinuous, wherein the antibody binds a linear epitope. Thus, if the peptide sequence is MTTRKESELE (amino acids 1-10 of SEQ ID NO: 2) a functional equivalent includes discontinuous epitopes, that can appear as follows (=any number of intervening amino acids): $NH_2$--MMTTRKESELE—COOH. In this example, the peptide is functionally equivalent to amino acids 1-10 of SEQ ID NO: 2 if the three dimensional structure of the peptide is such that it can bind a monoclonal antibody that binds amino acids 1-10 of SEQ ID NO: 2.

Glu98: Refers to the 98$^{th}$ amino acid in a *B. subtillis* QueF protein sequence (such as SEQ ID NO: 2), as well as the corresponding Glu in other nitrile oxido-reductases, which can be determined by aligning the sequences (for example see FIGS. 9A-G and 10A-K, the "E" highlighted in blue). For example, the corresponding Glu98 in the *E. coli* QueF protein is Glu230 (for example the Glu230 in SEQ ID NO: 4).

Hybridization: To form base pairs between complementary regions of two strands of DNA, RNA, or between DNA and RNA, thereby forming a duplex molecule, for example forming a duplex molecule between a first nucleic acid molecule and a second nucleic acid molecule (such as a nucleic acid molecule encoding a nitrile oxido-reductase, or fragment thereof). Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share 90% Identity)
   Hybridization: 5×SSC at 65° C. for 16 hours
   Wash twice: 2×SSC at room temperature (RT) for 15 minutes each
   Wash twice: 0.5×SSC at 65° C. for 20 minutes each
High Stringency (Detects Sequences that Share 80% Identity or Greater)
   Hybridization: 5×-6×SSC at 65° C.-70° C. for 16-20 hours
   Wash twice: 2×SSC at RT for 5-20 minutes each
   Wash twice: 1×SSC at 55° C.-70° C. for 30 minutes each
Low Stringency (Detects Sequences that Share Greater than 50% Identity)
   Hybridization: 6×SSC at RT to 55° C. for 16-20 hours
   Wash at least twice: 2×-3×SSC at RT to 55° C. for 20-30 minutes each.

Isolated: An "isolated" biological component (such as a nitrile oxido-reductase nucleic acid molecule or protein) has been substantially separated or purified away from other biological components in the cell of the organism in which the component naturally occurs (such as other chromosomal and extrachromosomal DNA and RNA, and proteins). Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

NADPH regeneration system: A reaction that can produce catalytic quantities of NADPH, for example enzymes that generate NADPH in situ using an enzymatic reaction. Examples of enzymes that can be used in an NADPH regeneration system include, but are not limited to, phosphite dehydrogenase, formate dehydrogenase, and soluble pyridine nucleotide transhydrogenase.

Nitrile containing compound: Any organic compound that includes the cyano radical CN, R—CN, where R is aliphatic or substituted aliphatic groups, including alkyl, alkenyl, or alkynyl groups (or combinations thereof); substituted aliphatic groups, including without limitation, aliphatic groups substituted with halogen, oxygen, sulfur, nitrogen, combinations of such substituents, and a functional group or groups defined by such elements; aromatic groups; substituted aromatic groups; heterocycles; or other groups, and all possible combinations of such groups. Particular examples include, but are not limited to: 7-cyano-7-deazaguanine (preQ$_0$), phenylacetonitrile, benzonitrile, p-amino-phenylacetonitrile, acrylonitrile, adiponitrile.

Nitrile oxido-reductase: An enzyme that can catalyze the conversion of a nitrile containing compound to the corresponding amine, such as a primary amine. In particular examples, a nitrile oxido-reductase includes a QueF motif sequence (SEQ ID NO: 5). Particular examples include QueF enzymes.

Includes any nitrile oxido-reductase gene, cDNA, RNA, or protein from any organism, such as a prokaryote. In one example, a nitrile oxido-reductase is a mutated QueF sequence having nitrile oxido-reductase activity. Nitrile oxido-reductases can be obtained from any organism, such as a prokaryote, for example *Bacillus subtilis* or *E. coli*, and mutated using any method known in the art.

In particular examples, a nitrile oxido-reductase nucleic acid sequence includes the sequence shown in SEQ ID NOS: 1 or 3, variants thereof (such as mutants, fusions, or fragments) that retain the ability to encode a peptide or protein having nitrile oxido-reductase activity. In another example, a nitrile oxido-reductase protein includes the amino acid sequence shown in SEQ ID NO: 2, 4, or any of 6-95, or variants thereof that retain nitrile oxido-reductase activity (such as a sequence that includes a Glu98 substitution).

In another example, a nitrile oxido-reductase sequence includes a full-length sequence, such as any of SEQ ID NOS: 2, 4, or 6-95, as well as shorter sequences which retain the ability to reduce a nitrile to a primary amine, such as amino acids 5-160, 10-130, or 60-110 of SEQ ID NO: 2, or amino acids 5-275, 50-240, or 100-240 of SEQ ID NO 4 (or the corresponding fragments of SEQ ID NOS: 6-95). This description includes nitrile oxido-reductase allelic variants, as well as any variant sequence which retains the ability to reduce a nitrile to an amine.

Particular examples of nitrile oxido-reductases include, but are not limited to, enzymes that catalyze the reduction of 7-cyano-7-deazaguanine to 7-aminomethyl-7-deazaguanine; enzymes that catalyze the reduction of aromatic and alkyl nitrites to the corresponding primary amines, such as enzymes that catalyze the reduction of phenylacetonitrile to phenethylamine, enzymes that catalyze the reduction of 3-cyano-indole to 3-amino-methylindole, enzymes that catalyze the reduction of benzonitrile to benzyl amine, enzymes that catalyze the reduction of acrylonitrile to propylene amine, enzymes that catalyze the reduction of p-carboxyphenylacetonitrile to p-carboxyphenethylamine, and enzymes that catalyze the reduction of p-carboxybenzonitrile to p-carboxybenzylamine.

Nitrile oxido-reductase activity: The ability of a nitrile oxido-reductase to reduce a nitrile to a primary amine. In one example, such activity occurs in a cell. In another example, such activity occurs in vitro. Such activity can be measured using any assay known in the art, for example the assays described in EXAMPLES 2 and 8. In addition, an enzyme with nitrile oxido-reductase activity can be identified by incubating the enzyme with a nitrile and NADPH and determining the resulting amount of NADPH oxidation, or by measuring the primary amine produced (for example by high-performance liquid chromatography or after derivatization of the amine to a fluorophore, such as the Dansyl group).

Nucleic acid molecule: Encompasses both RNA and DNA including, without limitation, cDNA, genomic DNA, mRNA. Includes synthetic nucleic acid molecules, such as those that are chemically synthesized or recombinantly produced. The nucleic acid molecule can be double-stranded or single-stranded. Where single-stranded, the nucleic acid molecule can be the sense strand or the antisense strand. In addition, nucleic acid molecules can be circular or linear.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence (such as a nitrile oxido-reductase coding sequence). Generally, operably linked DNA sequences are contiguous and, where necessary to join two protein coding regions, in the same reading frame. Configurations of separate genes that are transcribed in tandem as a single messenger RNA are denoted as operons. Thus placing genes in close proximity, for example in a plasmid vector, under the transcriptional regulation of a single promoter, constitutes a synthetic operon.

ORF (open reading frame): A series of nucleotide triplets (codons) coding for amino acids without any termination codons. These sequences are usually translatable into a peptide.

Phosphite dehydrogenase (PTDH): Includes any phosphate dehydrogenase that can be used to regenerate NADPH. Includes any PTDH gene, cDNA, RNA, or protein from any organism, such as a prokaryote.

In one example, a PTDH is a mutated PTDH sequence that can be used to regenerate NADPH. Particular examples of such mutants include PTDH-E175A/A176R (see Woodyer et al., *FEBS J.* 272:3816, 2005). PTDH can be obtained from any organism, such as a prokaryote, for example *Pseudomonas stutzer* and mutated using any method known in the art.

PTDH nucleic acid and protein sequences are publicly available, such as GenBank Accession Nos. AF061070 and CQ972047, which disclose PTDH nucleic acid sequences, and GenBank Accession Nos. CAI40127 and O69054, which disclose PTDH protein sequences. One skilled in the art will recognize that variants of these sequences can be used in an NADPH regeneration system, as long as such variants that retain the ability to regenerate NADPH.

Primary amine: An amine ($RNH_2$) having one organic substituent attached to the nitrogen atom.

Promoter: An array of nucleic acid control sequences that direct transcription of a nucleic acid molecule, such as nucleic acid molecule encoding a nitrile oxido-reductase. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

The term includes endogenous promoter sequences as well as exogenous promoter sequences (such as those introduced into the chromosome to promote expression of a nitrile oxido-reductase). Particular types of promoters that can be used to practice the methods disclosed herein include, but are not limited to, constitutive promoters and inducible promoters (such as a promoter responsive or unresponsive to a particular stimulus, for example such as light, oxygen, or chemical concentration, such as an IPTG or tetracycline inducible promoter).

QueF motif: A sequence of amino acids found in nitrile oxido-reductases, shown in SEQ ID NO: 5. Without being bound to a particular theory, it is proposed that this sequence interacts with NADPH, and that changes in this sequence could be made to change the nitrile oxido-reductase from an NADPH-dependent enzyme to an NADH-dependent enzyme.

Recombinant: A recombinant nucleic acid molecule or protein is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or proteins, such as genetic engineering techniques. Recombinant is also used to describe nucleic acid molecules that have been artificially manipulated, but contain the same regulatory sequences and coding regions that are found in the organism from which the nucleic acid was isolated.

Sequence identity/similarity: The identity/similarity between two or more nucleic acid sequences, or two or more amino acid sequences, is expressed in terms of the identity or similarity between the sequences (such as between a first sequence and a nitrile oxido-reductase). Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: –i is set to a file containing the first nucleic acid sequence to be compared (e.g., C:\seq1.txt); –j is set to a file containing the second nucleic acid sequence to be compared (e.g., C:\seq2.txt); –p is set to blastn; –o is set to any desired file name (e.g., C:\output.txt); –q is set to –1; –r is set to 2; and all other options are left at their default setting. For example, the following command can be used to generate an output file containing a comparison between two sequences: C:\B12seq -i c:\seq1.txt -j c:\seq2.txt -p blastn -o c:\output.txt -q -1 -r 2.

To compare two amino acid sequences, the options of B12seq can be set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (15÷20*100=75).

```
                          1                   20
Target Sequence:     AGGTCGTGTACTGTCAGTCA
                     | || ||| |||| ||||| |
Identified Sequence: ACGTGGTGAACTGCCAGTGA
```

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). Other programs use SEG. In addition, a manual alignment can be performed. Proteins with even greater similarity will show increasing percentage identities when assessed by this method, such as at least 80%, at least 90%, at least 95%, or at least 99% sequence identity to a nitrile oxido-reductase (such as at least this percent identity to any of SEQ ID NOS: 2, 4, and 6-95).

When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 80%, at least 85%, at least 90%, at least 95%, at least 98%, or at least 99% sequence identity to a nitrile oxido-reductase (such as at least this percent identity to any of SEQ ID NOS: 2, 4, and 6-95). When less than the entire sequence is being compared for sequence identity, homologs will typically possess at least 75% sequence identity over short windows of 10-20 amino acids, and can possess sequence identities of at least 85%, at least 90%, at least 95% or at least 98% depending on their identity to the reference sequence. Methods for determining sequence identity over such short windows are described at the NCBI web site.

One indication that two nucleic acid molecules are closely related is that the two molecules hybridize to each other under stringent conditions. Stringent conditions are sequence-dependent and are different under different environmental parameters. Nucleic acid molecules that hybridize under stringent conditions to a nitrile oxido-reductase gene sequence typically hybridize to a probe based on either an entire nitrile oxido-reductase gene or selected portions of the gene, respectively, under conditions described above.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 80%, at least 90%, at least 95%, at least 98%, or at least 99% sequence identity to a nitrile oxido-reductase (such as at least this percent identity to SEQ ID NO: 1 or 3) determined by this method.

One of skill in the art will appreciate that these sequence identity ranges are provided for guidance only; it is possible that strongly significant homologs could be obtained that fall outside the ranges provided.

An alternative (and not necessarily cumulative) indication that two nucleic acid sequences are substantially identical is that the peptide which the first nucleic acid sequence encodes is immunologically cross reactive with the peptide encoded by the second nucleic acid sequence (such as a nitrile oxido reductase).

Transformed cell: A cell into which a nucleic acid molecule has been introduced, for example by molecular biology techniques. Transformation encompasses all techniques by which a nucleic acid molecule can be introduced into such a cell, including, but not limited to, transfection with viral vectors, conjugation, transformation with plasmid vectors, and introduction of naked DNA by electroporation, lipofection, and particle gun acceleration. In particular examples, a transformed cell includes a nucleic acid encoding a nitrile oxido-reductase, such as a sequence that includes SEQ ID NO: 1 or 3 (or a sequence that encodes any of SEQ ID NOS: 2, 4, or 6-95, or variants thereof).

Under conditions sufficient for: A phrase that is used to describe any environment that permits the desired activity.

In one example, includes incubating a sample under conditions that permit reduction of a nitrile to an amine. For example, it can include incubating the sample at an appropriate temperature, for an appropriate time, and in the presence of appropriate compounds, for example NADPH. In particular examples, the sample includes a recombinant nitrile oxido-reductase.

In another example, includes culturing cells (such as bacterial or yeast cells) under conditions sufficient to permit reduction of a nitrile to an amine, such as culturing the cells under an appropriate temperature, for an appropriate time, and in the appropriate media. In particular examples, the cell includes an exogenous nitrile oxido-reductase.

Variant sequence: A native sequence, such as a native nitrile oxido-reductase sequence, that is modified at one or more nucleotides or one or more amino acids. Exemplary variants include mutants (such as sequences that include one or more nucleotide or amino acid substitutions, deletions, insertions, or combinations thereof), fragments (such as a fragment that retains the biological activity of the native protein), fusions (for example fusion to a sequence that permits purification of a protein, such as a His-tag), or combinations thereof. Variant sequences can retain the biological activity of the native sequence (for example the same nitrile substrate specificity as the native sequence), or can have different biological activity (for example, the variant may be a nitrile oxido-reductase with different nitrile substrate specificity from the native sequence)

Vector: A nucleic acid molecule as introduced into a cell, thereby producing a transformed cell. A vector can include nucleic acid sequences that permit it to replicate in the cell, such as an origin of replication. A vector can also include one or more selectable marker genes and other genetic elements known in the art.

Methods of Reducing a Nitrile to an Amine

The present application provides methods for reducing a nitrile to its corresponding amine, such as a primary amine. In addition, methods for producing an amine, such as a target amine, are disclosed.

Identification of nitrile oxido-reductases permits this reaction to be performed within a cell (in vivo) or outside a cell (in vitro, for example in a container or column). For example, a cell or microorganism disclosed herein can be used to reduce a nitrile to its corresponding amine, or an extract containing one or more nitrites and one or more proteins having nitrile oxido-reductase activity can be used to reduce the nitrile(s) to its corresponding amine.

In particular examples, the method of reducing a nitrile to its corresponding amine includes reducing a nitrile containing compound to a primary amine, and includes contacting the nitrile containing compound with a nitrile oxido-reductase under conditions sufficient for reducing the nitrile containing compound to the primary amine. In some examples, the method further includes providing a nitrile oxido-reductase (such as a nitrile oxido-reductase that is recombinant, purified, or both).

Methods are also provided for producing an amine, such as a commercially important primary amine. In particular examples the method includes providing a nitrile containing compound, that when reduced produces the amine and providing nitrile oxido-reductase. The nitrile containing compound is contacted with the nitrile oxido-reductase under conditions sufficient for substantially reducing the nitrile on the containing compound to the desired target amine.

Complete reduction of the nitrile containing compound is not required. In some examples, the nitrile containing compounds are substantially reduced using the disclosed methods. For example if the nitrile containing compound includes a single nitrile group, substantial reduction can include complete reduction of at least 70% of the compounds in the reaction mixture, for example at least 75%, at least 80%, at least 90%, at least 95%, at least 98%, or at least 99% of the compounds in the reaction mixture. In another example, the nitrile containing compound includes a two or more nitrile groups (such as two, three or four nitrites), and substantial reduction can include complete reduction of at least 50% of the nitrites on a compound, for example at least 75%, or at least 90% of the nitrites. For example, the method can be used to reduce only one specific nitrile of a nitrile-containing compound with two or more nitrites, while leaving the other nitrites unreduced.

Ideally, the reaction conditions permit the nitrile oxido-reductase to substantially retain its biological activity. Although particular examples of incubation are provided herein, one skilled in the art will appreciate that other conditions can be used.

Nitrile containing compounds and the corresponding amines are known in the art. In particular examples, the target amine to be produced is commercially important. For example, the nitrile containing compound can include a nitrile (—RCN). Exemplary R groups include, but art not limited to: an aromatic group, an alkyl group, or a mixed aromatic/alkyl group, such as an unsubstituted phenyl group, a phenyl group with amine, carboxyl, or halo-substitution, an aromatic substituted alkyl group, or an alkyl group. Specific examples include the phenyl group, the p-aminophenyl group, the p-carboxy-phenyl group, the benzyl group, the allyl group, or the ethyl, propyl, butyl, hexyl groups. In addition, commercially important target amines can include primary amines, such as a primary amine (—RNH2). Exemplary R groups include, but are not limited to: an aromatic group, an alkyl group, or a mixed aromatic/alkyl group, such as an unsubstituted phenyl group, a phenyl group with amine, carboxyl, or halo-substitution, an aromatic substituted alkyl group, or an alkyl group. Specific examples include the phenyl group, the p-amino-phenyl group, the p-carboxy-phenyl group, the benzyl group, the allyl group, or the ethyl, propyl, butyl, hexyl groups.

Nitrile Oxido-Reductases

Several nitrile oxido-reductases are disclosed herein. However, one skilled in the art will appreciate that the choice of nitrile oxido-reductase will depend on the nitrile to be reduced (or the amine to be produced). For example, if the nitrile is 7-cyano-7-dezazguanine (preQ$_0$) (and the corresponding primary amine is 7-aminomethyl-7-dezazguanine (preQ$_1$)), examples of nitrile oxido-reductases that can be used include but art not limited to QueF, such as those sequences shown in FIGS. 9A-G and 10A-K.

Nitrile oxido-reductases can include variants of a native sequence, such as a native QueF sequence. In particular examples, the nitrile oxido-reductase includes an amino acid sequence that has at least 90% sequence identity to any of the amino acid sequences of SEQ ID NO: 2, 4, or 6-95, such as at least 95%, at least 98%, or at least 99% sequence identity to any of the amino acid sequences of SEQ ID NO: 2, 4, or 6-95.

In some examples, the nitrile oxido-reductase includes one or more conservative amino acid substitutions in a native nitrile oxido-reductase amino acid sequence, such as 1, 2, 3, 4, 5, 6, 7, 8, 9, or 10 conservative amino acid substitutions to any of SEQ ID NOS: 2, 4, or 6-95, for example 1-10, 1-8, or 1-5 conservative amino acid substitutions to SEQ ID NO: 2, 4, or 6-95. Ideally, such substitutions do not significantly impair the nitrile oxido-reductase from reducing a nitrile to an amine (such as a primary amine), for example a reduction of no more than 20% (such as no more than 10%, or no more than 5%). In particular examples, the QueF motif is not altered (such as amino acids 79-86 of SEQ ID NO: 2).

In some examples, the method uses fragments of a full-length nitrile oxido-reductase that retain the ability to reduce a nitrile to an amine. For example, a fragment of a nitrile oxido-reductase can reduce a nitrile to an amine with the same activity as the full-length nitrile oxido-reductase, or can in some examples be slightly decreased (such as a decrease of no more than 20%, no more than 10%, or no more than 5%) as compared to the full-length nitrile oxido-reductase. Exemplary fragments include, but are not limited to, at least 130 contiguous amino acids of any of SEQ ID NO: 2, 4, or 6-95, such as at least 120 contiguous amino acids of any of SEQ ID NOS: 2, 4, or 6-95, at least 100 contiguous amino acids of any of SEQ ID NO: 2, 4, or 6-95, at least 90 contiguous amino acids of any of SEQ ID NO: 2, 4, or 6-95, at least 75 contiguous amino acids of any of SEQ ID NO: 2, 4, or 6-95, or at least 50 contiguous amino acids of any of SEQ ID NO: 2, 4, or 6-95. In particular examples, a fragment of a nitrile oxido-reductase includes the QueF motif (SEQ ID NO: 5). Particular nitrile oxido-reductase fragments that can be used in the disclosed methods include, but are not limited to, amino acids 10-140, 10-130, 25-140, 50-140, 60-140, 60-100, or 68-105 of SEQ ID NO: 2 and amino acids 20-250, 50-240, 100-240, or 85-230 of SEQ ID NO: 4 (or the corresponding fragments of SEQ ID NOS: 6-95, using the alignments shown in FIGS. 9A-G and 10 A-K). One skilled in the art will recognize that other fragments can be generated, and their ability to reduce a nitrile to its corresponding amine (such as a primary amine) determined using routine methods, such as measuring NADPH oxidation.

Other nitrile oxido-reductases that can be used in the disclosed methods are provided herein.

Nitrile/Nitrile Oxido Reductase Combinations

Although particular nitrile/nitile oxido-reductase combinations are provided herein, one skilled in the art will recognize that the disclosed nitrile oxido-reductase sequences can be altered to change the nitrile specificity of the enzyme.

In one example, the nitrile containing compound includes a 7-cyano-7-dezazguanine (preQ$_0$) and the corresponding primary amine includes a 7-aminomethyl-7-dezazguanine (preQ$_1$). Particular examples of nitrile oxido-reductases that can be used to perform this reduction include, but are not limited to, any of SEQ ID NOS: 2, 4, and 6-95, as well as variants thereof that retain the ability to reduce preQ$_0$ to preQ$_1$.

In another particular example, the nitrile containing compound includes an aromatic nitrile, such as phenylacetonitrile, 3-cyano-indole, or benzonitrile, or an alkyl nitrile, such as an acrylonitrile. Particular examples of nitrile oxido-reductases that can be used to reduce such nitrites to their corresponding amines include, but are not limited to QueF sequences that include one of the following substitutions at Glu98: E98A, E98L, E98I, E98M, E98V, E98Q, or E98N (wherein the Glu98 refers to SEQ ID NO: 2, but that one skilled in the art will recognize that the corresponding Glu can be identified in other QueF sequences, for example using the alignment provided in FIGS. 9A-G and 10A-K; the corresponding Glu98 is highlighted in blue).

In one particular example, the nitrile containing compound includes a carboxylate residue in the site occupied by the exocyclic amine of preQ$_0$, such as p-carboxyphenylacetonitrile or p-carboxybenzonitrile. Particular examples of nitrile oxido-reductases that can be used to reduce such nitrites to their corresponding amines include, but are not limited to QueF sequences that include one of the following substitutions at Glu98: E98K or E98R (wherein the Glu98 refers to SEQ ID NO: 2, but that one skilled in the art will recognize that the corresponding Glu can be identified in other QueF sequences, for example using the alignment provided in FIGS. 9A-G and 10A-K; the corresponding Glu98 is highlighted in blue).

Reduction of Nitriles In Vitro

Nitrile oxido-reductases can be used to reduce a nitrile to its corresponding primary amine in vitro. For example, a preparation including a peptide having nitrile oxido-reductase activity can be used to catalyze the reduction of a nitrile to a primary amine, for example in the presence of NADPH. In some examples, the method is performed in a cell-free extract. Any method can be used to produce a cell-free extract. For example, osmotic shock, sonication, or a repeated freeze-thaw cycle followed by filtration or centrifugation can be used to produce a cell-free extract from intact cells.

NADPH can be provided in excess. In some examples, an NADPH regeneration system is included with the nitrile oxido-reductase and the nitrile containing compound. In a particular example, the NADPH regeneration system includes phosphite dehydrogenase. NADPH regeneration systems are known in the art, for example Woodyear et al. (*Biochemistry* 42:11604-14, 2003), the formate dehydrogenase system of Tishkov et al. (*Biotechnol. Bioeng.* 64:187-93, 1999), or the soluble pyridine nucleotide transhydrogenase and NADH system of Boonstra et al. (*Appl. Environ. Microbiol.* 66:5161-66, 2000) (all herein incorporated by reference as to the NADPH regeneration system methods).

In particular examples, reduction of a nitrile containing compound can be performed at 20-40° C. (such as 25-37° C., 25-30° C., such as 30° C.), at a pH of 6-8.5 (such as 6-8, 6-7.5, or 7-7.5, such as pH 7.2 or 7.5), for 30 seconds to several hours (such as 30 seconds to 6 hours, 1 minute to 3 hours, or 30 minutes to 2 hours). In a specific example, reduction of a nitrile containing compound is performed at 30° C. in 20-100 mM HEPES buffer (pH 7.5), 0.2-2.0 mM DTT or BME, 10-100 mM KCl, 0.2-150 μM preQ$_0$, and 2.0-200 μM NADPH, with an assay time from 30 seconds to 2 hours. One skilled in the art will appreciate that changes to the specific conditions used can be made to achieve substantial reduction for other nitrile oxido-reductases.

In one example, using UV detection and measuring the loss of NADPH at 334 nm, 340 nm, or 365 nm, the formation of ~0.2 μM primary amine can be measured in an assay volume of about 0.08 mL.

Reduction of Nitriles in a Cell

The nitrile oxido-reductase nucleic acid and amino acid sequences provided herein can be used with cells to reduce a nitrile to its corresponding amine (such as a primary amine). The cells can be eukaryotic or prokaryotic. For example, genetically modified cells can be mammalian cells (such as human, murine, or bovine cells), plant cells (such as corn, wheat, rice, or soybean cells), fungal cells (such as *Aspergillus* or *Rhizopus* cells), yeast cells, or bacterial cells (such as *Bacillus, Escherichia,* or *Clostridium* cells). In one example, a cell is a microorganism. The term "microorganism" refers to any microscopic organism including, but not limited to, bacteria, algae, fungi, and protozoa. Thus, *E. coli, B. subtilis, S. cerevisiae, K. lactis, Candida blankii,* and *Pichia pastoris* are microorganisms and can be used as described herein. In another example, the cell is part of a larger organism, such as a plant, such as a transgenic plant.

In one example, a cell is genetically modified such that a particular target amine is produced. For example, a cell or microorganism can contain one or more exogenous nucleic acid molecules that encode a peptide having nitrile oxido-reductase activity. In one example, cells are transfected with a nucleic acid molecule encoding one or more nitrile oxido-reductases.

A cell can be given an exogenous nucleic acid molecule that encodes a nitrile oxido-reductase that catalyzes the production of an amine not normally produced by that cell. Alternatively, a cell can be given an exogenous nucleic acid molecule that encodes a nitrile oxido-reductase that catalyzes the production of an amine that is normally produced by that cell. In this case, the genetically modified cell can produce more of the amine, or can produce the amine more efficiently, than a similar cell not having the genetic modification.

In some examples, the produced amine can be secreted from the cell, eliminating the need to disrupt cell membranes to retrieve the organic compound. For example, the exogenous nitrile oxido-reductase nucleic acid molecule can be operably linked to a secretory sequence, thereby producing a nitrile oxido-reductase fusion protein that is secreted from the cell. In other examples, the amine is not secreted, and the cell is disrupted and the amine isolated. In one example, the cell produces the desired primary amine, with the concentration of the product(s) being at least about 1 mg per L (such as at least about 10 mg/L, 50 mg/L, 100 mg/L, 1 g/L, or 1.5 g/L). When determining the yield of the amine for a particular cell, any method can be used. A cell within the scope of the disclosure can utilize a variety of carbon sources.

Methods of identifying cells that contain exogenous nucleic acid molecules encoding nitrile oxido-reductase are well known. Such methods include, without limitation, PCR and nucleic acid hybridization techniques such as Northern and Southern analysis (see hybridization described herein). In some cases, immunohistochemical and biochemical techniques can be used to determine if a cell contains particular nucleic acid molecule(s) by detecting the expression of the nitrile oxido-reductase encoded by that particular nucleic acid molecule(s). For example, an antibody having specificity for a nitrile oxido-reductase can be used to determine whether or not a particular cell contains nucleic acid encoding that nitrile oxido-reductase. Further, biochemical techniques can be used to determine if a cell contains a particular nucleic acid molecule encoding a nitrile oxido-reductase by detecting an organic product produced as a result of the expression of the nitrile oxido-reductase. For example, detection of a primary amine after introduction of exogenous nucleic acid that encodes a nitrile oxido-reductase into a cell that does not normally express such an amine can indicate that the cell not only contains the introduced exogenous nucleic acid molecule but also expresses the encoded peptide from that introduced exogenous nucleic acid molecule. Methods for detecting specific enzymatic activities or the presence of particular primary amines are well known, for example, the presence of an amine can be determined using HPLC methods.

Methods of recombinantly expressing a nucleic acid molecule (such as a nitrite oxido-reductase) are commonly used in the art. For example, one or more nitrile oxido-reductases (such as those described herein, for example those shown in SEQ ID NOS: 2, 4, and 6-95), can be produced in a host cell. Moreover, the nitrile oxido-reductase can be naturally-occurring or non-naturally-occurring. A naturally-occurring peptide is any peptide having an amino acid sequence as found in nature, including wild-type and polymorphic polypeptides. Naturally-occurring peptides can be obtained from any species including, but not limited to, plant, fungal, and bacterial species. A non-naturally-occurring peptide is any peptide having an amino acid sequence that is not found in nature. Thus, a non-naturally-occurring peptide can be a mutated version of a naturally-occurring peptide, or an engineered polypeptide. For example, a non-naturally-occurring peptide having nitrile oxido-reductase activity (such as a variant of those shown in SEQ ID NOS: 2, 4, and 6-95) can be a mutated version of a naturally-occurring peptide having nitrile oxido-reductase activity that has at least some nitrile oxido-reductase activity. In one example, the naturally-occurring nitrile oxido-reductase is mutated in order to alter the substrate specificity of the peptide (for example variants that include a Glu98 substitution)). In another example, the naturally-occurring nitrile oxido-reductase is mutated in order to provide preferred codons to the cell. A peptide can be mutated by, for example, sequence additions, deletions, substitutions, or combinations thereof.

The cells described herein can contain a single copy, or multiple copies (such as at least 5, at least 10, at least 20, at least 35, at least 50, at least 75, at least 100 or at least 150 copies), of an exogenous nitrile oxido-reductase nucleic acid molecule. The cells described herein can contain more than one particular exogenous nucleic acid. For example, a particular cell can contain about 50 copies of exogenous nucleic acid molecule X as well as about 75 copies of exogenous nucleic acid molecule Y.

A cell can contain an exogenous nucleic acid molecule that encodes a peptide having nitrile oxido-reductase activity, for example SEQ ID NO: 1 or 3 (or variants, fragments, or fusions thereof that retain nitrile oxido-reductase activity). Such cells can have any detectable level of nitrile oxido-reductase activity, including activity detected by the production of the appropriate primary amine or by the oxidation of NADPH. For example, a cell containing an exogenous nucleic acid molecule that encodes a peptide having nitrile oxido-reductase activity can have nitrile oxido-reductase activity with a specific activity greater than about 0.015 µmol min$^{-1}$ mg$^{-1}$, such as at least 0.02 µmol min$^{-1}$ mg$^{-1}$, such as at least 0.024 µmol min$^{-1}$ mg$^{-1}$. As described above, in one example, using UV detection and measuring the loss of NADPH at 334 nm, 340 nm, or 365 nm permits detection of the formation of ~0.2 µM primary amine in an assay volume of about 0.08 mL.

Any method can be used to introduce an exogenous nucleic acid molecule into a cell. For example, heat shock, lipofection, electroporation, conjugation, fusion of protoplasts, and biolistic delivery are common methods for introducing nucleic acid into bacteria and yeast cells. (See, for example, Ito et al., *J. Bacterol.* 153:163-8, 1983; Durrens et al., *Curr. Genet.* 18:7-12, 1990; Sambrook et al., Molecular cloning: A laboratory manual, Cold Spring Harbour Laboratory Press, New York, USA, second edition, 1989; and Becker and Guarente, *Methods in Enzymology* 194:182-7, 1991). Other methods for expressing a nitrile oxido-reductase amino acid sequence from an exogenous nucleic acid molecule include, but are not limited to, constructing a nucleic acid molecule such that a regulatory element promotes the expression of a nucleic acid sequence that encodes a nitrile oxido-reductase. Typically, regulatory elements are DNA sequences that regulate the expression of other DNA sequences at the level of transcription. Thus, regulatory elements include, without limitation, promoters, enhancers, and the like. Any type of promoter can be used to express a nitrile oxido-reductase amino acid sequence from an exogenous nucleic acid molecule. Examples of promoters include, without limitation, constitutive promoters, tissue-specific promoters, and promoters responsive or unresponsive to a particular stimulus (such as light, oxygen, chemical concentration). Methods for transferring nucleic acids into mammalian cells are also known, such as using viral vectors.

An exogenous nucleic acid molecule contained within a particular cell of the disclosure can be maintained within that cell in any form. For example, exogenous nucleic acid molecules can be integrated into the genome of the cell or maintained in an episomal state. That is, a cell can be a stable or transient transformant.

The cell having nitrile oxido-reductase activity is cultured in the presence of one or more nitrile containing compounds, under conditions sufficient for the production of the corresponding amine, such as a primary amine. In general, the culture media or culture conditions can be such that the microorganisms grow to an adequate density and produce the product efficiently. For large-scale production processes, any method can be used such as those described elsewhere (Manual of Industrial Microbiology and Biotechnology, $2^{nd}$ Edition, Editors: Demain and Davies, ASM Press; and Principles of Fermentation Technology, Stanbury and Whitaker, Pergamon).

For example, a large vessel (such as vessel having a capacity of at least 100 gallons, at least 200 gallons, or at least 500 gallons) containing appropriate culture medium with, for example, a glucose carbon source is inoculated with a particular cell. After inoculation, the cells are incubated to allow biomass to be produced. Once a desired biomass is reached, the broth containing the cells can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank. For example, the first tank can contain medium with xylose, while the second tank contains medium with glucose.

Once transferred, the cells can be incubated to allow for the production of the amine (such as a primary amine). Once produced, any method can be used to isolate the formed product. For example, common separation techniques can be used to remove the biomass from the broth, and common isolation procedures (such as extraction, distillation, and ion-exchange procedures) can be used to obtain the primary amine from the microorganism-free broth. Alternatively, the amine can be isolated while it is being produced, or it can be isolated from the broth after the amine production phase has been terminated.

Nitrile Oxido-Reductase Nucleic Acids and Peptides

Sequences encoding nitrile oxido reductases, as well as the corresponding peptide sequences, are disclosed herein, and can be used in the disclosed methods. The disclosure provides native nitrile oxido reductases, such as the native QueF sequences shown in FIGS. 9A-G and 10A-K (and SEQ ID NOS: 2, 4, and 6-95), as well as variant sequences thereof. Variant sequences include fragments, fusions, and mutations (such as one or more insertions, deletions, or substitutions), or combinations thereof. In some examples, the variant sequence retains the same biological activity as the native sequence, such as a conservative amino acid substitution, or a substitution of one or more nucleotides that does not result in a changed amino acid sequence. In other examples, the variant sequence retains the same generally biological activity as the native sequence (such as the ability to reduce a nitrile to its corresponding amine), but has a different nitrile substrate specificity. For example, changes to Glu98 in a QueF sequence can change the substrate specificity of the enzyme.

Examples of native peptide sequences having nitrile oxido reductase activity are shown in SEQ ID NOS: 2, 4 and 6-95. However, the disclosure also encompasses variants of SEQ ID NOS: 2, 4 and 6-95 that retain nitrile oxido reductase activity (such as a mutant, fusion, or fragment of a native nitrile oxido reductase). In one example, the peptide is a variant nitrile oxido reductase amino acid sequence, such as a variant of the sequences shown in SEQ ID NOS: 2, 4 and 6-95. In particular examples, such variants retain a native QueF motif (SEQ ID NO: 5).

In one example, the variant nitrile oxido-reductase is a fragment of a native nitrile oxido-reductase that retains the ability to reduce a nitrile to its corresponding amine. In one example, the fragment nitrile oxido-reductase peptide includes at least 25 contiguous amino acids that are identical to a native nitrile oxido-reductase sequence, such as at least 50 contiguous amino acids of any of SEQ ID NOS: 2, 4 and 6-95. It will be appreciated that the disclosure also provides nitrile oxido-reductase fragments greater than at least 25 amino acid residues (such as at least 50, at least 75, at least 100, at least 150, or at least 200 contiguous amino acid residues of any of SEQ ID NOS: 2, 4 and 6-95). Particular examples of nitrile oxido-reductase fragments that can be used include, but are not limited to: amino acids 10-140, 10-130, 25-140, 50-140, 60-140, 60-100, or 68-105 of SEQ ID NO: 2 and amino acids 20-250, 50-240, 100-240, or 85-230 of SEQ ID NO: 4 (or the corresponding fragments of SEQ ID NOS: 6-95, using the alignments shown in FIGS. 9A-G and 10 A-K). In particular examples, the fragment includes the sequence shown in SEQ ID NO: 5.

In a particular example, the variant nitrile oxido-reductase is a fusion protein that includes a nitrile oxido-reductase (or variant thereof), for example any of SEQ ID NOS: 2, 4 and 6-95, linked to other amino acid sequences that do not significantly inhibit the biological activity of nitrile oxido-reductase, for example the ability to reduce a nitrile to a primary amine. In one example, the other amino acid sequences are no more than about 10, 12, 15, 20, 25, 30, or 50 amino acids in length. In a specific example, the nitrile oxido-reductase is fused to a secretory peptide, to permit secretion of the peptide from a cell. The secretory peptide can be linked directly to the nitrile oxido-reductase, or indirectly via a spacer peptide (such as a spacer of at least 2, at least 5 or at least 10 amino acids). In another example, the nitrile oxido-reductase is fused to a peptide that permits isolation of the peptide, such as a His-tag.

In addition, the disclosure provides nitrile oxido-reductases that include an amino acid sequence having a variation (such as a mutation) of the amino acid sequence. Such altered sequences can contain a single insertion, a single deletion, a single substitution, multiple insertions, multiple deletions, multiple substitutions, or any combination thereof (such as single deletion together with multiple insertions). Such peptides share at least 80%, at least 85%, at least 90%, at least 95%, at least 97%, at least 98%, or at least 99% sequence identity with a nitrile oxido-reductase (such as those shown in SEQ ID NOS: 2, 4 and 6-95), as long as the peptide encoded by the amino acid sequence retains the desired nitrile oxido-reductase activity. Examples of particular substitutions which can be made to a nitrile oxido-reductase, while still retaining nitrile oxido-reductase activity, include, but are not limited to: L9T, Y22P, K58M, K58I, I103T, D132V, K139A, E149W and N154Y of SEQ ID NO: 2, and A11E, G32P, H52Q, Y82A, K126E, T156E, or E174L of SEQ ID NO: 4, as well as combinations of these substitutions (similar substitutions can be made to SEQ ID NOS: 6-95, using the alignment provided in FIGS. 9A-G and 10A-K).

It has been observed that substitutions of the Cys56 of SEQ ID NO: 2 with an Ala or Ser (or the corresponding Cys in other nitrile oxido-reductases) decreases the biological activity of the QueF enzyme by at least 30%, such as at least 50%, or at least 80%, such as 30-80%. Therefore, substitutions with an Ala or a Ser at this position allow the enzyme to retain its ability to reduce $preQ_0$.

Substitution of Glu98 in SEQ ID NO: 2 to Ala or Met significantly decreased the ability of the QueF enzyme to reduce $PreQ_0$. Therefore, changes to this residue are ideally not made if QueF enzyme activity is desired. However, substitution of Glu98 in SEQ ID NO: 2 (or the corresponding Glu in other nitrile oxido-reductases), can change the nitrile specificity of the enzyme. For example substitution of Glu98 as follows: E98A, E98L, E98I, E98M, E98V, E98Q, or E98N (wherein the Glu98 refers to SEQ ID NO: 2, but that one skilled in the art will recognize that the corresponding Glu can be identified in other QueF sequences, for example using the alignment provided in FIGS. 9A-G and 10A-K), can be used to change the enzyme to one that reduces an aromatic nitrile (such as phenylacetonitrile, 3-cyano-indole, or benzonitrile) or an alkyl nitrile (such as an acrylonitrile), to the corresponding amine. In addition, substitution of Glu98 as follows: E98K or E98R (wherein the Glu98 refers to SEQ ID NO: 2, but that one skilled in the art will recognize that the corresponding Glu can be identified in other QueF sequences, for example using the alignment provided in FIGS. 9A-G and 10A-K) can be used to change the enzyme to one that reduces a nitrile containing compound that includes a carboxylate residue in the site occupied by the exocyclic amine of $preQ_0$ (such as p-carboxyphenylacetonitrile or p-carboxybenzonitrile) to the corresponding amine. These substitutions to Glu98 can be made in combination with other conservative or non-conservative substitutions, such as those disclosed herein.

In addition, changes in the QueF motif (SEQ ID NO: 5), can be used to change nitrile oxido-reductase from an NADPH-dependent enzyme, to an NADH-dependent enzyme. For example, changing the Lys residues in the QueF motif to a non-conserved residue may change this dependency.

One particular type of variation includes the substitution of one or more amino acid residues, such as no more than 10 amino acids, for amino acid residues having a similar biochemical property, that is, a conservative substitution. In particular examples, a nitrile oxido reductase includes 10, 9, 8, 7, 6, 5, 4, 3, 2, or 1 conservative amino acid substitutions (for example to any of SEQ ID NOS: 2, 4, and 6-95). For example, one or more of the following conservative substitutions can be made to SEQ ID NO: 2: F24L, F24Y, A27S, Glu75D, T142S, or Y158W, and one or more of the following conservative substitutions can be made to SEQ ID NO: 4: A11S, H52N, H52Q, K126R, Y166W, or T277S. Based on these teachings, one skilled in the art can make corresponding conservative substitutions to other nitrile oxido reductases (for example in combination with FIGS. 9A-G and 10A-K).

More substantial changes can be obtained by selecting substitutions that are less conservative, such as selecting residues that differ more significantly in their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, such as serine or threonine, is substituted for (or by) a hydrophobic residue, such as leucine, isoleucine, phenylalanine, valine or alanine; (b) a cysteine or proline is substituted for (or by) any other residue; (c) a residue having an electropositive side chain, such as lysine, arginine, or histidine, is substituted for (or by) an electronegative residue, such as glutamic acid or aspartic acid; or (d) a residue having a bulky side chain, such as phenylalanine, is substituted for (or by) one not having a side chain, such as glycine.

Methods of producing variant sequences are known in the art. For example, Variant nitrile oxido-reductase amino acid sequences can be produced by manipulating the nucleotide sequence encoding the corresponding peptide using standard procedures such as site-directed mutagenesis or PCR. In addition, variant nitrile oxido reductase peptides (such as mutants, fusions, or fragments) can be produced using chemical synthesis of the peptide.

The effects of these amino acid variations on the ability of the variant to function as a nitrile oxido-reductase (for example to determine whether the changes alter the substrate specificity of the nitrile oxido-reductase) can be assessed by analyzing the ability of the variant peptide to catalyze the reduction of a nitrile to a primary amine, for example relative to the native nitrile oxido-reductase. In a specific example, NADPH oxidation is monitored in the presence of the variant nitrile oxido-reductase and the corresponding nitrile. In another example, production of the corresponding amine is measured, for example by using HPLC.

Also disclosed are isolated nucleic acid molecules that encode peptides having nitrile oxido-reductase activity, for example a sequence that includes SEQ ID NO: 1 or 3. However, the disclosure also encompasses variants of SEQ ID NOS: 1 and 3 (such as mutants, fusions or fragments of these sequences) that retain the ability to encode a protein having nitrile oxido-reductase activity. These isolated nucleic acid molecules can be used in the disclosed methods.

In one example an isolated nucleic acid encoding a peptide having nitrile oxido-reductase activity is operably linked to a promoter sequence, and can be part of a vector. This vector can be introduced into cells, thereby making transformed cells. Once inside the cell, the vector allows the protein to be produced. In particular examples, the nucleic acid sequence encoding a nitrile oxido-reductase is altered to optimize codon preference, for example to facilitate the protein to be expressed in a particular cell, such as yeast cells, bacterial cells, insect cells, or plant cells.

Transformed cells including at least one exogenous nucleic acid molecule which encodes a peptide having nitrile oxido-reductase activity (such as SEQ ID NO: 1 or 3, or variants thereof that retain nitrile oxido-reductase activity), are disclosed. In one example, such a transformed cell reduces a nitrile to a primary amine.

Nucleic acid sequences encoding a nitrile oxido-reductase (such as SEQ ID NO: 1 and 3), can contain an entire nucleic acid sequence encoding the enzyme, as well as a portions thereof that retain the desired nitrile oxido-reductase activity. For example, a nitrile oxido-reductase nucleic acid sequence can contain at least 24 contiguous nucleotides of a nitrile oxido-reductase nucleic acid sequence. It will be appreciated that the disclosure also provides isolated nitrile oxido-reductase nucleic acid molecules that contain greater than 24 contiguous nucleotides (such as at least 25, at least 26, at least 27, at least 28, at least 29, at least 30, at least 40, at least 50, at least 75, at least 10, at least 200, or at least 500 contiguous nucleotides) of any portion of a nitrile oxido-reductase nucleic acid sequence (such as those shown in SEQ ID NO: 1 or 3).

In addition, the disclosure provides isolated nitrile oxido-reductase nucleic acid sequences which contain a variation of in the sequence. Variants can contain a single insertion, a single deletion, a single substitution, multiple insertions, multiple deletions, multiple substitutions, or any combination thereof (such as a single deletion together with multiple insertions) as long as the peptide encoded thereby retains nitrile oxido-reductase. Variant nitrile oxido-reductase nucleic acid molecules can share at least 90%, at least 92%, at least 95%, at least 97%, at least 98, or at least 99% sequence identity with a native nitrile oxido-reductase sequence, as long as the peptide encoded by the nucleic acid retains the desired nitrile oxido-reductase activity. For example, the following variations can be made to a nitrile oxido-reductase nucleic acid sequence: for SEQ ID NO: 1, the "a" at position 96 can be substituted with an "g"; the "g" at position 195 can be substituted with an "a", "c", or "t"; the "a" at position 384; can be substituted with an "g", "t", or "c"; the "t" at position 432 can be substituted for a "c"; and the "a" at positions 483 can be substituted for a "g", "c", or "t". For SEQ ID NO: 3, the "a" at position 48 can be substituted with a "g", "t", or "c"; the "t" at position 288 can be substituted with a "c"; the "g" at position 387 can be substituted with a "c", "t", or "a"; the "c" at position 576 can be substituted with a "t" or an "a"; and the "t" at position 771; can be substituted with an "a", "g", or "c." Similar substitutions can be made to other nitrile oxido-reductase nucleic acid sequences, for example, by using a genetic code table.

Codon preferences and codon usage tables for a particular species can be used to engineer isolated nitrile oxido-reductase nucleic acid molecules that take advantage of the codon usage preferences of that particular species. For example, the nitrile oxido-reductases disclosed herein can be designed to have codons that are preferentially used by a particular organism of interest.

The disclosure also provides isolated nucleic acid sequences that encode a nitrile oxido-reductase that is at least 24 bases in length (such as at least 25, at least 30, at least 40, at least 50, at least 60, at least 100, at least 250, at least 500, at least 750, or at least 1000 bases in length) and hybridizes, under moderately or highly stringent hybridization conditions, to the sense or antisense strand of a nucleic acid encoding the nitrile oxido-reductase.

Variant nitrile oxido-reductase nucleic acid molecules can be produced by standard DNA mutagenesis techniques, for example, M13 primer mutagenesis. Details of these techniques are provided in Sambrook et al. (ed.), Molecular Cloning: A Laboratory Manual 2nd ed., vol. 1-3, Cold Spring Harbor Laboratory Press, Cold Spring, Harbor, N.Y., 1989, Ch. 15. Nucleic acid molecules can contain changes of a coding region to fit the codon usage bias of the particular organism into which the molecule is to be introduced.

Alternatively, the coding region can be altered by taking advantage of the degeneracy of the genetic code to alter the coding sequence in such a way that, while the nucleic acid sequence is substantially altered, it nevertheless encodes a nitrile oxido-reductase peptide having an amino acid sequence identical or substantially similar to the native amino acid sequence. For example, because of the degeneracy of the genetic code, alanine is encoded by the four nucleotide codon triplets: GCT, GCA, GCC, and GCG. Thus, the nucleic acid sequence of the open reading frame can be changed at an alanine position to any of these codons without affecting the amino acid sequence of the encoded peptide or the characteristics of the peptide. Based upon the degeneracy of the genetic code, nucleic acid variants can be derived from a nucleic acid sequence using standard DNA mutagenesis techniques as described herein, or by synthesis of nucleic acid sequences. Thus, this disclosure also encompasses nucleic acid molecules that encode a nitrile oxido-reductase but vary in nucleic acid sequence by virtue of the degeneracy of the genetic code.

Identification of Other Nitrite Oxido-Reductases

A nucleic acid molecule encoding a peptide having nitrile oxido-reductase activity can be identified and obtained using any method known in the art. For example, nucleic acid molecules that encode a peptide having nitrile oxido-reductase activity can be identified and obtained using common molecular cloning or chemical nucleic acid synthesis procedures and techniques, including PCR. In addition, standard nucleic acid sequencing techniques and software programs that translate nucleic acid sequences into amino acid sequences based on the genetic code can be used to determine whether or not a particular nucleic acid has any sequence homology with a nitrile oxido-reductase peptides. Sequence alignment software such as MEGALIGN (DNASTAR, Madison, Wis., 1997) can be used to compare a sequence to a known nitrile oxido-reductase sequence.

In addition, nucleic acid molecules encoding known nitrile oxido-reductases can be mutated using common molecular cloning techniques (such as site-directed mutagenesis). Possible mutations include, without limitation, deletions, insertions, and base substitutions, as well as combinations of deletions, insertions, and base substitutions. Further, nucleic acid and amino acid databases (such as GenBank and EMBL) can be used to identify a nucleic acid sequence that encodes a peptide having nitrile oxido-reductase activity. Briefly, any amino acid sequence having some homology to a peptide having nitrile oxido-reductase activity, or any nucleic acid sequence having some homology to a sequence encoding a peptide having nitrile oxido-reductase activity can be used as a query to search GenBank or EMBL. The identified peptides then can be analyzed to determine whether or not they exhibit nitrile oxido-reductase activity, or have specificity for a particular nitrile.

In addition, nucleic acid hybridization techniques can be used to identify and obtain a nucleic acid molecule that encodes a peptide having nitrile oxido-reductase activity. Briefly, any nucleic acid molecule that encodes a known nitrile oxido-reductase polypeptide, or fragment thereof, can be used as a probe to identify similar nucleic acid molecules by hybridization under conditions of moderate to high stringency. Such similar nucleic acid molecules then can be isolated, sequenced, and analyzed to determine whether the encoded polypeptide has nitrile oxido-reductase activity, or has specificity for a particular nitrile.

Expression cloning techniques also can be used to identify and obtain a nucleic acid molecule that encodes a peptide having nitrile oxido-reductase activity. For example, a nitrile substrate known to interact with a particular nitrile oxido-reductase polypeptide can be used to screen a phage display library containing that nitrile oxido-reductase polypeptide.

Phage display libraries can be generated as described (Burritt et al., *Anal. Biochem.* 238:1-13, 1990), or can be obtained from commercial suppliers such as Novagen (Madison, Wis.).

Further, peptide sequencing techniques can be used to identify and obtain a nucleic acid molecule that encodes a peptide having nitrile oxido-reductase activity. For example, a purified peptide can be separated by gel electrophoresis, and its amino acid sequence determined by, for example, amino acid microsequencing techniques. Once determined, the amino acid sequence can be used to design degenerate oligonucleotide primers. Degenerate oligonucleotide primers can be used to obtain the nucleic acid encoding the polypeptide by PCR. Once obtained, the nucleic acid can be sequenced, cloned into an appropriate expression vector, and introduced into a microorganism.

Cells with Nitrile Oxido-Reductase Activity

Cells having nitrile oxido-reductase activity are disclosed, and can be used in the methods described herein. Such cells can be used to produce one or more desired amines (referred to herein as target amines), such as a primary amine, from a nitrile containing compound. Cells including nitrile oxido-reductase activity can be eukaryotic or prokaryotic. Examples of such cells include, but are not limited to *Lactobacillus, Lactococcus, Bacillus, Escherichia*, fungal, plant, and yeast cells. In one example, a plant cell is part of a plant, such as a transgenic plant.

In one example, cells having nitrile oxido-reductase activity are transformed cells. Such cells can include at least one exogenous nucleic acid molecule that encodes a nitrile oxido-reductase, for example a sequence that includes SEQ ID NO: 1 or 3, or variants thereof that retain the ability to encode a protein having nitrile oxido-reductase activity. Therefore, in some examples, the disclosed cells express an exogeous nitrile oxido-reductase, for example an enzyme that includes at least 98% sequence identity to any of SEQ ID NOS: 2, 4, and 6-95.

In one example, the exogenous nucleic acid molecule is a variant nitrile oxido-reductase, such as a variant prokaryotic QueF sequence (for example a sequence having at least 98% sequence identity to any of SEQ ID NOS: 2, 4, and 6-95). In specific examples, the variant prokaryotic nitrile oxido-reductase is a mutated *B. subtilis* or *E. coli* QueF sequence. Other nitrile oxido-reductase can be identified by using methods known in the art, for example by searching for similar sequences on BLAST or by using hybridization methods.

In a particular example, the variant nitrile oxido-reductase includes 1-10 conservative amino acid substitutions. In other particular examples, the variant nitrile oxido-reductase includes an E98A, E98L, E98I, E98M, E98V, E98Q, E98N, E98K, or E98R substitution (wherein the substitution refers to the sequence shown in SEQ ID NO: 2, but one skilled in the art can identify the corresponding Glu residue, for example by using FIGS. 9A-G and 10A-K).

Methods of Producing a Peptide Having Nitrile Oxido-Reductase Activity

A method is disclosed for producing peptides having nitrile oxido-reductase activity. The method includes culturing the disclosed cells having nitrile oxido-reductase activity under conditions that allow the cell to produce the nitrile oxido-reductase peptide. In one example, the method includes culturing cells having one or more exogenous nucleic acid molecules which encode for a nitrile oxido-reductase (such as a sequence which includes SEQ ID NO: 1 or 3 or variants thereof that retain nitrile oxido-reductase activity), such that the nitrile oxido-reductase is produced. The resulting nitrile oxido-reductase can be isolated from the cell or culture medium. In particular examples, the nitrile oxido-reductase includes a secretory signal sequence, thereby permitting isolation of the nitrile oxido-reductase peptide from the culture medium.

A method for making a primary amine from a nitrile is also disclosed. In one example, the method includes culturing the disclosed cells having nitrile oxido-reductase activity under conditions that allow the cell to produce a primary amine from a nitrile. In one example, the method includes culturing cells having one or more exogenous nucleic acid molecules which encode for a nitrile oxido-reductase, such that the nitrile oxido-reductase is capable of producing the corresponding primary amine from a nitrile. In one example, the exogenous nucleic acid is a sequence that includes SEQ ID NO: 1 or 3, or variants thereof that retain nitrile oxido-reductase activity.

The subject matter of the present disclosure is further illustrated by the following non-limiting Examples.

EXAMPLE 1

Cloning and Over-Expression of *B. subtillis* and *E. coli* QueF

This example describes methods used to identify bacterial nitrile oxido-reductases using a genomics based search. One skilled in the art will appreciate that similar methods can be used to identify other nitrile oxido-reductases in addition to QueF.

A genomics based search was performed for missing enzymes in the queuosine and archaeosine pathways. Specifically, a search for a GTP cyclohydrolase-like enzyme (the first putative step of queuosine biosynthesis) in the COG database (Tatusov et al., *Nucl. Acids Res.* 29:22-8, 2001) identified the two GTP cyclohydrolase families (FolE and RibA) and the COG0780 family (annotated as "enzymes related to GTP cyclohydrolase I"). Alignments of proteins of the COG0780 family with members of the GTP cyclohydrolase I (FolE) family using clustalw software (Thompson et al., *Nucl. Acids Res.* 22:4673-80, 1994) indicated that while the two families clearly share a common ancestor, the exact function of these enzymes might not be conserved.

When analyzing the neighboring regions of COG0780 family members, in *B. subtilis*, the COG0780 member ykvM was the last gene of the ykvJKLM operon. In 80% of the completely sequenced organisms different combinations containing two or three of these four genes are found in operonic structures.

The results of the bioinformatics analysis were consistent with YkvM catalyzing a GTP cyclohydrolase-like activity.

The ykvM gene from *B. subtilis* JH642 (GeneID No: 939296) and the *E. coli* K12 MG1655 homolog, yqcD (GeneID No: 947270) were amplified by PCR using genomic DNA, and cloned into pET30 expression vectors (Novagen, Madison, Wis.) using standard molecular biology methods. pET30 vectors allow expression of the recombinant proteins as N-terminal $His_6$ proteins. A Factor Xa cleavage site immediately precedes the starting Met of the target protein, and allows for the isolation of the wild-type protein following Factor Xa proteolysis of the affinity-purified fusion construct. A typical purification of recombinant *E. coli* or *B. subtilis* $His_6$-QueF involved cell lysis by French press, sonication, or lysozyme treatment, and centrifugation to generate a cell-free extract (CFE). The enzymes were then purified from the CFE by chromatography on a $Ni^{2+}$-agarose affinity column according to the manufactures protocols. After dialyzing the purified $His_6$-QueF into an appropriate buffer, the $His_6$-fusion was cleaved by incubation overnite with Factor Xa according to the manufactures instructions. The wt QueF was then isolated from the reaction mixture by rechromatography on the $Ni^{2+}$-agarose affinity column according to the manufactures protocols.

Both yqcM and ykvD were cloned because the encoded enzymes form two subclasses (referred to herein as QueF Class I and QueF Class II, respectively), with YqcD approximately 40% larger than YkvM, and to confirm the activity of both and investigate any structural and functional consequences of these differences. The YqcD N-terminal domain has been annotated as a membrane-spanning domain, but transmembrane prediction programs run on YqcD do not detect any transmembrane segment.

Both QueF Class I and QueF Class II recombinant proteins were obtained as soluble proteins, and Factor Xa cleavage of the N-terminal fusion constructs provided the wild-type proteins in good yields. The *E. coli* genes encoding GTP cyclohydrolase I (folE) and GTP cyclohydrolase II (ribA) were cloned in parallel so that the enzymes would serve as positive controls for cyclohydrolase activity assays of QueF Class I and QueF Class II.

The sequences of *B. subtilis* QueF Class I nucleic acid and protein sequences are shown in SEQ ID NOS: 1 and 2, respectively, and *E. coli* QueF Class II nucleic acid and protein sequences are shown in SEQ ID NOS: 3 and 4, respectively.

EXAMPLE 2

Biochemical Characterization of QueF

This example describes methods used to determine the biological function of YkvM/YqcD (referred to herein as QueF).

GTP cyclohydrolase activity was investigated using three different assays (radiochemical based release of $[^{14}C]$formic acid, fluorescence, or HPLC analysis of reactions) and a large screen of assay conditions (including those for cyclohydrolase I, II, and III activity). Surprisingly, no GTP cyclohydrolase activity was detected for YkvM/YqcD, and therefore these enzymes are not GTP cyclohydrolases.

The failure to observe cyclohydrolase activity with QueF Class I or QueF Class II prompted consideration of alternative roles the QueF gene family. One potential enzymatic activity included the conversion of $preQ_0$ to $preQ_1$, which involves the conversion of a nitrile to an amine.

Figure 2A:
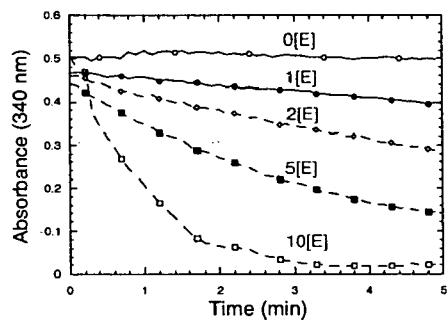
FIG. 2A are plots showing QueF assays monitoring the disappearance of NADPH.

$PreQ_0$ oxido-reductase activity was determined using a number of redox cofactors, and activity was observed only in the presence of NADPH. Using a continuous UV-based assay (FIG. 2), the rate of NADPH oxidation was shown to be dependent on enzyme (QueF Class I or QueF Class II) and substrate concentrations, consistent with QueF acting as the catalyst in the redox reaction of $preQ_0$ and NADPH. Assays were typically carried out at 30° C. in a final volume of 80 μL in a solution of 50 mM HEPES (pH 7.5), 50 mM KCl, 1 mM DTT, 2-150 μM NADPH, 0.2-150 μM $preQ_0$, and 10-1000 nM QueF. Assays were run from 30 seconds to 2 hours.

To confirm that $preQ_1$ was the reduced product as predicted, reaction assays were analyzed by reverse-phase HPLC (Bondclone 10 C-18, 300×3.9 mm) with a mobile phase of 20 mM ammonium acetate (pH 6.0) and methanol. With a flow-rate of 1 mL/min a series of linear gradients were developed from 20 mM ammonium acetate (pH 6.0) (buffer U) to 75% methanol in buffer U (buffer V) in the following manner (beginning time and ending time and linear increase to % V): 0-20.0 min, 0% V; 20.0-30.0 min, 8% V; 30.0-40.0 min, 20% V; 40.0-42.0 min, 100% V; 42.0-50.0 min, 100% V; and 50.0.0-52.0 min, 0% V. $PreQ_0$ and $preQ_1$ were detected with a diode array detector.

Figure 2B:
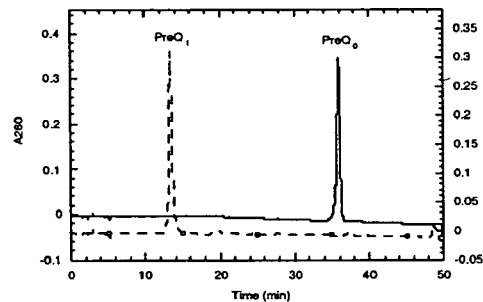
FIGS. 2B and 2C are HPLC chromatograms of (B) authentic preQ$_1$ (dashed line) and preQ$_0$ (solid line) and (C) of a reaction of *B. subtilis* QueF with preQ$_0$ (solid line) and the reaction with added preQ$_1$ (dashed line).
Figure 2C:
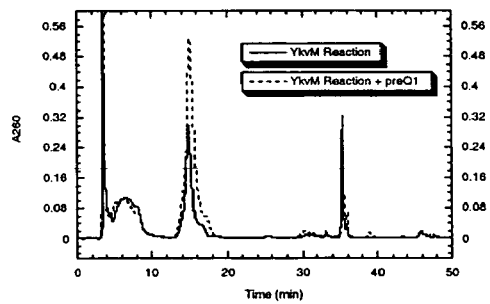

As shown in FIGS. 2B and 2C, HPLC analysis of an incubation of either YkvM (QueF Class I) or YqcD (QueF Class II) with NADPH and $preQ_0$ clearly shows the formation of a product that co-elutes with authentic $preQ_1$ prepared synthetically. Furthermore, the product of the reaction was isolated and its NMR, IR, and UV spectra were found to be identical to authentic $preQ_1$.

Having established that QueF is a nitrile oxido-reductase, a biochemical characterization of the enzymes was performed. The presence of the N-terminal $His_6$ fusion did not affect catalytic activity; both the fusion and cleaved recombinant enzymes exhibited identical molar specific activities. Other than NADPH, no other organic cofactors (such as NADH, $FADH_2$, riboflavin, and $FMNH_2$) were associated with the QueF enzyme nor were necessary for catalysis. The QueF enzymes had no observable metal ion requirements, and exhibited optimal activity at pH ~7.2. The equilibrium lies far to the side of $preQ_1$, <1% of $preQ_0$ was generated when the reaction was run in reverse with $preQ_1$ and $NADP^+$.

Analysis of velocity data with variable NADPH and constant, saturating $preQ_0$ provided a $K_M$ for NADPH of 36 μM, consistent with the $K_M$ values for other bacterial NADPH-dependent oxidoreductases (Smith et al. in The Enzymes, $3^{rd}$ Ed., XI:293-367, 1975). The measured $k_{cat}$ of 0.6 $min^{-1}$, while low, is comparable to the two subsequent enzymes in the pathway (Hoops et al. *Biochem.* 34:15539-44, 1995; Van Lanen et al. *Biochem.* 42:5312-20, 2003). The $K_M$ for $preQ_0$ was observed to be $K_M$<1 μM. Based on the chemistry it is predicted that the kinetic mechanism is a bi uni uni ping pong ter ter system (Segel, I. *Enzyme Kinetics: Behavior and Analysis of Rapid-Equilibrium and Steady-State Enzyme Systems*, John Wiley & Sons, 1975), with NADPH binding and reacting twice.

EXAMPLE 3

Structural Analysis of QueF

This example describes methods used to analyze the structure of the QueF Class I (YkvM) and Class II (YqcD) families. Based on the teachings herein, one skilled in the art can make variants of QueF sequences, for example to generate QueF proteins having specificity for a different nitrile substrate, or to make a variant QueF protein having a different sequence but having specificity for the same nitrile substrate.

FolE and QueF class I are members of the same structural superfamily; the homology score between the two families (detected by Psi-BLAST, available on the Internet) is around 25% sequence identity and 40% similarity in a 100 amino acid stretch.

Figure 3:
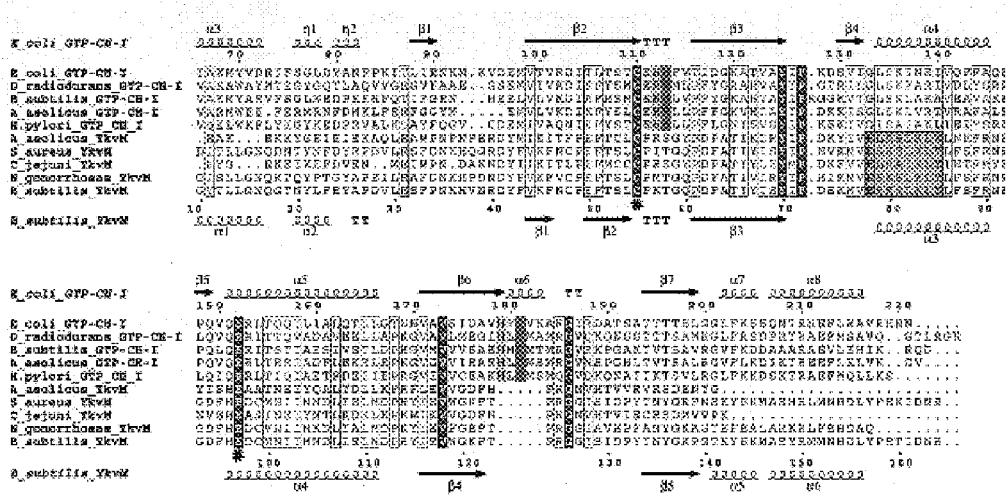
FIG. 3 is a schematic drawing showing the alignment of unimodular FolE (GTP cyclohydrolase I) and class I QueF sequences. For clarity and space, only sequences from select organisms are shown from among 60 sequences in the original alignment, and the N-terminii have been truncated. Sequence numbers of every 10$^{th}$ residue are shown for *E. coli* FolE and *B. subtilis* QueF. Secondary structure elements and nomenclature as defined by the crystal structure of *E. coli* FolE, and by the 3D homology model of *B. subtilis* QueF are shown on the top and bottom, respectively. The conserved Cys and Glu found in the substrate binding pocket of both protein families are indicated by asterisks. The QueF motif, specific for the QueF family, is highlighted in green. The zinc binding His and Cys residues found in FolE and not in QueF are highlighted in blue. Other catalytic residues in FolE not found in QueF are highlighted in yellow. The absence of the zinc binding and catalytic residues of FolE is the best identifier of YkvM sequences in genome databases.

To differentiate the QueF Class I family from the FolE family, as they are both annotated as GTP cyclohydrolase I enzymes in the databases, a clustalw alignment was generated using 30 unimodular FolE sequences and 30 QueF Class I sequences (FIG. 3).

Two major features differentiate the QueF Class I and FolE families. First, the strictly conserved pattern $E_{79}(S/L)K(S/A)hK(L/Y)(Y/F/W)_{86}$ (residue numbers are those of *B. subtilis* QueF, h is hydrophobic amino acid; SEQ ID NO: 5) is characteristic of the QueF family but is not found in the FolE family and is referred to herein as the QueF motif. Two residues, Cys56 and Glu98 flank the QueF motif and are strictly conserved in both protein families, and correspond to Cys110 and Glu152 in *E. coli* FolE. Second, four catalytically important residues in FolE, His112, 113 and 179, and Cys181 (*E. coli* FolE numbering), are absent in YkvM sequences (FIG. 3). Notably, His113 and Cys181 provide ligands for $Zn^{2+}$, indicating the absence of a zinc-binding site in QueF.

The FolE family contains two structural subfamilies: homodecameric enzymes of unimodular 26-kDa subunits exemplified by bacterial and mammalian FolE, and bimodular 50-kDa proteins of two tandem FolE-like domains—each containing half the active site residues—and forming lower-order quaternary structures, as found in plant FolE. Similarly, the QueF proteins appear to form two subfamilies, QueF class I proteins exemplified by *B. subtilis* QueF, and QueF class II proteins exemplified by *E. coli* QueF (FIG. 4). The QueF class I proteins are comparable in size to bacterial and mammalian FolE, while the QueF class II proteins are larger, similar to plant FolE. Exemplary QueF class I and class II proteins are listed in Tables 1 and 2, and an alignment of some of the sequences is shown in FIGS. 9A-G and 10A-K, respectively.

TABLE 1

QueF family: Class I (YkvM)

| Organism | Alignment Abbreviation[1] | Accession # | Databank Definition |
|---|---|---|---|
| *Aeropyrum pernix* K1 | | BAA80469 | 147aa long hypothetical GTP cyclohydrolase I |
| *Agrobacterium tumefaciens* str. C58 | A. tum | NP_355229 | hypothetical protein AGR_C_4128 |
| *Anabaena variabilis* ATCC 29413 | | ZP_00162432 | COG0780: Enzyme related to GTP cyclohydrolase I |
| *Aquifex aeolicus* VF5 | A. aeo | NP_213635 | hypothetical protein aq_931 |
| *Bacillus anthracis* str. A2012 | B. ant | NP_655246 | hypothetical protein BA_1886 |
| *Bacillus anthracis* str. Ames | | NP_843820 | hypothetical protein BA1362 |
| *Bacillus anthracis* str. Sterne | | YP_027529 | hypothetical protein BAS1260 |
| *Bacillus cereus* ATCC 10987 | | NP_977782 | hypothetical protein BCE1461 |
| *Bacillus cereus* ATCC 14579 | | NP_831125 | GTP cyclohydrolase I |
| *Bacillus cereus* G9241 | | ZP_00237259 | conserved hypothetical protein |
| *Bacillus cereus* ZK | | YP_082834 | possible GTP cyclohydrolase I |
| *Bacillus clausii* KSM-K16 | | YP_175622 | GTP cyclohydrolase I |
| *Bacillus halodurans* C-125 | | BAB05960 | BH2241 |
| *Bacillus licheniformis* ATCC 14580 | | AAU23077 | GTP cyclohydrolase I |
| *Bacillus subtilis* | | D69868 | conserved hypothetical protein ykvM |
| *Bacillus subtilis* subsp. *subtilis* str. 168 | B. sub1 | NP_389258 | hypothetical protein BSU13750 |
| *Bacillus thuringiensis serovar konkukian* str. 97-27 | | YP_035568 | possible GTP cyclohydrolase I |
| *Bacteroides fragilis* NCTC 9343 | | CAH07109 | putative GTP-cyclohydrolase protein |
| *Bacteroides fragilis* YCH46 | | YP_098751 | hypothetical protein BF1466 |
| *Bacteroides thetaiotaomicron* VPI-5482 | B. the | AAO76671 | conserved hypothetical protein |
| *Bdellovibrio bacteriovorus* HD100 | | NP_967112 | GTP cyclohydrolase I |
| *Bradyrhizobium japonicum* USDA 110 | B. jap | BAC50061 | blr4796 |
| *Brucella abortus biovar* 1 str. 9-941 | B. abo | YP_221888 | hypothetical protein BruAb1_1189 |
| *Brucella melitensis* 16M | B. mel | NP_539721 | Hypothetical Cytosolic Protein |
| *Brucella suis* 1330 | B. sui | NP_698188 | hypothetical protein BR1183 |
| *Campylobacter coli* RM2228 | | ZP_00370699 | GTP cyclohydrolase I subfamily, putative |
| *Campylobacter jejuni* RM1221 | | YP_179862 | GTP cyclohydrolase I family protein |
| *Campylobacter jejuni* subsp. *jejuni* NCTC 11168 | C. jej1 | CAB73710 | hypothetical protein Cj1724c |
| *Campylobacter lari* RM2100 | | ZP_00369623 | GTP cyclohydrolase I subfamily, putative |
| *Campylobacter upsaliensis* RM3195 | | ZP_00372144 | GTP cyclohydrolase I subfamily, putative |
| *Caulobacter crescentus* CB15 | C. cre | NP_421453 | hypothetical protein CC2654 |
| *Chlorobium tepidum* TLS | C. tep | NP_66252 | hypothetical protein CT1638 |
| *Crocosphaera watsonii* WH 8501 | | ZP_00176699 | COG0780: Enzyme related to GTP cyclohydrolase I |
| *Desulfovibrio vulgaris* subsp. *vulgaris* str. Hildenborough | | YP_010184 | GTP cyclohydrolase I family protein |
| *Erythrobacter litoralis* HTCC2594 | | ZP_00377404 | probable GTP cyclohydrolase I |
| *Geobacillus kaustophilus* HTA426 | | YP_146831 | hypothetical protein GK0978 |
| *Gloeobacter violaceus* PCC 7421 | G. vio | BAC91534 | gll3593 |
| *Gluconobacter oxydans* 621H | | YP_191070 | hypothetical protein GOX0637 |
| *Helicobacter pylori* 26695 | H. pyl1 | AAD08456 | conserved hypothetical protein |
| *Helicobacter pylori* J99 | H. pyl2 | NP_224026 | hypothetical protein jhp 1308 |
| JGlenv acid_mining-1 | JGle1 | ? | |
| JGlenv acid_mining-2 | JGle2 | ? | |

TABLE 1-continued

QueF family: Class I (YkvM)

| Organism | Alignment Abbreviation[1] | Accession # | Databank Definition |
|---|---|---|---|
| *K. pneumoniae* MGH78578-1 | *K. pne*1 | ? | |
| *K. pneumoniae* MGH78578-2 | *K. pne*2 | ? | |
| *Leptospira interrogans serovar Lai* str. 56601 | *L. int*1 | NP_712266 | hypothetical protein LA2085 |
| *Leptospira interrogans serovar Copenhageni* str. Fiocruz L1-130 | | YP_001781 | hypothetical protein LIC11832 |
| *Magnetococcus* sp. MC-1 | | ZP_00290453 | COG0780: Enzyme related to GTP cyclohydrolase I |
| *Magnetospirillum magnetotacticum* MS-1 | *M. mag* | ZP_00054688 | COG0780: Enzyme related to GTP cyclohydrolase I |
| *Mesorhizobium loti* MAFF303099 | *M. lot* | NP_108416 | hypothetical protein mll8291 |
| *Mesorhizobium* sp. BNC1 | | ZP_00193845 | COG0780: Enzyme related to GTP cyclohydrolase I |
| *Methylobacillus flagellatus* KT | | ZP_00350262 | COG0780: Enzyme related to GTP cyclohydrolase I |
| *Methylococcus capsulatus* str. Bath | | AAU91450 | conserved hypothetical protein |
| *Micromonospora echinospora* | | CAF34041 | conserved hypothetical protein |
| *Neisseria gonorrhoeae* FA 1090 | *N. gon* | YP_208721 | hypothetical protein NGO1684 |
| *Neisseria meningitidis* MC58 | *N. men*1 | AAF40762 | conserved hypothetical protein |
| *Neisseria meningitidis* Z2591 | *N. men*2 | CAB85382 | conserved hypothetical protein |
| *Nitrosomona europaea* ATCC 19718 | *N. eur* | NP_842285 | hypothetical protein NE2285 |
| *Nostoc punctiforme* PCC 73102 | *N. pun* | ZP_00111265 | COG0780: Enzyme related to GTP cyclohydrolase I |
| *Nostoc* sp. PCC 7120 | N. PCC | BAB73119 | all1162 |
| *Novosphingobium aromaticivorans* DSM 12444 | *N. aro* | ZP_00301998 | COG0780: Enzyme related to GTP cyclohydrolase I |
| *Oceanobacillus iheyensis* HTE831 | *O. ihe* | BAC14166 | hypothetical conserved protein |
| *Prochlorococcus marinus* str. MIT 9313 | *P. mar* | CAE21653 | conserved hypothetical protein |
| *Prochlorococcus marinus* subsp. *pastoris* str. CCMP1986 | *P. mar*1 | NP_893578 | hypothetical protein PMM1461 |
| *Prochlorococcus marinus* subsp. *marinus* str. CCMP1375 | *P. mar*2 | NP_876005 | GTP cyclohydrolase I family enzyme |
| *Porphyromonas gingivalis* W83 | *P. gin* | AAQ66412 | conserved hypothetical protein |
| *Rhodopirellula baltica* SH 1 | | CAD72755 | conserved hypothetical protein-putative GTP cyclohydrolase I |
| *Rhodopseudomonas palustris* CGA009 | | NP_948216 | GTP cyclohydrolase I |
| *Rubrivivax gelatinosus* PM1 | | ZP_00245616 | COG0780: Enzyme related to GTP cyclohydrolase I |
| *Silicibacter pomeroyi* DSS-3 | | AAV96974 | GTP cyclohydrolase family protein |
| *Silicibacter* sp. TM1040 | S. TM | ZP_00336449 | COG0780: Enzyme related to GTP cyclohydrolase I |
| *Sinorhizobium meliloti* 1021 | | NP_386491 | hypothetical protein SMc02723 |
| *Sinorhizobium meliloti* | *S. mel* | CAC46964 | CONSERVED HYPOTHETICAL PROTEIN |
| *Staphylococcus aureus* subsp. *aureus* MRSA252 | | YP_040209 | hypothetical protein SAR0782 |
| *Staphylococcus aureus* subsp. *aureus* COL | | YP_185663 | GTP cyclohydrolase I |
| *Staphylococcus aureus* subsp. *aureus* Mu50 | | BAB56890 | similar to GTP cyclohydrolase I |
| *Staphylococcus aureus* subsp. *aureus* MW2 | | BAB94555 | conserved hypothetical protein |
| *Staphylococcus aureus* subsp. *aureus* N315 | | NP_373938 | hypothetical protein SA0683 |
| *Staphylococcus epidermidis* ATCC 12228 | | NP_764065 | hypothetical protein SE0510 |
| *Staphylococcus epidermidis* RP62A | | YP_187987 | hypothetical protein SERP0394 |
| *Streptococcus mutans* UA159 | *S. mut* | AAN58623 | conserved hypothetical protein |
| *Streptococcus thermophilus* CNRZ1066 | | YP_141234 | hypothetical protein str0828 |
| *Streptococcus thermophilus* LMD-9 | | ZP_00388194 | COG0780: Enzyme related to GTP cyclohydrolase I |
| *Streptococcus thermophilus* LMG 18311 | | YP_139319 | hypothetical protein stu0828 |
| *Synechococcus elongatus* PCC 6301 | | YP_172960 | hypothetical protein syc2250_d |
| *Synechococcus* sp. PCC 7942 | | AAN46170 | unknown protein |
| *Synechococcus* sp. WH 8102 | S. WH | CAE06978 | conserved hypothetical protein |
| *Synechocystis* sp. PCC 6803 | S. PC | S77065 | hypothetical protein slr0711 |
| *Thermoanaerobacter tengcongensis* MB4 | *T. ten* | NP_623163 | Enzyme related to GTP cyclohydrolase I |
| *Thermosynechococcus elongatus* BP-1 | *T. elo*1 | NP_681009 | hypothetical protein tll0218 |
| *Thermotoga maritima* MSB8 | *T. mar* | NP_228600 | hypothetical protein TM0791 |
| *Thiobacillus denitrificans* ATCC | | ZP_00335625 | COG0780: Enzyme related to GTP |

TABLE 1-continued

QueF family: Class I (YkvM)

| Organism | Alignment Abbreviation[1] | Accession # | Databank Definition |
|---|---|---|---|
| 25259 | | | cyclohydrolase I |
| *Trichodesmium erythraeum* IMS101 | | ZP_00324960 | COG0780: Enzyme related to GTP cyclohydrolase I |
| *Wolinella succinogenes* DSM 1740 | W. suc | NP_906277 | hypothetical protein WS0003 |
| *Zymomonas mobilis* subsp. *mobilis* ZM4 | | AAV88950 | probable GTP cyclohydrolase I |
| *Zymomonas mobilis* | | AAD56930 | hypothetical protein; zm12orf10 |

[1]Representative sequences that are shown in alignment figures.

TABLE 2

QueF family: Class II (YqcD)

| Organism | Alignment Abbreviation[1] | Accession # | Databank Definition |
|---|---|---|---|
| *Acinetobacter* sp. ADP1 | | YP_046874 | hypothetical protein ACIAD2261 |
| *A. actinomycetemcomitans*-1 | A. act | ? | ? |
| *Actinobacillus pleuropneumoniae* serovar 1 str. 4074 | A. ple | ZP_00135322 | COG0780: Enzyme related to GTP cyclohydrolase I |
| *Azoarcus* sp. EbN1 | | YP_157993 | conserved hypothetical protein, predicted GTP cyclohydrolase I family |
| *Azobacter vinelandii* | A. vin | ZP_00342251 | COG0780: Enzyme related to GTP cyclohydrolase I |
| *Bacteriophage* KVP40 | | AAQ64194 | GTP cyclohydrolase I family protein |
| *Buchnera aphidicola* str. Sg (*Schizaphis graminum*) | B. aph | NP_660633 | hypothetical 29.0 kDa protein |
| *Bordetella bronchiseptica* RB50 | B. bro | NP_889875 | hypothetical protein BB3340 |
| *Bordetella parapertussis* 12822 | B. par | NP_884039 | hypothetical protein BPP1768 |
| *Bordetella pertussis* Tohama I | B. per | NP_880745 | hypothetical protein BP2084 |
| *Buchnera aphidicola* str. Sg (*Schizaphis graminum*) | | NP_660633 | hypothetical 29.0 kDa protein |
| *Burkholderia cepacia* R1808 | | ZP_00222733 | COG2904: Uncharacterized protein conserved in bacteria |
| *Burkholderia cepacia* R18194 | | ZP_00215787 | COG2904: Uncharacterized protein conserved in bacteria |
| *Burkholderia fungorum* LB400 | | ZP_00282699 | COG0780: Enzyme related to GTP cyclohydrolase I |
| *Burkholderia mallei* ATCC 23344 | | YP_102019 | GTP cyclohydrolase family protein |
| *Burkholderia pseudomallei* K96243 | | YP_107261 | putative GTP cyclohydrolase I |
| *Chromobacterium violaceum* ATCC 12472 | C. vio | AAQ61412 | conserved hypothetical protein |
| *Coxiella burnetii* RSA 493 | C. bru | NP_819201 | hypothetical protein CBU0151 |
| *Dechloromonas aromatica* RCB | | ZP_00151388 | COG0780: Enzyme related to GTP cyclohydrolase I |
| *Desulfotalea psychrophila* LSv54 | | CAG34897 | conserved hypothetical protein |
| *Escherichia coli* 0157:H7 EDL933 | E. col1 | AAG57908 | orf, hypothetical protein |
| *Escherichia coli* 0157:H7 | E. col2 | BAB37077 | hypothetical protein |
| *Escherichia coli* CFT073 | E. col3 | NP_755237 | Hypothetical protein yqcD |
| *Escherichia coli* K12 | E. col4 | NP_417274 | hypothetical protein b2794 |
| *Haemophilus influenzae* Rd KW20 | H. inf | NP_439443 | hypothetical protein HI1291 |
| *Haemophilus influenzae* R2866 | | ZP_00157353 | COG0780: Enzyme related to GTP cyclohydrolase I |
| *Haemophilus influenzae* 86-028NP | | ZP_00321341 | COG0780: Enzyme related to GTP cyclohydrolase I |
| *Haemophilus ducreyi* 35000HP | H. duc | AAP96437 | possible GTP cyclohydrolase I |
| *Haemophilus somnus* 129PT | H. som | ZP_00122278 | COG0780: Enzyme related to GTP cyclohydrolase I |
| *Haemophilus somnus* 2336 | H. som | ZP_00133538 | COG0780: Enzyme related to GTP cyclohydrolase I |
| *Idiomarina loihiensis* L2TR | | YP_155244 | GTP cyclohydrolase I related protein |
| *Legionella pneumophila* str. Lens | | YP_126016 | hypothetical protein lpl0654 |
| *Legionella pneumophila* str. Paris | | YP_123008 | hypothetical protein lpp0670 |
| *Legionella pneumophila* subsp. *pneumophila* str. Philadelphia 1 | | YP_094652 | GTP cyclohydrolase I PLUS perhaps regulatory protein |

TABLE 2-continued

QueF family: Class II (YqcD)

| Organism | Alignment Abbreviation[1] | Accession # | Databank Definition |
|---|---|---|---|
| *Mannheimia succiniciproducens* MBEL55E | | YP_088261 | hypothetical protein MS1069 |
| *Microbulbifer degradans* 2-40 | | ZP_00314723 | COG0780: Enzyme related to GTP cyclohydrolase I |
| *Pasteurella multocida* Pm70 | P. mul | NP_245413 | hypothetical protein PM0476 |
| *Photorhabdus luminescens* subsp. *laumondii* TTO1 | | NP_928007 | hypothetical protein plu0662 |
| *Photorhabdus luminescens* | P. lum | AAO39145 | putative GTP cyclohydrolase I |
| *Photobacterium profundum* SS9 | | YP_131118 | hypothetical protein PBPRA2982 |
| *Polaromonas* sp. JS666 | | ZP_00361530 | COG0780: Enzyme related to GTP cyclohydrolase I |
| *Pseudomonas aeruginosa* PA01 | P. aer | NP_251496 | hypothetical protein PA2806 |
| *Pseudomonas aeruginosa* UCBPP-PA14 | | ZP_00135913 | COG0780: Enzyme related to GTP cyclohydrolase I |
| *Pseudomonas fluorescens* PfO-1 | | ZP_00263760 | COG0780: Enzyme related to GTP cyclohydrolase I |
| *Pseudomonas putida* KT2440 | P. put | AAN67773 | conserved hypothetical protein |
| *Pseudomonas yringae* pv. syringae B728a | P. syr2 | ZP_00124356 | COG0780: Enzyme related to GTP cyclohydrolase I |
| *Pseudomonas syringae* pv. Tomato str. DC3000 | | NP_791934 | GTP cyclohydrolase I, putative |
| *Psychrobacter* sp. 273-4 | | ZP_00147132 | COG0780: Enzyme related to GTP cyclohydrolase I |
| *Ralstonia eutropha* JMP134 | | ZP_00203010 | COG0780: Enzyme related to GTP cyclohydrolase I |
| *Ralstonia metallidurans* CH34 | R. met | ZP_00272373 | COG0780: Enzyme related to GTP cyclohydrolase I |
| *Ralstonia solanacearum* GM1000 | R. sol | NP_518569 | hypothetical protein RSc0448 |
| *Rickettsia rickettsii* | | ZP_00153168 | COG0780: Enzyme related to GTP cyclohydrolase I |
| *Rickettsia akari* str. Hartford | | ZP_00339820 | COG0780: Enzyme related to GTP cyclohydrolase I |
| *Rickettsia conorii* str. Malish 7 | R. con | NP_359739 | hypothetical protein RC0102 |
| *Rickettsia prowazekii* | R. pro | H71715 | hypothetical protein RP072 |
| *Rickettsia prowazekii* str. Madrid E | | NP_220466 | hypothetical protein RP072 |
| *Rickettsia sibirica* 246 | R. sib | EAA25828 | unknown |
| *Rickettsia typhi* str. Wilmington | | YP_067028 | hypothetical protein RT0060 |
| *Salmonella enterica* subsp. *enterica* serovar paratyphi A str. ATCC 9150 | | YP_151992 | hypothetical protein SPA2832 |
| *Salmonella enterica* subsp. *enterica* serovar Typhi Ty2 | S. ent1 | NP_806572 | hypothetical protein t2876 |
| *Salmonella enterica* subsp. *enterica* serovar Typhi str. CT18 | S. ent2 | NP_457363 | hypothetical protein STY3107 |
| *Salmonella enterica* subsp. *enterica* serovar choleraesuis str. SC-B67 | | YP_217894 | putative GTP cyclohydrolase I |
| *Salmonella typhimurium* LT2] | S. typ | AAL21847 | putative GTP cyclohydrolase I |
| *Shewanella oneidensis* MR-1 | S. one | NP_717220 | hypothetical protein SO1608 |
| *Shigella flexneri* 2a str. 301 | S. fle1 | AAN44295 | orf, conserved hypothetical protein |
| *Shigella flexneri* 2a str. 2457T | S. fle2 | AAP18120 | hypothetical protein S3002 |
| *Shewanella oneidensis* MR-1 | | NP_717220 | hypothetical protein SO1608 |
| *Vibrio cholerae* O1 biovar eltor str. N16961 | V. chl | AAF94064 | conserved hypothetical protein |
| *Vibrio fischeri* ES114 | | YP_203981 | hypothetical protein VF0598 |
| *Vibrio parahaemolyticus* RIMD 2210633 | V. par | NP_797080 | hypothetical protein VP0701 |
| *Vibrio vulnificus* CMCP6 | V. vul1 | AAO08830 | GTP cyclohydrolase I-like protein |
| *Vibrio vulnificus* YJ016 | V. vul2 | NP_933680 | GTP cyclohydrolase I-like protein |
| *Xanthomonas campestris* pv. Campestris str. ATCC 33913 | X. cam | NP_639130 | hypothetical protein XCC3785 |
| *Xanthomonas axonopodis* pv. citri str. 306 | X. axo | AAM38688 | conserved hypothetical protein |
| *Xanthomonas oryzae* pv. oryzae KACC10331 | | YP_202824 | hypothetical protein XOO4185 |
| *Xylella fastidiosa* 9a5c | X. fas1 | NP_299662 | hypothetical protein XF2383 |
| *Xylella fastidiosa* Ann-1 | X. fas2 | ZP_00041649 | COG0780: Enzyme related to GTP cyclohydrolase I |
| *Xylella fastidiosa* Dixon | X. fas3 | ZP_00039169 | COG0780: Enzyme related to GTP cyclohydrolase I |

TABLE 2-continued

QueF family: Class II (YqcD)

| Organism | Alignment Abbreviation[1] | Accession # | Databank Definition |
|---|---|---|---|
| *Xylella fastidiosa* Temecula1 | *X. tem* | NP_779599 | hypothetical protein PD1401 |
| *Yersinia pestis* biovar Medievalis str. 91001 | | AAS63001 | Enzyme related to GTP cyclohydrolase I |
| *Yersinia pestis* C092 | *Y. pes*1 | CAC89876 | conserved hypothetical protein |
| *Yersinia pestis* KIM | *Y. pes*2 | NP_670446 | hypothetical protein y3147 |
| *Yersinia pseudotuberculosis* IP 32953 | | YP_071518 | hypothetical protein YPTB3012 |

[1]Representative sequences that are shown in alignment figures.

QueF class II contains two domains (FIG. 4). The C-terminal domain of contains the region of homology to the GTP cyclohydrolase superfamily containing FolE and QueF class I. The N-terminal domain has often been annotated as a membrane-spanning domain, but transmembrane prediction programs (Hofmann and Stoffel. *Comput. Appl. Biosci.* 8(4):331-7, 1992) run on QueF class II do not detect any transmembrane segments. The fact that the QueF class I signature motif is located between the strictly conserved cysteine and glutamate residues in the QueF class I family but is located in the N-terminal domain in the QueF class II family indicates that a gene duplication occurred, with each domain retaining half the residues of the active site. Such a duplication event and redistribution of active site residues could allow QueF class II to evolve a simpler quaternary structure, potentially monomeric or homodimeric.

The native quaternary structures of *B. subtilis* and *E. coli* QueF were determined by gel filtration chromatography (FIG. 5). Chromatography was carried out on sepharose CL-6B in Tris buffer (pH 7.5) containing 100 mM KCl and 1 mM DTT. The elution volume of *B. subtilis* QueF (His$_6$-tagged and wild type) was consistent with a MW corresponding to a dodecamer (12.2 and 11.9 subunits, respectively), similar to the quaternary structure of FolE (decamer), while both the His$_6$-tagged and wild type YqcD eluted with a volume consistent with the molecular weight of a dimer (1.8 and 1.9 subunits, respectively).

FolE has been studied extensively, and several critical active site residues have been identified from structural and site-directed mutagenesis studies (Rebelo et al. *J. Mol. Biol.* 326:503-16, 2003). The crystal structure of *E. coli* FolE reveals a homodecamer of two pentameric substructures, each constructed by a cyclic arrangement of the 4-stranded β-sheets of the five monomers to form a 20-stranded β-barrel (Nar et al. *Structure*, 3:459-66, 1995). The interfaces between the monomeric subunits each contain a zinc and a GTP binding site. The three residues C110, H113 and C181 are involved in zinc binding (Rebelo et al. *J. Mol. Biol.* 326:503-16, 2003; Auerbach et al. *Proc. Natl. Acad. Sci. USA* 97:13567-72, 2000), while Glu152 forms a salt bridge with the $C_2$—$NH_2$ of the guanine moiety of bound GTP. FolE is part of a structural superfamily of functionally distant pterin/purine binding proteins which utilize a common oligomerization of the characteristic T-fold (Tunneling-fold), comprised of an antiparallel β-sheet and two helices, to form a $β_{2n}α_n$ barrel (Colloc'h et al. *Proteins* 39:142-54, 2000). Two barrels join in a head-to-head fashion to form a tunnel-like center. Other members of the FolE structural superfamily are 6-pyruvol tetrahydropterin synthase (n=3) (Nar et al. *EMBO J* 13(6):1255-62, 1994), urate oxidase (n=4) (Colloc'h et al. *Nat. Struct. Biol.* 4:947-52, 1997), and dihydroneopterin adolase (n=4) (Hennig et al. *Nat. Struct. Biol.* 5:357-62, 1998) which all similarly bind planar substrates of purine/pterin at the interface of monomers and use a positionally conserved Glu/Gln to anchor the substrate, although their chemistries and catalytic mechanisms are unrelated. The homology of QueF class I and FolE families demonstrates that QueF class I belongs to the T-fold structural superfamily.

EXAMPLE 4

Homology Modeling of QueF

This example describes methods used to generate a model of QueF. Based on the results, one skilled in the art can design QueF variants having the desired substrate specificity.

Using the homology between *B. subtilis* QueF and *E. coli* FolE, a homology model of the 3D structure of *B. subtilis* QueF (FIG. 6) was generated using the standard protocols of the homology program MODELLER-6 (version 1). The X-ray crystal structure of *E. coli* FolE (Nar et al., *Structure* 3:459-66, 1995) (GTP-CH-I; PDB entry 1FBX) was used as a template. The *B. subtilis* QueF sequence was obtained from GenBank (accession no. NP_389258, GeneID 939296).

To obtain an accurate model, the pair-wise alignment of *B. subtilis* QueF and *E. coli* FolE was extracted from the multiple sequence alignment (FIG. 3) and used in MODELLER. The resulting model was energy minimized in CNS (Brunger et al., *Acta Crystall. D* 54:905-21, 1998). The similarity in quaternary structure to *E. coli* FolE predicted a similarly located active site for *B. subtilis* QueF at the inter-subunit interface. Therefore, using the symmetry of the FolE multimer, a homodimer of the *B. subtilis* QueF monomeric model was generated and energy minimized in CNS. Then, a 7-cyano-7-deazaguanine molecule was docked onto the putative active site, located at the inter-subunit interface using the coordinates of bound GTP in the FolE structure as a starting model. The complexed model was energy minimized again.

The model was validated in PROCHECK (Vaguine et al. *Acta Crystallogr. D Biol. Crystallogr.* 55(1):191-205, 1999). The model (FIG. 6) includes residues Glu8-Ile161 of the *B. subtilis* QueF sequence (amino acids 8-161 of SEQ ID NO: 2), and lacks the 7 N-terminal and 3 C-terminal residues. It has a standard Ramachandran plot with 90.2% of residues falling in its favored regions, and 8.3%, 1.5% in the allowed and generously allowed regions, respectively. There are no residues in disallowed conformations (the model contains 10 glycine and 11 proline residues). The r.m.s. deviations of bonds and angles from standard values are 0.019 Å and 2.33°, respectively. A least square superposition with the FolE structure yields a r.m.s. deviation of 0.64 Å over 318 $C_\alpha$-atoms, indicating a good fit.

Figure 6:
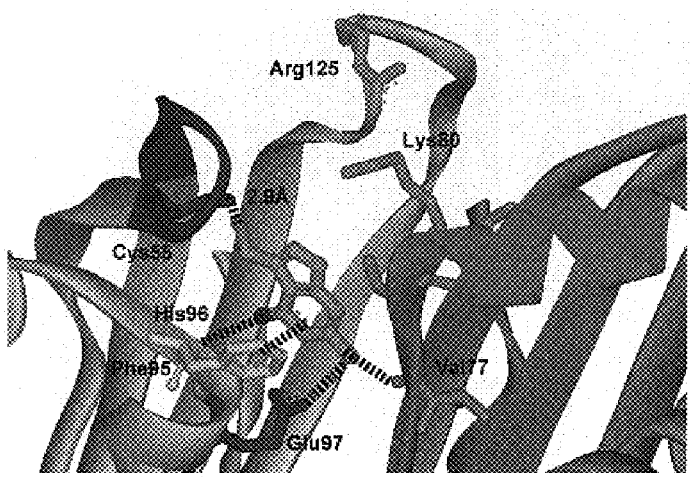
FIG. 6 is a schematic drawing showing the putative active site of *B. subtilis* QueF based on the homology model built from the crystal structure of *E. coli* FolE. A partial view is shown of the two monomers in the model (dark and light grey ribbons) and the putative substrate-binding mode at the interface. Potential active site interactions are indicated. The conserved QueF motif is in green, and the side-chains of the Glu and Cys residues conserved in both QueF and FolE are in red.

The model reveals a putative active site formed by residues at the interface of two QueF monomers (FIG. 6). The bound $preQ_0$ makes contacts with the two strictly conserved side chains Glu98 and Cys56, two interactions also found in the structure of the FolE/GTP complex. An additional side chain contact is a ring stacking interaction with Phe96, which is not present in FolE. All other interactions are with protein backbone atoms.

The specificity of the QueF motif (SEQ ID NO: 5) to the QueF family indicates that these residues might be involved in forming the binding site for NADPH. The model shown in FIG. 6 is consistent with this proposal and provides additional details of the putative NADPH binding pocket. In the model, three basic residues (Lys81, Lys84, Arg126), line a pocket formed by the conserved QueF motif. The two lysines are from one monomer, the arginine from the other.

EXAMPLE 5

Crystal Structure of B. subtilis QueF

This example describes methods used to determine the crystal structure of B. subtilis QueF at a resolution of 3.0 Å. One skilled in the art will recognize that similar methods can be used to determine the structure of other nitrile oxidoreductases, such as QueF variants. In addition, one skilled in the art will recognize that other crystallography methods can be used to determine a higher resolution crystal structure.

Several constructs and complexes were targeted, and a high throughput approach was used to increase the chance of success in obtaining crystals with quality X-ray diffraction. Native and $His_6$-tagged forms of QueF from B. subtillis were used (as noted in Example 2, the $His_6$-tagged proteins are fully enzymatically active). N-terminally $His_6$-tagged constructs of the proteins were expressed in E. coli and affinity purified as described in Example 1 (>10 mg pure protein per liter of cell culture was obtained). Wild-type proteins were prepared by enzymatic cleavage of the $His_6$ tag at the Factor Xa site.

Prior to use in crystallization, the enzyme was dialyzed against Tris (100 mM, pH 7.5), KCl (100 mM) and dithiothreitol (2 mM). Initial crystallization conditions were obtained for the wild-type B. subtilis QueF (15 mg/mL, apo enzyme) after subjecting the enzyme to high-throughput sparse-matrix and grid crystallization screens using the vapor diffusion method. Briefly, sitting drops (200 nL) were set up using the Mosquito crystallization robot (Molecular Dimensions, Ltd., U.K.) in 96-well low-profile Greiner microplates (Greiner BioOne, Fla.), and imaged with the CrystalPro imaging system (Tritek Corp., VA). Crystallization (1536 experiments) was performed at 20° C. and 4° C.

Attempts to crystallize the apo enzyme (the enzyme without substrate present) led to showers of single or clustered hexagonal crystal plates (0.05×0.1×0.1 $mm^3$, space group $P6_1$) that grew from 15 mg/mL enzyme, any of PEG3350, PEG2000, PEG1000, or PEG550 mme as the precipitant, a variety of buffers in the pH range 6.0-9.0, and 50 mM $CaCl_2$. After refinement of conditions, the showering and clustering effects were controlled by lowering the $CaCl_2$ and protein concentrations to 30 mM, and 4 mg/mL, respectively (FIG. 7A, left). However, the crystals remained highly mosaic (2.0-3.0°) and their diffraction quality poor as assessed by lack of detectable diffraction beyond 7-8 Å resolution. Because these initial crystals diffracted only to 8 Å at the synchrotron, further improvement of crystal quality was obtained.

The similarity between B. subtilis QueF and E. coli FolE in sequence and multimeric quaternary structure predicted a similar location for the active site of B. subtilis QueF at the inter-subunit interface. Based on the crystal structure of E. coli FolE, a 3D homology model of two adjacent QueF monomers was built and a $preQ_0$ molecule was docked in the putative active site (FIG. 6). In one monomer, the docked substrate interacts with the two invariant side chains of Glu98 and Cys56 (two interactions also found in the structure of the FolE/GTP complex (residue numbers are those of B. subtilis QueF), the conserved Phe96, and the backbone NH of His97. In the other monomer, the side chain of Glu98 and the backbone CO of Val78 interact with substrate. Significantly, the QueF motif lies in a nearby α-helix. This model demonstrates that $preQ_0$ plays a role in stabilizing and tying together the functional, multimeric enzyme structure, bridging the two halves of the active site, that is, the QueF motif from one monomer and the invariant Glu and Cys from the other. In view of this information, $preQ_0$ was included in the crystallization of QueF.

The refined conditions for crystal growth obtained for the apo enzyme (4 mg/mL protein, 20% PEG550 mme, 100 mM HEPES, 30 mM $CaCl_2$) were applied to samples containing enzyme pre-incubated with $preQ_0$ (concentrations of 0.2, 0.4, 0.6, 0.8, 1.0, 1.2, 2, and 5 mM, that is an enzyme:$preQ_0$ molar ratio of 1:1-1:25). To rule out the effect of DMSO, control experiments were set up simultaneously using enzyme pre-incubated with the same added volume of DMSO.

A second, trigonal crystal form (space group $P3_121$) appeared as the sole form only in drops containing $\geq 1.2$ mM $preQ_0$ (enzyme:$preQ_0$ molar ratio $\geq 1:6$, FIG. 7A, right). $PreQ_0$ concentrations $\leq 0.8$ mM (molar ratio $\leq 1:4$) yielded the hexagonal form and middle concentrations yielded a mixture of both forms in the same drop. The trigonal form diffracted synchrotron X-rays to 2.25 Å with apparent mosaicity of 0.29°. Analysis of the solvent content with the CCP4 package (Collaborative Computational Project, Acta Crystallo. D 50: 760-3, 1994,) gave a unique solution consisting of half a dodecamer in the asymmetric unit (FIG. 6B, Table 3). Growth of larger crystals was aided by inclusion of 1% (w/v) dextran sulfate or 100 mM imidazole in the crystallization buffer. Pre-incubation of enzyme with DMSO alone, or with the cofactor for catalysis α-NADP, failed to produce the trigonal crystals. A self-rotation search in CNS (Brunger et al., Acta Crystall. D 54: 905-21, 1998) detected 6-fold non-crystallographic symmetry around an axis parallel to the c-axis of the unit cell.

TABLE 3

| X-ray data collection parameters | |
|---|---|
| Wavelength (Å) | 0.97944 |
| Space group | $P3_121$ |
| Unit Cell parameters (Å) | A = b = 93.52, c = 193.76 |
| Crystal mosaicity (°) | 0.29 |
| Resolution range (Å) | 2.25-50.0 (2.25-2.33) |
| No. observations | 278757 (17116) |
| No. unique reflections | 46429 (3890) |
| Completeness (%) | 97.8 (83.3) |
| Redundancy | 6.0 (4.3) |
| $R_{merge}$ | 0.078 (0.39) |
| $<I/\sigma(I)>$ | 9.9 (7.9) |
| Matthews coefficient ($Å^3 Da^{-1}$) | 2.1 |

TABLE 3-continued

X-ray data collection parameters

| | |
|---|---|
| Solvent content (%) | 40.1 |
| Asymmetric unit content | 6 monomers |

A structure determination was attempted by molecular replacement, using both the homology model and the structure of E. coli FolE, but failed to provide a solution. Therefore, the Se-MAD (selenium-multiple anomalous dispersion) method was used (Terwilliger, Acta Crystallo., D 50:17-23, 1994). Briefly, selenomethionine-labeled proteins were prepared using standard procedures (Hendrickson et al., EMBO J 9(5):1665-72, 1990, herein incorporated by reference for the method), and crystals of the selenomethionine-labeled protein were produced using standard methods, and these diffracted synchrotron X-rays to 3.0 Å. This data-set can be used to solve the structure by seleno-multiwavelength anomalous diffraction.

Crystals were screened for diffraction quality at beam line 11-1 of the Stanford Synchrotron Research Laboratory (SSRL), using a robot for mounting of crystals (using the SSRL crystal freezing cassette kit which holds 96 crystals at a time). A single-wavelength data set was collected from a crystal of the enzyme-preQ$_0$ complex on an ADSC Quantum 315 CCD detector at SSRL beamline 1-5 (crystal-to-detector distance 240 mm). Data were processed using the HKL package (Otwinowski & Minor, Methods In Enzymology 276:307-26, 1997).

EXAMPLE 6

Substitutions at Cys56

This example describes methods used to alter the amino acid present at position Cys56 in B. subtilis QueF. One skilled in the art will recognize that similar methods can be used to substitute any amino acid in any QueF sequence.

Utilizing the QuickChange (Stratagene) mutagenesis protocol Cys56 of B. subtilis QueF was changed to Ala and Ser. The recombinant mutant His$_6$-QueF(Cys56Ala) and His$_6$-QueF(Cys56Ser) proteins were purified as described above for the native proteins. Both mutants retained the ability to reduce preQ$_0$ under the standard nitrile oxido-reductase assay conditions, although activity was reduced up to 10-fold.

EXAMPLE 7

Changing Substrate Specificity by Altering Glu98

This example describes methods that can be used to alter the Glu98 residue in B. subtilis QueF to another amino acid, thereby changing the substrate specificity of the nitrile oxido-reductase. One skilled in the art can use similar methods to alter the corresponding Glu in other QueF sequences (for example using the alignment provided in FIGS. 9A-G and 10A-K). Although particular methods are described, one skilled in the art will appreciate that other routine methods can be used to change this residue, and well as any other desired residue.

Based on the conservation of Glu98 in the sequences of both the FolE and Que families and the proposed model of B. subtilis QueF (FIG. 6), it is likely that structural and functional conservation will be observed for this residue, with Glu98 located at the bottom of the substrate-binding pocket of QueF where it can interact with the C$_2$—NH$_2$ group of preQ$_0$. Thus, changing this residue can be used to create a nitrile oxido-reductase enzyme with altered substrate specificity with regards to functional groups located at positions equivalent to C$_2$.

For example, substitution of Glu98 with an amino acid possessing a neutral side chain (such as Ala, Leu, Ile, Met, Val, Gln, or Asn) would result in a nitrile oxido-reductase enzyme better able to accept substrates that lack an amine at the C$_2$-postion, such as the aromatic nitrites phenylacetonitrile, 3-cyano-indole, and benzonitrile, as well as alkyl nitrites such as acrylonitrile. Conversely, mutation of Glu98 to a basic residue such as Lys or Arg will generate a nitrile oxido-reductase enzyme better able to accept substrates with a carboxylate residue in the site occupied by the exocyclic amine of preQ$_0$ such as p-carboxyphenylacetonitrile, p-carboxybenzonitrile, and so forth. Particular examples of substitutions to QueF sequences are shown in Table 3. However, one skilled in the art can identify the appropriate Glu in any nitrile oxido reductase sequence, for example using the alignment shown in FIGS. 9A-G and 10A-K.

TABLE 4

Changes to QueF that can be made to alter substrate specificity

| Nitrile Substrate | Substitution to SEQ ID NO:2 | Substitution to SEQ ID NO:4 |
|---|---|---|
| Nitriles lacking an amine at the C$_2$-postion, such as aromatic nitriles (for example phenylacetonitrile, 3-cyano-indole and benzonitrile) and alkyl nitriles (for example acrylonitrile) | Glu98Ala Glu98Leu Glu98Ile Glu98Met Glu98Val Glu98Gln Glu98Asn | Glu230Ala Glu230Leu Glu230Ile Glu230Met Glu230Val Glu230Gln Glu230Asn |
| Nitriles with a carboxylate residue in the site occupied by the exocyclic amine of preQ$_0$ (for example p-carboxyphenylacetonitrile and p-carboxybenzonitrile) | Glu98Lys Glu98Arg | Glu230Lys Glu230Arg |

The Glu98 QueF mutants can be constructed using the QuickChange protocol (Stratagene) with the appropriate mutagenic primers and the pET30 construct harboring a queF coding sequence with the 5'-His$_6$ cassette. Substitutions of Glu98 in SEQ ID NO: 2 with Ala, Leu, or Lys have been made. Mutated plasmids are sequenced to confirm incorporation of the desired mutation, and the mutant recombinant enzymes can be over-produced by transforming E. coli BL21 (DE3) with the plasmids. Purification of the mutant enzymes can be carried out with Ni-affinity chromatography following the protocols used for the wild-type enzyme.

Figure 11:
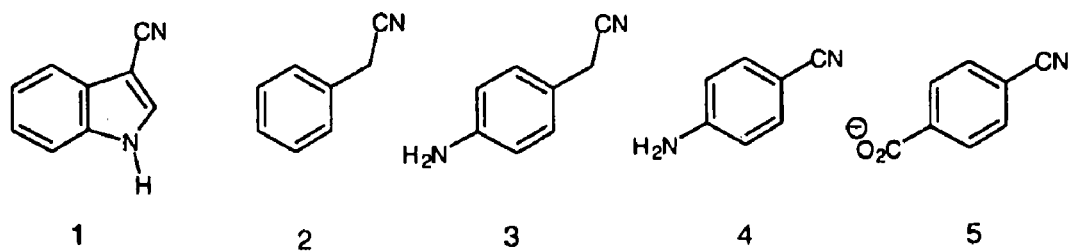
FIG. 11 is a schematic drawing showing exemplary nitrile containing compounds. Compound 1 retains the overall bicyclic core and nitrile group position while removing all the heteroatoms from the 6-membered ring. Compound 2 removes the remaining heteroatom in the 5-membered ring, leaving the potential for only hydrophobic interactions. Compound 3 reintroduces the exocyclic amine at position "C$_2$" to permit investigation of that interaction in the absence of the other heteroatoms, while compound 4 eliminates the methylene so that the position of the nitrile relative to Cys56 can be determined. Compound 5 reverses the polarity observed with 4, and permits an assessment of how well the enzyme tolerates such a charge reversal between the enzyme and substrate. Binding of 5 the Arg mutant may approximate preQ$_0$ binding to the wild-type enzyme since the loss of the methylene group in 5 will be offset (at least partially) by the longer length of Arg relative to Glu.
Figure 10A:
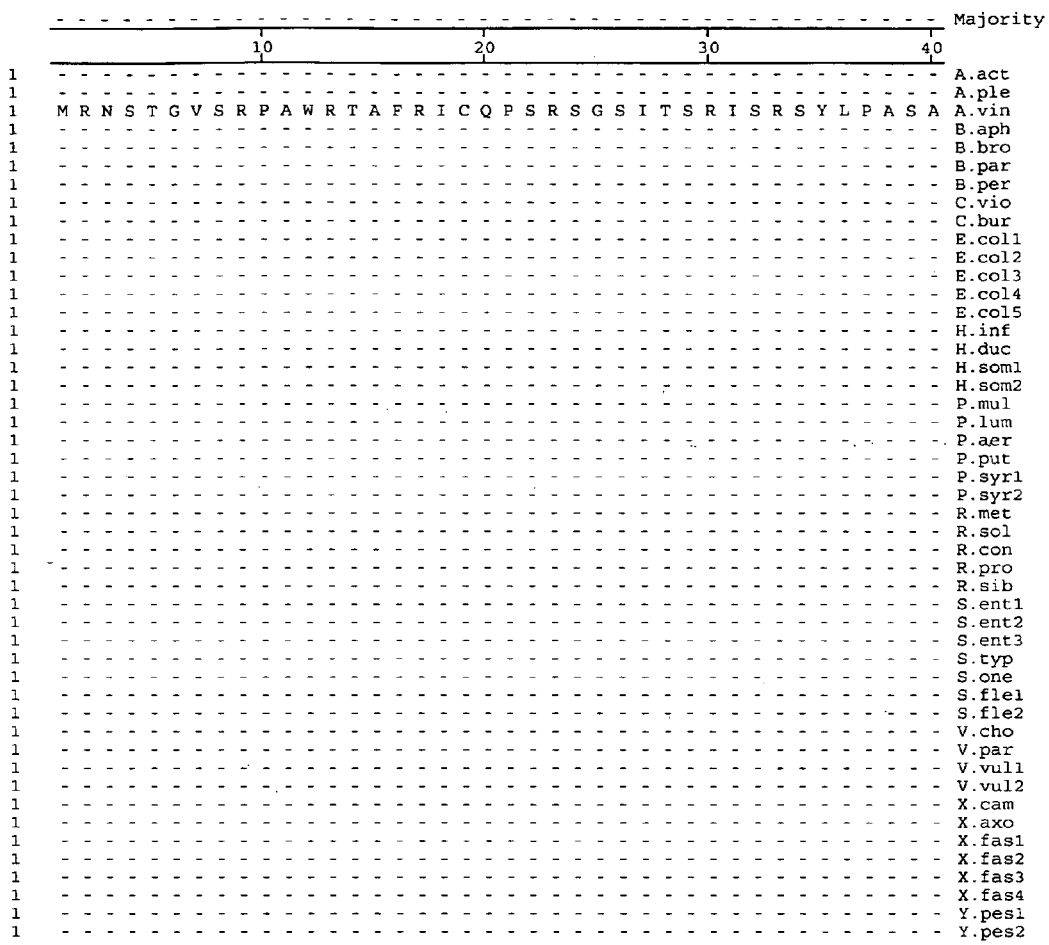
Figure 10B:
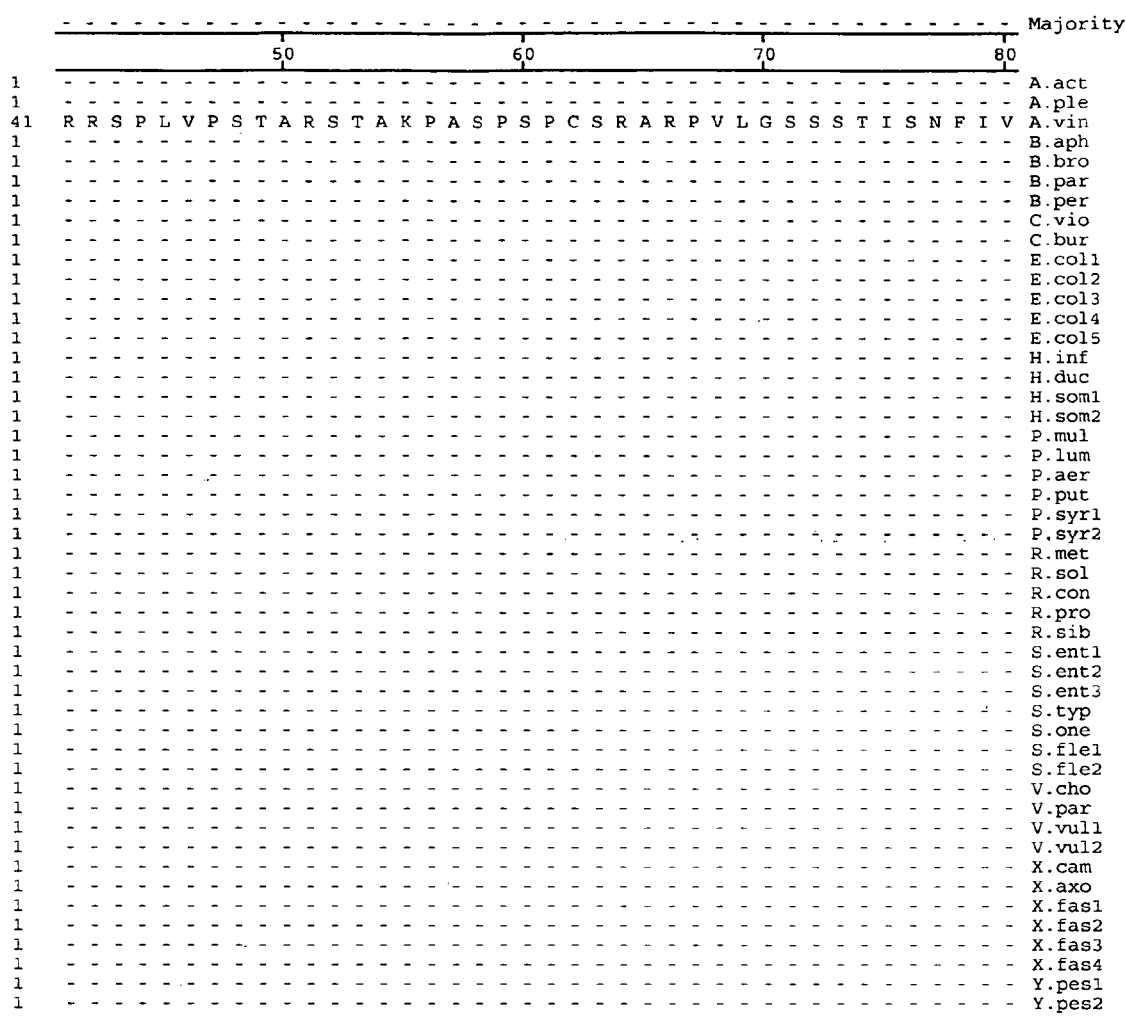

The purified nitrile oxido-reductase enzymes are screened for activity with the desired nitrile (such as phenylacetonitrile, PreQ$_0$, 3-cyanoindole, benzonitrile, and the nitrites shown in FIG. 11), for example using the standard continuous UV-assay developed for wild-type QueF (see Example 2), or to monitor for very low turnover the HPLC system developed for monitoring wild-type activity described in Example 2 can be used.

For example the Glu98Ala mutant has significantly reduced ability to reduce PreQ$_0$, while the Km for NADPH is not significantly impacted.

Enzymes showing the ability to significantly reduce a nitrile to the desired amine can be selected. In particular examples, the nitrile oxidoreductase has a similar or greater specific activity for the nitrile, than the specific activity of $PreQ_0$ reduction by wild-type QueF (such as SEQ ID NOS: 2, 4, and 6-95).

EXAMPLE 8

Screening for QueF Variants

Based on the QueF crystal structure and other information provided herein, those skilled in the art can design variants of QueF enzymes, for example using rational-design and directed-evolution. In particular examples, variant QueF enzymes have altered substrate specificity. In other examples, variant QueF enzymes include one or more conservative amino acid substitutions that do not alter the substrate specificity of the enzyme. Such variant enzymes can be used to reduce nitrites to amines in vitro or in vivo.

Figure 8:
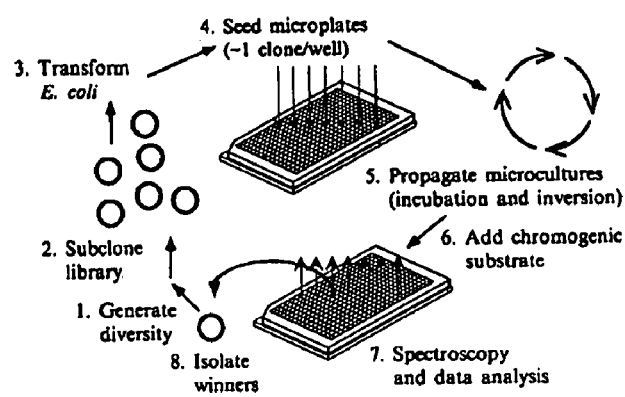
FIG. 8 is a schematic drawing of the screening protocol that can be employed for the detection of mutant QueF enzymes with phenylacetonitrile reductase activity. A 96-well format can be used instead of the 384-well format shown.

A throughput screen can be used to assay for nitrile reductase activity in libraries generated through directed evolution of a QueF enzyme. The utilization of NADPH in the reaction catalyzed by QueF provides an optical handle for screening variant enzyme activity. In one example, the screening method is similar to that developed by Geddie et al. (*Methods Enzymol.* 388:134-45, 2004). However, one skilled in the art will appreciate that other types of multi-welled plates can be used, such as a 96-well or 384-well format. A schematic for the method is presented in FIG. 8. In this method, culture growth and assays all occur in the same microtiter well. Under normal growth the wells will contain both lysed and viable cells, such that free enzyme is released into the culture medium. This eliminates the need for time-consuming replica plating, cell lysis, and centrifugation steps, as assays are carried out directly on these solutions, and cells from positive wells can be propagated from the assay solution.

Briefly, the method involves introducing molecular diversity into gene sequences. The resulting mutant library is seeded into wells at ~1 colony/well (colony density calculated by plating the transformed cells and determining the transformation frequency), sealing the plates and growing the cultures overnight at 37° C., adding the assay solution, which can contain a buffer (such as HEPES or Tris) at an appropriate pH (such as 7.0, 7.25, or 7.5) and concentration (such as 10-100 mM), the nitrile of interest (such as $preQ_0$ or phenylacetonitrile) at an appropriate concentration (such as 10-500 μM), and NADPH at an appropriate concentration (such as 20-150 μM), and stacking the plates at a 45° angle to allow the cells to settle (about 4 hrs), and then placing the plates in the plate reader to measure the consumption of NADPH. Quantitation of NADPH concentration can then be carried out by measuring, for example, the absorption at 340 nm in the microplate reader.

The assay results can be validated by separately transforming *E. coli* with wild-type QueF in the appropriate vector and empty vector, seeding microplates with cells from these transformation mixtures, propagating the colonies, and carrying out the assays as described above. Results from cells expressing a wild-type QueF protein provide a positive control, and cells transformed with empty vector provide a negative control.

An alternative method that can be used is based on the methods disclosed in (Franke et al. *Methods Enzymol.* 338:224-38, 2004; Schmidt et al. *Methods Enzymol.* 338: 199-207, 2004). Briefly, nucleic acid molecules are mutagenized as described above, replica plating of the microcultures, cell growth, lysis and centrifugation to generate a cell-free lysate, and then performing activity assays in a separate microtiter plate. The availability of microtiter plates incorporating immobilized $Ni^{2+}$ allows for the assay of essentially pure QueF protein when cell lysis screens are utilized, which may be useful if the presence of endogenous dehydrogenases result in a high background and eliminates the need to centrifuge the microtiter plate and subsequent transfer of the supernatents. Analysis of nitrile oxido-reductase activity in the microtiter plates can then be carried as described above.

Generating a Mutant Library

Methods of generating a mutant library are known in the art (for example see Arnold, F. *Nature* 409:253-7, 2001; Lutz et al. *Curr. Opin. Biotechnol.* 15:291-7, 2004) In one example, the method includes combining early rounds of error-prone PCR (Caldwel & Joyce *PCR Methods and Applications* 2:28-33, 1992; Vartanian et al. *Nucleic Acids Res.* 24:2627-2631, 1996) with latter rounds of recombination to produce catalysts with optimal characteristics (for example, Aguinaldo & Arnold, *Methods Mol. Biol.* 231:105-10, 2003). For example, a native QueF sequence (such as a sequence that includes the sequence shown in SEQ ID NO: 1 or 3) can be subjected to standard error-prone PCR under conditions that result in a nucleotide error frequency of ~2%. For example, *B. subtilis* QueF (SEQ ID NO: 2) is 165 amino acids, and the frequency of amino acid mutation is 0.745 per nucleotide change, an average of ~2.5 amino-acid mutations per peptide is expected. This will create a population of sequences containing a significant percentage of single, double, and triple mutants, and only a small percentage of wild-type sequences. The resulting sequences can be inserted into a vector, such as a pET vector, or a vector that allows constitutive expression (such as pBAD (Invitrogen) and pPROTtet (Clontech)).

Microplates are seeded and propagated with the mutagenized library and controls (wild-type QueF vector and empty vector) as described above. Controls can be assayed at a frequency of 1% within each run of 20 microtiter plates. Positive clones can be subjected to a secondary screen to confirm activity. If many positive hits are observed, the secondary screen can utilize the 96-well format. Specifically, an aliquot from each of the microculture/assay solutions exhibiting apparent activity is removed and diluted into fresh LB (w/antibiotic) followed by aliquoting replicate samples into a new, sterile 96-well microplate. After incubating overnight the assay solution lacking NADPH will be added, the cells allowed to settle out as above, and NADPH added immediately prior to monitoring the reaction in a kinetic run on the plate reader. If there are only a small number of positive hits these will be diluted into fresh LB (w/antibiotic) and grown in culture tubes, and the supernatants assayed after standard cell lysis with lysozyme and centrifugation to obtain cell-free extracts. The best clones can be archived by storing in 30% glycerol at −80° C., the plasmids isolated for DNA sequencing, and the mutant enzymes purified via nickel-affinity chromatography for more thorough characterization.

In some examples, error-prone PCR can be combined with recombination (for example see (Zhao et al. *Nat. Biotechnol.* 16:258-61, 1998; Aguinaldo & Arnold, *Methods Mol. Biol.* 192:235-9, 2002; Aguinaldo & Arnold, *Methods Mol. Biol.* 231:105-10, 2003). Since recombination is a more effective strategy with templates incorporating more substitutions, we will create a new mutant library by error-prone PCR under conditions in which the nucleotide error frequency is ~3% (Vartanian et al. *Nucleic Acids Res.* 24:2627-2631, 1996), giving an average of 3.7 amino acid substitutions per polypeptide. Screening of the library generated after recombination will follow the protocols described above.

Measuring NADPH Oxidation

NADPH oxidation can be measured by the loss of absorption of NADPH in the UV (for example at 340 nm). Briefly, the absorption of reaction assays over varying time (seconds to hours) is measured in a standard UV spectrophotometer or in a microtiter plate reader (for example one capable of analyzing plates with 96 wells).

In addition, NADPH oxidation can be measured by measuring the loss of the intrinsic NADPH fluorescence. Excitation occurs at 340 nm and emission is observed at 455 nm (for example see Hara et al. *Biochem. J.* 313:373-6, 1996 and Matsuura et al. *Biochem. J.* 313:179-84, 1996).

Measuring Amine Production

As an alternative to (or in addition to) measuring NADPH oxidation, the formation of the amine from the nitrile can be measured by detecting the primary amine by post-analysis derivation to form fluorescent adducts. For example, the amine can be reacted with dansyl chloride followed by excitation at 348 nm and emission at 535 and 560 nm (for example using the method of Kasai et al. *Nucleic Acids Res.* 7:231-8, 1979). Alternatively, the amine can be reacted with fluorescamine (excitation at 390 nm, emission at 475 nm) (for example using the method of Takashashi et al. *J. Biol. Chem.* 272:3437-43, 1997; Weigele et al. *J. Am. Chem. Soc.* 94:5927-8, 1972). In yet another example, the amine can be reacted with o-phthalaldehyde (excitation at 340 nm, emission at 455 nm) (for example using the method of Benson & Hare, *Proc. Nat. Acad. Sci. USA* 72:619-22, 1975).

Exemplary Nitriles

The ability of both wild-type and mutant nitrile oxido-reductase enzymes to bind and react with a variety of aromatic nitrites (such as those shown in FIG. 11) designed to interrogate structural interactions in the vicinity of the $C_2$—$NH_2$ can be determined. In addition, the ability of wild-type and mutant nitrile oxido-reductase enzymes to bind and react with other nitrites, such as alkyl nitrites (for example such as acrylonitrile and adiponitrile), can be determined using the method disclosed herein.

All of the compounds listed in FIG. 11 are commercially available, and differ in the presence of an amine, a carboxylate, or no substitution at the position equivalent to $C_2$ of $preQ_0$.

The ability of purified mutant and wild-type nitrile oxido-reductase enzymes to reduce each nitrile compound in FIG. 11 (or other nitrile of interest) can be determined using the methods described above. Enzymes demonstrating an ability to reduce one or more nitrites can be selected and cloned to identify the mutation that provides the nitrile oxido-reductase the ability to reduce that nitrile.

Compounds 1 and 2, which lack an exocyclic amine, may show the greatest relative activity/binding with the Glu98Leu/Gln mutants, since the substitution of a neutral residue for Glu is expected to favor the binding of these neutral aromatics. Conversely, compounds 3 and 4 should exhibit the highest relative activity/binding with the wild-type enzyme, while compound 5 should show no activity/binding to the wild-type enzyme and the strongest activity/binding to the Arg mutant.

EXAMPLE 9

Biocatalytic Reduction of Nitriles to Amines In Vitro

This example describes methods that can be used to reduce nitrites to the corresponding amine in vitro. Although particular niriles and nitrile oxido-reductases are disclosed, one skilled in the art will appreciate that similar methods can be used for other combinations of niriles and nitile oxido-reductases.

The method includes incubating one or more nitrites with one or more nitrile oxido-reductases under conditions that permit substantial reduction of the nitrites to the appropriate amine. For example, the nitrile is contacted with a substantially purified nitrile oxido-reductase in the presence of NADPH to drive the reduction of the nitrile. In some examples, the reaction chamber excess NADPH is used to promoted complete reduction of the nitrile. In other examples, the reaction chamber includes a catalytic amount of NADPH and an NADPH regeneration system (such as phosphite dehydrogenase), which has been engineered to utilize NADPH instead of NADH, or formate dehydrogenase engineered to utilize NADPH.

In some examples, the reaction is performed at 20-40° C., such as 30° C., for about 30 seconds to two hours, at a pH of 6.0-8.5 (such as pH 7.5). In particular examples, NADPH is present at concentrations of 500 μM to 50 mM). The reaction can include water and buffers (such as those that can buffer in the ranges described above, for example a thiol reductant, such as DTT or BME. In some examples, the reaction includes salt, salt such as NaCl or KCl.

EXAMPLE 10

Biocatalytic Reduction of Nitriles to Amines In Vivo

This example describes methods that can be used to reduce nitrites to the corresponding amine in vivo. Although particular niriles and nitile oxido-reductases are disclosed, one skilled in the art will appreciate that similar methods can be used for other combinations of niriles and nitile oxido-reductases.

The method includes contacting a cell expressing one or more exogenous nitile oxido-reductases with one or more nitrites under conditions that permit substantial reduction of the nitrites to the appropriate amines. The exogenous nitile oxido-reductases can be a fusion peptide that includes an amino acid sequence that permits secretion of the peptide from the cell. The secretory signal peptide can be linked to the N- or C-terminus of a nitile oxido-reductase, in the presence or absence of spacer amino acids. Examples of secretory signal peptide sequences are known. For example, signal peptides generally include several (4 to 12) hydrophobic residues, and a basic residue a few residues before the hydrophobic sequence. Particular examples include, but are not limited to: MKWVTFLLLLFISGSAFS (SEQ ID NO: 96), MDMRAPAQIFGFLLLLFPGTRC (SEQ ID NO: 97), and MKATKLVLGAVILGSTLLAG (SEQ ID NO: 98). In particular examples, the exogenous nitile oxido-reductases are a degenerate nucleotide sequence that permits expression of the exogenous nitile oxido-reductases in the particular cell used.

One skilled in the art will appreciate that the culture medium will depend on the cell used. For example, if the cell is a bacterial cell, a bacterial growth medium such as Luria broth can be used, if the cell is a yeast cell a yeast growth medium such as YPD yeast growth medium can be used, and if the cell is a mammalian cell a mammalian growth medium such as RPMI or DMEM can be used. Cells are generally grown at 25-37° C., depending on the cell type.

In some examples, the cell over-expresses an NADPH regeneration system, such as phosphite dehydrogenase, but that would also require a transport system for the co-substrate. Phosphite dehydrogenase sequences are publicly available.

The resulting amine(s) can be isolated from the cell or the culture medium.

EXAMPLE 11

QueF Sequences Containing Conservative Substitutions

This example provides specific examples of conservative amino acid substitutions that can be made to a nitrile oxido-reductase sequence, such as those shown in SEQ ID NOS: 2 and 4. Conservative amino acid substitutions can be made to a nitrile oxido-reductase that has the same nitrile substrate specificity as the native sequence, or to a nitrile oxido-reductase that has a nitrile substrate specificity that differs from the native sequence (such as a nitrile oxido-reductase that includes a mutation at Glu98, see Example 7). Although particular substitutions are provided herein, one skilled in the art will recognize that other such substitutions can be made, without substantially altering the biological activity of the nitrile oxido-reductase.

Based on the alignment of QueF sequences shown in FIGS. 9A-G and 10A-K, one skilled in the art can identify amino acid residues that can be changed, without substantially altering the biological activity of the nitrile oxido-reductase. For example, positions containing several different amino acids between different species (such as at least 4, at least 5, at least 6, or at least 7 different amino acids at a position) are not likely conserved, and therefore less likely to be important for the biological function of the protein. Examples of such positions include, but are not limited to E6, I103, and G141 (position numbers refer to SEQ ID NO: 2, and one skilled in the art can determine the corresponding position in the homolog sequences shown in FIGS. 9A-G and 10A-K).

In contrast, positions containing fewer or no different amino acids between different species (such as no more than 3, no more than 2, no more than 1, or 0 different amino acids at a position) are more likely conserved, and therefore more likely to be important for the biological function of the protein. Examples of such positions include, but are not limited to the QueF motif (SEQ ID NO: 5), and amino acids G16, Q61, and R126 (position numbers refer to SEQ ID NO: 2, and one skilled in the art can determine the corresponding position in the homolog sequences shown in FIGS. 9A-G and 10A-K).

While this disclosure has been described with particular embodiments, it will be obvious to those of ordinary skill in the art that variations of the disclosed embodiments may be used and it is intended that the disclosure may be practiced otherwise than as specifically described herein. Accordingly, this disclosure includes all modifications encompassed within the spirit and scope of the disclosure as defined by the claims below.

We claim:

1. A method of reducing a nitrile containing compound to an amine, comprising;
   contacting the nitrile containing compound with a nitrile oxido-reductase under conditions sufficient for substantially reducing the nitrile containing compound to the amine, wherein the nitrile oxido-reductase comprises at least 90% sequence identity to the amino acid sequence of SEQ ID NO: 4, includes the amino acid sequence of SEQ ID NO: 5, and retains the ability to reduce the nitrile containing compound to the amine.

2. The method of claim 1, wherein the amine is a primary amine.

3. The method of claim 1, wherein the provided nitrile oxido-reductase is substantially isolated.

4. The method of claim 1, wherein the nitrile containing compound comprises the structure —RCN, wherein R is an aromatic group, an alkyl group, or a mixed aromatic/alkyl group.

5. The method of claim 1, wherein the amino acid sequence comprising at least 90% sequence identity to SEQ ID NO: 4 comprises 1-10 conservative amino acid substitutions and retains the ability to reduce the nitrile containing compound to the amine.

6. The method of claim 1, wherein the nitrile oxido-reductase comprises the amino acid sequence of SEQ ID NO: 4.

7. The method of claim 2, wherein the nitrile containing compound comprises a 7-cyano-7-dezazguanine (preQ$_0$) and the primary amine comprises a 7-aminomethyl-7-dezazguanine (preQ$_1$).

8. The method of claim 1, wherein the amino acid sequence comprising at least 90% sequence identity to the amino acid sequence of SEQ ID NO: 4 comprises a substitution at Glu230.

9. The method of claim 8, wherein the substitution at Glu230 comprises Glu230Ala, Glu230Leu, Glu230Ile, Glu230Met, Glu230Val, Glu230Gln, or Glu230Asn.

10. The method of claim 9, wherein the nitrile containing compound comprises an aromatic nitrile.

11. The method of claim 10, wherein the aromatic nitrile comprises phenylacetonitrile, 3-cyano-indole, or benzonitrile.

12. The method of claim 9, wherein the nitrile containing compound comprises an alkyl nitrile.

13. The method of claim 12, wherein the alkyl nitrile comprises an acrylonitrile.

14. The method of claim 8, wherein the substitution at Glu230 comprises Glu230Lys or Glu230Arg.

15. The method of claim 14, wherein the nitrile containing compound comprises a carboxylate residue in the site occupied by the exocyclic amine of preQ$_0$.

16. The method of claim 15, wherein the compound comprising a carboxylate residue in the site occupied by the exocyclic amine of preQ$_0$ comprises p-carboxyphenylacetonitrile or p-carboxybenzonitrile.

17. The method of claim 1, wherein the nitrite containing compound is contacted with the nitrite oxido-reductase in the presence of NADPH.

18. The method of claim 1, wherein the nitrite containing compound is contacted with the nitrite oxido-reductase in the presence of an NADPH regeneration system.

19. The method of claim 17, wherein the NADPH regeneration system comprises phosphite dehydrogenase.

20. The method of claim 1, wherein the method is performed in vitro.

21. The method of claim 1, wherein the method is performed in a cell comprising a recombinant nitrite oxido-reductase.

22. A method of producing an amine, comprising:
   providing a nitrite, that when reduced produces the amine;
   providing a nitrile oxido-reductase comprising at least 90% sequence identity to the amino acid sequence of SEQ ID NO: 4, wherein the nitrile oxido-reductase includes the amino acid sequence of SEQ ID NO: 5 and retains the ability to reduce the nitrile to the amine; and
   contacting the nitrite with the nitrite oxido-reductase under conditions sufficient for substantially reducing the nitrite to the amine.

23. The method of claim 22, wherein the amine is a primary amine.

24. The method of claim 23, wherein R comprises an aromatic group, an alkyl group, or mixed aromatic/alkyl groups.

25. The method of claim 1, wherein the nitrite oxido-reductase comprises at least 95% sequence identity to the amino acid sequence of SEQ ID NO: 4 and retains the ability to reduce the nitrite containing compound to the amine.

26. The method of claim 1, wherein the nitrile oxido-reductase comprises at least 98% sequence identity to the amino acid sequence of SEQ ID NO: 4 and retains the ability to reduce the nitrile containing compound to the amine.

27. The method of claim 1, wherein the nitrile oxido-reductase comprises at least 99% sequence identity to the amino acid sequence of SEQ ID NO: 4 and retains the ability to reduce the nitrile containing compound to the amine.

28. The method of claim 1, wherein the nitrile oxido-reductase consists of the amino acid sequence of SEQ ID NO: 4.

29. The method of claim 1, wherein the nitrite oxido-reductase comprises amino acids 5-275, 50-240, 85-230, or 100-240 of SEQ ID NO: 4 and retains the ability to reduce the nitrile containing compound to the amine.

30. The method of claim 22, wherein the nitrite oxido-reductase comprises at least 95% sequence identity to the amino acid sequence of SEQ ID NO: 4 and retains the ability to reduce the nitrite to the amine.

31. The method of claim 22, wherein the nitrite oxido-reductase comprises at least 98% sequence identity to the amino acid sequence of SEQ ID NO: 4 and retains the ability to reduce the nitrite to the amine.

32. The method of claim 22, wherein the nitrile oxido-reductase comprises at least 99% sequence identity to the amino acid sequence of SEQ ID NO: 4 and retains the ability to reduce the nitrite to the amine.

33. The method of claim 22, wherein the nitrile oxido-reductase consists of the amino acid sequence of SEQ ID NO: 4.

34. The method of claim 22, wherein the nitrile oxido-reductase comprises amino acids 5-275, 50-240, 85-230, or 100-240 of SEQ ID NO: 4 and retains the ability to reduce the nitrile containing compound to the amine.

35. A method of reducing a nitrile containing compound to an amine, comprising;
   contacting a nitrile containing compound with a nitrile oxido-reductase under conditions sufficient for substantially reducing the nitrile containing compound to the amine, wherein the nitrile oxido-reductase comprises at least 95% sequence identity to the amino acid sequence of SEQ ID NO: 4 and retains the ability to reduce the nitrile containing compound to the amine.

36. The method of claim 35, the nitrile oxido-reductase comprises SEQ ID NO: 5.

* * * * *

UNITED STATES PATENT AND TRADEMARK OFFICE
CERTIFICATE OF CORRECTION

PATENT NO. : 7,364,882 B1
APPLICATION NO. : 11/235933
DATED : April 29, 2008
INVENTOR(S) : Iwata-Reuyl et al.

It is certified that error appears in the above-identified patent and that said Letters Patent is hereby corrected as shown below:

In the Specification

Column 1, Lines 12-18, the paragraph STATEMENT OF GOVERNMENT SUPPORT should be changed to:
-- STATEMENT OF GOVERNMENT LICENSE RIGHTS
This invention was made with government support under grant number GM023562 awarded by the National Institutes of Health and under grant numbers MCB0128901 and MCB9733746 awarded by the National Science Foundation. The government has certain rights in the invention. --

Signed and Sealed this
Seventh Day of April, 2020

Andrei Iancu
*Director of the United States Patent and Trademark Office*